US012742206B2

(12) United States Patent
André et al.

(10) Patent No.: US 12,742,206 B2
(45) **Date of Patent: *Sep. 22, 2026**

(54) MULTIPLEX DROP-OFF DIGITAL POLYMERASE CHAIN REACTION METHODS

(71) Applicant: Stilla Technologies, Villejuif (FR)

(72) Inventors: Barbara André, Paris (FR); Rémi Dangla, Paris (FR); Jordan Madic, Villejuif (FR); Allison Mallory, Villejuif (FR)

(73) Assignee: Stilla Technologies, Villejuif (FR)

( * ) Notice: Subject to any disclaimer, the term of this patent is extended or adjusted under 35 U.S.C. 154(b) by 942 days.

This patent is subject to a terminal disclaimer.

(21) Appl. No.: 17/787,866

(22) PCT Filed: Dec. 22, 2020

(86) PCT No.: PCT/EP2020/087704

§ 371 (c)(1),
(2) Date: Jun. 21, 2022

(87) PCT Pub. No.: WO2021/130271

PCT Pub. Date: Jul. 1, 2021

(65) Prior Publication Data

US 2023/0057726 A1 Feb. 23, 2023

Related U.S. Application Data

(63) Continuation-in-part of application No. 17/013,222, filed on Sep. 4, 2020, now Pat. No. 11,060,141.

(30) Foreign Application Priority Data

Dec. 23, 2019 (EP) .................................... 19306765

(51) Int. Cl.
*C12Q 1/6876* (2018.01)
*C12Q 1/6827* (2018.01)
(Continued)

(52) U.S. Cl.
CPC ......... *C12Q 1/6876* (2013.01); *C12Q 1/6827* (2013.01); *C12Q 1/6853* (2013.01);
(Continued)

(58) Field of Classification Search
None
See application file for complete search history.

(56) References Cited

U.S. PATENT DOCUMENTS 4,683,195 A 7/1987 Mullis
4,683,202 A 7/1987 Mullis
(Continued)

FOREIGN PATENT DOCUMENTS

CN 104937600 A 9/2015
CN 107406842 A 11/2017
(Continued)

OTHER PUBLICATIONS

Falabella et al. G3 Genes|Genomes|Genetics. 2017. 7(10):3533-3542 and Table S1 (Year: 2017).*
(Continued)

*Primary Examiner* — Joseph G. Dauner
(74) *Attorney, Agent, or Firm* — Morrison & Foerster LLP

(57) ABSTRACT

The present application provides multiplex digital polymerase chain reaction (dPCR) assays such as multiplex drop-off dPCR assays, methods, systems, and kits. The methods described herein are useful in a variety of applica-
(Continued)

tions, such as detection of microsatellite instability and quantification of site-specific genome-edited products.

18 Claims, 23 Drawing Sheets

Specification includes a Sequence Listing.

(51) Int. Cl.

| | |
|---|---|
| ***C12Q 1/6853*** | (2018.01) |
| ***C12Q 1/6858*** | (2018.01) |
| ***C12Q 1/686*** | (2018.01) |
| ***G16B 25/20*** | (2019.01) |
| ***G16B 30/00*** | (2019.01) |

(52) U.S. Cl.

CPC .......... *C12Q 1/6858* (2013.01); *C12Q 1/686* (2013.01); *G16B 25/20* (2019.02); *G16B 30/00* (2019.02); *C12Q 2600/156* (2013.01); *C12Q 2600/16* (2013.01)

(56) References Cited

U.S. PATENT DOCUMENTS

| | | | |
|---|---|---|---|
| 5,210,015 | A | 5/1993 | Gelfand |
| 8,384,899 | B2 | 2/2013 | Oldham et al. |
| 8,697,359 | B1 | 4/2014 | Zhang |
| 8,932,814 | B2 | 1/2015 | Cong |
| 9,023,649 | B2 | 5/2015 | Mali |
| 9,057,057 | B2 | 6/2015 | Chandrasegaran et al. |
| 9,074,199 | B1 | 7/2015 | Chavez |
| 9,222,128 | B2 | 12/2015 | Saxonov |
| 10,501,789 | B2 | 12/2019 | Baroud |
| 11,060,141 | B1 | 7/2021 | Andréet al. |
| 2010/0173394 | A1 | 7/2010 | Colston, Jr. |
| 2011/0092373 | A1 | 4/2011 | Colston, Jr. |
| 2011/0092376 | A1 | 4/2011 | Colston, Jr. |
| 2018/0024061 | A1 | 1/2018 | Anazawa et al. |
| 2019/0256925 | A1 | 8/2019 | Litterst |
| 2021/0189486 | A1 | 6/2021 | André et al. |

FOREIGN PATENT DOCUMENTS

| | | | |
|---|---|---|---|
| WO | 2010036352 | A1 | 4/2010 |
| WO | 2013026027 | A1 | 2/2013 |
| WO | 2014/043581 | A1 | 3/2014 |
| WO | 2014097888 | A1 | 6/2014 |
| WO | 2015071474 | A2 | 5/2015 |
| WO | 2015071474 | A3 | 8/2015 |
| WO | 2016112351 | A1 | 7/2016 |
| WO | 2017115128 | A2 | 7/2017 |
| WO | 2017115128 | A3 | 8/2017 |
| WO | 2019011971 | A1 | 1/2019 |
| WO | 2019162240 | A1 | 8/2019 |
| WO | 2019175323 | A1 | 9/2019 |

OTHER PUBLICATIONS

Madic et al. Oncotarget. 2018. 9(100):37393-37406. (Year: 2018).*
Watanabe et al. EBioMedicine. 2017. 21:86-93. (Year: 2017).*
Chuvilin et al. PLOS ONE. 2016 11(11):e0166911, 17 pages. (Year: 2016).*
Walton et al. Bioconjugate Chem. 2002. 13:1155-1158. (Year: 2002).*
Yoshikawa et al. Analytical Biochemistry. 1998. 256:82-91. (Year: 1998).*
Bacher, J.W. et al. (2004). "Development of a Fluorescent Multiplex Assay for Detection of MSI-High Tumors," Disease Markers 20(4-5):237-250.
Baker, M. (Jun. 2012). "Digital PCR Hits Its Stride," Nature Methods 9(6):541-544.
Beerli, R.R. et al. (Dec. 8, 1998). "Toward Controlling Gene Expression at Will: Specific Regulation of the erbB-2/HER-2 Promoter by Using Polydactyl Zinc Finger Proteins Constructed From Modular Building Blocks," Proc. Natl. Acad. Sci USA 95(25):14628-14633.
Bhakta, M. et al. (Mar. 2013, e-pub. Dec. 5, 2012). " Highly Active Zinc-Finger Nucleases by Extended Modular Assembly," Genome Research 23(3):530-538.
Boch, J. et al. (Dec. 11, 2009). "Breaking the Code of DNA Binding Specificity of TAL-Type III Effectors," Science 326(5959):1509-1512.
Boland, C.R. et al. (Jun. 2010). "Microsatellite Instability in Colorectal Cancer," Gastroenterology 138(6):2073-2087. e3, 30 pages.
Cermak, T. et al. (Jul. 2011, e-pub. Apr. 14, 2011). "Efficient Design and Assembly of Custom TALEN and Other TAL Effector-Based Constructs for DNA Targeting," Nucleic Acids Research 39(12):e82, 11 pages.
Chevalier, B.S. et al. (Sep. 15, 2001). "Homing Endonucleases: Structural and Functional Insight Into the Catalysts of Intron/Intein Mobility," Nucleic Acids Research 29(18):3757-3774.
Cho, S.W. et al. (Mar. 2013, e-pub. Jan. 29, 2013). "Targeted Genome Engineering in Human Cells With the Cas9 RNA-Guided Endonuclease," Nature Biotechnology 31(3):230-232, 14 pages.
Christian, M. et al. (Oct. 2010, e-pub. Jul. 26, 2010). "Targeting DNA Double-Strand Breaks With TAL Effector Nucleases," Genetics 186(2):757-761.
Decraene, C. et al. (2018). "Multiple Hotspot Mutations Scanning by Single Droplet Digital PCR," Clinical Chemistry 64(2):317-328.
Deng, D. et al. (Feb. 10, 2012, e-pub. Jan. 5, 2012). "Structural Basis for Sequence-Specific Recognition of DNA by TAL Effectors," Science 335(6069):720-723, 9 pages.
Dobnik, D. et al. (Oct. 14, 2016). "Multiplex Quantification of Four DNA Targets in One Reaction With Bio-Rad Droplet Digital PCR System for GMO Detection," Scientific Report 6(35451):1-9.
Fan, H.C. et al. (Oct. 1, 2007, e-pub. Aug. 24, 2007). "Detection of Aneuploidy With Digital Polymerase Chain Reaction," Anal Chem 79(19):7576-7579.
Gaj, T. et al. (2016). "Genome-Editing Technologies: Principles and Applications," Cold Spring Harbor Perspectives in Biology 8:a023754, 21 pages.
gene-pi.com (Aug. 2019). "Drop-Off Assay for Determining Mutant DNA Population," Retrieved from https://www.gene-pi.com/tutorial/drop-off-assay/, last visited Dec. 3, 2020, 6 pages.
Hause, R.J. et al. (Nov. 2016, e-pub. Oct. 3, 2016). "Classification and Characterization of Microsatellite Instability Across 18 Cancer Types," Nat Medicine 22(11):1342-1350.
Hindson, B. et al. (2011). "High-Throughput Droplet Digital PCR System for Absolute Quantitation of DNA Copy Number," Analytical Chemistry 83(22):8604-8610.
Barra, G.S.R. et al. (Aug. 23, 2016). "Efficient Modification of the CCR5 Locus in Primary Human T Cells With megaTAL Nuclease Establishes HIV-1 Resistance," Molecular Therapy-Nucleic Acids 5:e352, 10 pages.
Innis, M.A et al. (1990). Optimization of PCRs, in PCR Protocols: A Guide to Methods and Applications, 11 pages.
International Preliminary Report on Patentability, issued Nov. 5, 2021, for PCT Application No. PCT/EP2020/087704, filed Dec. 22, 2022, 7 pages.
International Search Report and Written Opinion, mailed Apr. 19, 2021, for PCT Application No. PCT/EP2020/087704, , filed Dec. 22, 2022, 14 pages.
Jinek, M. et al. (Aug. 17, 2012, e-pub. Jun. 28, 2012). "A Programmable Dual-RNA-Guided DNA Endonuclease in Adaptive Bacterial Immunity," Science 337(6096):816-821, 14 pages.
Maar, D. et al. (Sep. 11, 2019). "Expanded Droplet Digital PCR Multiplexing Capability Using Two Different Strategies," Retrieved from https://bioradiations.com/expanded-droplet-digital=pcr-multiplexing-capability-using-two-different-strategies/, last visited Dec. 3, 2020, 5 pages.
Madic, J. et al. (2016, e-pub. Nov. 3, 2016). "Three-Color Crystal Digital PCR," Biomolecular Detection and Quantification 10:34-36.

(56) References Cited

OTHER PUBLICATIONS

Miller, J.C. et al. (Feb. 2011, e-pub. Dec. 22, 2010). "A Tale Nuclease Architecture for Efficient Genome Editing," Nature Biotechnology 29(2):143-148.
Morrison, T. et al. (2006, e-pub. Sep. 25, 2006). "Nanoliter High-Throughput Quantitative PCR," Nucleic Acids Res 34:e123, 9 pages.
Nazarenko, I.A. et al. (Jun. 15, 1997). "A Closed Tube Format for Amplification and Detection of DNA Based on Energy Transfer," Nucleic Acids Research 25(12):2516-2521.
Osborn, M. et al. (Mar. 2016, e-pub. Oct. 27, 2015). "Evaluation of TCR Gene Editing Achieved by TALENs, CRISPR/Cas9, and megaTAL Nucleases," Molecular Therapy. 24(3):570-581.
Ottesen, E.A. et al. (Dec. 1, 2006). "Microfluidic Digital PCR Enables Multigene Analysis of Individual Environmental Bacteria," Science 314(5804):1464-1467, 6 pages.
Pinheiro, L.B. et al. (Jan. 17, 2012, e-pub. Dec. 21, 2011). Evaluation of a Droplet Digital Polymerase Chain Reaction Format for DNA Copy Number Quantification, Anal. Chem. 84(2):1003-1011.
Pohl, G. et al. (Jan. 2004). "Principle and Applications of Digital PCR," Expert Rev Mol. Diagn, 4:41-47.
Ran, F.A. et al. (Nov. 2013). "Genome Engineering Using the CRISPR-Cas9 System," Nature Protocols 8 (11):2281-2308, 49 pages.
Sather, B. et al. (Sep. 30, 2015). "Efficient Modification Of CCR5 in Primary Human Hematopoietic Cells Using a megaTAL Nuclease and AAV Donor Template," Sci Transl Med 7(307):307ra156, 29 pages.
Sundberg, S.O. et al. (Feb. 15, 2010). "Spinning Disk Platform for Microfluidic Digital Polymerase Chain Reaction," Anal Chem 82(4):1546-1550.
Sykes, P.j. et al. (Sep. 1992). "Quantitation of Targets for PCR by Use of Limiting Dilution," BioTechniques 13:444-449.
Tyagi, S. et al. (Jan. 1998). "Multicolor Molecular Beacons for Allele Discrimination," Nature Biotechnology 16 (1):49-53.
Uniprot Accession No. CDJ55032 (Feb. 4, 2016). "CRISPR Associated Protein [*Streptococcus pyogenes*]," 2 pages.
Uniprot Accession No. Q99ZW2.1 (Oct. 7, 2020). "RecName: Full=CRISPR-Associated Endonuclease Cas9/Csn1; AltName: Full=SpCas9; AltName: Full=SpyCas9," 13 pages.
Vogelstein, B. et al. (Aug. 3, 1999). "Digital PCR," Proc Natl Acad Sci USA 96(16):9236-9241.
Wang, Y. et al. (Jun. 2014, e-pub. Mar. 25, 2014). "Progressive Engineering of a Homing Endonuclease Genome Editing Reagent for the Murine X-Linked Immunodeficiency Locus," Nucleic Acid Research 42(10):6463-6475.
Warren, L. et al. (Nov. 21, 2006, e-pub. Nov. 10, 2006). "Transcription Factor Profiling in Individual Hematopoietic Progenitors by Digital RT-PCR," Proc Natl Acad Sci USA 103(47):17807-17812.
Whale, A.S. et al. (2016, e-pub. May 27, 2016). "Fundamentals of Multiplexing With Digital PCR," Biomolecular Detection and Quantification 10:15-23.
Whitecombe, D. et al. (Aug. 1999). "Detection of PCR Products Using Self-Probing Amplicons and Fluorescence," Nature Biotechnology 17(8):804-807.
Zhong, Q. et al. (2011). "Multiplex Digital PCT: Breaking The One Target Per Color Barrier of Quantitative PCR," Lab Chip 11:2167-2174.

* cited by examiner

MULTIPLEX DROP-OFF DIGITAL POLYMERASE CHAIN REACTION METHODS

CROSS-REFERENCE TO RELATED APPLICATIONS

This application is a national stage application under 35 U.S.C. § 371 of International Application No. PCT/EP2020/087704, filed internationally on Dec. 22, 2020, which is a continuation-in-part on U.S. patent application Ser. No. 17/013,222, filed on Sep. 4, 2020, (issued as U.S. Pat. No. 11,060,141), the contents of each of which are hereby incorporated by reference in their entirety. International Application No. PCT/EP2020/087704 also claims the priority benefit of European Patent Application No. 19306765.9, filed on Dec. 23, 2019, the content of which is also hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 186142000630SEQLIST.TXT, date recorded: Jun. 16, 2022, size: 3,000 bytes).

FIELD

The present application is related to multiplex digital polymerase chain reaction (PCR) assays (such as multiplex drop-off dPCR assays), methods and systems, including methods for assessing microsatellite instability (MSI) and genome-editing products.

BACKGROUND

Digital polymerase chain reaction (dPCR) is a powerful and sensitive method that can be used to detect rare mutations in nucleic acid samples. Digital PCR assays using allele-specific fluorescent TAQMAN™ probes have been developed to detect somatic mutations in biomarker genes. In a conventional dPCR assay, a wildtype probe recognizing the wildtype allele and a mutant probe recognizing a specific mutant allele are used. Upon hybridization of a wildtype probe or a mutant probe to an amplicon in a dPCR partition, the probe releases its fluorophore through the exonuclease activity of a DNA polymerase. The released fluorophore from a wildtype probe is detected via a fluorescence detection channel that is distinct from the released fluorophore from a mutant probe. Such assays require a dPCR instrument with R detection channels to detect R mutations at one or more genetic loci. In contrast, drop-off assays allow the quantification of any number of mutations occurring at a mutation hotspot by using two probes in a dPCR reaction: a drop-off probe that recognizes a wildtype sequence at the mutation hotspot, and a reference probe that recognizes a sequence at a low-mutation region on the same amplicon. See, Decraene C. et al., *Clinical Chemistry* 64(2): 317-328 (2017). In a drop-off assay, two detection channels are required to detect any number of mutations at a single genetic locus.

Because dPCR instruments have limited fluorescence detection channels, there is a need to increase the multiplex levels of dPCR assays for different mutations and at different genetic loci. Such assays are especially useful in clinical and other applications involving samples that are limited in quantity. Robust methods for quantification of different genetic species based on data from multiplexed dPCR assays are also needed.

BRIEF SUMMARY

The present application provides methods, apparatus, systems and compositions, for detection and/or quantification of wildtype and mutant sequences at a plurality of target regions in nucleic acid samples using multiplex dPCR assays, such as multiplex drop-off dPCR assays. The assays described herein can be used to assess microsatellite instability (MSI) and detect genome-editing products (e.g., CRISPR-Cas system-edited products).

One aspect of the present application provides a method for quantification of wildtype and/or mutant sequences at a plurality of target regions in a sample comprising nucleic acid molecules, wherein the nucleic acid molecules are distributed among a plurality of partitions of the sample, and wherein substantially all partitions each comprises:

- a plurality of probe sets corresponding to the plurality of target regions, wherein each probe set of the plurality of probe sets comprises:
  - a drop-off probe comprising a drop-off label and an oligonucleotide drop-off sequence complementary to a wildtype sequence at a target region corresponding to the respective probe set;
  - a reference probe comprising a reference label and an oligonucleotide reference sequence complementary to a wildtype sequence at an adjacent reference region upstream or downstream to the target region corresponding to the respective probe set;
  - wherein a reference label and a drop-off label of each probe set of the plurality of probe sets are detectable via different detection channels; wherein reference labels of the plurality of probe sets are detectable via different detection channels with respect to each other; wherein drop-off labels of the plurality of probe sets are detectable via different detection channels with respect to each other; wherein at least one reference label of the plurality of probe sets and at least one drop-off label of the plurality of probe sets are detectable via the same detection channel;

wherein the method comprises detecting hybridization of reference probes of the plurality of probe sets to nucleic acid molecules or amplicons thereof comprising wildtype sequences at the reference regions in the plurality of partitions; and detecting hybridization of drop-off probes of the plurality of probe sets to nucleic acid molecules or amplicons thereof comprising wildtype sequences at the target regions in the plurality of partitions; thereby providing quantification of wildtype and/or mutants sequences at the plurality of target regions in the sample. In some embodiments, detection of a signal from a reference label and a signal from a drop-off label in a probe set indicates a wildtype sequence at the target region corresponding to the probe set, and detection of a signal from a reference label but no signal from a drop-off label in a probe set indicates a mutant sequence at the target region corresponding to the probe set. In some embodiments, wherein each probe set of the plurality of probe sets is a probe pair, the total number of detection channels is fewer than two times the total number of probe sets. In some embodiments, the total number of detection channels is equal to the total number of probe sets.

In some embodiments according to any one of the methods described above, the plurality of probe sets are R number of probe pairs, wherein a first probe pair of the R number of probe pairs comprises:

a first reference probe comprising a first reference sequence ($r_1$) and a first reference label detectable via a first detection channel ($X_1$), and a first drop-off probe comprising a first drop-off sequence ($w_1$) and a first drop-off label detectable via a second detection channel ($X_2$);

wherein a second probe pair of the R number of probe pairs comprises:

a second reference probe comprising a second reference sequence ($r_2$) and a second reference label detectable via the second detection channel ($X_2$), and a second drop-off probe comprising a second drop-off sequence ($w_2$) and a second drop-off label detectable via a third detection channel ($X_3$);

wherein, if (e.g., when) R is strictly larger than 3, an i-th probe pair ($2<i<R$) of the R number of probe pairs comprises:

an i-th reference probe comprising an i-th reference sequence ($r_i$) and an i-th reference label detectable via an i-th detection channel ($X_i$), and an i-th drop-off probe comprising an i-th drop-off sequence ($w_i$) and an i-th drop-off label detectable via an (i+1)-th detection channel ($X_{i+1}$);

wherein, if (e.g., when) R is strictly larger than 2, a R-th probe pair of the R number of probe pairs comprises:

a R-th reference probe comprising a R-th reference sequence ($r_R$) and a R-th reference label associated with a R-th detection channel ($X_R$), and a R-th drop-off probe comprising a R-th drop-off sequence ($w_R$) and a R-th drop-off label detectable by the first detection channel ($X_1$);

wherein the method comprises:

detecting hybridization of reference probes of the R number of probe pairs to nucleic acid molecules or amplicons thereof comprising wildtype sequences at the reference regions in the plurality of partitions via each of the detection channels $X_1$-$X_R$; and detecting hybridization of drop-off probes of the R number of probe pairs to nucleic acid molecules or amplicons thereof comprising wildtype sequences at the target regions in the plurality of partitions via each of the detection channels $X_1$-$X_R$.

In some embodiments, the method further comprises: obtaining a first count of one or more partitions that each produces a positive signal via the i-th detection channel and negative signals via any other of the detection channels $X_1$-$X_R$; obtaining a second count of one or more partitions that each produces negative signals via all of the detection channels $X_1$-$X_R$; and calculating a mutant probability ($\hat{P}(m_i)$) that a given partition contains a mutant sequence at the target region corresponding to the i-th probe pair, wherein the mutant probability is based on a ratio between the first count and a sum of the first count and the second count. In some embodiments, the method further comprises determining an estimated concentration of the mutant sequences at the target region corresponding to the i-th probe pair in the sample based on the mutant probability. In some embodiments, the estimated concentration of the mutant sequences at the target region corresponding to the i-th probe pair in the sample is determined according to:

$$\hat{C}(m_i) = -\frac{1}{v}\ln\left(1 - \hat{P}(m_i)\right)$$

wherein $\acute{C}(m_i)$ is indicative of the estimated concentration of mutant sequences at the target region corresponding to the i-the probe pair in the sample, wherein v is indicative of volume of a partition, and wherein $\hat{P}(m_i)$ is indicative of the mutant probability that a given partition contains a mutant sequence at the target region corresponding to the i-th probe pair in the sample. In some embodiments, the method further comprises determining a confidence interval and/or an uncertainty measure associated with the estimated concentration of the mutant sequences at the target region corresponding to the i-th probe pair in the sample.

In some embodiments according to any one of the methods described above, wherein the plurality of probe sets are R number of probe pairs, the method further comprises calculating a wildtype probability that a given partition contains a wildtype sequence at the target region corresponding to the i-th probe pair, wherein the wildtype probability is based on the mutant probability corresponding to the i-th probe pair and the mutant probability corresponding to the (i+1)-th probe pair, wherein the (i+1)-th probe pair refers to the first probe pair if (e.g., when) i=R. In some embodiments, the wildtype probability is calculated according to:

$$\hat{P}(w_i) = \left(\frac{n_{i,(i+1)}}{n_0 + n_i + n_{i+1} + n_{i,(i+1)}} - \hat{P}(m_i)\hat{P}(m_{i+1})\right)\frac{1}{1 - \hat{P}(m_i)\hat{P}(m_{i+1})}$$

wherein $\hat{P}(w_i)$ is indicative of the wildtype probability that a given partition contains a wildtype sequence at the target region corresponding to the i-th probe pair, wherein $n_{i,(i+1)}$ is indicative of a count of one or more partitions that each produces a positive signal via the $X_i$ detection channel, a positive signal via the $X_{i+1}$ detection channel, and negative signals via any other of the detection channels $X_1$-$X_R$;

wherein $n_{i,(i+1)}$ refers to $n_{R,1}$ if (e.g., when) i=R;

wherein $n_0$ is indicative of a count of one or more partitions that each produces negative signals via all the detection channels $X_1$-$X_R$;

wherein $n_i$ is indicative of a count of one or more partitions that each produces positive signal via the $X_i$ detection channel and negative signals via any other of the detection channels $X_1$-$X_R$;

wherein $n_{i+1}$ is indicative of a count of one or more partitions that each produces positive signal via the $X_{i+1}$ detection channel and negative signals via any other of the detection channels $X_1$-$X_R$;

wherein $n_{i+1}$ refers to $n_1$ if (e.g., when) i=R, wherein $\hat{P}(m_i)$ is indicative of the mutant probability that a given partition contains a mutant sequence at the target region corresponding to the i-th probe pair, wherein $\hat{P}(m_{i+1})$ is indicative of the mutant probability that a given partition contains a mutant sequence at the target region corresponding to the (i+1)-th probe pair, and wherein $\hat{P}(m_{i+1})$ refers to $\hat{P}(m_1)$ if (e.g., when) i=R. In some embodiments, the method further comprises determining an estimated concentration of the wildtype sequence at the target region corresponding to the i-th probe pair in the sample based on the wildtype probability. In some embodiments, the estimated concentration of the wildtype sequences at the target region corresponding to the i-th probe pair in the sample is determined according to:

$$\hat{C}(w_1) = -\frac{1}{v}\ln\left(1 - \hat{P}(w_1)\right)$$

wherein $\hat{C}(w_i)$ is indicative of the estimated concentration of wildtype sequences at the target region corresponding to the i-the probe pair in the sample, wherein v is indicative of volume of a partition, and wherein $\hat{P}(w_i)$ is indicative of the wildtype probability that a given partition contains a wildtype sequence at the target region corresponding to the i-th probe pair in the sample. In some embodiments, the method further comprises determining a confidence interval and/or a uncertainty measure associated with the estimated concentration of the wildtype sequence at the target region corresponding to the i-th probe pair in the sample.

In some embodiments according to any one of the methods described above, wherein the plurality of probe sets are R number of probe pairs, the method further comprises adjusting the concentration of nucleic acid molecules in the sample based on a count of partitions that each produces a positive signal via three or more of the detection channels $X_1$-$X_R$, wherein: (i) if (e.g., when) the count is larger than a pre-determined value, the adjusting is decreasing the concentration of the nucleic acid molecules in the sample by diluting the sample; or (ii) if (e.g., when) the count is smaller than a pre-determined value, the adjusting is increasing the concentration of the nucleic acid molecules in the sample by concentrating the sample. In some embodiments, the method further comprises determining a quality control measure by comparing a count of partitions that each produces a positive signal via each of the detection channels $X_1$-$X_R$ with an estimated count, wherein the estimated count is based on counts of partitions other than the count of partitions that each produces a positive signal via each of the detection channels $X_1$-$X_R$.

In some embodiments according to any one of the methods described above, wherein the plurality of probe sets are R number of probe pairs, R is between 2 and 6, such as 3.

In some embodiments according to any one of the methods described above, wherein the plurality of probe sets are three probe pairs, the method comprises obtaining a first count ($n_{100}$) of one or more partitions that each produces a positive signal via the detection channel $X_1$, a negative signal via the detection channel $X_2$, and a negative signal via the detection channel $X_3$; obtaining a second count ($n_{000}$) of one or more partitions that each produces negative signals on all of the detection channels $X_1$-$X_3$, and calculating a mutant probability ($\hat{P}(m_1)$) that a given partition contains a mutant sequence at the target region corresponding to the first probe pair, wherein the mutant probability is based on a ratio between the first count ($n_{100}$) and a sum of the first count ($n_{100}$) and the second count ($n_{000}$). In some embodiments, the method further comprises determining an estimated concentration C ($m_1$) of the mutant sequences at the target region corresponding to the first probe pair in the sample based on the mutant probability $\hat{P}(m_1)$. In some embodiments, the method further comprises determining a confidence interval and/or an uncertainty measure associated with the estimated concentration $\hat{C}(m_1)$ in the sample.

In some embodiments according to any one of the methods described above, wherein the plurality of probe sets are three probe pairs, the method further comprises calculating a wildtype probability ($\hat{P}(w_1)$) that a given partition contains a wildtype sequence at the target region corresponding to the first probe pair in the sample, wherein the wildtype probability is calculated based on $\hat{P}(m_1)$. In some embodiments, the wildtype probability is calculated based on $\hat{P}(m_1)$ and $\hat{P}(m_2)$. In some embodiments, the wildtype probability ($\hat{P}(w_1)$) is determined based on $$\hat{P}(w_1) = \left(\frac{n_{110}}{n_{000} + n_{100} + n_{010} + n_{110}} - \hat{P}(m_1)\hat{P}(m_2)\right)\frac{1}{1 - \hat{P}(m_1)\hat{P}(m_2)},$$

wherein $n_{110}$ is indicative of a count of one or more partitions that each produces a positive signal via the first detection channel, a positive signal via the second detection channel, and a negative signal via the third detection channel, wherein $n_{010}$ is indicative of a count of one or more partitions that each produces a negative signal via the first detection channel, a positive signal via the second detection channel, and a negative signal via the third detection channel, and wherein $\hat{P}(m_2)$ is indicative of a probability that a given partition contains a mutant sequence at the target region corresponding to the second probe pair.

In some embodiments according to any one of the methods described above, substantially all partitions each further comprises:

an allele-specific (AS) probe comprising an AS label and an oligonucleotide AS sequence complementary to an allelic sequence at a target region, wherein the AS label is detectable via a detection channel that is different from the detection channels corresponding to the reference probes and the drop-off probes of the plurality of probe sets; and wherein the method further comprises detecting hybridization of the AS probe to nucleic acid molecules or amplicons thereof comprising the allelic sequence at the target region in the sample, thereby providing quantification of the allelic sequence at the target region in the sample.

In some embodiments according to any one of the methods described above, each of the reference probes and the drop-off probes has a single detectable label. In some embodiments, the reference labels and drop-off labels are fluorophores. In some embodiments, one or more different detection channels have different excitation wavelength ranges and/or different emission wavelength ranges. In some embodiments, one or more different detection channels share the same excitation and/or emission wavelength ranges, but are associated with different fluorescence intensities. In some embodiments, probe sets corresponding to different target regions within a gene of interest comprise drop-off probes having drop-off labels associated with different detection channels that share the same excitation and/or emission wavelength ranges, wherein the drop-off probes are detected at different fluorescence intensities with respect to each other. In some embodiments, the reference labels and drop-off labels are selected from the group consisting of fluorescein, FAM, YAKIMA YELLOW®, CY3™, HEX, VIC, ROX, CY5™, CY5.5™, ALEXA FLUOR® 647, ALEXA FLUOR® 448, and Quasar705. In some embodiments, wherein the plurality of probe sets are three probe pairs, the first reference label, the second reference label and the third reference label are selected from the group consisting of CY3™, FAM and CY5™, or wherein the first reference label, the second reference label and the third reference label are selected from the group consisting of FAM, HEX and CY5™.

In some embodiments according to any one of the methods described above, the target regions are mutation hotspot regions in one or more genes selected from the group consisting of EGFR, NRAS, KRAS, ESR1, and BRAF.

In some embodiments according to any one of the methods described above, each partition further comprises:

(a) a plurality of primer sets corresponding to the plurality of target regions, and (b) a DNA-dependent DNA polymerase;

wherein each primer set of the plurality of primer sets comprises a forward oligonucleotide primer and a reverse oligonucleotide primer suitable for amplifying a target fragment comprising a target region corresponding to the primer set and the reference region corresponding to the target region; wherein the method comprises amplifying the target fragments from the nucleic acid molecules in the plurality of partitions; and wherein the detecting comprises detecting hybridization of the reference probes and the drop-off probes to amplicons of the target fragments. In some embodiments, the DNA-dependent DNA polymerase comprises 5' to 3' exonuclease activity and the detecting comprises detecting an increase in fluorescence caused by 5' to 3' exonuclease digestion of the reference labels from hybridized reference probes and/or the drop-off labels from hybridized drop-off probes in the plurality of partitions.

In some embodiments according to any one of the methods described above, the amplicons are about 100 to about 200 nucleotides long. In some embodiments, the reference regions are not associated with single nucleotide polymorphisms.

In some embodiments according to any one of the methods described above, the method further comprises forming a plurality of partitions having a pre-determined volume.

In some embodiments according to any one of the methods described above, the nucleic acid molecules are genomic DNA molecules, tumor DNA molecules, or cDNA molecules. In some embodiments, the method further comprises extracting the nucleic acid molecules from a biological sample. In some embodiments, the nucleic acid molecules are obtained from a formalin-fixed, paraffin-embedded (FFPE) sample, or a liquid biopsy sample. In some embodiments, the method comprises fragmenting nucleic acid molecules in the biological sample to provide the sample comprising nucleic acid molecules.

In some embodiments according to any one of the methods described above, the plurality of target regions are microsatellite sequence loci.

In some embodiments according to any one of the methods described above, the nucleic acid molecules are genomic DNA in a sample of cells, wherein the cells have been contacted with a site-specific genome-editing reagent configured to cleave target sites in the plurality of target regions, and wherein the mutant sequences are non-homologous end joining (NHEJ) edited sequences at the plurality of target regions. In some embodiments, the site-specific genome-editing reagent comprises a Cas nuclease, a TALEN, or a Zinc-finger nuclease. In some embodiments, the method further comprises contacting the cells with the site-specific genome-editing reagent.

In some embodiments according to any one of the methods described above, each probe set of the plurality of probe sets further comprises:

an allele-specific (AS) probe comprising an AS label and an oligonucleotide AS sequence complementary to an allelic sequence at the target region corresponding to the respective probe set, wherein the AS label is detectable via a detection channel that is different from the detection channel of the respective reference probe or the detection channel of the respective drop-off probe, and wherein AS labels of the plurality of probe sets are detectable via different detection channels with respect to each other, wherein the method further comprises detecting hybridization of AS probes of the plurality of probe sets to nucleic acid molecules or amplicons thereof comprising allelic sequences at the target regions in the plurality of partitions; thereby providing quantification of allelic sequences at the plurality of target regions in the sample. In some embodiments, wherein each probe set of the plurality of probe sets is a probe triplet, the total number of detection channels is fewer than three times the total number of probe sets. In some embodiments, the total number of detection channels is one more than the total number of probe sets. In some embodiments, the nucleic acid molecules are genomic DNA in a sample of cells, wherein the cells have been contacted with a site-specific genome-editing reagent and homology directed repair (HDR) template nucleic acids comprising HDR replacement sequences, wherein the site-specific genome-editing reagent is configured to cleave target sites in the plurality of target regions, wherein the mutant sequences are non-homologous end joining (NHEJ) edited sequences at the plurality of target regions, and wherein the allelic sequences are HDR replacement sequences inserted at the plurality of target regions. In some embodiments, the site-specific genome-editing reagent comprises a Cas nuclease, a TALEN, or a Zinc-finger nuclease. In some embodiments, the method further comprises contacting the cells with the site-specific genome-editing reagent.

One aspect of the present application provides a method for quantification of mutations at a plurality of microsatellite sequence loci in a sample comprising nucleic acid molecules, wherein the nucleic acid molecules are distributed among a plurality of partitions of the sample, and wherein substantially all partitions each comprises:

a plurality of primer sets corresponding to the plurality of microsatellite sequence loci, wherein each primer set of the plurality of primer sets comprises:

a forward oligonucleotide primer and a reverse oligonucleotide primer suitable for amplifying target fragments from the nucleic acid molecules, wherein each target fragment comprises the microsatellite sequence locus corresponding to the primer set and an adjacent reference region upstream or downstream to the microsatellite sequence locus;

a plurality of probe pairs corresponding to the plurality of microsatellite sequence loci, wherein each probe pair of the plurality of probe pairs comprises:

a drop-off probe comprising a drop-off label and an oligonucleotide drop-off sequence complementary to a wildtype sequence of a microsatellite sequence locus corresponding to the respective probe pair, a reference probe comprising a reference label and an oligonucleotide reference sequence complementary to a wildtype sequence of the reference region corresponding to the respective probe pair, wherein a reference label and a drop-off label of each probe pair of the plurality of probe pairs are detectable via different detection channels;

wherein reference labels of the plurality of probe pairs are detectable via different detection channels with respect to each other;

wherein drop-off labels of the plurality of probe pairs are detectable via different detection channels with respect to each other;

wherein at least one reference label of the plurality of probe pairs and at least one drop-off label of the plurality of probe pairs are detectable via the same detection channel;

wherein the method comprises amplifying the target fragments in the plurality of partitions; and detecting hybridization of reference probes and drop-off probes of the plurality of probe pairs to amplicons of the target fragments in the plurality of partitions, thereby providing quantification of mutations at the plurality of microsatellite sequence loci in the sample.

One aspect of the present application provides a method for quantification of unmodified, homology directed repair (HDR)-edited, and/or non-homologous end joining (NHEJ)-edited sequences at a plurality of target regions in nucleic acid molecules from a sample of cells, wherein the cells have been contacted with a site-specific genome-editing reagent and HDR template nucleic acids comprising HDR replacement sequences, wherein the site-specific genome-editing reagent is configured to cleave target sites in the plurality of target regions, wherein the nucleic acid molecules are distributed among a plurality of partitions of the sample, and wherein substantially all partitions each comprises:

a plurality of probe sets corresponding to the plurality of target regions, wherein each probe set of the plurality of probe sets comprises:

a HDR probe comprising a HDR label and an oligonucleotide HDR sequence complementary to a HDR replacement sequence inserted at a target region corresponding to the respective probe set, an NHEJ drop-off probe comprising an NHEJ drop-off label and an oligonucleotide drop-off sequence complementary to a wildtype sequence of the target region corresponding to the respective probe set, and wherein the drop-off sequence does not hybridize to NHEJ-edited mutant sequences at the target region corresponding to the respective probe set, a reference probe comprising a reference label and an oligonucleotide reference sequence complementary to a wildtype sequence at an adjacent reference region upstream or downstream to the target region corresponding to the respective probe set, wherein a HDR label, an NHEJ drop-off label, and a reference label of each probe set of the plurality of probe sets are detectable via different detection channels; wherein HDR labels of the plurality of probe sets are detectable via different detection channels with respect to each other; wherein NHEJ drop-off labels of the plurality of probe sets are detectable via different detection channels with respect to each other; wherein reference labels of the plurality of probe sets are detectable via different detection channels with respect to each other; wherein at least one reference label of the plurality of probe sets and at least one NHEJ drop-off label of the plurality of probe sets are detectable via the same detection channel, and/or at least one reference label of the plurality of probe sets and at least one HDR label of the plurality of probe sets are detectable via the same detection channel;

wherein the method comprises:

detecting hybridization of reference probes of the plurality of probe sets to nucleic acid molecules or amplicons thereof comprising wildtype sequences at the reference regions in the plurality of partitions;

detecting hybridization of HDR probes of the plurality of probe sets to nucleic acid molecules or amplicons thereof comprising the HDR replacement sequences at the target regions in the plurality of partitions; and detecting hybridization of NHEJ drop-off probes of the plurality of probe sets to nucleic acid molecules or amplicons thereof comprising wildtype sequences at the target regions in the plurality of partitions;

thereby providing quantification of unmodified, HDR-edited, and/or NHEJ-edited sequences at the plurality of target regions in the sample. In some embodiments, the plurality of probe sets are (R−1) number of probe triplets, wherein a first probe triplet of the (R−1) number of probe triplets comprises:

a first reference probe comprising a first reference sequence ($m_1$) and a first reference label detectable via a first detection channel ($X_1$);

a first NHEJ drop-off probe comprising a first NHEJ drop-off sequence ($r_1$) and a first NHEJ drop-off label detectable via a second detection channel ($X_2$); and a first HDR probe comprising a first HDR sequence ($w_1$) and a first HDR label detectable via a third channel ($X_3$);

wherein a second probe triplet of the (R−1) number of probe triplets comprises:

a second reference probe comprising a second reference sequence ($m_2$) and a second reference label detectable via the second detection channel ($X_2$);

a second NHEJ drop-off probe comprising a second drop-off sequence ($r_2$) and a second NHEJ drop-off label detectable via the third detection channel ($X_3$); and a second HDR probe comprising a second HDR sequence ($w_2$) and a second HDR label detectable via a fourth detection channel ($X_4$);

wherein, if (e.g., when) R is strictly larger than 3, an i-th probe triplet ($2<i<R-1$) of the (R−1) number of probe triplets comprises:

an i-th reference probe comprising an i-th reference sequence ($m_i$) and an i-th reference label detectable via an i-th detection channel ($X_i$);

an i-th NHEJ drop-off probe comprising an i-th drop-off sequence ($r_i$) and an i-th NHEJ drop-off label detectable via an (i+1)-th detection channel ($X_{i+1}$); and an i-th HDR probe comprising an i-th HDR sequence ($w_i$) and an i-th HDR label detectable via an (i+2)-th detection channel ($X_{i+2}$);

wherein, if (e.g., when) R is strictly larger than 3, a (R−1)-th probe triplet of the (R−1) number of probe triplets comprises:

a (R−1)-th reference probe comprising a (R−1)-th reference sequence ($m_{R-1}$) and a R-th reference label detectable via a R-th detection channel ($X_R$);

a (R−1)-th NHEJ drop-off probe comprising a (R−1)-th drop-off sequence ($r_{R-1}$) and a (R−1)-th NHEJ drop-off label detectable via a (R−1)-th detection channel ($X_{R-1}$); and a (R−1)-th HDR probe comprising a (R−1)-th HDR sequence ($w_R$-1) and a (R−1)-th HDR label detectable via the first detection channel ($X_1$);

wherein the method comprises detecting hybridization of reference probes of the (R−1) number of probe triplets to nucleic acid molecules or amplicons thereof comprising wildtype sequences at the reference regions in the plurality of partitions via each of the detection channels $X_1$-$X_{R-2}$ and $X_R$; detecting hybridization of NHEJ drop-off probes of the (R−1) number of probe triplets to nucleic acid molecules or amplicons thereof comprising wildtype sequences at the target regions in the plurality of partitions via each of the detection channels $X_2$-$X_{R-1}$; and detecting hybridization of HDR probes of the (R−1) number of probe triplets to nucleic acid molecules or amplicons thereof comprising the HDR replacement sequences at the target regions in the plurality of partitions via each of the detection channels $X_1$ and $X_3$-$X_R$. In some embodiments, the method further comprises:

if (e.g., when) 1≤i≤R−2:

obtaining a first count of one or more partitions that each produces a positive signal via the $X_i$ detection channel and negative signals via any other of the detection channels $X_1$-$X_R$; obtaining a second count of one or more partitions that each produces negative signals via all of the detection channels $X_1$-$X_R$;

or if (e.g., when) i is R−1:

obtaining a first count of one or more partitions that each produces a positive signal via the $X_R$ detection channel and negative signals via any other of the detection channel $X_1$-$X_R$; obtaining a second count of one or more partitions that each produces negative signals via all of the detection channels $X_1$-$X_R$; and calculating an NHEJ-edited probability ($\hat{P}(r_i)$) that a given partition contains an NHEJ-edited sequence at the target region corresponding to the i-th probe triplet, wherein the NHEJ-edited probability is based on a ratio between the first count and a sum of the first count and the second count. In some embodiments, the method further comprises:

if (e.g., when) 1≤i≤R−2:

obtaining a first count of one or more partitions that each produces a positive signal via the $X_i$ detection channel, a positive signal via the $X_{i+1}$ detection channel and negative signals via any other of the detection channels $X_1$-$X_R$; obtaining a second count of one or more partitions that each produces negative signals via each of the detection channels $X_1$-$X_{i-1}$, and negative signals via each of the detection channels $X_{i+2}$-$X_R$; and calculating an unmodified probability ($\hat{P}(m_i)$) that a given partition contains a wildtype sequence at the target region corresponding to the i-th probe triplet, wherein the unmodified probability is based on $\hat{P}(r_i)$, $\hat{P}(r_{i+1})$ and a ratio between the first count and a sum of the first count and the second count;

or if (e.g., when) i is R−1:

obtaining a first count of one or more partitions that each produces a positive signal via the $X_R$ detection channel, a positive signal at the $X_{R-1}$ detection channel and negative signals via any other of the detection channel $X_1$-$X_R$; obtaining a second count of one or more partitions that each produces negative signals via each of the detection channels $X_1$-$X_{R-2}$; and calculating an unmodified probability ($\hat{P}(m_{R-1})$) that a given partition contains a wildtype sequence at the target region corresponding to the (R−1)-th probe triplet, wherein the unmodified probability is based on a ratio between the first count and a sum of the first count and the second count. In some embodiments, the method further comprise:

if (e.g., when) 1≤i≤R−2:

obtaining a first count of one or more partitions that each produces a positive signal via the $X_i$ detection channel, a positive signal via the $X_{i+2}$ detection channel and negative signals via any other of the detection channels $X_1$-$X_R$; obtaining a second count of one or more partitions that each produces negative signals via each of the detection channels $X_1$-$X_{i-1}$, negative signal in $X_{i+1}$, and negative signals via each of the detection channels $X_{i+3}$-$X_R$; and calculating a HDR-edited probability ($\hat{P}(w_i)$) that a given partition contains a HDR replacement sequence at the target region corresponding to the i-th probe triplet, wherein the HDR-edited probability is based on $\hat{P}(r_i)$, $\hat{P}(r_{i+2})$, and a ratio between the first count and a sum of the first count and the second count;

or if (e.g., when) i is R−1:

obtaining a first count of one or more partitions that each produces a positive signal via the $X_R$ detection channel, a positive signal at the $X_1$ detection channel and negative signals via any other of the detection channel $X_1$-$X_R$; obtaining a second count of one or more partitions that each produces negative signals via each of the detection channels $X_2$-$X_{R-1}$; and calculating a HDR-edited probability ($\hat{P}(w_R$-1)) that a given partition contains a wildtype sequence at the target region corresponding to the (R−1)-th probe triplet, wherein the HDR-edited probability is based on ($r_{R-1}$), $\hat{P}(r_1)$, and a ration between the first count and a sum of the first count and the second count.

One aspect of the present application provides a method for quantification of wildtype and/or allelic sequences at R number of target regions in a sample comprising nucleic acid molecules, wherein the nucleic acid molecules are distributed among a plurality of partitions of the sample, wherein substantially all partitions each comprises R number of probe triplets corresponding to the R number of target regions, wherein a first probe triplet of the R number of probe triplets comprises:

a first reference probe corresponding to a first reference sequence ($w_1$) and a first reference label detectable via a first detection channel ($X_1$), a first AS probe of the first probe triplet ("first AS probe 1") corresponding to a first allelic sequence ($r_1$) and a first AS label of the first probe triplet ("first AS label 1") detectable via the first detection channel ($X_1$), and a second AS probe of the first probe triplet ("second AS probe 1") corresponding to the first allelic sequence ($r_1$) and a second AS label of the first probe triplet ("second AS label 1") detectable via the second detection channel ($X_2$);

wherein a second probe triplet of the R number of probe triplets comprises:

a second reference probe corresponding to a second reference sequence ($w_2$) and a second reference label detectable via the second detection channel ($X_2$), a first AS probe of the second probe triplet ("first AS probe 2") corresponding to a second allelic sequence ($r_2$) and a first AS label of the second probe triplet ("AS label 2") detectable via the second detection channel ($X_2$), and a second AS probe of the second probe triplet ("second AS probe 2") corresponding to the second allelic sequence second allelic sequence ($r_2$) and a second AS label of the second probe triplet ("second AS label 2") detectable via a third detection channel ($X_3$);

wherein, if (e.g., when) R is strictly larger than 3, an i-th probe triplet (2<i<R) of the R number of probe triplet comprises:

an i-th reference probe corresponding to an i-th reference sequence ($w_i$) and an i-th reference label detectable via an i-th detection channel ($X_i$), a first AS probe of the i-th probe triplet ("first AS probe i") corresponding to an i-th allelic sequence ($r_i$) and a first AS label of the i-th probe triplet ("first AS label i") detectable via the i-th detection channel ($X_i$), and a second AS probe of the i-th probe triplet ("second AS probe i") corresponding to an i-th allelic sequence ($r_i$) and a second AS label of the i-th probe triplet ("second AS label i") detectable via the (i+1)-th detection channel ($X_{i+1}$);

wherein, if (e.g., when) R is strictly larger than 2, a R-th probe triplet of the R number of probe triplets comprises:

a R-th reference probe corresponding to a R-th reference sequence ($w_R$) and a R-th reference label detectable via a R-th detection channel ($X_R$), a first AS probe of the R-th probe triplet ("first AS probe R") corresponding to an R-th allelic sequence (TR) and a first AS label of the R-th probe triplet ("first AS label R") detectable via the R-th detection channel ($X_R$), and a second AS probe of the R-th probe triplet ("second AS probe R") corresponding to a R-th allelic sequence (TR) and a second AS label of the R-th probe triplet ("second AS label R") detectable via the first detection channel ($X_1$);

wherein the first AS probe and the second AS probe of each probe triplet hybridize to the same allelic sequence, different portions within the same allelic sequence, or complementary sequences thereof at a target region corresponding to the respective probe triplet; wherein the reference sequence of each probe triplet is at a reference region corresponding to the respective probe triplet;

wherein the detection channels $X_1$-$X_R$ are different from each other;

wherein the method comprises detecting hybridization of reference probes of the R number of probe triplets to nucleic acid molecules or amplicons thereof comprising reference sequences or complementary sequences thereof at the reference regions in the plurality of partitions via each of the detection channels $X_1$-$X_R$; and detecting hybridization of the first AS probes and the second AS probes of the R number of probe triplets to nucleic acid molecules or amplicons thereof comprising allelic sequences or complementary sequences thereof at the target regions in the plurality of partitions via each of the detection channels $X_1$-$X_R$; thereby providing quantification of wildtype and/or allelic sequences at the R number of target regions in the sample. In some embodiments, the reference region of a probe triplet is adjacent to (e.g., upstream or downstream) the target region corresponding to the respective probe triplet. In some embodiments, R is 3. In some embodiments, the allelic sequences are associated with copy number variations (CNVs). In some embodiments, the allelic sequences are associated with rare alleles. In some embodiments, the allelic sequences are related to one or more mutant allele fraction(s) (MAFs). In some embodiments, the allelic sequences are related to one of more variant allele fraction(s) (VAFs). In some embodiments, the method is used for simultaneous detection of CNVs, determination of multiple allelic frequencies (MAF) or variant allele fractions (VAF).

Also provided are compositions, systems, kits and articles of manufacture for any one of the methods described above.

BRIEF DESCRIPTION OF THE DRAWINGS

FIG. 1A shows a three-dimensional plot of fluorescent signals from dPCR reaction droplets of a sample having only wildtype sequences at the EGFR, NRAS and KRAS genetic loci. FIG. 1B shows a three-dimensional plot of fluorescent signals from dPCR reaction droplets of a sample having wildtype sequences at the NRAS and KRAS loci, and both wildtype and mutant sequences at the EGFR locus. FIG. 1C shows a three-dimensional plot of fluorescent signals from dPCR reaction droplets of a sample having wildtype sequences at the EGFR and KRAS loci, and both wildtype and mutant sequences at the NRAS locus. FIG. 1D shows a three-dimensional plot of fluorescent signals from dPCR reaction droplets of a sample having wildtype sequences at the EGFR and NRAS loci, and both wildtype and mutant sequences at the KRAS locus.

FIG. 4A shows a design with two distinct multiplex drop-off dPCR assays, one capable of detecting wildtype and mutant sequences at the A146, G12/13 and Q61 loci of KRAS using three probe pairs, and a second assay capable of detecting wildtype and mutant sequences at the G12/13 and Q61 loci of NRAS, and the V600E and V600K mutations of BRAF. In the second assay, the BRAF V600E and V600K mutations can be detected either using drop-off probes or allele-specific probes. FIG. 4B shows a design of a single multiplex assay that can detect all KRAS, NRAS and BRAF mutations using three fluorescence detection channels. The same fluorescence detection channel is used to detect wildtype and mutant sequences at different loci in the same gene. However, to distinguish different loci from the same gene, probe pairs associated with different loci are detected via different fluorescence intensities, which can be adjusted by using different concentrations of primers and probe pairs.

DETAILED DESCRIPTION

Figure 1A:
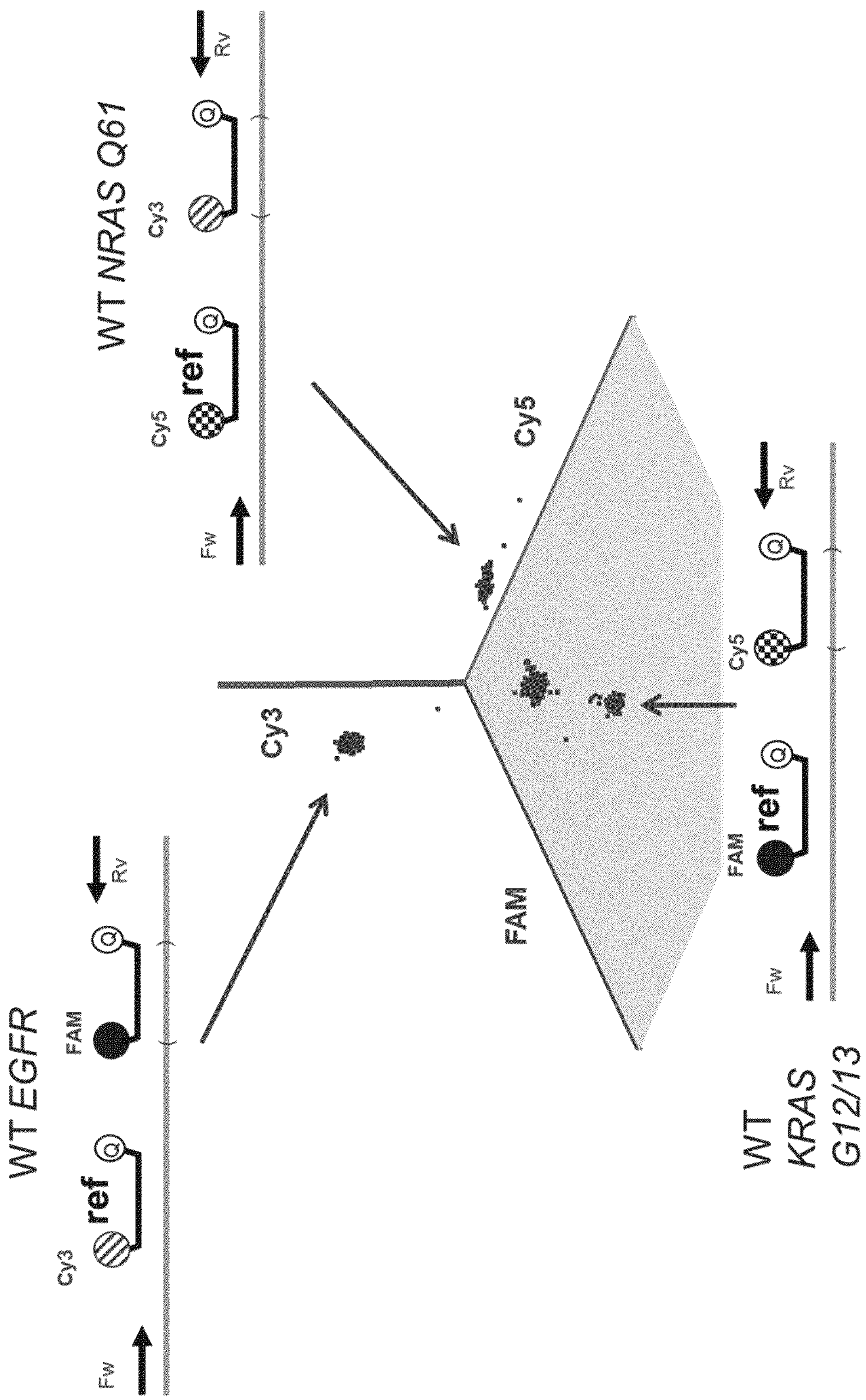
FIGS. 1A-1D show schematics of an exemplary triplex drop-off dPCR assay that can detect a total of six genetic populations, i.e., one wildtype sequence and all mutant sequences at each of the three genetic loci (e.g., KRAS, NRAS and EGFR mutation hotspots), using three fluorescence detection channels.
Figure 1B:
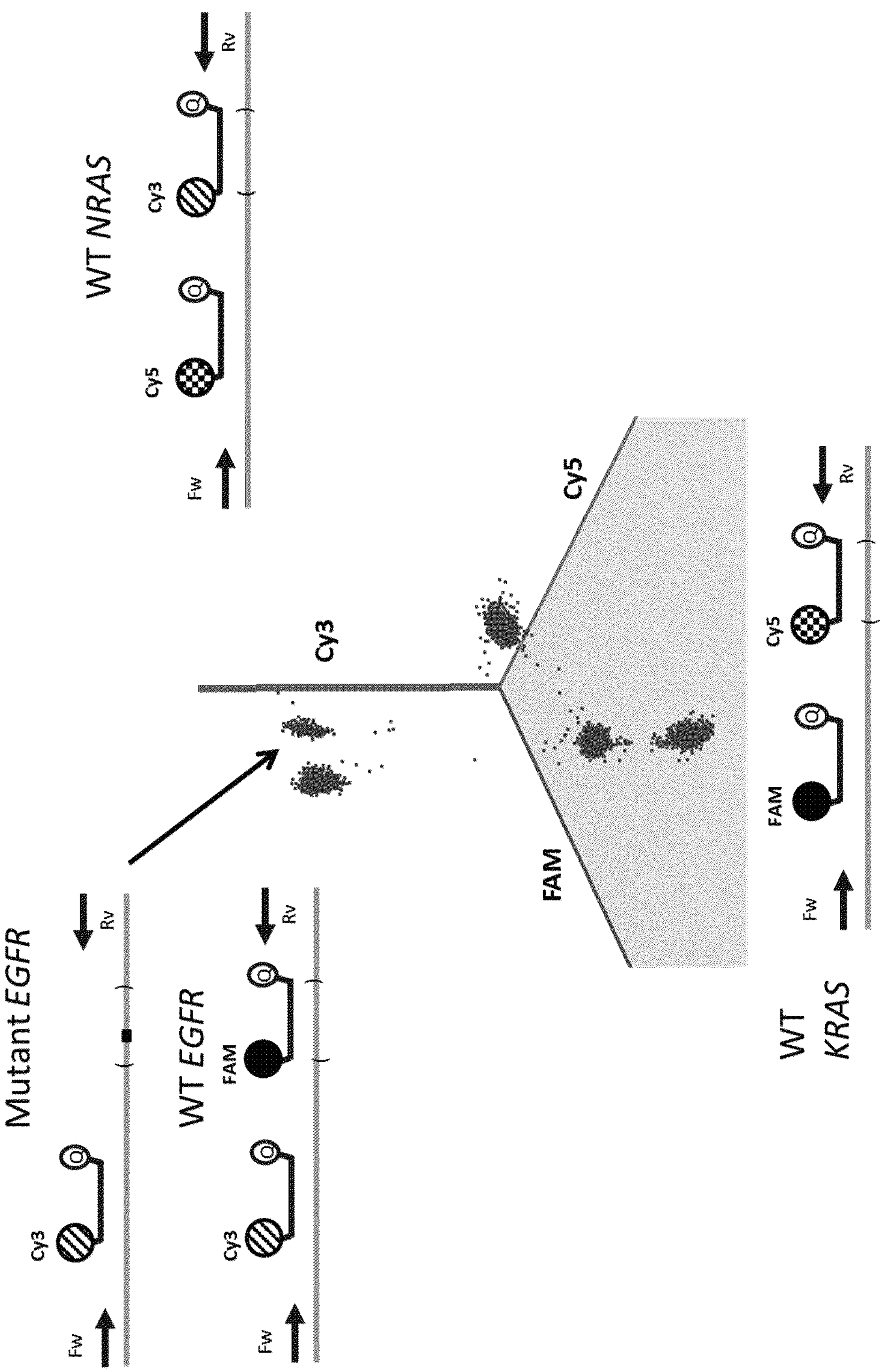
Figure 1C:
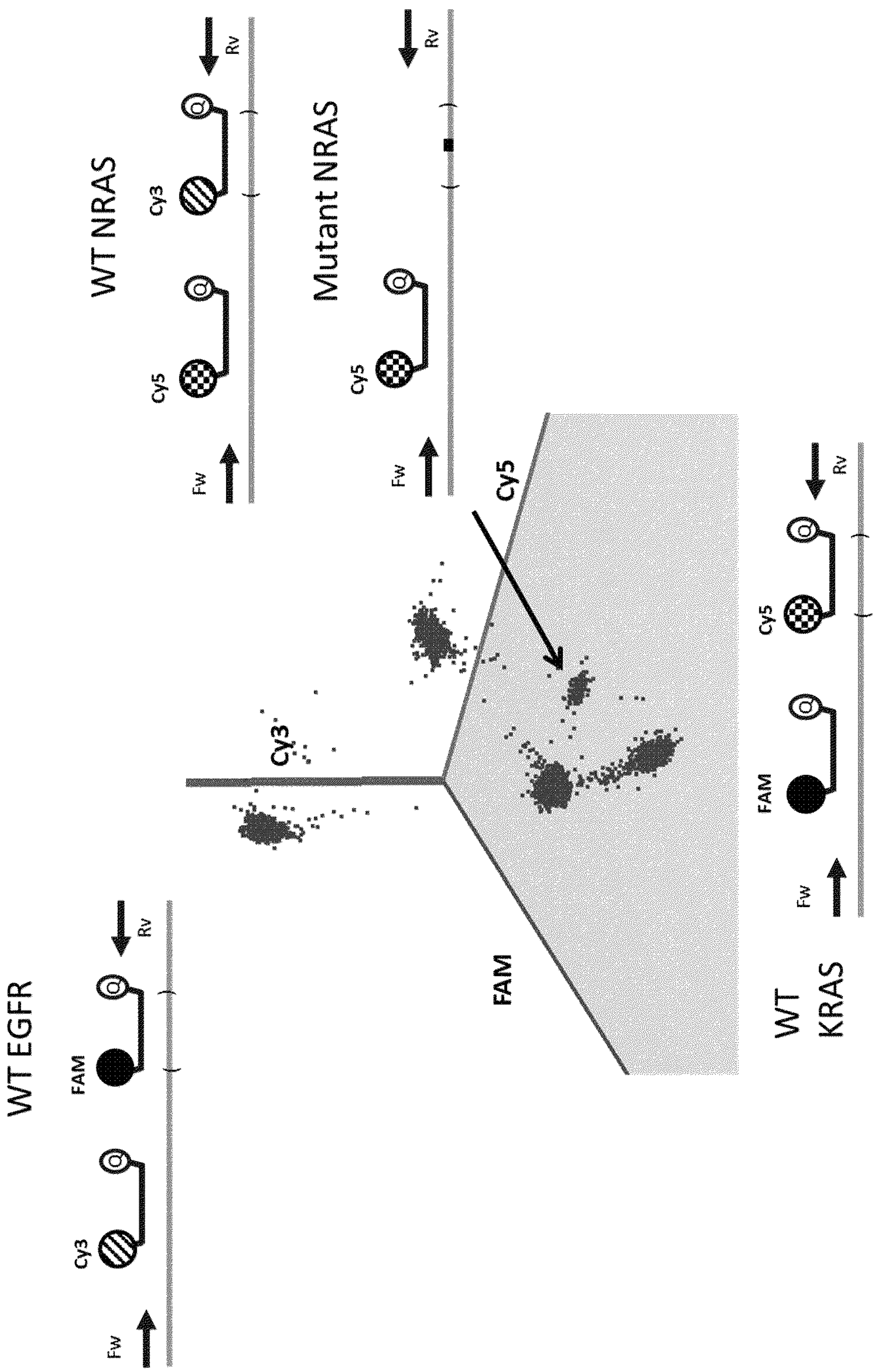
Figure 1D:
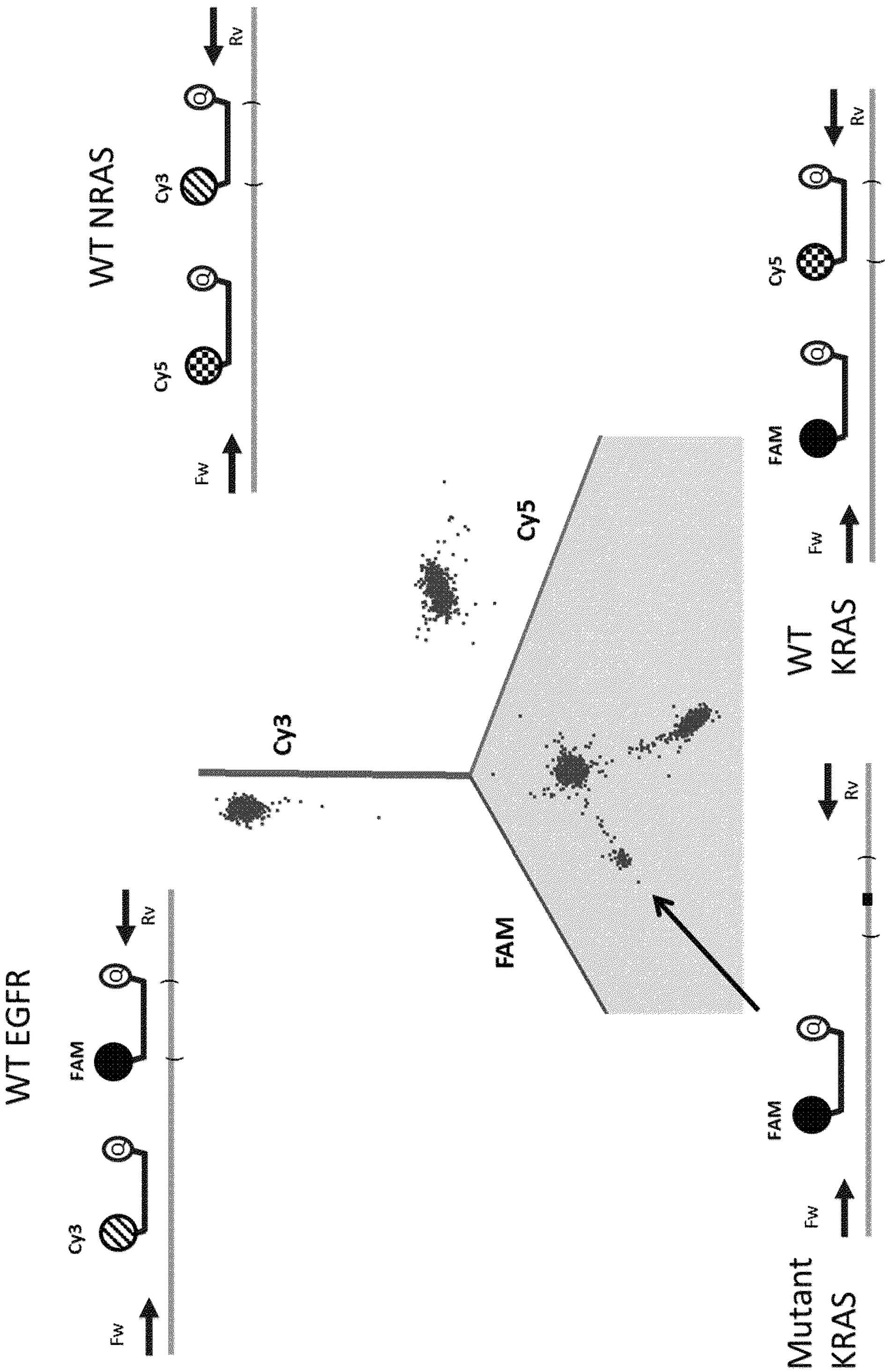

The present application provides multiplex digital polymerase chain reaction (dPCR) assays such as multiplex drop-off dPCR assays that can detect wildtype and mutant sequences at R different genetic loci using fewer than two times R number of detection channels, for example, by using reference probes and drop-off probes sharing overlapping sets of labels. The assays described herein may be used to assess microsatellites instability (MSI) and genome-editing products.

In some embodiments, the multiplex drop-off dPCR assays use R probe pairs each comprising a reference probe comprising a reference label and a drop-off probe comprising a drop-off label, in which the reference label and the drop-off label in each probe pair are detectable via different detection channels. In some embodiments, the set of the drop-off labels and the set of the reference labels used in the probe pairs are circular permutations with respect to each other, which allows detection of 2R number of genetic species (i.e., wildtype and mutant at each genetic locus) via only R number of different detection channels. Additionally, each drop-off probe is capable of detecting all mutation sequences associated with its respective target genetic locus, thereby increasing the multiplex level of the dPCR assay in terms of detectable mutations per assay.

In some embodiments, the multiplex drop-off dPCR assay uses R−1 probe triplets each comprising a reference probe comprising a reference label, a drop-off probe (e.g., an NHEJ drop-off probe) comprising a drop-off label, and an allele-specific probe (e.g., a HDR probe) comprising an allele-specific label, in which the reference label, the drop-off label and the allele-specific label in each probe triplet are detectable via different detection channels. In some embodiments, the set of the reference labels, the set of the drop-off labels, and the set of the allele-specific labels used in the probe triplets are permutations with respect to each other (e.g., as shown in FIG. 6B), thereby allowing detection of 3(R−1) species via only R number of detection channels.

In some embodiments, the multiplex dPCR assays use R probe sets each comprising a reference probe comprising a reference label, a first allele-specific probe comprising a first allele-specific label, and a second allele-specific probe comprising a second allele-specific label, wherein the second allele-specific probe hybridizes to the same allelic sequence or its complementary sequence as the first allele-specific probe or the first allele-specific probe and the second allele-specific probe hybridize to two different portions of the same allelic sequence or complementary sequences thereof, wherein the reference label and the first allele-specific label in each probe set are detectable via the same detection channel, and the reference label and the second allele-specific label in each probe set are detectable via different detection channels. In some embodiments, the set of the second allele-specific labels and the set of the reference labels used in the probe sets are circular permutations with respect to each other, which allows detection of 2R number of genetic species (i.e., wildtype and allelic sequences at each genetic locus) via only R number of different detection channels. The multiplex dPCR assays may be used for detecting multiple copy number variants (CNVs), assessing multiple allelic frequencies (MAF) and determining multiple variant allele fractions (VAF) in a sample.

The multiplex dPCR assays and methods described herein can be used in a variety of applications, such as detection of microsatellite mutations, and quantification of site-specific genome-edited products. Also provided are compositions, systems, methods of diagnosis, methods of treatment, methods of screening, kits and articles of manufacture.

I. Definitions

The terms "polynucleotide" and "nucleic acid" are used interchangeably herein to refer to a polymer of nucleotides of any length, and includes DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. Nucleic acids may be single-stranded, double-stranded, or in more highly aggregated hybridization forms, and may include chemical modifications. "Polynucleotide" or "nucleic acid" may also be used herein to refer to the sequence encoded by the nucleic acid, including the sense strand (i.e., coding strand) sequence and anti-sense strand (i.e., non-coding strand) sequence in a double-stranded nucleic acid molecule.

An "oligonucleotide," as used herein, generally refers to a short, generally single-stranded, generally synthetic, polynucleotide that is generally, but not necessarily, no more than about 200 nucleotides in length. The terms "oligonucleotide" and "polynucleotide" are not mutually exclusive. The description above for polynucleotides is equally and fully applicable to oligonucleotides.

The term "sample" as used herein refers to a sample that can be subject to the methods described herein with or without pre-processing such as nucleic acid extraction, fragmentation, dilution/concentration, or other pre-treatment. The sample may be a biological sample, or obtained by processing or manipulating a biological sample. In some embodiments, the sample is ready for loading onto a digital PCR instrument for analysis. In some embodiments, the sample has been diluted from a biological sample.

A "probe" refers to a molecule (e.g., a protein, nucleic acid, aptamer, etc.) that specifically interacts with or specifically binds to, and thus detects, a target polynucleotide. Non-limiting examples of molecules that specifically interact with or specifically bind to a target polynucleotide include nucleic acids (e.g., oligonucleotides), proteins (e.g., antibodies, transcription factors, zinc finger proteins, non-antibody protein scaffolds, etc.), and aptamers. Generally, a probe is labeled with a detectable label. The probe can indicate the presence or level of the target polynucleotide by either an increase or decrease in signal from the detectable label. In some embodiments, the probes detect the target polynucleotide in an amplification reaction by being digested by the 5' to 3' exonuclease activity of a DNA dependent DNA polymerase.

As used herein, "set," "pair" and "triplet" refers to an ordered list of members. For example, "set," "pair" and "triplet" correspond to "list", "couple" and "triple" respectively in mathematics. For example, each probe pair may have the order {reference probe, drop-off probe}; each probe triplet may have the order {reference probe, drop-off probe, and AS probe}, and the set of labels for reference probes may have the order {reference label of probe set 1, reference label of probe set 2, . . . reference label of probe set R}.

The terms "label," and "detectable label" are used interchangeably herein to refer to an agent detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, 32P and other isotopes, haptens. The term includes combinations of single labeling agents, e.g., a combination of fluorophores that provides a unique detectable signature, e.g., at a particular wavelength or combination of wavelengths. Any method known in the art for conjugating a label to a desired agent may be employed, e.g., using methods described in Hermanson, Bioconjugate Techniques 1996, Academic Press, Inc., San Diego.

The term "circular permutation" refers to the act of rearranging members (e.g., labels) of a set (e.g., a set of reference probes, and a set of drop-off probes) in a circular manner to generate another set having the same members without changing the relative positions of the members, e.g., by moving the final element of a linear arrangement of the members in the set to its front. Two circular permutations are equivalent if one can be rotated into the other (that is, cycled without changing the relative positions of the elements). Each set of n members has (n-1)! circular permutations. For example, a circular permutation of the set {fluorophore 1, fluorophore 2, fluorophore 3} can be {fluorophore 2, fluorophore 3, fluorophore 1}, or {fluorophore 3, fluorophore 1, fluorophore 2}.

The term "permutation" refers to the act of rearranging the members (e.g., labels) of a set (e.g., a set of reference probes, a set of drop-off probes and a set of allele-specific probes) into a sequence or order. For example, FIG. 6B shows permutation of a set of four, six, or ten labels in three, five, or nine sets of probe triplets, respectively.

A "primer" is generally a short single-stranded polynucleotide, generally with a free 3'-OH group, that binds to a target nucleic acid by hybridizing with a target sequence, and thereafter promotes polymerization of a polynucleotide complementary to the target nucleic acid. Primers can be of a variety of lengths and are often less than 50 nucleotides in length, for example 12-30 nucleotides, in length. Primers can be DNA, RNA, or a chimera of DNA and RNA portions. In some cases, primers can include one or more modified or non-natural nucleotide bases.

A nucleic acid sequence is "complementary" to another nucleic acid when at least two contiguous bases of, e.g., a first nucleic acid or a primer, can combine in an antiparallel association or hybridize with at least a subsequence of a second nucleic acid to form a duplex. In some embodiment, complementary refers to hydrogen-bonded base pair formation preferences between the nucleotide bases G, A, T, C and U, such that when two given polynucleotides or nucleotide sequences anneal to each other, A pairs with T and G pairs with C in DNA, and G pairs with C and A pairs with U in RNA.

A first nucleic acid sequence "corresponding to" a second nucleic acid sequence is a sequence that is identical to or complementary to the second nucleic acid sequence or a portion of the second nucleic acid sequence, or comprises the second nucleic acid sequence or its complementary sequence. When a second nucleic acid sequence contains a unique feature, such as a mutation, a nucleic acid sequence "corresponding to" the second nucleic acid sequence comprises a sequence having the unique feature or a complement thereof.

"Hybridization" and "annealing" as used interchangeably herein refer to a reaction in which one or more polynucleotides react to form a complex that is stabilized via hydrogen bonding between the bases of the nucleotide residues. The hydrogen bonding may occur by Watson-Crick base pairing, Hoogstein binding, or by any other sequence specific manner. A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is, or is about, 37, 40, 42, 45, 50, 55, 60, 65, 70, 75, or 80° C.

"Target region," "target locus" or "target genetic locus", as used herein, refers to a unique genomic location that defines the position of an individual nucleic acid sequence of interest, including one or more contiguous nucleotides. In some embodiments, a region or locus is a single nucleotide position of interest. In some embodiments, a region or locus is at least about any of 2, 3, 5, 10, 15, 20, 25 contiguous nucleotides. A gene may contain multiple target regions of interest. The sequence at a target region may refer to the sequence of either the sense strand or the anti-sense strand sequence of the target region, and may be a wildtype sequence or a mutant sequence. In some embodiments, the target region is associated with one or more variant sequences. In some embodiments, the target region is susceptible to mutation, and is associated with one or more mutant sequences.

"Reference region" used herein refers to a unique genomic location that defines a nucleic acid sequence (i.e., "reference sequence") that is associated with a wildtype sequence. In some embodiments, the reference region is not associated with mutations or variations. Reference regions and reference sequences can be selected and validated by a skilled person in the art. Different reference regions may be needed for different target regions. In some embodiments, the target region and the reference region corresponding to a probe set are overlapping or identical.

"Target fragment" used herein refers to the fragment of a nucleic acid molecule that is amplified by a primer set corresponding to the respective target region. "Reference fragment" used herein refers to the fragment of a nucleic acid molecule that is amplified by a primer set corresponding to the respective reference region. In some embodiments, the target fragment includes the target region (e.g., mutation hotspot, microsatellite sequence locus or target genetic locus in a genomic DNA that is subject to site-specific genome-editing) and an adjacent reference region upstream or downstream to the target region, which provides sequence that the reference probe can hybridize to. In this situation, the target fragment and the reference fragment are the same. In some embodiments, the target region and the reference region are located in different fragments (i.e., target fragment and reference fragment respectively) that are amplified with separate pairs of primers. As used herein, a target fragment may also refer to amplicons of the target fragment, and a reference fragment may also refer to amplicons of the reference fragment.

As used herein, "adjacent to" a target region refers to a region that may partially overlap with the target region or outside the target region in a target fragment or amplicon thereof.

"Allele", as used herein, refers to one of several alternative forms of a gene or DNA sequence at a specific genomic location (locus). In human, at each autosomal locus an individual possesses two alleles, one inherited from the father and one from the mother. "Allelic sequence" as used herein refers to the sequence of a specific allele. An allelic sequence may be longer than the sequence of an allele-specific (AS) probe, or shorter than the sequence of an AS probe. An AS probe hybridizes to its corresponding allelic sequence, or a portion thereof.

"Mutant sequence" and "variant sequence" as used interchangeably herein, refer to any sequence alteration in a sequence of interest in comparison to a reference sequence. "Wildtype sequence" and "reference sequence" are used interchangeably herein, to refer to a sequence to which one wishes to compare a sequence of interest, for example, a sequence corresponding to the dominant allele of a gene, or an unmodified sequence of a genetic locus. Mutant sequences include, but are not limited to, insertions, deletions, and substitutions, including single nucleotide changes, and alterations of more than one nucleotide in a sequence.

"Mutation hotspots" refer to genetic loci that are known to have naturally-occurring mutations, for example, in a diseased tissue or a diseased state. As used herein, the term "single nucleotide variant," or "SNV" for short, refers to the alteration of a single nucleotide at a specific position in a genomic sequence. When alternative alleles occur in a population at appreciable frequency (e.g., at least 1% in a population), a SNV is also known as "single nucleotide polymorphism" or "SNP".

As used herein, "specific" when used in the context of a primer specific for a target nucleic acid or a probe specific for a target nucleic acid refers to a level of complementarity between the primer and the target such that there exists an annealing temperature at which the primer or probe will anneal to and mediate amplification of the target nucleic acid and will not anneal to or mediate amplification of non-target sequences present in a sample.

"Amplification" as used herein, generally refers to the process of producing two or more copies of a desired sequence. Components of an amplification reaction may include, but are not limited to, for example, primers, a polynucleotide template, polymerase, nucleotides, dNTPs and the like.

"Polymerase chain reaction" or "PCR" refers to a method thereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two-step cycles have a denaturation step followed by a hybridization/elongation step. Three step cycles comprise a denaturation step followed by a hybridization step followed by a separate elongation step. Also contemplated herein are polymerase chain reactions that are carried out without thermal cycling, including, but not limited to, isothermal PCR and loop-mediated isothermal amplification (LAMP).

Figure 5A:
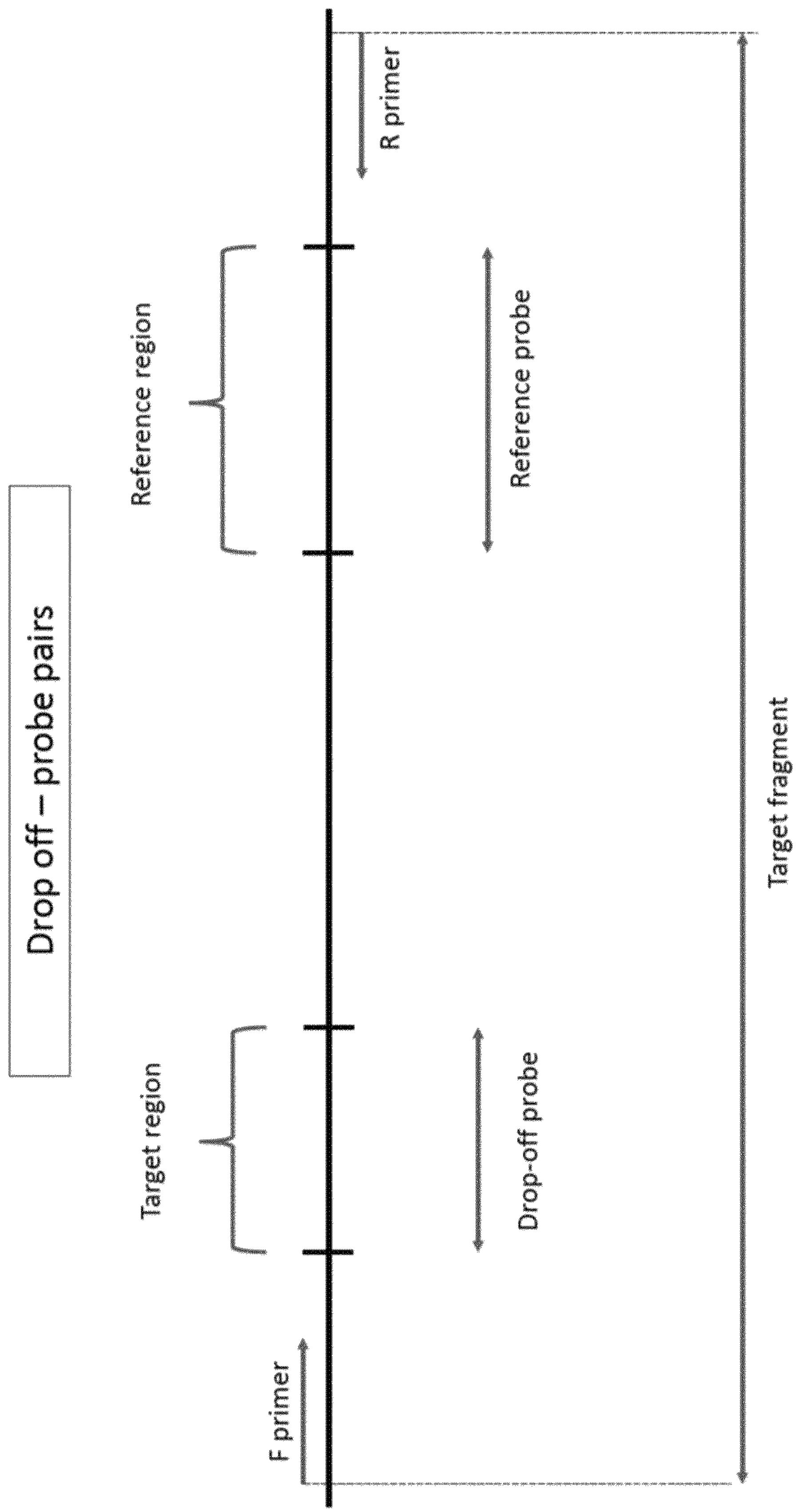
FIG. 5A shows schematics of an exemplary probe pair for detecting mutant sequences at a target region in a nucleic acid molecule. The probe pair includes: (a) a drop-off probe that hybridizes to a wildtype sequence at a target region, and (b) a reference probe that hybridizes to a wildtype sequence at a reference region that is adjacent to the target region. Both the target region and the reference region are found within the same template nucleic acid molecule or amplicons thereof. The reference region can be either upstream or downstream with respect to the target region. The reference probe and the drop-off probe may be designed to hybridize to the same strand of the nucleic acid molecule or amplicons thereof, or different strands of the nucleic acid molecule or amplicons thereof. The reference region is associated with low mutation frequency. Thus, the reference probe hybridizes to the nucleic acid molecule or amplicons thereof regardless whether the nucleic acid molecules contains a wildtype sequence or a mutant sequence at the target region. A forward primer (F primer) and a reverse primer (R primer) can be used to amplify a target fragment comprising the target region and the reference region in the nucleic acid molecule.
Figure 5B:
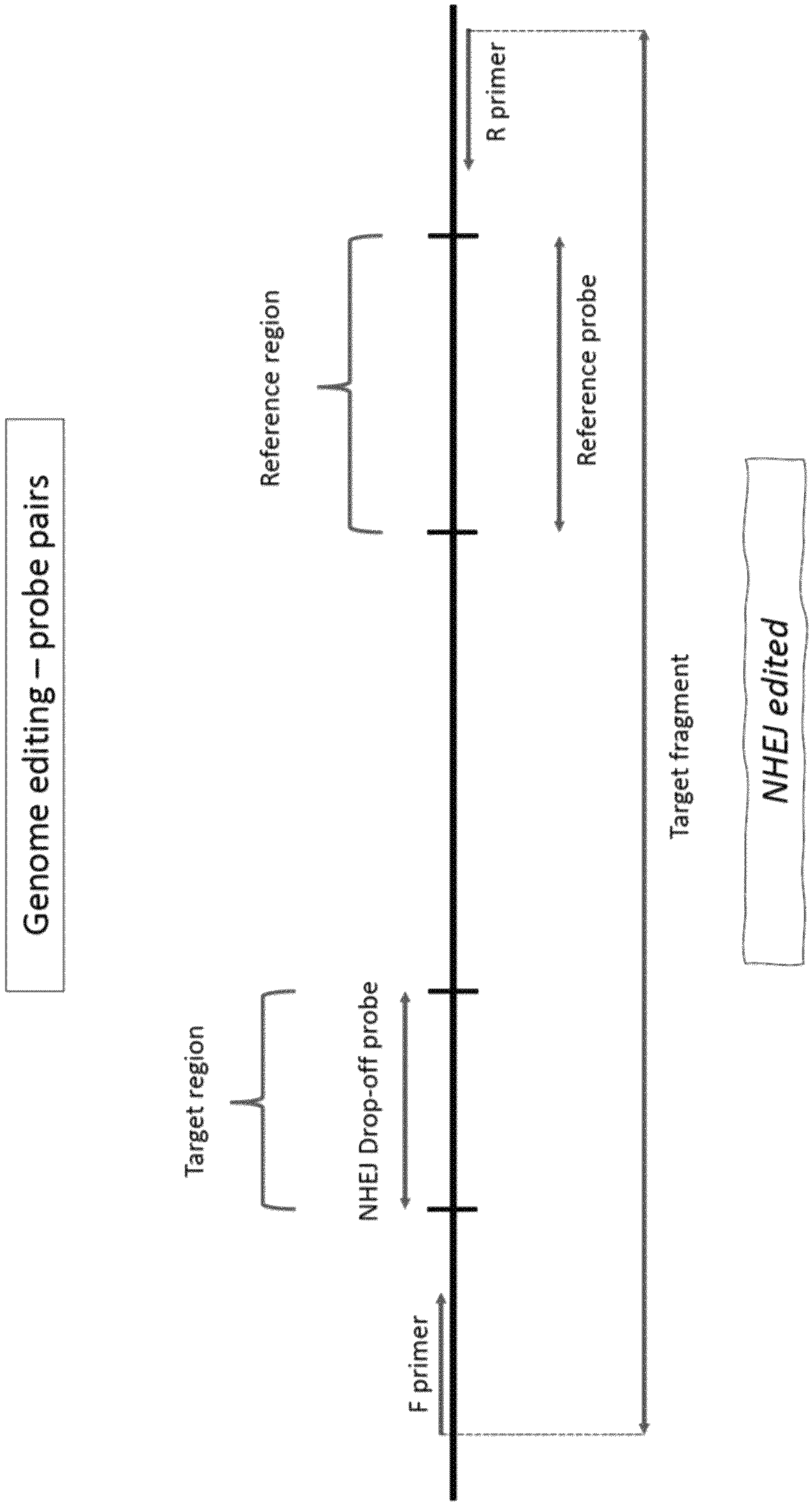
FIG. 5B shows schematics of an exemplary probe pair for detecting NHEJ-edited sequences at a target region in a nucleic acid molecule. The probe pair includes: (a) an NHEJ drop-off probe that hybridizes to an unmodified sequence (i.e., wildtype sequence) at a target region, and (b) a reference probe that hybridizes to a wildtype sequence at a reference region that is adjacent to the target region. Both the target region and the reference region are found within the same template nucleic acid molecule or amplicons thereof. The reference region can be either upstream or downstream with respect to the target region. The reference probe and the NHEJ drop-off probe may be designed to hybridize to the same strand of the nucleic acid molecule or amplicons thereof, or different strands of the nucleic acid molecule or amplicons thereof. The target region contains a target site of a site-specific genome-editing reagent (e.g., CRISPR-Cas), which can be cleaved and subject to repair by NHEJ. The reference region is associated with low mutation frequency. Thus, the reference probe hybridizes to the nucleic acid molecule or amplicons thereof regardless whether the nucleic acid molecules contains an unmodified sequence or a mutant NHEJ-edited sequence at the target region. A forward primer (F primer) and a reverse primer (R primer) can be used to amplify a target fragment comprising the target region and the reference region in the nucleic acid molecule.
Figure 5C:
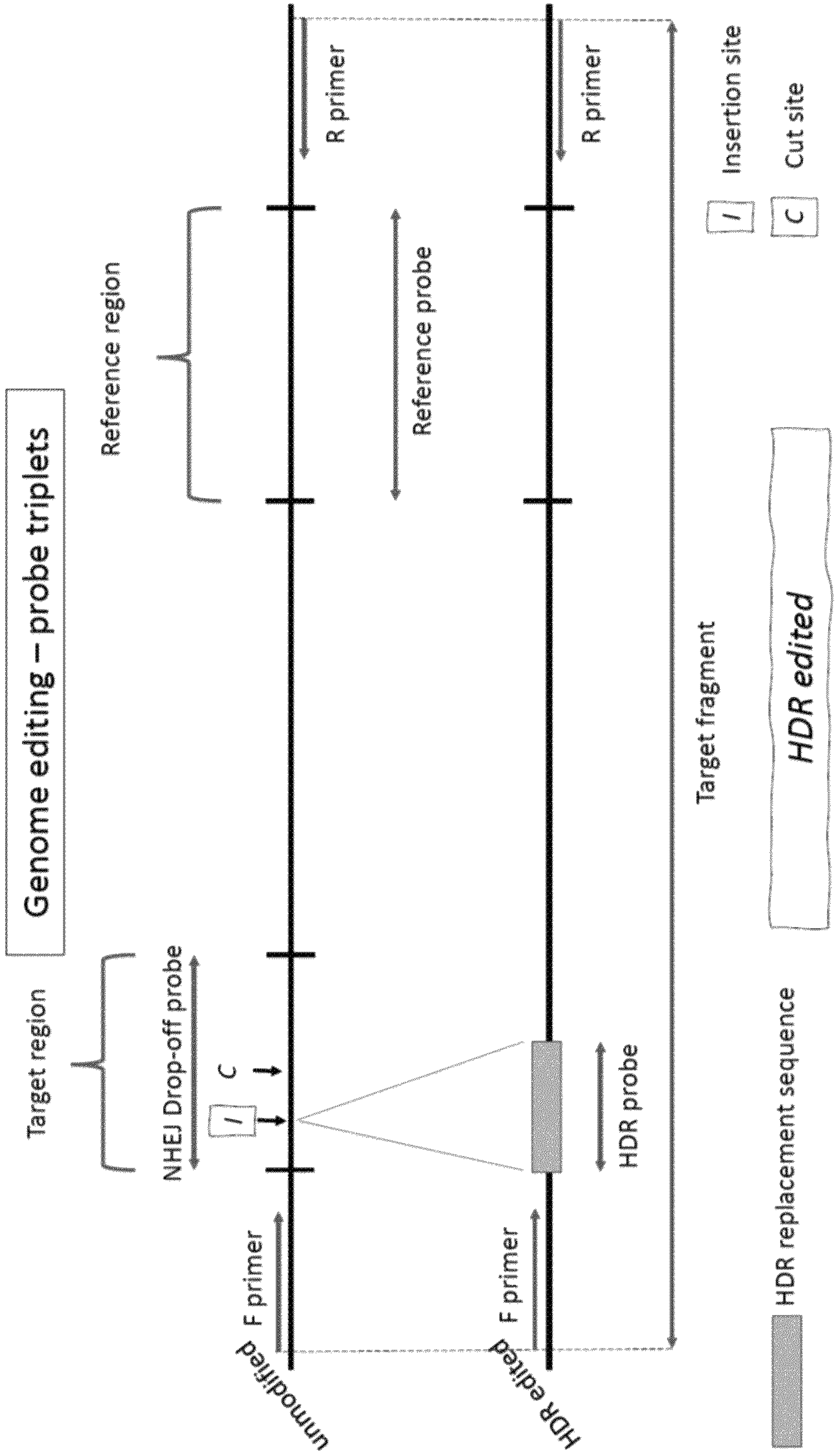
FIG. 5C shows schematics of an exemplary probe triplet for detecting both NHEJ-edited sequences and HDR-edited sequence at a target region in a nucleic acid molecule. The probe triplet includes: (a) an NHEJ drop-off probe that hybridizes to an unmodified sequence (i.e., wildtype sequence) at a target region, (b) a HDR probe that hybridizes to a HDR replacement sequence at the target region, and (c) a reference probe that hybridizes to a wildtype sequence at a reference region that is adjacent to the target region. Both the target region and the reference region are found within the same template nucleic acid molecule or amplicons thereof. The reference region can be either upstream or downstream with respect to the target region. The reference probe, the NHEJ drop-off probe, and the HDR probe may be designed to hybridize to the same strand of the nucleic acid molecule or amplicons thereof, or different strands of the nucleic acid molecule or amplicons thereof. The target region contains a target site of a site-specific genome-editing reagent (e.g., CRISPR-Cas), which can be cleaved and subject to repair by NHEJ or HDR. The reference region is associated with low mutation frequency. Thus, the reference probe hybridizes to the nucleic acid molecule or amplicons thereof regardless whether the nucleic acid molecules contains an unmodified sequence, a mutant NHEJ-edited sequence, or a HDR replacement sequence at the target region. A forward primer (F primer) and a reverse primer (R primer) can be used to amplify a target fragment comprising the target region and the reference region in the nucleic acid molecule.

An "amplicon" refers to a nucleic acid fragment formed as a product of a PCR amplification reaction that are copies of a portion of a particular target nucleic acid, e.g., a target fragment comprising a target region as illustrated in FIG. 5A. An amplicon, as described herein will generally be double-stranded DNA, although reference can be made to individual strands thereof.

As used herein, "digital PCR" refers to a PCR assay that separates a sample into a large number of partitions and PCR reactions are carried out in each partition. Signal from each partition is detected to allow quantification of nucleic acids by statistical analysis. See, e.g., Sykes et al., 1992 Quantitation of targets for PCR by use of limiting dilution. BioTechniques 13, 444-449, Vogelstein and Kinzler 1999 Digital PCR. Proc Natl Acad Sci USA, 96:9236-9241 and Pohl and Shihle 2004 Principle and applications of digital PCR. Expert Rev Mol Diagn, 4:41-47, see also, Monya Baker 2012 Nature Methods 9, 541-544.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microwell. In some embodiments, a partition is a fluid partition, e.g., a droplet. In some embodiments, a fluid partition (e.g., a droplet) is the result of a mixture of immiscible fluids (e.g., water and oil). In some embodiments, a fluid partition (e.g., a droplet) is an aqueous droplet that is surrounded by an immiscible carrier fluid (e.g., oil). As used herein, "substantially all partitions" refer to at least about any one of 70%, 75%, 80%, 85%, 90%, 95%, 98%, 99%, or more of the total number of partitions.

A "microsatellite sequence locus" refers to a region of genomic DNA that contains short, repetitive sequence elements of one to seven, such as one to five, or one to four basepairs in length. Each sequence repeated at least once within a microsatellite locus is referred to herein as a "repeat unit." Each microsatellite locus typically comprises at least seven repeat units, such as at least ten repeat units, or at least twenty repeat units.

A "site-specific genome-editing reagent" refers to a component or set of components that can be used for site-specific genome editing. Generally, such a reagent contains a targeting module and a nuclease module. Exemplary targeting modules include nucleic acids, e.g., guide RNAs, such as those utilized in CRISPR/Cas systems. Alternatively, the targeting module can be, or be derived from, a transcription factor domain, or a TAL effector DNA binding domain. For example, a zinc-finger domain can be employed as a targeting moiety. Exemplary nuclease modules include, but are not limited to a type IIS restriction endonuclease (e.g., FokI), a Cas nuclease (e.g., Cas9), or a derivative thereof. In some cases, the site-specific genome-editing reagent utilizes a combination of a guide RNA, a "dead" Cas nuclease, and a type IIS restriction endonuclease. Other variations are known in the art. Generally, site-specific genome-editing reagents target a genomic region and induce a double stranded cut ("cleave") into the DNA within the target region. Repair of the cutting can proceed via two alternative pathways. In non-homologous end joining (NHEJ), the cut ends of a DNA strand are directly ligated without the need for a homologous template nucleic acid. NHEJ can lead to addition, deletion, and/or substitution of one or more nucleotides at the repair site, and the resulting sequences are referred herein as "NHEJ-edited sequences." In homology directed repair (HDR), the cleaved ends of a DNA strand are repaired by polymerization from a homologous template nucleic acid, and the resulting sequence is referred herein as a "HDR-edited sequence."

The terms "individual" or "subject" are used interchangeably herein to refer to an animal; for example, a mammal. In some examples, an "individual" or "subject" refers to an individual or subject in need of treatment for a disease or disorder.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X". For example, a value of about X may be within (i.e., ±) 10%, 5%, 2%, 1% or less of X.

As used herein, reference to "not" a value or parameter generally means and describes "other than" a value or parameter.

As used herein and in the appended claims, the singular forms "a," "an," and "the" include plural referents unless the context clearly dictates otherwise.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the multiplex dPCR assays (e.g., multiplex drop-off dPCR assays) and methods are specifically embraced by the present invention and are disclosed herein just as if each and every combination was individually and explicitly disclosed. In addition, all subcombinations of the multiplex dPCR assays (e.g., multiplex drop-off dPCR assays) and methods listed in the embodiments describing such variables are also specifically embraced by the present invention and are disclosed herein just as if each and every such sub-combination of the multiplex dPCR assays (e.g., multiplex drop-off dPCR assays) and methods was individually and explicitly disclosed herein.

II. Multiplex dPCR Methods

The present application provides methods of quantifying reference (e.g., wildtype) sequences and/or variant sequences (e.g., mutant sequences) at two or more target regions in a nucleic acid sample using any of the probe set designs described in the "Probe sets" subsection, which include reference probes and drop-off probes that have overlapping sets of labels, and reference probes and allele-specific probes that have overlapping sets of labels. The methods described herein are useful as multiplex drop-off digital PCR assays.

Multiplex Drop-Off dPCR Methods

In some embodiments, there is provided a method for quantification of wildtype and/or mutant sequences at a plurality of target regions in a sample comprising nucleic acid molecules, wherein the nucleic acid molecules are distributed among a plurality of partitions of the sample, wherein substantially all partitions (e.g., all partitions) each comprises a plurality of probe sets corresponding to the plurality of target regions, wherein each probe set of the plurality of probe sets comprises:

- a drop-off probe comprising a drop-off label and an oligonucleotide drop-off sequence complementary to a wildtype sequence at a target region corresponding to the respective probe set;
- a reference probe comprising a reference label and an oligonucleotide reference sequence complementary to a wildtype sequence at an adjacent reference region upstream or downstream to the target region corresponding to the respective probe set; wherein a reference label and a drop-off label of each probe set of the plurality of probe sets are detectable via different detection channels; wherein reference labels of the plurality of probe sets are detectable via different detection channels with respect to each other; wherein drop-off labels of the plurality of probe sets are detectable via different detection channels with respect to each other;
- wherein at least one reference label of the plurality of probe sets and at least one drop-off label of the plurality of probe sets are detectable via the same detection channel;

wherein the method comprises: detecting hybridization of reference probes of the plurality of probe sets to nucleic acid molecules or amplicons thereof comprising wildtype sequences at the reference regions in the plurality of partitions; and detecting hybridization of drop-off probes of the plurality of probe sets to nucleic acid molecules or amplicons thereof comprising wildtype sequences at the target regions in the plurality of partitions; thereby providing quantification of wildtype and/or mutants sequences at the plurality of target regions in the sample. In some embodiments, detection of a signal from a reference label and a signal from a drop-off label in a probe set indicates a wildtype sequence at the target region corresponding to the probe set, and detection of a signal from a reference label but no signal from a drop-off label in a probe set indicates a mutant sequence at the target region corresponding to the probe set. In some embodiments, the set of reference labels of the plurality of probe sets and the set of drop-off labels of the plurality of probe sets have overlapping labels. In some embodiments, the set of reference labels of the plurality of probe sets and the set of drop-off labels of the plurality of probe sets are circular permutations with respect to each other.

In some embodiments, there is provided a method for quantification of wildtype and/or mutant sequences at R number of target regions in a sample comprising nucleic acid molecules, wherein the nucleic acid molecules are distributed among a plurality of partitions of the sample, wherein substantially all partitions (e.g., all partitions) each comprises R number of probe pairs corresponding to the R number of target regions,

- wherein a first probe pair of the R number of probe pairs comprises:
  - a first reference probe comprising a first reference sequence ($r_1$) and a first reference label detectable via a first detection channel ($X_1$), and
  - a first drop-off probe comprising a first drop-off sequence ($w_1$) and a first drop-off label detectable via a second detection channel ($X_2$);
- wherein a second probe pair of the R number of probe pairs comprises:
  - a second reference probe comprising a second reference sequence ($r_2$) and a second reference label detectable via the second detection channel ($X_2$), and
  - a second drop-off probe comprising a second drop-off sequence ($w_2$) and a second drop-off label detectable via a third detection channel ($X_3$);
- wherein, if (e.g., when) R is strictly larger than 3, an i-th probe pair ($2<i<R$) of the R number of probe pairs comprises:
  - an i-th reference probe comprising an i-th reference sequence ($r_i$) and an i-th reference label detectable via an i-th detection channel ($X_i$), and
  - an i-th drop-off probe comprising an i-th drop-off sequence ($w_i$) and an i-th drop-off label detectable via an (i+1)-th detection channel ($X_{i+1}$);
- wherein, if (e.g., when) R is strictly larger than 2, a R-th probe pair of the R number of probe pairs comprises:
  - a R-th reference probe comprising a R-th reference sequence (R) and a R-th reference label associated with a R-th detection channel ($X_R$), and
  - a R-th drop-off probe comprising a R-th drop-off sequence ($w_R$) and a R-th drop-off label detectable by the first detection channel ($X_1$);
- wherein the drop-off sequence of each probe pair is complementary to a wildtype sequence at a target region corresponding to the respective probe pair;
- wherein the reference sequence of each probe pair is complementary to a wildtype sequence at an adjacent reference region upstream or downstream to the target region corresponding to the respective probe pair;

wherein the detection channels $X_1$-$X_R$ are different from each other;

wherein the method comprises detecting hybridization of reference probes of the R number of probe pairs to nucleic acid molecules or amplicons thereof comprising wildtype sequences at the reference regions in the plurality of partitions via each of the detection channels $X_1$-$X_R$; and detecting hybridization of drop-off probes of the R number of probe pairs to nucleic acid molecules or amplicons thereof comprising wildtype sequences at the target regions in the plurality of partitions via each of the detection channels $X_1$-$X_R$; thereby providing quantification of wildtype and/or mutants sequences at the R number of target regions in the sample. R may be any suitable integer of 2 or larger. In some embodiments, R is between 2 and 6. In some embodiments, detection of a signal from a reference label and a signal from a drop-off label in a probe pair indicates a wildtype sequence at the target region corresponding to the probe pair, and detection of a signal from a reference label but no signal from a drop-off label in a probe pair indicates a mutant sequence at the target region corresponding to the probe pair.

In some embodiments, there is provided a method for quantification of wildtype and/or mutant sequences at three target regions in a sample comprising nucleic acid molecules, wherein the nucleic acid molecules are distributed among a plurality of partitions of the sample, wherein substantially all partitions (e.g., all partitions) each comprises three probe pairs corresponding to the three target regions, wherein the three probe pairs comprise:

a first probe pair comprising:

a first reference probe comprising a first reference sequence and a first reference label detectable via a first detection channel, and a first drop-off probe comprising a first drop-off sequence and a first drop-off label detectable via a second detection channel;

a second probe pair comprising:

a second reference probe comprising a second reference sequence and a second reference label detectable via a second detection channel, and a second drop-off probe comprising a second drop-off sequence and a second drop-off label detectable via a third detection channel;

a third probe pair comprising:

a third reference probe comprising a third reference sequence and a third reference label detectable via a third detection channel, and a third drop-off probe comprising a third drop-off sequence and a third drop-off label detectable via a first detection channel;

wherein the drop-off sequence of each probe pair is complementary to a wildtype sequence at a target region corresponding to the respective probe pair; wherein the reference sequence of each probe pair is complementary to a wildtype sequence at an adjacent reference region upstream or downstream to the target region corresponding to the respective probe pair; wherein the first detection channel, the second detection channel and the third detection channel are different with respect to each other;

wherein the method comprises detecting hybridization of reference probes of the three probe pairs to nucleic acid molecules or amplicons thereof comprising wildtype sequences at the reference regions in the plurality of partitions via each of the first, second, and third detection channels; and detecting hybridization of drop-off probes of the three probe pairs to nucleic acid molecules or amplicons thereof comprising wildtype sequences at the target regions in the plurality of partitions via each of the first, second, and third detection channels; thereby providing quantification of wildtype and/or mutants sequences at the three of target regions in the sample. In some embodiments, detection of a signal from a reference label and a signal from a drop-off label in a probe pair indicates a wildtype sequence at the target region corresponding to the probe pair, and detection of a signal from a reference label but no signal from a drop-off label in a probe pair indicates a mutant sequence at the target region corresponding to the probe pair. In some embodiments, the target regions are mutation hotspot regions in one or more genes selected from the group consisting of EGFR, NRAS, KRAS, ESR1 and BRAF. In some embodiments, the method is for quantification of wildtype and mutant sequences at mutation hotspot regions in EGFR, NRAS and KRAS. In some embodiments, the method is for quantification of wildtype and mutant sequences at mutation hotspot regions in NRAS, KRAS and BRAF. In some embodiments, the method is for quantification of wildtype and mutant sequences at G12/13, Q61, and/or A146 of KRAS, at G12/13 and/or Q61 of NRAS, at E19 of EGFR, and/or at V600 of BRAF.

In some embodiments, there is provided a method for quantification of wildtype, mutant and/or allelic sequences at a plurality of target regions in a sample comprising nucleic acid molecules, wherein the nucleic acid molecules are distributed among a plurality of partitions of the sample, wherein substantially all partitions (e.g., all partitions) each comprises a plurality of probe sets corresponding to the plurality of target regions, wherein each probe set of the plurality of probe sets comprises:

a drop-off probe comprising a drop-off label and an oligonucleotide drop-off sequence complementary to a wildtype sequence at a target region corresponding to the respective probe set;

a reference probe comprising a reference label and an oligonucleotide reference sequence complementary to a wildtype sequence at an adjacent reference region upstream or downstream to the target region corresponding to the respective probe set; an allele-specific (AS) probe comprising an AS label and an oligonucleotide AS sequence complementary to an allelic sequence at the target region corresponding to the respective probe set, wherein a reference label, a drop-off label, and an AS label of each probe set of the plurality of probe sets are detectable via different detection channels; wherein reference labels of the plurality of probe sets are detectable via different detection channels with respect to each other; wherein drop-off labels of the plurality of probe sets are detectable via different detection channels with respect to each other; wherein AS labels of the plurality of probe sets are detectable via different detection channels with respect to each other, wherein at least one reference label of the plurality of probe sets and at least one drop-off label of the plurality of probe sets are detectable via the same detection channel, and/or at least one reference label of the plurality of probe sets and at least one AS label of the plurality of probe sets are detectable via the same detection channel;

wherein the method comprises: detecting hybridization of reference probes of the plurality of probe sets to nucleic acid molecules or amplicons thereof comprising wildtype sequences at the reference regions in the plurality of partitions; and detecting hybridization of drop-off probes of the plurality of probe sets to nucleic acid molecules or amplicons thereof comprising wildtype sequences at the target regions in the plurality of partitions; detecting hybridization of AS probes of the plurality of probe sets to nucleic acid molecules or amplicons thereof comprising allelic sequences at the target regions in the plurality of partitions; thereby providing quantification of wildtype sequences, mutants sequences and/or allelic sequences at the plurality of target regions in the sample. In some embodiments, detection of a signal from a reference label and a signal from a drop-off label in a probe set indicates a wildtype sequence at the target region corresponding to the probe set; detection of a signal from a reference label but no signal from a drop-off label in a probe set indicates a mutant sequence at the target region corresponding to the probe set; and detection of a signal from an AS label indicates an AS sequence at the target region corresponding to the probe set. In some embodiments, the set of reference labels of the plurality of probe sets, the set of drop-off labels of the plurality of probe sets, and the set of AS labels of the plurality of probe sets have overlapping labels. In some embodiments, the set of reference labels of the plurality of probe sets, the set of drop-off labels of the plurality of probe sets, and the set of AS labels of the plurality of probe sets are permutations with respect to each other.

In some embodiments, there is provided a method for quantification of wildtype, mutant, and/or allelic sequences at (R−1) number of target regions in a sample comprising nucleic acid molecules, wherein the nucleic acid molecules are distributed among a plurality of partitions of the sample, wherein substantially all partitions (e.g., all partitions) each comprises (R−1) number of probe triplets corresponding to the (R−1) number of target regions,

- wherein a first probe triplet of the (R−1) number of probe triplets comprises:
  - a first reference probe comprising a first reference sequence ($m_1$) and a first reference label detectable via a first detection channel ($X_1$);
  - a first drop-off probe comprising a first drop-off sequence ($r_1$) and a first drop-off label detectable via a second detection channel ($X_2$); and
  - a first allele-specific (AS) probe comprising a first AS sequence ($w_1$) and a first AS label detectable via a third channel ($X_3$);
- wherein a second probe triplet of the (R−1) number of probe triplets comprises:
  - a second reference probe comprising a second reference sequence ($m_2$) and a second reference label detectable via the second detection channel ($X_2$);
  - a second drop-off probe comprising a second drop-off sequence ($r_2$) and a second drop-off label detectable via the third detection channel ($X_3$); and
  - a second AS probe comprising a second AS sequence ($w_2$) and a second AS label detectable via a fourth detection channel ($X_4$);
- wherein, if (e.g., when) R is strictly larger than 3, an i-th probe triplet (2<i<R−1) of the (R−1) number of probe triplets comprises:
  - an i-th reference probe comprising an i-th reference sequence ($m_i$) and an i-th reference label detectable via an i-th detection channel ($X_i$);
  - an i-th drop-off probe comprising an i-th drop-off sequence ($r_i$) and an i-th drop-off label detectable via an (i+1)-th detection channel ($X_{i+1}$); and
  - an i-th AS probe comprising an i-th AS sequence ($w_i$) and an i-th AS label detectable via an (i+2)-th detection channel ($X_{i+2}$);
- wherein, if (e.g., when) R is strictly larger than 3, a (R−1)-th probe triplet of the (R−1) number of probe triplets comprises:
  - a (R−1)-th reference probe comprising a (R−1)-th reference sequence ($m_{R-1}$) and a R-th reference label detectable via a R-th detection channel ($X_R$);
  - a (R−1)-th drop-off probe comprising a (R−1)-th drop-off sequence (TR−1) and a (R−1)-th drop-off label detectable via a (R−1)-th detection channel ($X_{R-1}$); and
  - a (R−1)-th AS probe comprising a (R−1)-th AS sequence ($w_R$-1) and a (R−1)-th AS label detectable via the first detection channel ($X_1$);
- wherein the drop-off sequence of each probe triplet is complementary to a wildtype sequence at a target region corresponding to the respective probe triplet; wherein the reference sequence of each probe triplet is complementary to a wildtype sequence at an adjacent reference region upstream or downstream to the target region corresponding to the respective probe triplet; wherein the AS sequence of each probe triplet is complementary to an allelic sequence at the target region corresponding to the respective probe triplet; wherein the detection channels $X_1$-$X_R$ are different from each other;
- wherein the method comprises detecting hybridization of reference probes of the (R−1) number of probe triplets to nucleic acid molecules or amplicons thereof comprising wildtype sequences at the reference regions in the plurality of partitions via each of the detection channels $X_1$-$X_R$; detecting hybridization of AS probes of the (R−1) number of probe triplets to nucleic acid molecules or amplicons thereof comprising the allelic sequences at the target regions in the plurality of partitions via each of the detection channels $X_1$-$X_R$; and detecting hybridization of drop-off probes of the (R−1) number of probe triplets to nucleic acid molecules or amplicons thereof comprising wildtype sequences at the target regions in the plurality of partitions via each of the detection channels $X_1$-$X_R$; thereby providing quantification of wildtype, mutant and/or allelic sequences at the plurality of target regions in the sample. R may be any integer of 3 or more. In some embodiments, R is 4. In some embodiments, detection of a signal from a reference label and a signal from a drop-off label in a probe set indicates a wildtype sequence at the target region corresponding to the probe set; detection of a signal from a reference label but no signal from a drop-off label in a probe set indicates a mutant sequence at the target region corresponding to the probe set; and detection of a signal from an AS label indicates an AS sequence at the target region corresponding to the probe set.

The methods described herein may further comprise one or more steps of forming the partitions, amplification, and/or sample preparation, etc., as described in the "Digital PCR" subsection below. In some embodiments, the method further comprises forming the plurality of partitions. In some embodiments, the method further comprises distributing a composition comprising the nucleic acid molecules and the plurality of probe sets into the plurality of partitions. In some embodiments, the method further comprises amplifying the nucleic acid molecules in the plurality of partitions using a plurality of primer sets corresponding to the plurality of target regions. In some embodiments, substantially all partitions (e.g., all partitions) each comprises a plurality of primer pairs corresponding to the plurality of target regions, wherein each primer pair comprises a forward oligonucleotide primer and a reverse oligonucleotide primer suitable for amplifying a target fragment comprising a target region corresponding to the primer set and the reference region corresponding to the target region. In some embodiments, method further comprises distributing a composition comprising the nucleic acid molecules, the plurality of probe sets, and optionally the plurality of primer sets into the plurality of partitions.

The methods may further comprise data analysis steps as described in the subsections "Embodiment Employing Three (3) Probe Pairs," "Embodiment Employing R number of probe pairs," and "Embodiment Employing (R−1) number of Probe Triplets." In some embodiments, said quantification comprises providing estimated concentrations of the wildtype sequences and/or mutant sequences at the plurality of target regions in the sample. In some embodiments, said quantification comprises providing confidence intervals of the estimated concentrations of the wildtype sequences and/or mutant sequences at the plurality of target regions in the sample. In some embodiments, said quantification comprises providing an uncertainty measure of the wildtype sequences and/or mutant sequences at the plurality of target regions. The confidence intervals and/or uncertainty measures may be at any given confidence level, such as at about any one of 80%, 85%, 90%, 95%, 98%, 99%, or higher confidence level. The quantification of the wildtype sequences and/or mutant sequences at the plurality of target regions in the sample may further be converted to quantification of the wildtype sequences and/or mutant sequences at the plurality of target regions in a biological sample, from which the sample is derived, for example, by multiplying with a dilution factor, if the sample is prepared by diluting the biological sample.

Figure 2:
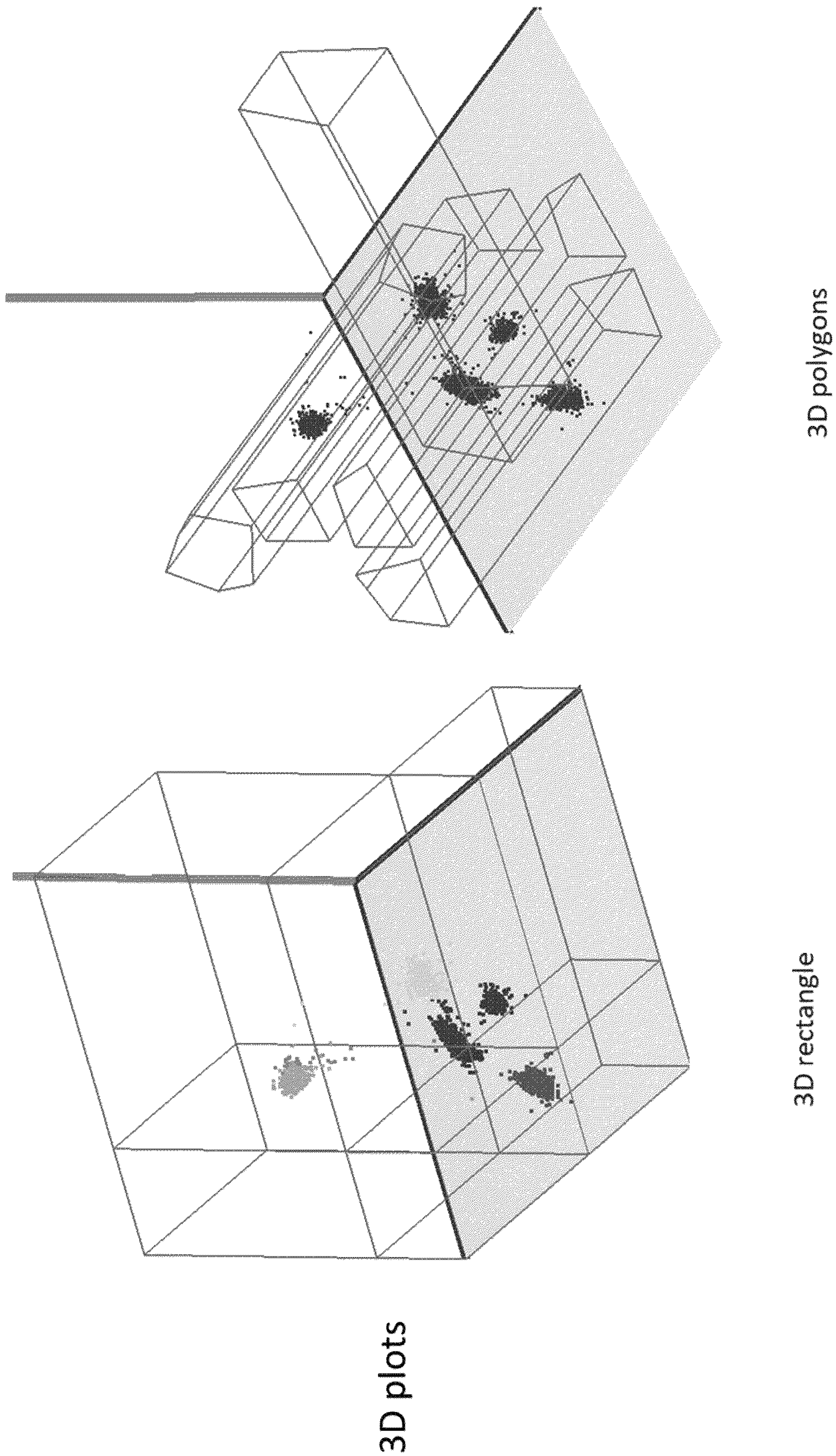
FIG. 2 shows an exemplary data analysis method. The populations of droplets corresponding to different characteristic signal readouts are identified in three-dimensional plots using space segmentation methods, such as using 3-dimensional rectangles or 3-dimensional polygons. The number of each population of droplets is counted in each space segment (e.g., designated as $n_{000}$, $n_{100}$, $n_{110}$, $n_{101}$, $n_{011}$, $n_{010}$, $n_{001}$, and $n_{111}$ for the 3-dimensional rectangle or polygon segments) and the counts are used to determine the concentration for each genetic population, i.e., wildtype or mutant population at the three genetic loci tested (e.g., designated as $C_{Mut1}$, $C_{Mut2}$, $C_{Mut3}$, $C_{WT1}$, $C_{WT2}$ and $C_{WT3}$).

FIGS. 1A-1D illustrate an exemplary triplex drop-off dPCR assay for detecting wildtype and mutant sequences at a target genetic locus in EGFR, NRAS and KRAS respectively. For each target genetic locus, a pair of forward and reverse primers and a pair of reference probe and drop-off probe were designed. The reference probe and drop-off probe hybridize to the same amplicon that is amplified by the forward and reverse primers from template nucleic acids in the sample. The drop-off probe hybridizes to a wildtype sequence at the respective target genetic locus, but not mutant sequences at the target genetic locus. The reference probe hybridizes to a wildtype sequence that is adjacent to but does not overlap with the target genetic locus. The reference probe and the drop-off probes are TAQMAN™ probes labeled with different fluorophores that are detectable via different fluorescence detection channels. For a nucleic acid containing the wildtype sequence at the target genetic locus, both the reference probe and the drop-off probe hybridize to the amplicons, thereby resulting in positive signals in the fluorescence channels that correspond to both the reference probe and the drop-off probe. For a nucleic acid containing mutant sequences at the target genetic locus, only the reference probe hybridizes to the amplicons, thereby resulting in positive signals in the fluorescence channel that corresponds to only the reference probe, but no signal in the fluorescence channel that corresponds to the drop-off probe. As shown in FIG. 2, the signals from dPCR droplets can be plotted in three-dimensions. Space segments corresponding to different clusters of signals are determined, and the number of droplets in each space segments is counted. The counts are used to estimate the concentration for each wildtype and mutant populations. Exemplary primers and probes that correspond to the KRAS, NRAS and EGFR genetic locus are shown in TABLE 12.

The methods described herein may further be multiplexed with conventional allele-specific dPCR assays by including allele-specific probes with labels detectable via detection channels that are distinct from those used in the plurality of probe sets (including probe pairs and probe triplets). An allele-specific ("AS") probe hybridizes to a specific allelic sequence, including wildtype sequence, mutant sequence, or SNP at a target region of interest. An AS probe is designed to confer its ability to bind properly to a specific allelic sequence at a target region, while preventing hybridization of the AS probe in the presence of any other sequence at the target region. In some embodiments, each AS probe is also used together with a dark probe to increase stringency of the assay by binding to a wildtype sequence of the allele, but not the allelic sequence associated with the AS probe.

Figure 4A:
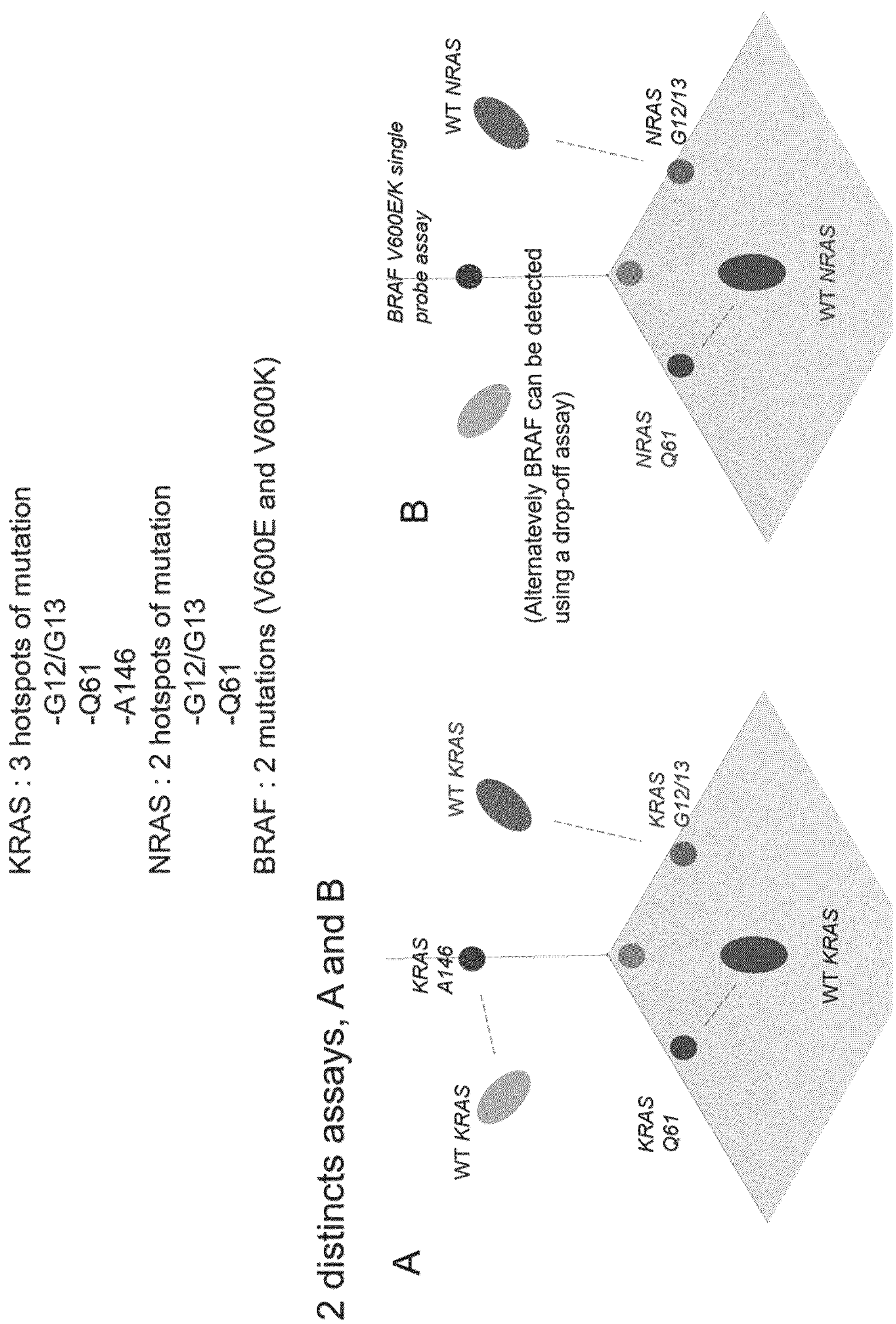
FIG. 4A-4B show two exemplary designs of multiplex drop-off dPCR assays that can detect wildtype and mutant sequences at 3 KRAS mutation hotspots, 2 NRAS mutation hotspots and 1 BRAF mutation hotspot using only three fluorescence detection channels.

For example, FIG. 4A illustrates an exemplary assay combining two sets of probe pairs comprising a reference probe and a drop-off probe (one set for detecting wildtype and mutant sequences at Q61 of NRAS, and a second set for detecting wildtype and mutant sequences at G12/13 of NRAS) with allele-specific probes for detecting V600E and V600K mutations in BRAF.

In some embodiments, the probes (e.g., reference probes, drop-off probes, AS probes) each has a single detectable label. In some embodiments, the labels (e.g., reference labels, drop-off labels, AS labels) are fluorophores. In some embodiments, different detection channels have different excitation wavelength ranges and/or different emission wavelength ranges.

The methods described herein that distinguish probes based on the excitation and/or emission wavelengths or wavelength ranges associated with different fluorophores may further be combined with multiplexing methods that distinguish probes having the same fluorophores but relying on different fluorescence intensities. In some embodiments, one or more detection channels are associated with different excitation wavelengths or wavelength ranges, and/or emission wavelengths or wavelength ranges, and one or more detection channels are associated with different fluorescence intensities. In some embodiments, probe sets that correspond to different target regions within the same gene of interest are labeled with the same sets of fluorophores, which are detected via different fluorescence intensities. In some embodiments, the probe sets corresponding to different target regions within a gene of interest comprise reference probes having reference labels detectable via detection channels that share the same excitation and/or emission wavelengths or wavelength ranges, wherein the reference probes are detected at different fluorescence intensities with respect to each other; drop-off probes having drop-off labels detectable via different detection channels that share the same excitation and/or emission wavelengths or wavelength ranges, wherein the drop-off probes are detected at different fluorescence intensities with respect to each other; and/or AS probes having AS labels detectable via different detection channels that share the same excitation and/or emission wavelengths or wavelength ranges, and wherein the AS probes are detected at different fluorescence intensities with respect to each other.

Figure 4B:
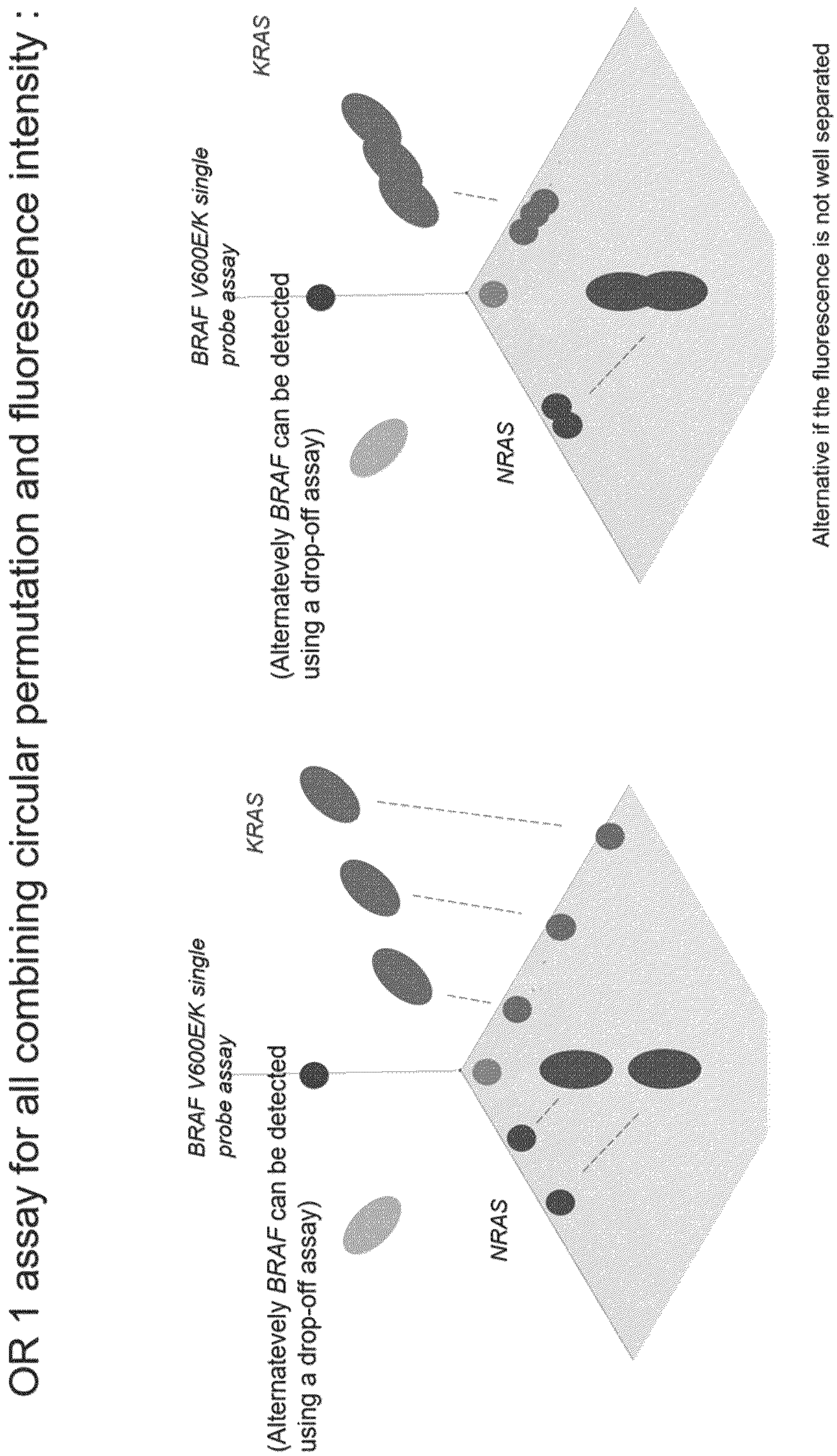

For example, FIG. 4B illustrates an exemplary assay that can simultaneously quantify twelve different genetic species (i.e., wildtype and mutant sequences at G12/G13, Q61, and A146 of KRAS; wildtype and mutant sequences at G12/G13 and Q61 of NRAS, and V600E and V600K at BRAF) by combining circular permutation of probe labeling with different fluorescence intensities. For example, genetic species associated with the same genes, e.g., KRAS, use the probe pairs that have the same reference and drop-off labels, but different probes and the corresponding primers are used at different concentrations for each probe pair so that signals from different probe pairs can be distinguished based on their fluorescence intensities.

Probe Sets

The methods described herein use a plurality of probe sets for detecting wildtype and mutant sequences at a plurality of target regions. Each probe set may comprise 2, 3, 4, 5, 6, or more probes. In some embodiments, a plurality of probe sets is a plurality of probe pairs each comprising a reference probe that always hybridizes to target fragments, and a drop-off probe that hybridizes to target fragments comprising wildtype sequences at the target region. In some embodiments, a plurality of probe sets is a plurality of probe triplets, each comprising a reference probe, a drop-off probe, and an allele-specific ("AS") probe that hybridizes to a specific allelic sequence at the target region. Any of the probe sets (including probe pairs and probe triplets) described herein may be used together with one or more "standalone" AS probes that are not part of the plurality of probe sets, e.g., the one or more AS probes may hybridize to target regions that are different from the target regions corresponding to the plurality of the probe sets. In some embodiments, at least 1, 2, 3, 4, 5, 6 or more standalone AS probes are used. Each probe comprises a detectable label.

In some embodiments, a plurality of probe sets is a plurality of probe triplets comprising a reference probe, a first AS probe and a second AS probe, wherein the first AS probe and the second AS probe hybridize to the same specific allelic sequence or its complementary sequence or different portions of the same specific allelic sequence. In some embodiments, the allelic sequence is at a junction of two repeats of a mutant gene associated with CNV at the target region. In some embodiments, the reference probe and one of the first AS probe and the second AS probe in each probe triplet have the same detectable label, and the other one of the first AS probe and the second AS probe has a different detectable label that can be detected via a different detection channel from that of the detectable label of the reference probe. In some embodiments, a plurality of probe sets is a plurality of probe pairs comprising a reference probe having a single detectable label and an AS probe with two detectable labels, in which one of the two detectable labels of the AS probe is the same as the detectable label of the reference probe, and the other detectable label of the AS probe can be detected via a different detection channel from that for the detectable label of the reference probe. The first AS probe and the second AS probe in the plurality of probe triplets or the AS probe with two detectable labels in the plurality of probe pairs are referred herein as "dual-labeled AS probes."

In some embodiments, the AS probe(s) hybridize to a mutant sequence at a target region and the reference probe hybridizes to a wildtype sequence at the same target region or a reference region that overlaps with the target region.

In some embodiments, the probes (e.g., reference probe, drop-off probe, or AS probe) are oligonucleotide probes. Exemplary probes include oligonucleotide primers having hairpin structures with a fluorescent molecule held in proximity to a fluorescent quencher until forced apart by primer extension, e.g., Whitecombe et al., Nature Biotechnology, 17:804-807 (1999) (AMPLIFLUOR™, hairpin primers). Exemplary probes may alternatively comprise an oligonucleotide attached to a fluorophore and a fluorescence quencher, wherein the fluorophore and quencher are in proximity until the oligonucleotide specifically binds to an amplification product, e.g., Gelfand et al., U.S. Pat. No. 5,210,015 (TAQMAN™ PCR probes); Nazarenko et al., Nucleic Acids Research, 25:2516-2521 (1997) ("scorpion probes"); and Tyagi et al., Nature Biotechnology, 16:49-53 (1998) ("molecular beacons"). Such probes may be used to measure the total amount of reaction product at the completion of a reaction or to measure the generation of amplification product during an amplification reaction. In some embodiments, the probes (e.g., reference probe, drop-off probe, or AS probe) are TAQMAN™ probes.

The probes (e.g., reference probe, drop-off probe, or AS probe) of the same probe set described herein hybridize within the same target fragments or amplicons thereof. However, standalone AS probes that are not part of the plurality of probe sets may or may not hybridize within the same target fragments or amplicons thereof as any one of the probes in the plurality of probe sets. The probes are designed according to the well-established practice in the art to minimize PCR artifact and to specifically hybridize to the target sequences. Specificity of hybridization of the oligonucleotide probes to target fragments or amplicons thereof can be achieved by altering the length of the probe, the GC content, or the amplification and/or detection conditions (e.g., temperature, salt content, etc.).

In some embodiments, the probes have a nucleotide sequence length of about 10 to about 50. In some embodiments, the probes have a nucleotide sequence length of about any one of 15-40, 25-50, 15-35, 20-40, 30-50 or 30-40. The probes may further comprise modifications that increase the specificity of the probes to their target sequences, e.g., by increasing the melting temperature (Tm) of the probe and stabilizing probe-target hybrids. In some embodiments, one or more probes include a minor groove binder (MGB) moiety at their 3' end. In some embodiments, the probes comprise a chemically modified nucleotide, such as a Locked Nucleic Acid (LNA).

The drop-off probe hybridizes to a wildtype sequence at a target region in a target fragment of a nucleic acid molecule or amplicon thereof. The target region may be a mutation hotspot in a gene of interest, including a microsatellite sequence locus. The target region may alternatively be a genomic locus edited by a site-specific genome-editing reagent (e.g., CRISPR-Cas). Preferably a drop-off probe covers the full wildtype sequence at a target region and extends further a few nucleotides on each extremity (typically 1 to 10 nucleotides, such as 2 to 8, 2 to 6, 2 to 5, or 2 to 4) to confer both its ability to bind properly and the resulting destabilization in case of a mutant sequence. In other words, the probe size is designed to confer its ability to bind properly to the wildtype sequence at the target region, while preventing hybridization of the drop-off probe in the presence of a mutation at the target region.

The reference probe hybridizes to a wildtype sequence at a reference region. The reference region is a region associated with low mutation or single nucleotide polymorphism frequency. In some embodiments, the reference probe hybridizes at a reference region that is located on a different fragment or amplicon than the AS probe. In some embodiments, the reference probe hybridizes at a reference region that is adjacent to a target region located on the same target fragment of a nucleic acid molecule of amplicon thereof.

For drop-off assays, the reference probe hybridizes to a wildtype sequence at an adjacent reference region in a target fragment of a nucleic acid molecule or amplicon thereof. The reference region is upstream or downstream of the target region, and does not overlap with the target region. A reference probe is designed to confer its ability to bind to substantially all target fragments or amplicons thereof that are associated with its respective target region, regardless of the mutation status at the target region.

FIG. 5A illustrates an exemplary pair of a reference probe and a drop-off probe.

An allele-specific (AS) probe in a probe set hybridizes to a specific allelic sequence at the target region that the corresponding drop-off probe and the corresponding reference probe hybridize to. Each standalone AS probe that is not part of the plurality of probe sets hybridizes to a specific allelic sequence at a target region that may or may not overlap with a target region corresponding to any one probe set of the plurality of probe sets. The AS probes may be used to detect specific sequences (e.g., wildtype sequence, mutant sequence, SNP, or amplification) in a gene of interest, or HDR-edited sequences at a target genomic locus edited by a site-specific genome-editing reagent (e.g., CRISPR-Cas). An AS probe is designed to confer its ability to bind properly to a specific allelic sequence at a target region, while preventing hybridization of the AS probe in the presence of any other sequence at the target region. In some embodiments, the AS probe has a single detectable label. In some embodiments, the AS probe has two different detectable labels. In some embodiments, two AS probes having different detectable labels are used to detect a specific allelic sequence at a target region.

In some embodiments, a probe set comprising an AS probe further comprises a dark probe that binds to a wildtype sequence of the allele, but not the allelic sequence associated with the AS probe. In some embodiments, an AS probe that is not part of the plurality of probe sets is used in combination with a dark probe that binds to a wildtype sequence of the allele, but not the allelic sequence associated with the AS probe. The dark probe can increase the stringency of the assay by decreasing erroneous signal provided by binding of the AS probe to the wildtype target genetic locus. Typically, the dark probe is designed to contain a non-extendible 3' end. An exemplary non-extendible 3' end includes, but is not limited to a 3' terminal phosphate. Alternative non-extendible 3' ends include, but not limited to, those disclosed in, e.g., international patent application publication No. WO 2013/026027.

In addition, since dPCR is performed as an endpoint reaction (PCR is run to completion before measuring fluorescence), having single or close to single (e.g., 2, 3, 4, 5, 6 copies etc., for example, as in a Poisson distribution of target molecules into partitions with each partition containing 0, 1, 2, 3, 4, 5 or more copies of target molecules) target molecules in isolation allows multiplexing based on probe intensity (Zhong, Bhattacharya, et al., 2011 Multiplex digital PCR: breaking the one target per color barrier of quantitative PCR. Lab Chip, 11:21 67-2 174). For example, by adding the target-specific fluorescent assay at a limiting concentration, a compartment with a first target will be PCR-positive, but with a limited brightness at PCR endpoint. To count a second target type, a different target-specific probe with the same "color" (i.e., with the same fluorophore) is added at a different concentration. A compartment with the second target will have a brighter signal at PCR endpoint than a compartment with the first target, providing separate clouds and thus enabling separate counts for each target. Thus, combinations of both different color probes and different concentration of probes can be used to multiplex at higher levels. Alternatively, different primer concentrations may be used for different target fragments in order to result in different signal intensity for different probe sets, thereby allowing multiplexing based on probe intensity.

In some embodiments, the probes (e.g., reference probe, drop-off probe, or AS probe) are detectably labeled with a fluorophore which can be selected, for example, from the group consisting of FAM (5- or 6-carboxyfluorescein), VIC, NED, Fluorescein, FITC, IRD-700/800, CY3™, CY5™, CY3.5™, CY5.5™, HEX, TET (5-tetrachloro-fluorescein), TAMRA, JOE, ROX, BODIPY TMR, Oregon Green, Rhodamine Green, Rhodamine Red, ALEXA FLUOR PET®, BIOSEARCH BLUE™, MARINA BLUE®, BOTHELL BLUE®, ALEXA FLUOR®, 350 FAM™, SYBR® Green 1, EvaGreen™, ALEXA FLUOR® 488 JOE™, 25 VIC™, HEX™, TET™, CAL FLUOR® Gold 540, YAKIMA YELLOW®, ROX™, CAL FLUOR® Red 610, CY3.5™, TEXAS RED®, ALEXA FLUOR® 568 CRY5™, QUASAR™ 670, LIGHTCYCLER RED640®, ALEXA FLUOR® 633 QUASAR™ 705, LIGHTCYCLER RED705®, ALEXA FLUOR® 680, SYT09, LC GREEN®, LC GREEN® Plus+, and EVAGREEN™. In some embodiments, the reference labels, drop-off labels and/or AS labels are selected from the group consisting of fluorescein, FAM, YAKIMA YELLOW®, CY3™, HEX, VIC, ROX, CY5™, CY5.5™, ALEXA FLUOR® 647, ALEXA FLUOR® 448, and Quasar705. In some embodiments, the reference labels, drop-off labels and/or AS labels are selected from the group consisting of CY3™, FAM and CY5™. In some embodiments, the reference labels, drop-off labels and/or AS labels are selected from the group consisting of FAM, HEX and CY5™.

In some embodiments, each fluorophore is detected via a detection channel having a characteristic excitation range and a characteristic emission range. In some embodiments, different fluorophores used in the probe sets have non-overlapping excitation wavelength ranges and/or non-overlapping emission wavelength ranges. TABLE 1 below shows exemplary detection channels and compatible fluorophores that are useful in a method with three probe pairs.

TABLE 1

| | Blue Channel | Green Channel | Red Channel |
|---|---|---|---|
| Excitation range | 415-480 nm | 530-550 nm | 615-645 nm |
| Emission range | 495-520 nm | 560-610 nm | 655-720 nm |
| Examples of Compatible Fluorophores | FAM, ALEXA FLUOR ®488 | VIC, HEX, YAKIMA YELLOW ®, Cy3, ROX . . . | Cy5, Quasar705 . . . |

The methods described herein use a total number of detection channels that is fewer than the total number of probes, including reference probes, drop-off probes and AS probes. In some embodiments, the plurality of probe sets is a plurality of probe pairs (e.g., a reference probe and a drop-off probe in each probe pair, or a reference probe and an AS probe with two different labels in each probe pair), and the total number of detection channels is fewer than two times the total number of probe pairs. In some embodiments, wherein R number of probe pairs are used, and R is 2 or more, the total number of detection channels is R, R+1, R+2, . . . or 2R−1. In some embodiments, the total number of detection channels is equal to the total number of probe pairs. In some embodiments, the plurality of probe sets is a plurality of probe triplets (e.g., a reference probe, a drop-off probe and an AS probe in each probe triplet), and the total number of detection channels is fewer than three times the total number of probe triplets. In some embodiments, wherein R number of probe triplets are used, and R is 2 or more, the total number of detection channels is R+1, R+2, R+3, . . . or 3R−1. In some embodiments, the total number of detection channels is equal to the total number of probe triplets plus 1. In some embodiments, the plurality of probe sets is a plurality of probe triplets (e.g., a reference probe, a first AS probe and a second AS probe that hybridize to the same allelic sequence in each probe triplet), and the total number of detection channels is fewer than two times the total number of probe triplets. In some embodiments, wherein R number of probe triplets are used, and R is 2 or more, the total number of detection channels is R, R+1, R+2, . . . or 2R−1. In some embodiments, the total number of detection channels is equal to the total number of probe triplets.

The quencher may be an internal quencher or a quencher located in the 3' end of the probe. Typical quenchers include, but are not limited to, tetramethylrhodamine, TAMRA, BLACK HOLE QUENCHER® (BHQ; e.g., BHQ-1, BHQ-2, BHQ-3), and nonfluorescent quencher (NFQ). Hydrolysis probes usable according to the invention are well-known in the field. In some embodiments, hydrolysis probes have a fluorophore covalently attached to their 5'-end of the oligonucleotide probe and a quencher. The quencher molecule quenches the fluorescence emitted by the fluorophore when excited by a light source typically via FRET (Forster Resonance Energy Transfer). As long as the fluorophore and the quencher are in proximity, quenching inhibits any fluorescence signals. In some embodiments, the probes (e.g., reference probe, drop-off probe, or AS probe) are designed such that they anneal within the target fragments amplified by a specific set of primers. As the DNA polymerase (e.g., Taq polymerase) extends the primer and synthesizes the nascent strand, the 5'-3' exonuclease activity inherent in the DNA polymerase then separates the 5' reporter from the 3' quencher, which provides a fluorescent signal that is proportional to the amplicon yield.

In addition, as discussed above, it is possible to multiplex the probes based on probe intensity, e.g., by varying probe concentrations and/or primer concentrations. See, Zhong, Bhattacharya, et al., 2011 Multiplex digital PCR: breaking the one target per color barrier of quantitative PCR. Lab Chip, 11:21 67-2 174. Thus, combinations of using overlapping sets of labels for the reference probes, drop-off probes and AS probes in the plurality of probe sets (such as permutation of labels among the different types of probes) and different concentration of probes and/or primers can be used to multiplex at higher levels.

Digital PCR

The methods described herein can be carried out in a digital PCR format, where substantially all partitions contain either 0, 1, or close to 1 target molecule.

In some embodiments, each partition contains 0 or 1 target molecule. In some embodiments, the plurality of partitions has a Poisson distribution of the target molecules, wherein each partition has 0, 1, 2, 3, 4, 5 or more target molecules, and wherein the average number of target molecules per partition is close to 1. In some embodiments, the average number of target molecules per partition is about any one of 0.5, 0.6, 0.7, 0.8, 0.9, 1, 1.1, 1.2, 1.3, 1.4, 1.5, 1.6, 1.7, 1.8, 1.9, or 2.0. For example, an optimal condition for the assays described herein may have a Poisson distribution of target molecules among the plurality of partitions with an average number of target molecules being about 1.6. In some embodiments, about 20% of the partitions each contain 0 target molecules, about 32.3% of the partitions each contain 1 target molecules; about 25.8% of the partitions each contain 2 target molecules; about 13.8% of the partitions each contain 3 target molecules; about 5.5% of the partitions each contain 4 target molecules; about 1.8% of the partitions each contain 5 target molecules; about 0.47% of the partitions each contain 6 target molecules; and about 0.12% of the partitions each contain 7 or more target molecules. In some embodiments, the number of target molecules referred in this paragraph are target molecules having a sequence of interest at a target region. In some embodiments, the number of target molecules referred in this paragraph are target molecules having a wildtype sequence at a target region. In some embodiments, the number of target molecules referred in this paragraph are target molecules having a mutant sequence or mutant sequences at a target region. In some embodiments, the number of target molecules referred in this paragraph are target molecules having either a wildtype or mutant sequence(s) at a target region.

In some embodiments, no more than about any one of 95%, 90%, 85%, 80%, 75%, 70%, 65%, or 60% of the plurality of partitions are occupied by one or more target molecules. In some embodiments, about any one of 60%-95%, 60%-70%, 70%-80%, 80%-90%, 70%-90%, 75%-85%, 76%-84%, 77%-83%, 78%-82%, or 79%-81% of the plurality of partitions are occupied by one or more target molecules. In some embodiments, about 80% of the plurality of partitions are occupied by one or more target molecules. In some embodiments, at least about any one of 5%, 10%, 15%, 20%, 25%, 30%, 35% or 40% of the plurality of partitions each have 0 target molecule. In some embodiments, about any one of 5%-40%, 10%-20%, 20%-30%, 30%-40%, 10%-30%, 15%-25%, 16%-24%, 17%-23%, 18%-22%, or 19%-21% of the plurality of partitions each have 0 target molecules. In some embodiments, the number of target molecules referred in this paragraph are target molecules having a sequence of interest at a target region. In some embodiments, the number of target molecules referred in this paragraph are target molecules having a wildtype sequence at a target region. In some embodiments, the number of target molecules referred in this paragraph are target molecules having a mutant sequence or mutant sequences at a target region. In some embodiments, the number of target molecules referred in this paragraph are target molecules having either a wildtype or mutant sequence(s) at a target region.

Because different sequences of interest (e.g., different alleles) at a target region may be present at different frequencies, in some embodiments, a first dPCR is carried out to detect a first sequence of interest with a first distribution of target molecules among the plurality of partitions, and a second dPCR is carried out to detect a second sequence of interest with a second distribution of target molecules among the plurality of partitions, e.g., by diluting the sample and redistributing the diluted sample among the plurality of partitions.

Techniques available for digital PCR include PCR amplification on a microfluidic chip (Warren et al., 2006 Transcription factor profiling in individual hematopoietic progenitors by digital RT-PCR. Proc Natl Acad Sci USA 103, 17807-1 781 2; Ottesen et al., 2006 Microfluidic digital PCR enables multigene analysis of individual environmental bacteria. Science 314, 1464-1467; Fan and Quake 2007 Detection of aneuploidy with digital polymerase chain reaction. Anal Chem 79, 7576-7579). Other systems involve separation onto microarrays (Morrison et al., 2006 Nanoliter high-throughput quantitative PCR. Nucleic Acids Res 34, e123) or spinning microfluidic discs (Sundberg et al., 201 0 Spinning disk platform for microfluidic digital polymerase chain reaction. Anal Chem 82, 1546-1 550) and droplet techniques based on oil-water emulsions (Hindson, Benjamin et al., 2011 High-Throughput Droplet Digital PCR System for Absolute Quantitation of DNA Copy Number. Analytical Chemistry 83 (22): 8604-8610; J. Madic et al. 2016, Three-Color crystal digital PCR, Biomolecular Detection and Quantification, 10:34-36). Typically, digital PCR is selected from DROPLET DIGITAL™ PCR (ddPCR), CRYSTAL DIGITAL™ PCR, chamber (e.g., microwell-based) digital PCR, BEAMing (beads, emulsion, amplification, and magnetic) based digital PCR, and microfluidic chip-based digital PCR. In some embodiments, the dPCR is DROPLET DIGITAL™ PCR. In some embodiments, the dPCR is CRYSTAL DIGITAL™ PCR.

Examples of suitable digital PCR systems include the NAICA™ CRYSTAL DIGITAL™ PCR system by Stilla Technologies, which partitions samples into 25,000-30,000 nanoliter-sized droplets; QX100™ DROPLET DIGITAL™ PCR System by Bio-Rad, which partitions samples containing nucleic acid template into 20,000 nanoliter-sized droplets; and the RAINDROP™ digital PCR system by RainDance, which partitions samples containing nucleic acid template into 1,000,000 to 10,000,000 picoliter-sized droplets. Droplet PCR systems have been described, for example, in U.S. Pat. No. 10,501,789B2, the contents of which are incorporated herein by reference in their entirety.

In a typical digital PCR experiment, a PCR solution is made similarly to a classical TAQMAN™ probe assay, which typically comprises the DNA sample, fluorescence-quencher probes (i.e., hydrolysis probes), primers, and a PCR master mix, which generally contains DNA polymerase, dNTPs, $MgCl_2$, and reaction buffers at optimal concentrations. The PCR solution is then randomly distributed into discrete (i.e. individual) partitions, such that some contain no target DNA and others contain one or more target DNA copies, e.g., an average of about 1.6 target DNA copy per partition. The partitions are individually amplified to the terminal plateau phase of PCR (or end-point) and then read for fluorescence, to determine the fraction of positive partitions.

If the partitions are of uniform volume, the number of target DNA molecules present may be calculated from the fraction of positive end-point reactions using Poisson statistics, according to the following equation: $\lambda=-\ln(1-p)$ wherein $\lambda$ is the average number of target DNA molecules per partition (i.e., replicate reaction) and p is the fraction of positive end-point reactions. From $\lambda$, together with the volume of each partition and the total number of partitions analyzed, an estimate of the absolute target DNA concentration is calculated.

The methods described herein use multiple probe sets in which different types of probes share overlapping sets (e.g., circular permutation sets, or permutations as shown in FIG. 6B) of labels. As a result, signals that are positive via two or more detection channels may be ambiguous, since partitions with 2 or more different target regions that give rise to signals that are positive via individual detection channels may add up to provide a composite signal that would seemingly correspond to a specific genetic species at a single target region. The data analysis methods described herein in some steps discard or otherwise account for errors arising from such ambiguous signals in order to estimate the concentrations of mutant sequences at the target regions.

Primer Sets and Amplification

The nucleic acid molecules in each partition may be subject to amplification. Each partition may comprise a plurality of primer sets corresponding to the plurality of target regions. In some embodiments, one or more primer sets each further comprises a forward primer and a reverse primer for amplifying the reference region corresponding to the target region. Each primer pair in a primer set comprises a forward primer and a reverse primer. In some embodiments, the forward primer and the reverse primer are oligonucleotide primers that anneal to opposite strands of a nucleic acid molecule and that flank the target region and the reference region (i.e., target fragment). The primer set allows production of an amplicon specific to the target fragment during the PCR reaction. The corresponding probe sets can thus hybridize to the amplicons.

In some embodiments, substantially all partitions (e.g., all partitions) each comprise (a) a plurality of primer sets corresponding to the plurality of target regions, and (b) a DNA-dependent DNA polymerase; wherein each primer set of the plurality of primer sets comprises a forward oligonucleotide primer and a reverse oligonucleotide primer suitable for amplifying a target fragment comprising a target region corresponding to the primer set and the reference region corresponding to the target region; wherein the method comprises amplifying the target fragments from the nucleic acid molecules in the plurality of partitions; and wherein the method comprises detecting hybridization of the reference probes, the drop-off probes and/or the AS probes to amplicons of the target fragments. In some embodiments, the method comprises detecting hybridization of the reference probes and the drop-off probes to amplicons of the target fragments.

In some embodiments, substantially all partitions (e.g., all partitions) each comprise (a) a plurality of primer sets corresponding to the plurality of target regions and reference regions, and (b) a DNA-dependent DNA polymerase; wherein each primer set of the plurality of primer sets comprises a forward oligonucleotide primer and a reverse oligonucleotide primer suitable for amplifying a target fragment comprising a target region corresponding to the primer set; wherein each primer set of the plurality of primer sets comprises a forward oligonucleotide primer and a reverse oligonucleotide primer suitable for amplifying a reference fragment comprising a reference region corresponding to the target region; wherein the method comprises amplifying the target fragments from the nucleic acid molecules and the reference fragments from the nucleic acid molecules in the plurality of partitions; and wherein the method comprises detecting hybridization of the reference probes to amplicons of the reference fragments, and detecting hybridization of the AS probes (e.g., the first AS probe and the second AS probe) to amplicons of the target fragments.

The primers may be of any suitable length and GC contents. In some embodiments, the plurality of primer sets can be designed using available computer programs such that upon amplification the resulting amplicons are predicted to have the same melting temperature.

The primers are designed to provide an amplicon having a suitable length so that an amplicon is long enough to allow hybridization of the respective reference probe, drop-off probe (and AS probe in some experiments), but at the same time, the amplicon is sufficiently short to avoid excessive nonspecific binding by any of the probes in the reaction mixture. In some embodiments, the amplicons are at least about any one of 50, 100, 150, 200, 250, 300, 350, 400, 450, or 500 basepairs long. In some embodiments, the amplicons are no more than about any one of 500, 450, 400, 350, 300, 250, 200, 150, or 100 basepairs long. In some embodiments, the amplicons are about any one of 100-500, 100-400, 100-300, 100-250, 100-200, 150-250, or 150-300 basepairs long.

Each partition may comprise a polymerase, which is an enzyme that performs template-directed synthesis of polynucleotides, e.g., DNA and/or RNA. The term "polymerase" encompasses both the full-length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga* maritime, or modified versions thereof. Additional examples of commercially available polymerase enzymes include, but are not limited to: Klenow fragment (New England Biolabs Inc.), Taq DNA polymerase (QIAGEN), 9° WM DNA polymerase (New England Biolabs Inc.), Deep Vent™ DNA polymerase (New England Biolabs Inc.), Manta DNA polymerase (Enzymat-ics), Bst DNA polymerase (New England Biolabs Inc.), and phi29 DNA polymerase (New England Biolabs Inc.). In some embodiments, the polymerase is a DNA-dependent polymerase. In some embodiments, the polymerase is an RNA-dependent polymerase, such as reverse transcriptase.

A droplet supports PCR amplification of template molecule(s) using homogenous assay chemistries and workflows similar to those widely used for real-time PCR applications (Hinson et al., 2011, Anal. Chem. 83:8604-8610; Pinheiro et al., 2012, Anal. Chem. 84:1003-1011). Once droplets are generated, they can be transferred on a PCR plate and emulsified PCR reactions can be run on a thermal cycler using a classical PCR program. Alternatively, droplets generated on a Sapphire chip of the NAICA™ system can be subject to thermal cycling using a classical PCR program. Thermal cycling is performed to endpoint.

To circumvent the technical challenges associated with the amplification of low complexity sequence such as a microsatellite sequence, the annealing temperature and/or extension time of the amplification step may be increased. For example, typical annealing temperature is 55° C., and for microsatellite loci detection, the annealing temperature may be increased by an amount from 3 to 15° C.

The PCR data collection step is typically performed using an optical detector (for example, the NAICA™ PRISM 3 system by Stilla, or the Bio-Rad QX-100 droplet reader). A detection system having a suitable number of detection channels, e.g., a three-color detection system, is used.

Partitioning

The partitions described herein can be in any suitable format. Microwell plates, capillaries, oil emulsion, and arrays of miniaturized chambers with nucleic acid binding surfaces can be used to partition the samples in distinct partitions or droplets. Thus, digital PCR as used herein includes a variety of formats, including chamber digital PCR, DROPLET DIGITAL™ PCR (ddPCR), CRYSTAL DIGITAL™ PCR, BEAMing (beads, emulsion, amplification, and magnetic)-based digital PCR, and microfluidic chip-based digital PCR.

Samples can be partitioned into a plurality of mixture partitions. The use of partitioning can be advantageous to reduce background amplification, reduce amplification bias, increase throughput, provide absolute or relative quantitative detection, or a combination thereof. Partitions can include any of a number of types of partitions, including solid partitions (e.g., wells or tubes) or fluid partitions (e.g., aqueous droplets within an oil phase). In some embodiments, the partitions are droplets. In some embodiments, the partitions are microwells. In some embodiments, the partitions are two-dimensional monolayers of droplets in microchambers. Methods and compositions for partitioning a sample are described, for example, in published patent applications WO 2010/036352, US 2010/0173394, US2011/0092373, US2011/0092376, U.S. Pat. No. 10,501,789B2, the entire content of each of which is incorporated by reference herein.

In some cases, samples are partitioned and detection reagents (e.g., probes, enzyme, etc.) are incorporated into the partitioned samples. In other cases, samples are contacted with detection reagents (e.g., probes, enzyme, etc.) and the sample is then partitioned. In some embodiments, reagents such as probes, primers, buffers, enzymes, substrates, nucleotides, salts, etc. are mixed together prior to partitioning, and then the sample is partitioned. In some cases, the sample is partitioned shortly after mixing reagents together so that substantially all, or the majority, of reactions (e.g., DNA amplification, DNA cleavage, etc.) occur after partitioning. In other cases, the reagents are mixed at a temperature in which reactions proceed slowly, or not at all, the sample is then partitioned, and the reaction temperature is adjusted to allow the reaction to proceed. For example, the reagents can be combined on ice, at less than 5° C., or at about 0, 1, 2, 3, 4, 5, 6, 7, 8, 9, 10, 11, 12, 13, 14, 15, 16, 17, 18, 19, 20, 20-25, 25-30, or 30-35° C. In general, one of skill in the art will know how to select a temperature at which the one or more reactions are inhibited. In some cases, a combination of temperature and time are utilized to avoid substantial reaction prior to partitioning. In some embodiments, reagents and sample can be mixed using one or more hot start enzymes, such as a hot start DNA-Dependent DNA polymerase. Thus, sample and one or more of buffers, salts, nucleotides, probes, labels, enzymes, etc. can be mixed and then partitioned. Subsequently, the reaction catalyzed by the hot start enzyme, can be initiated by heating the mixture partitions to activate the one or more hot-start enzymes.

In some embodiments, sample and reagents (e.g., one or more of buffers, salts, nucleotides, probes, labels, enzymes, etc.) can be mixed together without one or more reagents necessary to initiate an intended reaction (e.g., DNA amplification). The mixture can then be partitioned into a set of first partition mixtures and then the one or more essential reagents can be provided by fusing the set of first partition mixtures with a set of second partition mixtures that provide the essential reagent. In some embodiments, the essential reagent can be added to the first partition mixtures without forming second partition mixtures. For example, the essential reagent can diffuse into the set of first partition mixture water-in-oil droplets. As another example, the missing reagent can be directed to a set of microchannels, which contain the set of first partition mixtures.

In some embodiments, the sample is partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes.

In some embodiments, the droplets are formed by flowing an oil phase against an aqueous sample comprising nucleic acid molecules to be detected. In some embodiments, the droplets are formed by flowing an aqueous sample through microchannels comprising wall portions that diverge to detach a droplet of the aqueous sample under the effect of surface tension of the solution into a storage zone with an oil-phase carrier fluid in a microfluidic device. The oil phase can comprise a fluorinated base oil, which can additionally be stabilized by combination with a fluorinated surfactant such as a perfluorinated polyether. In some embodiments, the oil phase further comprises an additive for tuning the oil properties, such as vapor pressure, viscosity, or surface tension.

In some embodiments, the emulsion is formulated to produce highly monodisperse droplets having a liquid-like interfacial film that can be converted by heating into microcapsules having a solid like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or not. The microcapsules can be resistant to coalescence and/or flocculation across a wide range of thermal and mechanical processing. In some embodiments, these capsules are useful for storage or transport of partition mixtures. For example, a sample can be collected at one location, partitioned into droplets containing enzymes, buffers, probes, and/or primers, optionally one or more amplification reactions can be performed, the partitions can then be heated to perform microencapsulation, and the microcapsules can be stored or transported for further analysis.

In some embodiments, the sample is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300, 000 partitions, at least 400,000 partitions, at least 500,000 partitions, at least 600,000 partitions, at least 700, 000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000, 000 partitions, or at least 200,000,000 partitions.

In some embodiments, the NAICA™ dPCR platform is used to carry out the methods described herein. In some embodiments, the Sapphire chip of the NAICA™ dPCR platform is used to partition the sample. Typically, a Sapphire chip contains 4 microchambers, each with a 2-dimensional monolayer of droplets. In some embodiments, data from dPCR reactions in droplets from different microchambers in a Sapphire chip is combined to provide quantification of the genetic species (e.g., wildtype and mutant sequences at a plurality of target regions) that the method is designed to detect.

In some embodiments, the sample is partitioned into a sufficient number of partitions such that at least a majority of partitions has no more than 1-5 target regions or amplicons thereof (e.g., no more than about 1, 2, 3, 4, or 5 target regions or amplicons thereof). In some embodiments, on average about 0.5, 1, 2, 3, 4, or 5 target regions or amplicons thereof are present in each partition. In some embodiments, no more than about any one of 95%, 90%, 85%, 80%, 75%, 70%, 65%, 60%, 55%, 50%, 45%, 40%, or less of all partitions each contains at least 1 target region or amplicon thereof. In some embodiments, at least one partition contains no target regions or amplicons thereof (the partition is "empty"). In some embodiments, at least about 1%, 2%, 3%, 4%, 5%, 6%, 7%, 8%, 9%, 10%, 11%, 12%, 13%, 14%, 15%, 16%, 17%, 18%, 19%, 20%, 22%, 25%, 30%, or 40% of the partitions contain no target regions or amplicons thereof. Generally, partitions can contain an excess of enzyme, probes, and primers such that each mixture partition is likely to successfully amplify any target regions present in the partition.

In some embodiments, the droplets that are generated are substantially uniform in shape, size and/or volume. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 pico liter, 5 pico liters, 10 picoliters, 100 pico liters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

Sample Preparation

The sample analyzed by the methods in the application contain nucleic acid molecules. In some embodiments, the nucleic acid molecules are DNA molecules, such as genomic DNA, or DNA obtained from reverse transcription of RNA (e.g., cDNA). The genomic DNA may be chromosomal DNA, DNA originating from a tumor (i.e., tumor genomic DNA), fetal DNA, or a genomic DNA subject to site-specific genome editing. In some embodiments, the nucleic acid molecules are cell-free DNA (cfDNA), such as circulating DNA, for example, circulating tumor DNA, or cell-free fetal DNA.

In some embodiment, the nucleic acid molecules are RNA molecules. In such cases, the sample may be further subjected to a reverse transcription step.

The methods described herein may further comprise one or more of sample preparation steps, including, but not limited to, obtaining a biological sample from an individual, extraction of nucleic acid molecules from a biological sample, fragmenting nucleic acid molecules, and diluting nucleic acid molecules.

The sample may be prepared from a biological sample, such as a biological fluid or a biological tissue. Examples of biological fluids include urine, blood, plasma, serum, saliva, semen, stool, sputum, cerebrospinal fluid, tears, mucus, pancreatic juice, gastric juice, amniotic fluid, serous fluids such as pericardial fluid, pleural fluid or peritoneal fluid.

Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumor tissue, lymph nodes, arteries and disseminated cell(s). The tissue can be fresh, freshly frozen, or fixed, such as formalin-fixed paraffin-embedded (FFPE) tissues. The biological sample can be obtained by any means, for example via a surgical procedure, such as a biopsy, or by a less invasive method, including, but not limited to, abrasion or fine needle aspiration.

In some embodiments, the biological sample is selected from the group consisting of tumor tissue, disseminated cells, feces, blood cells, blood plasma, serum, lymph nodes, urine, saliva, semen, stool, sputum, cerebrospinal fluid, tears, mucus, pancreatic juice, gastric juice, amniotic fluid, cerebrospinal fluid, serous fluids. In some embodiments, the method further comprises extracting nucleic acid molecules from a biological sample.

In some embodiments, the sample comprises microbes such as bacterial cells, archaeal cells, and/or yeast cells, or nucleic acids derived from the microbes. In some embodiments, the sample comprises viruses, or nucleic acids derived from viruses. In some embodiments, the sample comprises one or more pathogens, or nucleic acids derived from the pathogens.

In some embodiments, the sample is derived from an animal, such as a pet, a farm animal, or a model animal, e.g., a mammal. In some embodiments, the sample comprises animal cells, such as cells from a primary cell or a cell line. In some embodiments, the sample is derived from a plant, such as a crop or a model plant, including genetically modified (GM) plants and genetically edited (GE) plants. In some embodiments, the sample comprise genetically engineered cells, such as genome-engineered plant cell or animal cell. In some embodiments, the sample comprises nucleic acids derived from one or more cells.

In some embodiments, the sample is an environmental sample. In some embodiments, the sample is obtained from sewage water.

In some embodiments, the nucleic acid molecules in the sample have a low molecular weight. For example, the nucleic acid molecules may be no more than about any one of 1000, 900, 800, 700, 600, 500, 400, 300, or 200 nucleotides long. In some embodiments, the method further comprises fragmenting high molecular weight nucleic acid molecules (e.g., chromosomal DNA) into nucleic acid molecules of suitable size, for example, for sonication or restriction digestion.

In some embodiments, the concentration of the nucleic acid molecules in a sample is adjusted, e.g., by dilution of the sample or by concentrating the sample (e.g., by dialysis, or by lyophilization and reconstitution), to provide a suitable concentration for dPCR. In some embodiments, the method is carried out with a first sample, and the concentration of the nucleic acid molecules in the sample is adjusted based on a count of partitions that each produces a positive signal via three or more detection channels, wherein if (e.g., when) the count is larger than a pre-determined value, the adjusting is decreasing the concentration of the nucleic acid molecules in the sample by diluting the sample; or wherein if (e.g., when) the count is smaller than a pre-determined value, the adjusting is increasing the concentration of the nucleic acid molecules in the sample by concentrating the sample. In some embodiments, the dilution factor or the concentration factor is based on the count of partitions that each produces a positive signal via three or more detection channels. In some embodiments, the concentration of the nucleic acid molecules in the sample is adjusted based on the estimated concentration of the wildtype sequence, the estimated concentration of the mutant sequences, or the estimated concentration of the specific allelic sequences at one or more of the plurality of target regions in the sample. In some embodiments, the method is repeated with the sample diluted to one or more concentrations in order to provide optimal concentrations for accurate quantification of different genetic species (e.g., wildtype, mutant and/or allelic sequences) at different target regions. In some embodiments, the concentration of a genetic species in a sample is at least about any one of 0.01, 0.05, 0.1, 0.5, 1, 2, 5, 10, 15, 20, 25, 30, 35, 50, 75, 100, 150, 200, 250, 500, 1000, 2000, 5000, 7500, 10000, 15000, 20000, 100000 or more copies per µL. In some embodiments, the methods are designed to detect mutations at different target regions that occur at comparable frequencies, such as frequencies that differ by no more than about 100×, 50×, 20×, 10×, 5×, 2×, or less.

In some embodiments, the method comprises determining a quality control measure based on a count of partitions that each produces a positive signal via each of the detection channels. In some embodiments, the quality control measure is determined by comparing a count of partitions that each produces a positive signal via each of the detection channels with an estimated count, wherein the estimated count is based on counts of partitions other than the count of partitions that each produces a positive signal via each of the detection channels $X_1$-$X_R$. In some embodiments, the estimated count is based on counts of partitions that each produces a positive signal via one of the detection channels and negative signals via each of the other detection channels.

For example, the probability of partitions that each produces a positive signal via each of the detection channels can be estimated as a product of each probability of partitions that each produces a positive signal via one of the detection channels and negative signals via each of the other detection channels.

In some embodiments, the sample is obtained from an individual. In some embodiments, the individual is a mammal, such as a primate, e.g., a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

In some embodiments, the individual has a cancer, is in remission of a cancer, or is at risk of suffering from a cancer notably based on family history. In some embodiments, the individual has familial tumor predisposition.

In some embodiment, the individual is suffering from, is in remission, or has familial cancer predisposition. In some embodiments, the individual is suffering from or is at risk of suffering from a disease caused by mutations in mismatch repair (MMR) genes, such as Constitutional mismatch repair deficiency syndrome (CMMRD syndrome) or Lynch syndrome.

The cancer may be a solid cancer or a “liquid tumor” such as cancers affecting the blood, bone marrow and lymphoid system, also known as tumors of the hematopoietic and lymphoid tissues, which notably include leukemia and lymphoma. Liquid tumors include for example acute myelogenous leukemia (AML), chronic myelogenous leukemia (CML), acute lymphocytic leukemia (ALL), and chronic lymphocytic leukemia (CLL), (including various lymphomas such as mantle cell lymphoma or non-Hodgkin’s lymphoma (NHL).

Solid cancers include cancers affecting one of the organs selected from the group consisting of colon, rectum, skin, endometrium, lung (including non-small cell lung carcinoma), uterus, bones (such as Osteosarcoma, Chondrosarcomas, Ewing’s sarcoma, Fibrosarcomas, Giant cell tumors, Adamantinomas, and Chordomas), liver, kidney, esophagus, stomach, bladder, pancreas, cervix, brain (such as Meningiomas, Glioblastomas, Lower-Grade Astrocytomas, Oligodendrocytomas, Pituitary Tumors, Schwannomas, and Metastatic brain cancers), ovary, breast, head and neck region, testis, prostate and the thyroid gland.

Embodiment Employing Three (3) Drop-Off Probe Pairs

Figure 7:
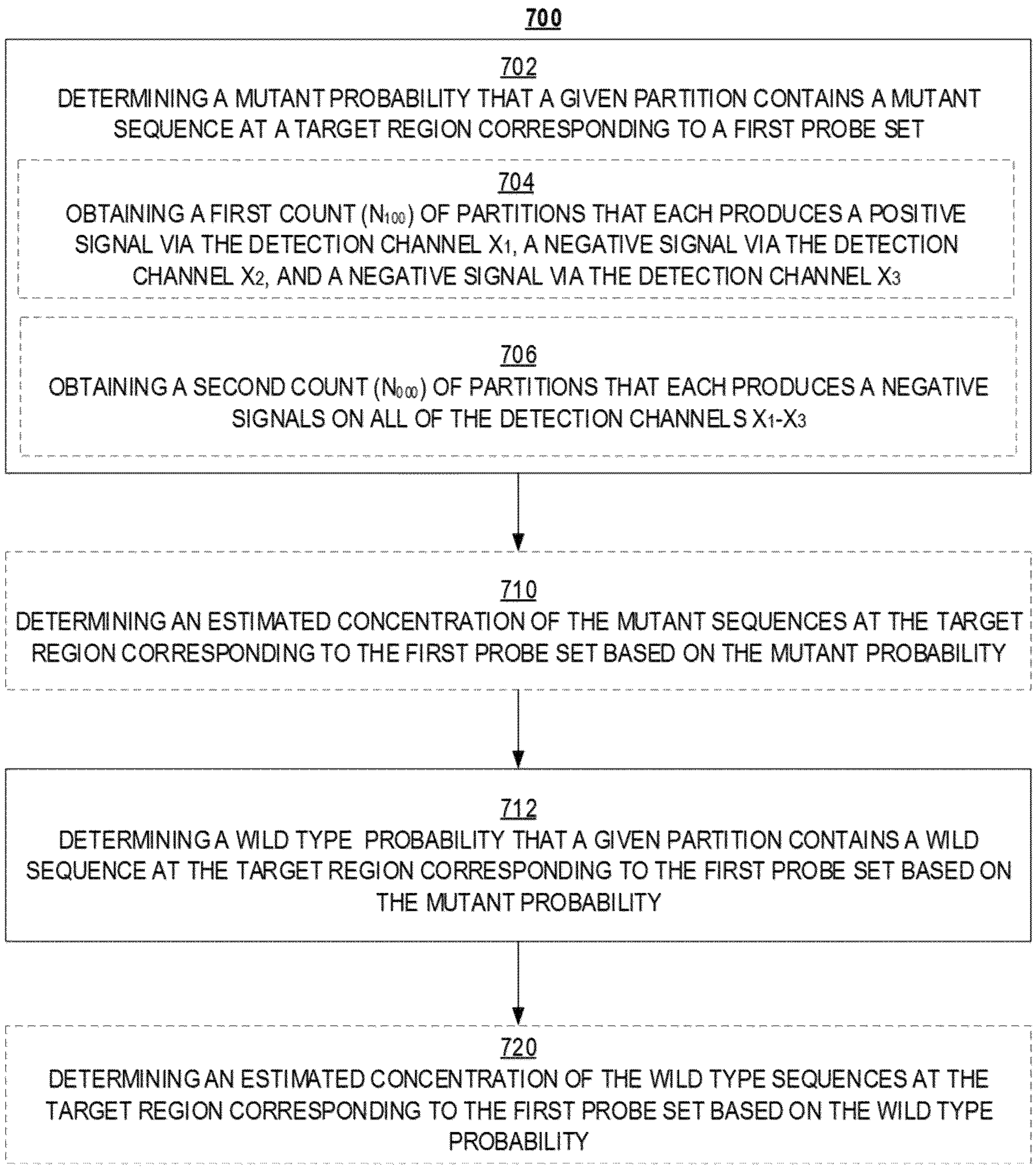
FIG. 7 shows a flow chart for data analysis of an exemplary method for detection of wildtype and mutant sequences at three target regions using three probe pairs.

FIG. 7 illustrates an exemplary process 700 for quantification of wildtype and/or mutant sequences at three (3) target regions in a sample comprising nucleic acid molecules, according to some embodiments. Process 700 is performed, for example, using one or more electronic devices implementing a software platform, by one or more human users, or any combination thereof. In some examples, process 700 is performed using a client-server system, and the blocks of process 700 are divided up in any manner between the server and a client device. In other examples, the blocks of process 700 are divided up between the server and multiple client devices. Thus, while portions of process 700 are described herein as being performed by particular devices of a client-server system, it will be appreciated that process 700 is not so limited. In other examples, process 700 is performed using only a client device or on multiple client devices.

In process 700, some blocks are, optionally, combined, the order of some blocks is, optionally, changed, and some blocks are, optionally, omitted. In some examples, additional steps may be performed in combination with the process 700. Accordingly, the operations as illustrated (and described in greater detail below) are exemplary by nature and, as such, should not be viewed as limiting.

In some embodiments, one or more variables of process 700 can be obtained via a drop-off digital PCR process in which three (3) probe pairs corresponding to the three target regions are employed. Each probe pair of the three probe pairs comprises a drop-off probe comprising a drop-off label and an oligonucleotide drop-off sequence complementary to a wildtype sequence, and not to the mutant sequence(s), at a target region corresponding to the respective probe pair, and a reference probe comprising a reference label and an oligonucleotide reference sequence complementary to a wildtype sequence at an adjacent reference region upstream or downstream to the target region corresponding to the respective probe pair.

In some embodiments, a reference label and a drop-off label of each probe pair of the three probe pairs are detectable via different detection channels. In an exemplary scheme shown in TABLE 2, each of the three probe pairs has a reference label and a drop-off label detectable via different detection channels (i.e., blue vs. green; green vs. red; red vs. blue). In some embodiments, the reference labels of the three probe pairs are detectable via different detection channels with respect to each other, and the drop-off labels of the three probe pairs are detectable via different detection channels with respect to each other. In the exemplary scheme shown in TABLE 2, the reference labels of the three probe pairs are detectable via a blue detection channel, a green detection channel, and a red detection channel, respectively. Further, the drop-off labels of the three probe pairs are detectable via a green detection channel, a red detection channel, and a blue detection channel, respectively.

TABLE 2

| Sequences | Detection Channel |
|---|---|
| Wildytype sequence (w1) and mutant sequence(s) (m1) at target region 1 | Blue fluorophore (B) on reference probe 1 (r1)<br>Green fluorophore (G) on drop-off probe 1 (w1) |
| Wildytype sequence (w2) and mutant sequence(s) (m2) at target region 2 | Green fluorophore (G) on reference probe 2 (r2)<br>Red fluorophore (R) on drop-off probe 2 (w2) |
| Wildytype sequence (w3) and mutant sequence(s) (m3) at target region 3 | Red fluorophore (R) on reference probe 3 (r3)<br>Blue fluorophore (B) on drop-off probe 3 (w3) |

The exemplary scheme in TABLE 2 employs circular permutation. Specifically, the detection channel for one of the three reference labels is also the detection channel for one of the three drop-off labels. For example, the detection channel for the drop-off label corresponding to the first probe pair (i.e., the green detection channel) is the same as the detection channel for the reference label corresponding to the second probe pair. Further, the number of detection channels (i.e., 3) is the same as the number of probe pairs (i.e., 3).

It should be appreciated, however, that the scheme TABLE 2 is merely exemplary and circular permutation is not required for performing process 700. For example, the drop-off label corresponding to the third probe pair can be yellow rather than blue. In some embodiments, the total number of detection channels can be the same or fewer than twice the number of probe pairs (i.e., 6).

In a digital drop-off PCR process, a sample comprising nucleic acid molecules is distributed among a plurality of partitions, and substantially all partitions each comprises the three probe pairs. Hybridization of reference probes of the three probe pairs to nucleic acid molecules or amplicons thereof comprising wildtype sequences at the reference regions in the plurality of partitions can be detected. Furthermore, hybridization of drop-off probes of the three probe pairs to nucleic acid molecules or amplicons thereof comprising wildtype sequences at the target regions in the plurality of partitions can be detected. Process 700 can then be performed to provide quantification of wildtype and/or mutants sequences at the three target regions in the sample.

Process 700 is based on the assumption of independence of the partition encapsulation of nucleic acid molecules containing target regions 1, 2, and 3. Indeed, despite the fact that in the exemplary scheme in TABLE 2, due to the biomolecular design, there is no independence of the partition encapsulation of fluorophores Blue, Green and Red, there is nonetheless independence of the partition encapsulation of nucleic acid molecules containing target regions 1, 2 and 3.

Process 700 is described below in accordance to the following notations:

TABLE 3

| Variable | Definition |
|---|---|
| P(X) | probability of the event X |
| $\overline{X}$ | negation of event X |
| $m_i$ | the event "a partition contains mutant sequence(s) at target region i" |
| $w_i$ | the event "a partition contains a wild-type sequence at target region i" |
| N | total number of partitions in the digital PCR experiment |
| v | volume of a partition (e.g., in μL), assumed to be constant |
| $C(m_i)$ | real concentration of mutant sequence(s) at target region number i in the digital PCR experiment (in cp/μL) |
| $C(w_i)$ | real concentration of wildtype sequence at target region number i in the digital PCR experiment (in cp/μL) |
| $P(m_i)$ | probability that a partition contains mutant sequence(s) at target region number i |
| $P(w_i)$ | probability that a partition contains a wildtype sequence at target region number i |
| $n_{BGR}$ | number of observed partitions in the digital PCR experiment that are positive (B = 1)/negative (B = 0) in Blue channel (B) and positive (G = 1)/negative (G = 0) in Green channel (G) and positive (R = 1)/negative (R = 0) in Red channel (R). For example: $n_{000}$ is the number of observed partitions in the digital PCR experiment that are triple negatives and $n_{101}$ is number of observed partitions in the digital PCR experiment that are positive in Blue and positive in Red. |
| $\hat{P}(m_i)$ | estimated probability that a partition contains a mutant sequence(s) at target region number i |
| $\hat{P}(w_i)$ | estimated probability that a partition contains a wildtype sequence at target region number i |
| $\hat{C}(m_i)$ | estimated concentration of mutant sequence(s) at target region number i in the digital PCR experiment (in cp/μL) |
| $\hat{C}(w_i)$ | estimated concentration of wildtype sequence at target region number i in the digital PCR experiment (in cp/μL) |
| $\hat{C}_{min}(m_i)$, $\hat{C}_{max}(m_i)$, $\hat{U}(m_i)$ | minimum value, maximum value and uncertainty at 95% confidence level for the estimated concentration of mutant sequence(s) at target region number i in the digital PCR experiment (in cp/μL) |
| $\hat{C}_{min}(w_i)$, $\hat{C}_{max}(w_i)$, $\hat{U}(w_i)$ | minimum value, maximum value and uncertainty at 95% confidence level for the estimated concentration of wildtype sequence at target region number i in the digital PCR experiment (in cp/μL) |

At block 702, a system (e.g., one or more electronic devices) determines a mutant probability ($\hat{P}(m_1)$) that a given partition contains a mutant sequence at the target region corresponding to the first probe pair.

In some embodiments, block 702 includes blocks block 704 and block 706. At block 704, the system obtains a first count ($n_{100}$) of one or more partitions that each produces a positive signal via the detection channel $X_1$, a negative signal via the detection channel $X_2$, and a negative signal via the detection channel $X_3$.

Further, at block 706, the system obtains a second count ($n_{000}$) of one or more partitions that each produces negative signals on all of the detection channels $X_1$-$X_3$.

In some embodiments, the system calculates $\hat{P}(m_1)$ based on a ratio between the first count ($n_{100}$) and a sum of the first count ($n_{100}$) and the second count ($n_{000}$), as shown below.

$$\hat{P}(m_1) = \frac{n_{100}}{n_{000} + n_{100}}$$

In some embodiments, the first count and/or the second count is zero. For example, if a mutant sequence is absent, there will be no single positive partitions and the exemplary method is unable to detect the mutant sequence(s), but it is able to provide an upper limit for its real concentration. In some embodiments, if the mutant (or the other targets) are excessively highly concentrated, there will be no full negative partitions and the exemplary method is able to detect its presence and provide a lower limit for its real concentration.

The formula above is derived as follows:

$$\hat{P}(m_1) = P(m_1|\overline{w_1}\cap\overline{w_2}\cap\overline{m_2}\cap\overline{w_3}\cap\overline{m_3}) = P(\text{partition is positive in Blue} \mid \text{partition is negative in Green and negative in Red}) = \frac{n_{100}}{n_{000}+n_{100}}$$

In some embodiments, the system can calculate $\hat{P}(m_2)$ and $\hat{P}(m_3)$ in a similar manner. For example:

$$\hat{P}(m_2) = \frac{n_{010}}{n_{000}+n_{010}}$$

$$\hat{P}(m_3) = \frac{n_{001}}{n_{000}+n_{001}}$$

In some embodiments, at block 710, the system determines an estimated concentration $\hat{C}(m_1)$ of the mutant sequence(s) at the target region corresponding to the first probe pair in the sample based on the mutant probability $\hat{P}(m_1)$ in the sample. For example, the system can calculate the estimated concentration based on Poisson's Law in accordance with the following formula:

$$\hat{C}(m_1) = -\frac{1}{v}\ln(1-\hat{P}(m_1)) = -\frac{1}{v}\ln\left(1-\frac{n_{100}}{n_{000}+n_{100}}\right) = -\frac{1}{v}\ln\left(\frac{n_{000}}{n_{000}+n_{100}}\right)$$

In some embodiments, the system determines a confidence interval and/or an uncertainty measure associated with the estimated concentration $\hat{C}(m_1)$ in the sample. For example, the confidence interval and uncertainty at 95% confidence level can be calculated as follows $$\hat{C}_{max}(m_1) = -\frac{1}{v}\ln(1-\hat{P}(m_1) - 1.96\sqrt{\frac{\hat{P}(m_1)(1-\hat{P}(m_1))}{n_{000}+n_{100}}}) = -\frac{1}{v}\ln(1-\frac{n_{100}}{n_{000}+n_{100}} - 1.96\sqrt{\frac{n_{000}*n_{100}}{(n_{000}+n_{100})^3}})$$

$$\hat{C}_{min}(m_1) = -\frac{1}{v}\ln(1-\hat{P}(m_1) + 1.96\sqrt{\frac{\hat{P}(m_1)(1-\hat{P}(m_1))}{n_{000}+n_{100}}}) = -\frac{1}{v}\ln(1-\frac{n_{100}}{n_{000}+n_{100}} + 1.96\sqrt{\frac{n_{000}*n_{100}}{(n_{000}+n_{100})^3}})$$

In some embodiments, the uncertain measure refers to uncertainty of the digital PCR method and can be calculated as provided below. One of ordinary skill in the art should appreciate that other types of uncertainty (e.g., sample taking, sample handling, processing) may be factored in $$\hat{U}(m_1) = \frac{\hat{C}_{max}(m_1) - \hat{C}_{min}(m_1)}{2\,\hat{C}(m_1)}$$

In some embodiments, the system can calculate $\hat{C}(m_2)$, $\hat{C}(m_3)$, $\hat{C}_{max}(m_2)$, $\hat{C}_{max}(m_3)$, $\hat{C}_{min}(m_2)$, $\hat{C}_{min}(m_3)$, $\hat{U}(m_2)$ and $\hat{U}(m_3)$ in a similar manner.

At block 712, the system determines a wildtype probability ($\hat{P}(w_1)$) that a given partition contains a wildtype sequence at the target region corresponding to the first probe pair. In some embodiments, the wildtype probability is based on $\hat{P}(m_1)$. In some embodiments, the wildtype probability is calculated based on $\hat{P}(m_1)$ and $\hat{P}(m_2)$.

In some embodiments, the system calculates $\hat{P}(w_1)$ in accordance with the following formula:

$$\hat{P}(w_1) = \left(\frac{n_{110}}{n_{000}+n_{100}+n_{010}+n_{110}} - \hat{P}(m_1)\hat{P}(m_2)\right)\frac{1}{1-\hat{P}(m_1)\hat{P}(m_2)} = \frac{n_{110} - \frac{n_{100}*n_{010}}{n_{000}}}{n_{000}+n_{100}+n_{010}+n_{110}}$$

The formula is derived as follows:

$$P(\text{partition is positive in Blue and positive in Green partitionis negative in Red}) = P(w_1 \mid \overline{w_2}\cap\overline{m_3}) + P(m_1\cap m_2\cap\overline{w_1} \mid \overline{w_2}\cap\overline{w_3}\cap\overline{m_3}) = \hat{P}(w_1) + \hat{P}(m_1)\hat{P}(m_2)(1-\hat{P}(w_1))$$

$$P(\text{partition is positive in Blue and positive in Green} \mid \text{partition is negative in Red}) = \frac{n_{110}}{n_{000}+n_{100}+n_{010}+n_{110}}$$

Thus, $$\hat{P}(w_1) + \hat{P}(m_1)\hat{P}(m_2)(1-\hat{P}(w_1)) = \frac{n_{110}}{n_{000}+n_{100}+n_{010}+n_{110}},$$

and the calculation of $\hat{P}(w_1)$ can be derived accordingly.

In some embodiments, at block 720, the system determines an estimated concentration $\hat{C}(w_1)$ of the wildtype sequences at the target region corresponding to the first probe pair in the sample based on the wildtype probability $\hat{P}(w_1)$. For example, the system can calculate the estimated concentration based on Poisson's Law in accordance with the following formula:

$$\hat{C}(w_1) = -\frac{1}{v}\ln(1-\hat{P}(w_1))$$

In some embodiments, if the wildtype concentrations obtained on each probe pairs are expected to be the same, a more robust wildtype concentration estimate can be obtained by averaging the three estimated values.

In some embodiments, the system can calculate $\hat{P}(w_2)$ and $\hat{P}(w_3)$, $\hat{C}(w_2)$ and $\hat{C}(w_3)$ in a similar manner.

In some embodiments, the confidence interval, including $\hat{C}_{max}(w_i)$ and $\hat{C}_{min}(w_i)$, the uncertainty measure ($\hat{U}(w_i)$) at 95% confidence level can be derived from the variance of $\hat{P}(w_i)$, respectively, where i is 1, 2, or 3.

The embodiments described in this section are applicable to dPCR methods using three sets of probes comprising dual-labeled AS probes (e.g., each probe set contains a reference probe and an AS probe with two detectable labels, or each probe set contains a reference probe, a first AS probe and a second AS probe). An exemplary scheme for a dual-labeled AS assay capable of detecting six genetic species using three fluorophores is shown in TABLE 4 below.

TABLE 4

| Sequences | Detection Channel |
|---|---|
| allelic sequence (w1) at target region 1 and reference sequence (m1) at reference region 1 | Blue fluorophore (B) on second AS probe 1<br>Green fluorophore (G) on reference probe 1 and first AS probe 1 |
| allelic sequence (w2) at target region 2 and reference sequence (m2) at reference region 2 | Green fluorophore (G) on second AS probe 2<br>Red fluorophore (R) on reference probe 2 and first AS probe 2 |
| allelic sequence (w3) at target region 3and reference sequence (m3) at reference region 3 | Red fluorophore (R) on second AS probe 3<br>Blue fluorophore (B) on reference probe 3 and first AS probe 3 |

Embodiment Employing R Number of Drop-Off Probe Pairs

Figure 8:
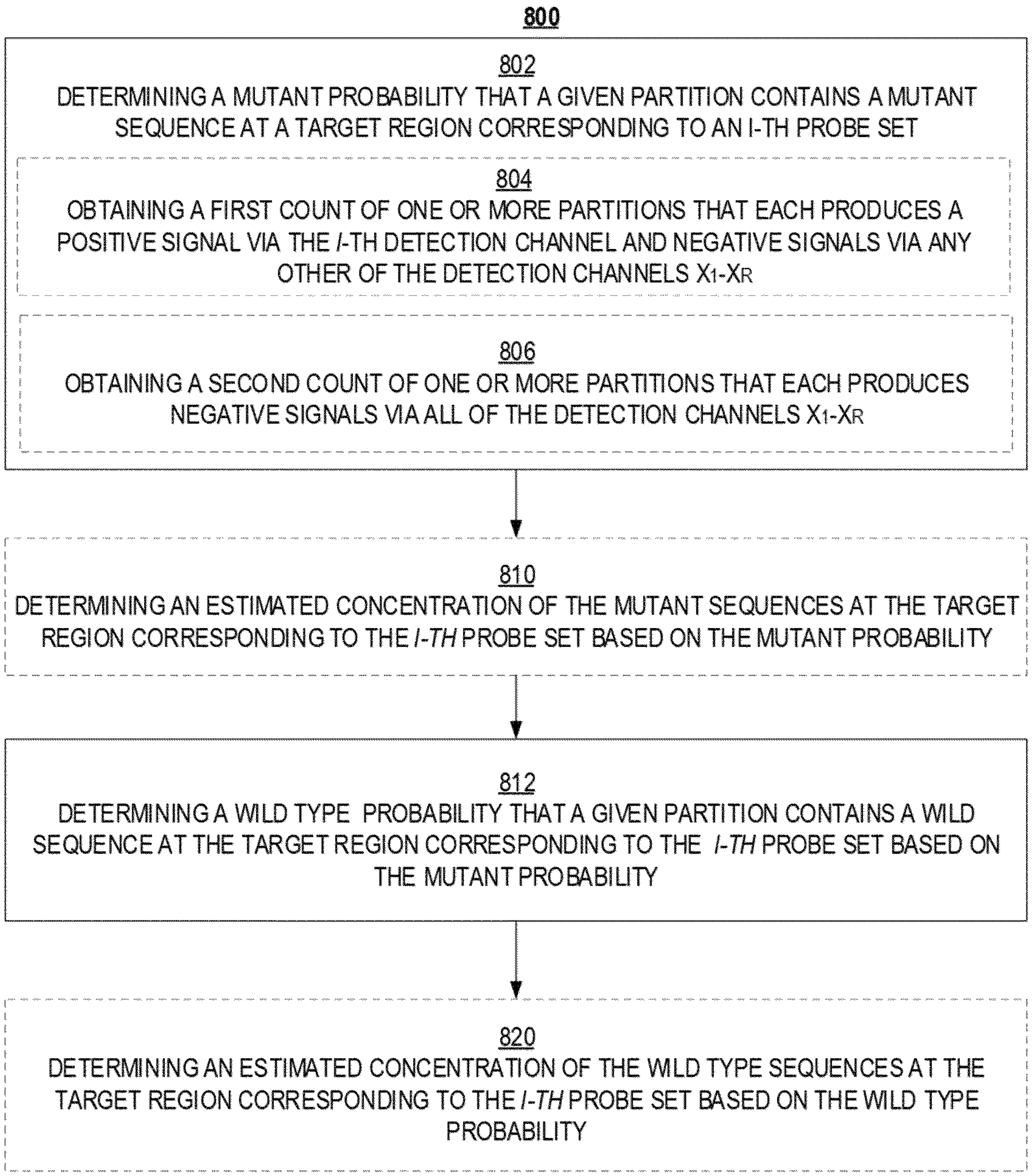
FIG. 8 shows a flow chart for data analysis of an exemplary method for detection of wildtype and mutant sequences at R number of target regions using R number of probe pairs.

FIG. 8 illustrates an exemplary process 800 for quantification of wildtype and/or mutant sequence(s) at a R number of target regions in a sample comprising nucleic acid molecules, according to some embodiments. Process 800 is performed, for example, using one or more electronic devices implementing a software platform, by one or more human users, or any combination thereof. In some examples, process 800 is performed using a client-server system, and the blocks of process 800 are divided up in any manner between the server and a client device. In other examples, the blocks of process 800 are divided up between the server and multiple client devices. Thus, while portions of process 800 are described herein as being performed by particular devices of a client-server system, it will be appreciated that process 800 is not so limited. In other examples, process 800 is performed using only a client device or on multiple client devices.

In process 800, some blocks are, optionally, combined, the order of some blocks is, optionally, changed, and some blocks are, optionally, omitted. In some examples, additional steps may be performed in combination with the process 800. Accordingly, the operations as illustrated (and described in greater detail below) are exemplary by nature and, as such, should not be viewed as limiting.

In some embodiments, one or more variables of process 800 can be obtained via a drop-off digital PCR process in which a R number of probe pairs corresponding to the R number of target regions are employed. Each probe pair of the R probe pairs comprises a drop-off probe comprising a drop-off label and an oligonucleotide drop-off sequence complementary to a wildtype sequence, and not to the mutant sequence(s), at a target region corresponding to the respective probe pair, and a reference probe comprising a reference label and an oligonucleotide reference sequence complementary to a wildtype sequence at an adjacent reference region upstream or downstream to the target region corresponding to the respective probe pair.

In some embodiments, a reference label and a drop-off label of each probe pair of the plurality of probe pairs are detectable via different detection channels. In an exemplary scheme shown in TABLE 5, each probe pair of the plurality of probe pairs has a reference label and a drop-off label detectable via different detection channels (i.e., $X_i$ v. $X_{i+1}$). In some embodiments, the reference labels of the plurality of probe pairs are detectable via different detection channels with respect to each other, and the drop-off labels of the plurality of probe pairs are detectable via different detection channels with respect to each other. In the exemplary scheme shown in TABLE 5, the reference labels of the plurality of probe pairs are detectable via $X_1$-$X_R$ respectively. Further, the drop-off labels of the three probe pairs are detectable via $X_1$-$X_R$ respectively.

TABLE 5

| Sequences | Detection Channel |
|---|---|
| Wildtype sequence (w1) and mutant sequence(s) (m1) at target region 1 | $X_1$ fluorophore (detection channel 1) on reference probe 1 ($r_1$)<br>$X_2$ fluorophore (detection channel 2) on drop-off probe 1 ($w_1$) |
| Wildtype sequence (w2) and mutant sequence(s) (m2) at target region 2 | $X_2$ fluorophore (detection channel 2) on reference probe 2 ($r_2$)<br>$X_3$ fluorophore (detection channel 3) on drop-off probe 2 ($w_2$) |
| . . . | . . . |
| Wildtype sequence ($w_i$) and mutant sequence(s) ($m_i$) at target region i | $X_i$ fluorophore (detection channel i) on reference probe i ($r_i$)<br>$X_{i+1}$ fluorophore (detection channel i + 1) on drop-off probe i ($w_i$) |
| Wildtype sequence ($w_R$) and mutant sequence(s) ($m_R$) at target region R | $X_R$ fluorophore (detection channel R) on reference probe R ($r_R$)<br>$X_1$ fluorophore (detection channel 1) on drop-off probe R ($w_R$) |

The exemplary scheme in TABLE 5 employs circular permutation. Specifically, the detection channel for one of the plurality of reference labels is also the detection channel for one of the plurality of drop-off labels. For example, the detection channel for the drop-off label corresponding to the probe pair i (i.e., $X_{i+1}$) is the same as the detection channel for the reference label corresponding to the probe pair i+1. Further, the number of detection channels (i.e., R) is the same as the number of probe pairs (i.e., R).

It should be appreciated, however, that the scheme TABLE 5 is merely exemplary and circular permutation is not required for performing process 800. In some embodiments, the total number of detection channels can be the same or fewer than twice the number of probe pairs (i.e., 2R).

In a multiplex drop-off digital PCR process, a sample comprising nucleic acid molecules is distributed among a plurality of partitions, and substantially all partitions each comprises the R number of probe pairs. Hybridization of reference probes of the plurality of probe pairs to nucleic acid molecules or amplicons thereof comprising wildtype sequences at the reference regions in each partition can be detected via each of the detection channels $X_1$-$X_R$. Further, hybridization of drop-off probes of the plurality of probe pairs to nucleic acid molecules or amplicons thereof comprising wildtype sequences in each partition can be detected via each of the detection channels $X_1$-$X_R$. Process 800 can then be performed to provide quantification of wildtype and/or mutants sequences at the R target regions in the sample.

Process 800 is based on the assumption of independence of the partition encapsulation of nucleic acid molecules containing target regions 1 to R. Indeed, despite the fact that in the exemplary scheme in TABLE 5, due to the biomolecular design, there is no independence of the partition encapsulation of fluorophores $X_1$ to $X_R$, there is nonetheless independence of the partition encapsulation of nucleic acid molecules containing target regions 1 to R.

Process 800 is described below in accordance to the following notations:

TABLE 6

| Variable | Definition |
|---|---|
| P(X) | probability of the event X |
| $\overline{X}$ | negation of event X |
| $m_i$ | the event "a partition contains mutant sequence(s) at target region i", where i = 1 . . . R |
| $w_i$ | the event "a partition contains a wildtype sequence at target region i", where i = 1 . . . R |
| N | total number of partitions in the digital PCR experiment |
| v | volume of a partition (e.g., in μL), assumed to be constant |
| $C(m_i)$ | real concentration of mutant sequence(s) at target region number i in the digital PCR experiment (e.g., in cp/μL), where i = 1 . . . R |
| $C(w_i)$ | real concentration of wildtype sequence at target region number i in the digital PCR experiment (e.g., in cp/μL), where i = 1 . . . R |
| $P(m_i)$ | probability that a partition contains mutant sequence(s) at target region number i, where i = 1 . . . R |
| $P(w_i)$ | probability that a partition contains a wildtype sequence at target region number i, where i = 1 . . . R |
| $n_0$ | number of observed partitions in the digital PCR experiment that are negative for all detection channels 1 to R (they are the full negative partitions) |
| $n_i$ | number of observed partitions in the digital PCR experiment that are positive for detection channel i and negative for all the other detection channels, where i = 1 . . . R |
| $n_{i,j}$ | number of observed partitions in the digital PCR experiment that are positive for detection channel i, positive for detection channel j, and negative for all the other detection channels, where i = 1 . . . R and j = 1 . . . R |
| $\hat{P}(m_i)$ | estimated probability that a partition contains mutant sequence(s) at target region number i, where i = 1 . . . R |
| $\hat{P}(w_i)$ | estimated probability that a partition contains a wildtype sequence at target region number i, where i = 1 . . . R |
| $\hat{C}(m_i)$ | estimated concentration of mutant sequence(s) at target region number i in the digital PCR experiment (e.g., in cp/μL) , where i = 1 . . . R |
| $\hat{C}(w_i)$ | estimated concentration of wildtype sequence at target region number i in the digital PCR experiment (e.g., in cp/μL), where i = 1 . . . R |
| $\hat{C}_{min}(m_i)$, $\hat{C}_{max}(m_i)$, $\hat{U}(m_i)$ | minimum value, maximum value and uncertainty at 95% confidence level for the estimated concentration of mutant sequence(s) at target region number i in the digital PCR experiment (e.g., in cp/μL), where i = 1 . . . R |

At block 802, a system (e.g., one or more electronic devices) determines a mutant probability ($\hat{P}(m_i)$) that a given partition contains mutant sequence(s) at the target region corresponding to the i-th probe pair.

In some embodiments, block 802 includes block 804 and block 806. At block 804, the system obtains a first count of one or more partitions that each produces a positive signal via the i-th detection channel and negative signals via any other of the detection channels $X_1$-$X_R$. Further, at block 806, the system obtains a second count of one or more partitions that each produces negative signals via all of the detection channels $X_1$-$X_R$.

In some embodiments, the system calculates $\hat{P}(m_i)$ based on a ratio between the first count ($n_i$) and a sum of the first count ($n_i$) and the second count ($n_0$), as shown below.

$$\hat{P}(m_i) = \frac{n_i}{n_0 + n_i}$$

In some embodiments, the first count and/or the second count is zero for reasons discussed above.

The formula above is derived as follows:

$$\hat{P}(m_i) = P\left(m_i \,\middle|\, \bigcap_{j\neq i}\overline{m_j} \cap \bigcap_{k}\overline{w_k}\right) = P(\text{partition is positive in detection channel } i \mid \text{partition is negative in all other channels}) = \frac{n_i}{n_0 + n_i}$$

In some embodiments, at block 810, the system determines an estimated concentration $\hat{C}(m_i)$ of the mutant sequence(s) at the target region corresponding to the i-th probe pair in the sample based on the mutant probability $\hat{P}(m_i)$. For example, the system can calculate the estimated concentration based on Poisson's Law in accordance with the following formula:

$$\hat{C}(m_i) = -\frac{1}{v}\ln\left(1 - \hat{P}(m_i)\right) = -\frac{1}{v}\ln\left(1 - \frac{n_i}{n_0 + n_i}\right) = -\frac{1}{v}\ln\left(\frac{n_0}{n_0 + n_i}\right)$$

In some embodiments, the system determines a confidence interval and/or an uncertainty measure associated with the estimated concentration $\hat{C}(m_i)$ in the sample. For example, the confidence interval and uncertainty at 95% confidence level can be calculated as follows $$\hat{C}_{max}(m_i) = -\frac{1}{v}\ln\left(1 - \hat{P}(m_i) - 1.96\sqrt{\frac{\hat{P}(m_i)\left(1-\hat{P}(m_i)\right)}{n_0+n_i}}\right) = -\frac{1}{v}\ln\left(1 - \frac{n_i}{n_0+n_i} - 1.96\sqrt{\frac{n_0 * n_i}{(n_0+n_i)^3}}\right)$$

$$\hat{C}_{min}(m_i) = -\frac{1}{v}\ln\left(1 - \hat{P}(m_i) + 1.96\sqrt{\frac{\hat{P}(m_i)\left(1-\hat{P}(m_i)\right)}{n_0+n_i}}\right) = -\frac{1}{v}\ln\left(1 - \frac{n_i}{n_0+n_i} + 1.96\sqrt{\frac{n_0 * n_i}{(n_0+n_i)^3}}\right)$$

$$\hat{U}(m_i) = \frac{\hat{C}_{max}(m_i) - \hat{C}_{min}(m_i)}{2\hat{C}(m_i)}$$

At block 812, the system determines a wildtype probability ($\hat{P}(w_i)$) that a given partition contains a wildtype sequence at the target region corresponding to the i-th probe pair. In some embodiments, the wildtype probability is based on $\hat{P}(m_i)$. In some embodiments, the wildtype probability is calculated based on $\hat{P}(m_i)$ and $(m_{i+1})$.

In some embodiments, the system calculates $\hat{P}(w_i)$ in accordance with the following formula:

$$\hat{P}(w_i) = \left(\frac{n_{i,(i+1)}}{n_0 + n_i + n_{i+1} + n_{i,(i+1)}} - \hat{P}(m_i)\hat{P}(m_{i+1})\right)\frac{1}{1 - \hat{P}(m_i)\hat{P}(m_{i+1})}$$

The formula is derived as follows:

$$P\begin{pmatrix}\text{partition is positive in detection channel } i \text{ and positive in} \\ \text{detection channel } i+1 \mid \text{partition is negative in all} \\ \text{other detection channels}\end{pmatrix} = P\left(w_i \,\middle|\, \bigcap\nolimits_{j\neq i \text{ and } j\neq i+1} \overline{m_J} \cap_{k\neq i} \overline{w_k}\right) + P\left(m_i \cap m_{i+1} \cap \overline{w_i} \,\middle|\, \bigcap\nolimits_{j\neq i \text{ and } j\neq i+1} \overline{m_J} \cap_{k\neq i} \overline{w_k}\right) = \hat{P}(w_i) + \hat{P}(m_i)\hat{P}(m_{i+1})\left(1-\hat{P}(w_i)\right)$$

$$P\begin{pmatrix}\text{partition is positive in detection channel } i \text{ and positive in} \\ \text{detection channel } i+1 \mid \text{partition is negative in all} \\ \text{other detection channels}\end{pmatrix} = \frac{n_{i,(i+1)}}{n_0 + n_i + n_{i+1} + n_{i,(i+1)}}$$

Thus, by equating the two above-referenced formulas, the calculation of $\hat{P}(w_1)$ can be derived accordingly:

$$\hat{P}(w_i) = 1 + \frac{\frac{n_{i,(i+1)}}{n_0 + n_i + n_{i+1} + n_{i,(i+1)}} - 1}{1 - \hat{P}(m_i)\hat{P}(m_{i+1})}$$

And subsequently:

$$\hat{P}(w_i) = 1 + \frac{\frac{n_{i,(i+1)}}{n_0 + n_i + n_{i+1} + n_{i,(i+1)}} - 1}{1 - \frac{n_i n_{i+1}}{(n_0+n_i)(n_0+n_{i+1})}} = \frac{n_{i,(i+1)} - \frac{n_i * n_{i+1}}{n_0}}{n_0 + n_i + n_{i+1} + n_{i,(i+1)}}$$

In some embodiments, at block 820, the system determines an estimated concentration $\hat{C}(w_i)$ of the wildtype sequences at the target region corresponding to the i-th probe pair in the sample based on the wildtype probability $\hat{P}(w_i)$. For example, the system can calculate the estimated concentration based on Poisson's Law in accordance with the following formula:

$$\hat{C}(w_i) = -\frac{1}{v}\ln\left(1 - \hat{P}(w_i)\right) = -\frac{1}{v}\ln\left(1 - \frac{n_{i,(i+1)} - \frac{n_i * n_{i+1}}{n_0}}{n_0 + n_i + n_{i+1} + n_{i,(i+1)}}\right)$$

In some embodiments, if the wildtype concentrations are expected to be the same, a more robust wildtype concentration estimate can be obtained by averaging the R estimated values.

In some embodiments, the confidence interval and the uncertainty measure at 95% confidence level can be derived from the variance of $\hat{P}(w_i)$, noted as Var ($\hat{P}(w_i)$) as follows:

$$\hat{C}_{max}(w_i) = -\frac{1}{v}\ln\left(1 - \hat{P}(w_i) - 1.96\sqrt{\text{Var}\left(\hat{P}(w_i)\right)}\right);$$

$$\hat{C}_{min}(w_i) = -\frac{1}{v}\ln\left(1 - \hat{P}(m_i) + 1.96\sqrt{\text{Var}\left(\hat{P}(w_i)\right)}\right);$$

$$\hat{U}(w_i) = \frac{\hat{c}_{max}(w_i) - \hat{c}_{min}(w_i)}{2\hat{c}(w_i)};$$

where the variance of $\hat{P}(w_i)$ can itself be derived from $$X = \frac{n_{i,(i+1)}}{n_0 + n_i + n_{i+1} + n_{i,(i+1)}}$$

from $$A = \hat{P}(m_i)\hat{P}(m_{i+1}) = \frac{n_i n_{i+1}}{(n_0+n_i)(n_0+n_{i+1})}$$

and from the variance of X and from the variance of A. Indeed:

$$\hat{P}(w_i) = 1 + \frac{X-1}{1-A}$$

$$\text{Var}\left(\hat{P}(w_i)\right) = \text{Var}\left(1 + \frac{X-1}{1-A}\right) = \text{Var}\left(\frac{X-1}{1-A}\right)$$

$$\text{Var}(X) = \frac{X(1-X)}{n_o + n_i + n_{i+1} + n_{i,(i+1)}}$$

$$\text{Var}(X) = \frac{n_{i,(i+1)}(n_0 + n_i + n_{i+1})}{(n_0 + n_i + n_{i+1} + n_{i,(i+1)})^2}$$

$$\text{Var}(A) = \text{Var}\left(\hat{P}(m_i)\hat{P}(m_{i+1})\right)$$

As $\hat{P}(m_i)$ and $\hat{P}(m_{i+1})$ are independent, we have:

$$\text{Var}\left(\hat{P}(m_i)\hat{P}(m_{i+1})\right) = \text{Var}\left(\hat{P}(m_i)\right)\text{Var}\left(\hat{P}(m_{i+1})\right) + \hat{P}(m_i)^2\text{Var}\left(\hat{P}(m_{i+1})\right) + \hat{P}(m_{i+1})^2\text{Var}\left(\hat{P}(m_i)\right)$$

$$\text{Var}(A) = \frac{n_0 n_i n_{i+1}(n_0 + n_i + n_{i+1})}{(n_0+n_i)^2(n_0+n_{i+1})^2}$$

Knowing that:

$$\mathrm{Var}\left(\frac{R}{S}\right) \approx \frac{R^2}{S^2}\left(\frac{1}{N_R}\frac{\mathrm{Var}(R)}{R^2} + \frac{1}{N_S}\frac{\mathrm{Var}(S)}{S^2} - 2\frac{1}{\sqrt{N_R N_S}}\frac{Cov(R, S)}{R\,S}\right)$$

where $N_R$ is the sample size of R and $N_S$ is the sample size of S.

The sample size of X is $N_X=n_0+n_i+n_{i+1}+n_{i,(+1)}$.

The sample size of A is $N_A=n_0+n_i+n_{i+1}$.

As the event of A are included in the event of X, we have: Cov(X, A)=Var(A) We deduce:

$$\mathrm{Var}(\hat{P}(w_i)) \approx \frac{(X-1)^2}{(1-A)^2}\left(\frac{1}{N_X}\frac{\mathrm{Var}(X)}{(X-1)^2} + \frac{1}{N_A}\frac{\mathrm{Var}(A)}{(1-A)^2} + 2\frac{1}{\sqrt{N_X N_A}}\frac{\mathrm{Var}(A)}{(X-1)(1-A)}\right)$$

$$\mathrm{Var}(\hat{P}(w_i)) \approx \frac{\left(\frac{n_{i,(i+1)}}{n_0+n_i+n_{i+1}+n_{i,(i+1)}}-1\right)^2}{\left(1-\frac{n_i\,n_{i+1}}{(n_0+n_i)(n_0+n_{i+1})}\right)^2}\left(\frac{\frac{n_{i,(i+1)}(n_0+n_i+n_{i+1})}{(n_0+n_i+n_{i+1}+n_{i,(i+1)})^3}}{\left(\frac{n_{i,(i+1)}}{n_0+n_i+n_{i+1}+n_{i,(i+1)}}-1\right)^2} + \right.$$

$$\frac{\frac{n_0 n_i n_{i+1}(n_0+n_i+n_{i+1})}{(n_0+n_i)^2(n_0+n_{i+1})^2}}{1-\frac{n_i\,n_{i+1}}{(n_0+n_i)(n_0+n_{i+1})}}\left(\frac{1}{(n_0+n_i+n_{i+1})\left(1-\frac{n_i\,n_{i+1}}{(n_0+n_i)(n_0+n_{i+1})}\right)}\right) +$$

$$\frac{\frac{n_0 n_i n_{i+1}(n_0+n_i+n_{i+1})}{(n_0+n_i)^2(n_0+n_{i+1})^2}}{1-\frac{n_i\,n_{i+1}}{(n_0+n_i)(n_0+n_{i+1})}}\left(\frac{1}{(n_0+n_i+n_{i+1})\left(1-\frac{n_i\,n_{i+1}}{(n_0+n_i)(n_0+n_{i+1})}\right)} + \right.$$

$$\left.\left.\frac{2}{\sqrt{(n_0+n_i+n_{i+1}+n_{i,(i+1)})(n_0+n_i+n_{i+1})}\left(\frac{n_{i,(i+1)}}{n_0+n_i+n_{i+1}+n_{i,(i+1)}}-1\right)}\right)\right)$$

With this biomolecular design, the higher the wildtype concentration, the higher the uncertainty of the mutant concentration.

In some embodiments, R is an integer between 2 and 6. FIG. 7 and the corresponding descriptions are directed to the embodiment in which R equals 3.

The embodiments described in this section are applicable to dPCR methods using R sets of probes comprising dual-labeled AS probes (e.g., each probe set contains a reference probe and an AS probe with two detectable labels, or each probe set contains a reference probe, a first AS probe and a second AS probe). An exemplary scheme for a dual-labeled AS assay capable of detecting 2R number of genetic species using R fluorophores is shown in TABLE 7 below.

TABLE 7

| Sequences | Detection Channel |
|---|---|
| allelic sequence (w1) at target region 1 and reference sequence (m1) at reference region 1 | $X_1$ fluorophore (detection channel 1) on reference probe 1 and first AS probe 1<br>$X_2$ fluorophore (detection channel 2) on second AS probe 1 |
| allelic sequence (w2) at target region 2 and reference sequence (m2) at reference region 2 | $X_2$ fluorophore (detection channel 2) on reference probe 2 and first AS probe 2<br>$X_3$ fluorophore (detection channel 3) on second AS probe 2 |
| . . . | . . . |

TABLE 7-continued

| Sequences | Detection Channel |
|---|---|
| allelic sequence ($w_i$) at target region i and reference sequence ($m_i$) at reference region i | $X_i$ fluorophore (detection channel i) on reference probe i and first AS probe i<br>$X_{i+1}$ fluorophore (detection channel i + 1) on second AS probe i |
| allelic sequence ($w_R$) at target region R and reference sequence ($m_R$) at reference region R | $X_R$ fluorophore (detection channel R) on reference probe R and first AS probe R<br>$X_1$ fluorophore (detection channel 1) on second AS probe R |

Embodiment Employing (R−1) Number of Drop-Off Probe Triplets

Figure 9:
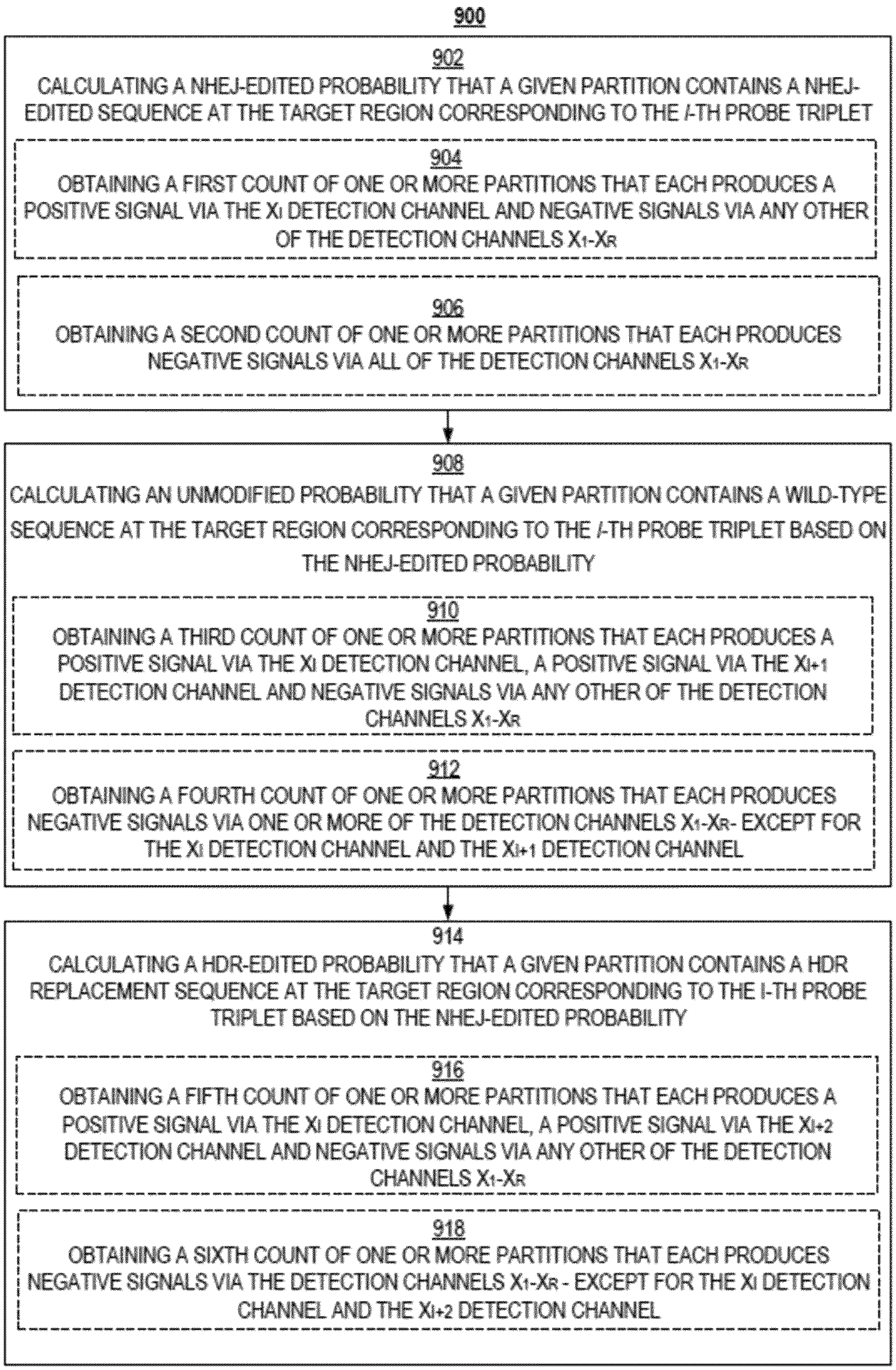
FIG. 9 shows a flow chart for data analysis of an exemplary method for detecting unmodified, NHEJ-edited and HDR-edited sequences at (R−1) number of target regions employing (R−1) number of probe triplets.

FIG. 9 illustrates an exemplary process 900 for quantification of unmodified, homology directed repair (HDR)-edited, and/or non-homologous end joining (NHEJ)-edited sequences at a plurality of target regions in nucleic acid molecules from a sample of cells, according to some embodiments. The cells have been contacted with a site-specific genome-editing reagent and HDR template nucleic acids comprising HDR replacement sequences, and the site-specific genome-editing reagent is configured to cleave target sites in the plurality of target regions.

Process 900 can be performed, for example, using one or more electronic devices implementing a software platform, by one or more human users, or any combination thereof. In some examples, process 900 can be performed using a client-server system, and the blocks of process 900 can be divided up in any manner between the server and a client device. In other examples, the blocks of process 900 can be divided up between the server and multiple client devices. Thus, while portions of process 900 are described herein as being performed by particular devices of a client-server system, it will be appreciated that process 900 are not so limited. In other examples, process 900 can be performed using only a client device or only multiple client devices.

In process 900, some blocks are, optionally, combined, the order of some blocks is, optionally, changed, and some blocks are, optionally, omitted. In some examples, additional steps may be performed in combination with the process 900. Accordingly, the operations as illustrated (and described in greater detail below) are exemplary by nature and, as such, should not be viewed as limiting.

In some embodiments, one or more variables of process 900 can be obtained via a drop-off digital PCR process in which a (R−1) number of probe triplets corresponding to the (R−1) number of target regions are employed. Each probe triplet of the (R−1) number of probe triplets comprises a HDR probe comprising a HDR label and an oligonucleotide HDR sequence complementary to a HDR replacement sequence inserted at a target region corresponding to the respective probe triplet, an NHEJ drop-off probe comprising an NHEJ drop-off label and an oligonucleotide drop-off sequence complementary to a wildtype sequence of the target region corresponding to the respective probe triplet, and wherein the drop-off sequence does not hybridize to NHEJ-edited mutant sequence(s) at the target region corresponding to the respective probe triplet, a reference probe comprising a reference label and an oligonucleotide reference sequence complementary to a wildtype sequence at an adjacent reference region upstream or downstream to the target region corresponding to the respective probe triplet.

In some embodiments, a HDR label, an NHEJ drop-off label, and a reference label of each probe triplet of the plurality of probe triplets are detectable via different detection channels. In an exemplary scheme shown in TABLE 8, each probe triplet of the plurality of probe triplets has a HDR label, an NHEJ drop-off label, and a reference label of each probe triplet of the plurality of probe triplets are detectable via different detection channels (i.e., $X_i$ v. $X_{i+1}$ v. $X_{i+2}$). In some embodiments, the reference labels of the plurality of probe triplets are detectable via different detection channels with respect to each other, the HDR labels of the plurality of probe triplets are detectable via different detection channels with respect to each other, and the NHEJ drop-off labels of the plurality of probe triplets are detectable via different detection channels with respect to each other. In the exemplary scheme shown in TABLE 8, the reference labels of the (R−1) number of probe triplets are detectable via $X_1$-$X_{R-2}$ and $X_R$ respectively. Further, the NHEJ drop-off labels of the (R−1) number of probe triplets are detectable via $X_2$-$X_{R-1}$ and $X_{R-1}$ respectively. The HDR labels of the (R−1) number of probe triplets are detectable via $X_1$, $X_3$-$X_R$ respectively.

TABLE 8

| Target region | Detection Channel |
|---|---|
| 1 | $X_1$ fluorophore (detection channel 1): unmodified sequence $m_i$, HDR-edited sequence $w_1$ and NHEJ-edited sequence(s) $r_i$ at the first target region |
| | $X_2$ fluorophore (detection channel 2): unmodified sequence $w_1$ at the first target region |
| | $X_3$ fluorophore (detection channel 3): HDR-edited sequence $w_1$ at the first target region |
| i (for i = 2 . . . (R − 2)) | $X_i$ fluorophore (detection channel i): unmodified sequence $m_i$, HDR-edited sequence $w_i$, and NHEJ-edited sequence(s) $r_i$ at the i-th target region |
| | $X_{i+1}$ fluorophore (detection channel i + 1): unmodified sequence $m_i$ at the i-th reference region |
| | $X_{i+2}$ fluorophore (detection channel i + 2): HDR-edited sequence $w_i$ at the i-th reference region |
| R − 1 | $X_R$ fluorophore (detection channel R): unmodified sequence $m_{R-1}$ HDR-edited sequence $w_{R-1}$, NHEJ-edited sequence(s) $r_{R-1}$ at the R − 1 target region |
| | $X_{R-1}$ fluorophore (detection channel R − 1): unmodified sequence $m_{R-1}$ at the R − 1 target region |
| | $X_1$ fluorophore (detection channel 1): of HDR-edited sequence $w_{R-1}$ at the R − 1 target region |

The exemplary scheme in TABLE 8 employs permutation of labels in the probe triplets. FIG. 6B shows exemplary permutation of four labels, six labels, or ten labels among three sets of probe triplets, five sets of probe triplets, or nine sets of probe triplets respectively. For example, with three probe triplets, the first probe triplet includes a first reference probe labeled with fluorophore 1, a first NHEJ drop-off probe labeled with fluorophore 2, and a first HDR probe labeled with fluorophore 3; a second probe triplet includes a second reference probe labeled with fluorophore 2, a second NHEJ drop-off probe labeled with fluorophore 3, and a second HDR probe labeled with fluorophore 4; a third probe triplet includes a third reference probe labeled with fluorophore 4, a third NHEJ drop-off probe labeled with fluorophore 3, and a third HDR probe labeled with fluorophore 1. The number of detection channels (i.e., R) is one more than the number of probe triplets (i.e., R−1).

It should be appreciated, however, that the scheme TABLE 8 is merely exemplary and permutation as shown in FIG. 6B is not required for performing process 800. In some embodiments, the total number of detection channels can be the same or fewer than three times the number of probe triplets (i.e., 3 (R−1)).

In a multiplex drop-off digital PCR process, a sample comprising nucleic acid molecules is distributed among a plurality of partitions, and substantially all partitions each comprises the (R−1) number of probe triplets. Hybridization of reference probes of the (R−1) number of probe triplets to nucleic acid molecules or amplicons thereof comprising wildtype sequences at the reference regions in each partition can be detected via each of the detection channels $X_1$-$X_{R-2}$ and $X_R$. Hybridization of NHEJ drop-off probes of the (R−1) number of probe triplets to nucleic acid molecules or amplicons thereof comprising the wildtype sequences at the target regions in each partition can be detected via each of the detection channels $X_2$-$X_{R-1}$. Further, hybridization of HDR probes of the (R−1) number of probe triplets to nucleic acid molecules or amplicons thereof comprising HDR-edited sequences (i.e., HDR replacement sequences) at the target regions in each partition can be detected via each of the detection channels $X_1$, and $X_3$-$X_R$. In an alternative setup, hybridization of HDR probes of the (R−1) number of probe triplets to nucleic acid molecules or amplicons thereof comprising HDR-edited sequences (i.e., HDR replacement sequences) at the target regions in each partition can be detected via each of the detection channels $X_2$-$X_{R-1}$. Further, hybridization of NHEJ drop-off probes of the (R−1) number of probe triplets to nucleic acid molecules or amplicons thereof comprising wildtype sequences at the target regions in each partition can be detected via each of the detection channels $X_1$, and $X_3$-$X_R$. Process 800 can then be performed to provide quantification of unmodified, NHEJ-edited and/or HDR-edited sequences at the (R−1) target regions in the sample.

Process 900 is based on the assumption of independence of the partition encapsulation of all types of sequences at the target regions 1 to R−1. Indeed, despite the fact that in the exemplary scheme in TABLE 8, due to the biomolecular design, there is no independence of the partition encapsulation of fluorophores $X_1$ to $X_R$, there is nonetheless independence of the partition encapsulation of nucleic acid molecules containing target regions 1 to R−1.

Process 900 is described below in accordance to the following notations:

TABLE 9

| Variable | Definition |
|---|---|
| P(X) | probability of the event X |
| $\overline{X}$ | negation of event X |
| $m_i$ | the event "a partition contains an unmodified sequence $m_i$ at target region i", where i = 1 . . . R − 1 |
| $r_i$ | the event "a partition contains NHEJ-edited sequence(s) $r_i$ at target region i", where i = 1 . . . R − 1 |
| $w_i$ | the event "a partition contains a HDR-edited sequence $w_i$ at target region i", where i = 1 . . . R − 1 |
| N | total number of partitions in the digital PCR experiment |
| v | volume of a partition (e.g., in uL), assumed to be constant |
| $C(m_i)$ | real concentration of unmodified sequence at target region number i in the digital PCR experiment (e.g., in cp/μL), where i = 1 . . . R − 1 |
| $C(r_i)$ | real concentration of NHEJ-edited sequence(s) at target region number i in the digital PCR experiment (e.g., in cp/μL), where i = 1 . . . R − 1 |
| $C(w_i)$ | real concentration of HDR-edited sequence at target region number i in the digital PCR experiment (e.g., in cp/μL), where i = 1 . . . R − 1 |
| $P(m_i)$ | probability of $m_i$, where i = 1 . . . R − 1 |
| $P(r_i)$ | probability of $r_i$, where i = 1 . . . R − 1 |
| $P(w_i)$ | probability of $w_i$, where i = 1 . . . R − 1 |
| $n_0$ | number of observed partitions in the digital PCR experiment that are negative for all detection channels 1 to R (they are the full negative partitions) |
| $n_i$ | number of observed partitions in the digital PCR experiment that are positive for detection channel i and negative for all the other detection channels, where i = 1 . . . R |
| $n_{i,j}$ | number of observed partitions in the digital PCR experiment that are positive for detection channel i, positive for detection channel j, and negative for all the other detection channels, where i = 1 . . . R and j = 1 . . . R |
| $\hat{P}(m_i)$ | estimated probability of $m_i$, where i = 1 . . . R − 1 |
| $\hat{P}(r_i)$ | estimated probability of $r_i$, where i = 1 . . . R − 1 |
| $\hat{P}(w_i)$ | estimated probability of $w_i$, where i = 1 . . . R − 1 |
| $\hat{C}(m_i)$ | estimated concentration of unmodified sequence at target region number i in the digital PCR experiment (e.g., in cp/μL), where i = 1 . . . R − 1 |
| $\hat{C}(r_i)$ | estimated concentration of NHEJ-edited sequence(s) at target region number i in the digital PCR experiment (e.g., in cp/μL), where i = 1 . . . R − 1 |
| $\hat{C}(w_i)$ | estimated concentration of HDR-edited sequence at target region number i in the digital PCR experiment (e.g., in cp/μL), where i = 1 . . . R − 1 |
| $\hat{C}_{min}(r_i)$, $\hat{C}_{max}(r_i)$, $\hat{U}(r_i)$ | minimum value, maximum value and uncertainty at 95% confidence level for the estimated concentration of NHEJ-edited sequence(s) at target region number i in the digital PCR experiment (e.g., in cp/μL), where i = 1 . . . R − 1 |

Process 900 depicts an exemplary process for calculating an NHEJ-edited probability ($\hat{P}(r_i)$), an unmodified probability ($\hat{P}(m_i)$), and an HDR-edited probability ($\hat{P}(w_i)$) corresponding to the i-th probe triplet if 1≤i≤R−2, in accordance with some embodiments.

At block 902, a system (e.g., one or more electronic devices) calculates an NHEJ-edited probability (($r_i$)) that a given partition contains NHEJ-edited sequence(s) at the target region corresponding to the i-th probe triplet.

In some embodiments, block 902 includes blocks block 904 and block 906. At block 904, the system obtains a first count ($n_i$) of one or more partitions that each produces a positive signal via the $X_i$ detection channel and negative signals via any other of the detection channels $X_1$-$X_R$. At block 906, the system obtains a second count ($n_0$) of one or more partitions that each produces negative signals via all of the detection channels $X_1$-$X_R$. In some embodiments, the first count and/or the second count is zero.

In some embodiments, the system calculates ($\hat{P}(r_i)$) based on a ratio between the first count and a sum of the first count and the second count, as shown below:

$$\hat{P}(r_i) = \frac{n_i}{n_0 + n_i}$$

The formula above is derived as follows:

$$\hat{P}(r_i) = P\left(r_i \middle| \bigcap_{j \neq i} \overline{r_i} \bigcap_k \overline{m_k} \bigcap_k \overline{w_k}\right) =$$

$$P(\text{partition is positive in detection channel } i \mid \text{partition is negative in all other channels}) = \frac{n_i}{n_0 + n_i}$$

In some embodiments, the system determines an estimated concentration $\hat{C}(r_i)$ of NHEJ-edited sequence(s) at target region number i in the sample based on the NHEJ-edited probability $\hat{P}(r_i)$. For example, the system can calculate the estimated concentration based on Poisson's Law in accordance with the following formula:

$$\hat{C}(r_i) = -\frac{1}{v}\ln\left(1 - \hat{P}(r_i)\right) = -\frac{1}{v}\ln\left(\frac{n_0}{n_0 + n_i}\right)$$

In some embodiments, the system determines a confidence interval and/or an uncertainty measure associated with the estimated concentration $\hat{C}(r_i)$ in the sample. For example, the confidence interval and uncertainty at 95% confidence level can be calculated as follows $$\hat{C}_{max}(r_i) = -\frac{1}{v}\ln\left(1 - \hat{P}(r_i) - 1.96\sqrt{\frac{\hat{P}(r_i)\left(1 - \hat{P}(r_i)\right)}{n_0 + n_i}}\right) = -\frac{1}{v}\ln\left(1 - \frac{n_i}{n_0 + n_i} - 1.96\sqrt{\frac{n_0 * n_i}{(n_0 + n_i)^3}}\right)$$

$$\hat{C}_{min}(r_i) = -\frac{1}{v}\ln\left(1 - \hat{P}(r_i) + 1.96\sqrt{\frac{\hat{P}(\tau_i)\left(1 - \hat{P}(r_i)\right)}{n_0 + n_i}}\right) = -\frac{1}{v}\ln\left(1 - \frac{n_i}{n_0 + n_i} + 1.96\sqrt{\frac{n_0 * n_i}{(n_0 + n_i)^3}}\right)$$

$$\hat{U}(r_i) = \frac{\hat{C}_{max}(r_i) - \hat{C}_{min}(r_i)}{2\hat{C}(r_i)}$$

At block 908, the system calculates an unmodified probability ($\hat{P}$(m;)) that a given partition contains a wildtype sequence at the target region corresponding to the i-th probe triplet.

In some embodiments, block 908 includes blocks 910 and 912. At block 910, the system obtains a third count of one or more partitions that each produces a positive signal via the $X_i$ detection channel, a positive signal via the $X_{i+1}$ detection channel and negative signals via any other of the detection channels $X_1$-$X_R$. At block 912, the system obtains a fourth count of one or more partitions that each produces negative signals via one or more of the detection channels $X_1$-$X_R$ except for the $X_i$ detection channel and the $X_{i+1}$ detection channel. In some embodiments, the fourth count is calculated as $n_0+n_i+n_{i+1}+n_{i,(i+1)}$. In some embodiments, the first count, the second count, the third count and/or the fourth count is zero.

In some embodiments, the system calculates ($\hat{P}(m_i)$) in accordance with the following formula for i<R−1:

$$\hat{P}(m_i) = \left(\frac{n_{i,(i+1)}}{n_0 + n_i + n_{i+1} + n_{i,(i+1)}} - \hat{P}(r_i)\hat{P}(r_{i+1})\right)\frac{1}{1 - \hat{P}(r_i)\hat{P}(r_{i+1})}$$

The formula above is derived as follows:

$$P(\text{partition is positive in detection channel } i \text{ and positive in detection channel } i+1 \mid \text{partition is negative in all other detection channels})$$

$$= P\left(m_i \middle| \bigcap\nolimits_{j \neq i \text{ and } j \neq i+1} \overline{r_j} \bigcap\nolimits_{k \neq i} \overline{m_k} \bigcap\nolimits_l \overline{w_l}\right) + P\left(r_i \cap r_{i+1} \cap \overline{m_i} \middle| \bigcap\nolimits_{j \neq i \text{ and } j \neq i+1} \overline{r_j} \bigcap\nolimits_{k \neq i} \overline{m_k} \bigcap\nolimits_l \overline{w_l}\right)$$

$$= \hat{P}(m_i) + \hat{P}(r_i)\hat{P}(r_{i+1})\left(1 - \hat{P}(m_i)\right)$$

$$P(\text{partition is positive in detection channel } i \text{ and positive in detection channel } i+1 \mid \text{partition is negative in all other detection channels})$$

$$= \frac{n_{i,(i+1)}}{n_0 + n_i + n_{i+1} n_{i,(i+1)}}$$

By equating the two formulas above, the formula for ($\hat{P}(m_i)$) can be derived accordingly.

$$\hat{P}(m_i) = \frac{n_{i,(i+1)} - \frac{n_i * n_{i+1}}{n_0}}{n_0 + n_i + n_{i+1} + n_{i,(i+1)}}$$

$\hat{P}(m_i)$ is maximized (or minimized) when $\hat{P}(r_i)$ and $\hat{P}(r_{i+1})$ are minimized (or maximized).

In some embodiments, the system determines an estimated concentration $\hat{C}$(m;) of unmodified sequence at target region number i in the sample based on the unmodified probability $\hat{P}(m_i)$. For example, the system can calculate the estimated concentration based on Poisson's Law in accordance with the following formula:

$$\hat{C}(m_i) = -\frac{1}{v}\ln\left(1 - \hat{P}(m_i)\right) = -\frac{1}{v}\ln\left(1 - \frac{n_{i,(i+1)} - \frac{n_i * n_{i+1}}{n_0}}{n_0 + n_i + n_{i+1} + n_{i,(i+1)}}\right)$$

At block 914, the system calculates a HDR-edited probability ($\hat{P}(w_i)$) that a given partition contains a HDR-edited sequence at the target region corresponding to the i-th probe triplet. In some embodiments, block 914 includes blocks 916 and 918.

At block 916, the system obtains a fifth count of one or more partitions that each produces a positive signal via the $X_i$ detection channel, a positive signal via the $X_{i+2}$ detection channel and negative signals via any other of the detection channels $X_1$-$X_R$. At block 918, the system obtains a sixth count of one or more partitions that each produces negative signals via the detection channels $X_1$-$X_R$ except for the $X_i$ detection channel and the $X_{i+2}$ detection channel. In some embodiments, the sixth count is calculated as $n_0+n_i+n_{i+2}+n_{i,(i+2)}$. In some embodiments, the fifth count, and/or the sixth count is zero.

In some embodiments, ($\hat{P}$(w;)) is calculated in accordance with the following formula, for i<R−1:

$$\hat{P}(w_i) = \left(\frac{n_{i,(i+2)}}{n_0 + n_i + n_{i+2} + n_{i,(i+2)}} - \hat{P}(r_i)\hat{P}(r_{i+2})\right)\frac{1}{1 - \hat{P}(r_i)\hat{P}(r_{i+2})}$$

The formula above is derived as follows:

$$P(\text{partition is positive in detection channel } i \text{ and positive in detection channel } i+2 \mid \text{partition is negative in all other detection channels})$$

$$= P\left(m_i \middle| \bigcap_{j\neq i \text{ and } j\neq i+2} \overline{r_j} \cap_{k\neq i} \overline{w_k} \cap_l \overline{m_l}\right) + P\left(r_i \cap r_{i+2} \cap \overline{w_i} \middle| \bigcap_{j\neq i \text{ and } j\neq i+2} \overline{r_j} \cap_{k\neq i} \overline{w_k} \cap_l \overline{m_l}\right) = \hat{P}(w_i) + \hat{P}(r_i)\hat{P}(r_{i+2})(1-\hat{P}(w_i))$$

Further:

$$P(\text{partition is positive in detection channel } i \text{ and positive in detection channel } i+2 \mid \text{partition is negative in all other detection channels}) = \frac{n_{i,(i+2)}}{n_0 + n_i + n_{i+2} + n_{i,(i+2)}}$$

In some embodiments, the system determines an estimated concentration $\hat{C}(w_i)$ of HDR-edited sequence at target region number i in the sample based on the HDR-edited probability $\hat{P}(w_i)$. For example, the system can calculate the estimated concentration based on Poisson's Law in accordance with the following formula:

$$\hat{C}(w_i) = -\frac{1}{v}\ln(1-\hat{P}(w_i))$$

As described above, process 900 depicts an exemplary process for calculating an NHEJ-edited probability ($\hat{P}(r_i)$), an unmodified probability ($\hat{P}(m_i)$), and an HDR-edited probability $((w_i))$ corresponding to the i-th probe triplet if $1 \leq i < R-2$, in accordance with some embodiments.

If $i=R-1$, the following formulas are used. The formulas are derived in a similar manner as those described with reference to FIG. 9.

$$\hat{P}(r_{R-1}) = P\left(r_{R-1} \middle| \bigcap_{j\neq R-1} \overline{r_i} \bigcap_k \overline{m_k} \bigcap_k \overline{w_k}\right) = P(\text{partition is positive in detection channel } R \mid \text{paetition is negative in all other channels}) = \frac{n_R}{n_0 + n_R}$$

$$\hat{C}(r_{R-1}) = -\frac{1}{v}\ln(1-\hat{P}(r_{R-1}))$$

$$\hat{C}_{max}(r_{R-1}) = -\frac{1}{v}\ln\left(1-\hat{P}(r_{R-1}) - 1.96\sqrt{\frac{\hat{P}(r_{R-1})(1-\hat{P}(r_{R-1}))}{n_0+n_R}}\right)$$

$$\hat{C}_{min}(r_{R-1}) = -\frac{1}{v}\ln\left(1-\hat{P}(r_{R-1}) + 1.96\sqrt{\frac{\hat{P}(r_{R-1})(1-\hat{P}r_{R-1})}{n_0+n_R}}\right)$$

$$\hat{U}(r_{R-1}) = \frac{\hat{C}_{max}(r_{R-1}) - \hat{C}_{min}(r_{R-1})}{2\hat{C}(r_{R-1})}$$

$$P\begin{pmatrix}\text{partition is positive in detection channel } R-1 \text{ and positive in detection channel} \\ R \mid \text{partition is negative in all other detection channel}\end{pmatrix} =$$

$$P(m_{R-1} \mid \cap_{j\neq R-1 \text{ and } j\neq R}\overline{r_j}\cap_{k\neq R-1}\overline{m_k}\cap_l\overline{w_l}) + P(r_{R-1}\cap r_R\cap\overline{m_{R-1}} \mid \cap_{j\neq R-1 \text{ and } j\neq R}\overline{r_j}\cap_{k\neq R-1}\overline{m_k}\cap_l\overline{w_l}) = \hat{P}(m_{R-1})$$

Indeed, by definition "$r_{R-1}$" is an impossible event, so $\hat{P}(r_{R-1})=0$ Thus:

$$\hat{P}(m_{R-1}) = \frac{n_{R,(R-1)}}{n_0 + n_R + n_{R-1} + n_{R,(R-1)}}$$

$$\hat{C}(m_{R-1}) = -\frac{1}{v}\ln(1-\hat{P}(m_{R-1}))$$

$$P\begin{pmatrix}\text{partition is positive in detection channel } R \\ \text{and positive in detection channel} \\ 1 \mid \text{partition is negative in all other detection channel}\end{pmatrix} =$$

$$P(w_{R-1} \mid \cap_{j\neq R-1 \text{ and } j\neq 1}\overline{r_j}\cap_{k\neq R-1}\overline{w_k}\cap_l\overline{m_l}) + P(r_{R-1}\cap r_1\cap\overline{w_{R-1}} \mid \cap_{j\neq R-1 \text{ and } j\neq 1}\overline{r_j}\cap_{k\neq R-1}\overline{w_k}\cap_l\overline{m_l}) = \hat{P}(w_{R-1}) + \hat{P}(r_R)\hat{P}(r_1)(1-\hat{P}(w_{R-1}))$$

Thus:

$$\hat{P}(w_{R-1}) = \left(\frac{n_{R,1}}{n_0 + n_R + n_1 + n_{R,1}} - \hat{P}(r_{R-1})\hat{P}(r_1)\right)\frac{1}{1-\hat{P}(r_{R-1})\hat{P}(r_1)}$$

$$\hat{C}(w_{R-1}) = -\frac{1}{v}\ln(1-\hat{P}(w_{R-1}))$$

Although described in the context of detection of CRISPR-Cas genome-edited sequences, the above analysis is generally applicable to methods for detection of genome editing using any tailored to any site-specific genome-editing reagent that edits genomic DNA via NHEJ or HDR-mediated repair of cleaved genomic DNA. Furthermore, the above embodiment of detection of site-specific genome-editing products is also generally applicable to any of the methods described herein for detection of wildtype, mutant and/or allelic sequences at (R−1) number of target regions using (R−1) number of probe triplets, in which the wildtype sequences correspond to the unmodified sequences in the CRISPR embodiment, and the mutant sequences correspond to the NHEJ-edited sequences in the CRISPR embodiment, and the allelic sequences correspond to the HDR-edited sequences in the CRISPR embodiment.

Multiplex dPCR Methods with Dual-Labelled Allele-Specific Probes

The present application further provides multiplex dPCR methods that do not use drop-off probes, but use the same concept of circular permutation of labels in the probe sets in order to allow high-order multiplexing of dPCR assays. In some embodiments, the method uses a plurality of probe sets, wherein each probe set comprises a reference probe and a dual-labelled allele-specific (AS) probe or AS probe pair, wherein the dual-labelled AS probe or AS probe pair has a first detectable label that can be detected via the same detection channel as the detectable label of the reference probe, and a second detectable label that can be detected via a different detection channel as the detectable label of the reference probe. Each probe set and its associated primers allow quantification of a target species (i.e., allelic sequence), such as a mutation (e.g., SNP, insertion, deletion, etc.) or a copy number variation (CNV), with respect to a reference species, thereby allowing detection and quantification of the target species in a sample.

In some embodiments, there is provided a method for quantification of wildtype and/or allelic sequences (e.g., rare allele or CNV) at a plurality of target regions in a sample comprising nucleic acid molecules, wherein the nucleic acid molecules are distributed among a plurality of partitions of the sample, wherein substantially all partitions (e.g., all partitions) each comprises a plurality of probe sets corresponding to the plurality of target regions, wherein each probe set of the plurality of probe sets comprises:

- a first allele-specific (AS) probe comprising a first AS label and an oligonucleotide AS sequence complementary to an allelic sequence or a first portion thereof at a target region corresponding to the respective probe set;
- a second AS probe comprising a second AS label and an oligonucleotide AS sequence complementary to the allelic sequence, a second portion thereof, or a complementary sequence thereof at the target region corresponding to the respective probe set;
- a reference probe comprising a reference label and an oligonucleotide sequence complementary to a reference sequence at a reference region corresponding to the respective probe set;
- wherein the reference label and the first AS label of each probe set of the plurality of probe sets are detectable via the same detection channel;
- wherein the reference label and the second AS label of each probe set of the plurality of probe sets are detectable via different detection channels;
- wherein reference labels of the plurality of probe sets are detectable via different detection channels with respect to each other;
- wherein the second AS labels of the plurality of probe sets are detectable via different detection channels with respect to each other;
- wherein at least one reference label of the plurality of probe sets and at least one second AS label of the plurality of probe sets are detectable via the same detection channel;

wherein the method comprises: detecting hybridization of reference probes of the plurality of probe sets to nucleic acid molecules comprising reference sequences at the reference regions in the plurality of partitions; and detecting hybridization of the first AS probes and the second AS probes of the plurality of probe sets to nucleic acid molecules or amplicons thereof comprising allelic sequences or portions thereof at the target regions in the plurality of partitions; thereby providing quantification of wildtype and/or allelic sequences at the plurality of target regions in the sample. In some embodiments, the reference region corresponding to each probe set is adjacent to (e.g., upstream or downstream) the target region. In some embodiments, the reference region overlaps with the target region. In some embodiments, the reference region is identical to the target region. In some embodiments, detection of a signal from a reference label and no signal from a second AS probe in a probe set indicates a wildtype sequence at the target region corresponding to the probe set, and detection of a signal from a reference label and a signal from a second AS label in a probe set indicates an allelic sequence at the target region corresponding to the probe set. In some embodiments, the reference label and the first AS label of each probe set are identical to each other. In some embodiments, the set of reference labels of the plurality of probe sets and the set of second AS labels of the plurality of probe sets have overlapping labels. In some embodiments, the set of reference labels of the plurality of probe sets and the set of second AS labels of the plurality of probe sets are circular permutations with respect to each other.

In some embodiments, there is provided a method for quantification of wildtype and/or allelic sequences (e.g., rare allele or CNV) at R number of target regions in a sample comprising nucleic acid molecules, wherein the nucleic acid molecules are distributed among a plurality of partitions of the sample, wherein substantially all partitions (e.g., all partitions) each comprises R number of probe triplets corresponding to the R number of target regions,

- wherein a first probe triplet of the R number of probe triplets comprises:
  - a first reference probe corresponding to (e.g., comprising) a first reference sequence ($w_1$) and a first reference label detectable via a first detection channel ($X_1$), a first AS probe of the first probe triplet ("first AS probe 1") corresponding to (e.g., comprising) a first allelic sequence ($r_1$) and a first AS label of the first probe triplet ("first AS label 1") detectable via the first detection channel ($X_1$), and
  - a second AS probe of the first probe triplet ("second AS probe 1") corresponding to (e.g., comprising) the first allelic sequence ($r_1$) and a second AS label of the first probe triplet ("second AS label 1") detectable via the second detection channel ($X_2$);
- wherein a second probe triplet of the R number of probe triplets comprises:
  - a second reference probe corresponding to (e.g., comprising) a second reference sequence ($w_2$) and a second reference label detectable via the second detection channel ($X_2$),
  - a first AS probe of the second probe triplet ("first AS probe 2") corresponding to (e.g., comprising) a second allelic sequence ($r_2$) and a first AS label of the second probe triplet ("AS label 2") detectable via the second detection channel ($X_2$), and
  - a second AS probe of the second probe triplet ("second AS probe 2") corresponding to (e.g., comprising) the second allelic sequence second allelic sequence ($r_2$) and a second AS label of the second probe triplet ("second AS label 2") detectable via a third detection channel ($X_3$);
- wherein, if (e.g., when) R is strictly larger than 3, an i-th probe triplet (2<i<R) of the R number of probe triplet comprises:
  - an i-th reference probe corresponding to (e.g., comprising) an i-th reference sequence ($w_i$) and an i-th reference label detectable via an i-th detection channel ($X_i$),
  - a first AS probe of the i-th probe triplet ("first AS probe i") corresponding to (e.g., comprising) an i-th allelic sequence ($r_i$) and a first AS label of the i-th probe triplet ("first AS label i") detectable via the i-th detection channel ($X_i$), and
  - a second AS probe of the i-th probe triplet ("second AS probe i") corresponding to (e.g., comprising) an i-th allelic sequence ($r_i$) and a second AS label of the i-th probe triplet ("second AS label i") detectable via the (i+1)-th detection channel ($X_{i+1}$);
- wherein, if (e.g., when) R is strictly larger than 2, a R-th probe triplet of the R number of probe triplets comprises:
  - a R-th reference probe corresponding to (e.g., comprising) a R-th reference sequence ($w_R$) and a R-th reference label detectable via a R-th detection channel ($X_R$),
  - a first AS probe of the R-th probe triplet ("first AS probe R") corresponding to (e.g., comprising) an R-th allelic sequence (FR) and a first AS label of the R-th probe triplet ("first AS label R") detectable via the R-th detection channel ($X_R$), and
  - a second AS probe of the R-th probe triplet ("second AS probe R") corresponding to (e.g., comprising) a R-th allelic sequence ($r_R$) and a second AS label of the R-th probe triplet ("second AS label R") detectable via the first detection channel ($X_1$);

wherein the first AS probe and the second AS probe of each probe triplet hybridize to the same allelic sequence, different portions within the same allelic sequence, or complementary sequences thereof at a target region corresponding to the respective probe triplet;

wherein the reference sequence of each probe triplet is at a reference region corresponding to the respective probe triplet;

wherein the detection channels $X_1$-$X_R$ are different from each other;

wherein the method comprises detecting hybridization of reference probes of the R number of probe triplets to nucleic acid molecules or amplicons thereof comprising reference sequences or complementary sequences thereof at the reference regions in the plurality of partitions via each of the detection channels $X_1$-$X_R$; and detecting hybridization of the first AS probes and the second AS probes of the R number of probe triplets to nucleic acid molecules or amplicons thereof comprising allelic sequences or complementary sequences thereof at the target regions in the plurality of partitions via each of the detection channels $X_1$-$X_R$; thereby providing quantification of wildtype and/or allelic sequences at the R number of target regions in the sample. In some embodiments, the reference region of a probe triplet is adjacent to (e.g., upstream or downstream) the target region corresponding to the respective probe triplet. In some embodiments, the reference region of a probe triplet overlaps with the target region corresponding to the respective probe triplet. In some embodiments, the reference region of a probe triplet is identical to the target region corresponding to the respective probe triplet. R may be any suitable integer of 2 or larger. In some embodiments, R is between 2 and 6. In some embodiments, detection of a signal from a reference label and a signal from a second AS label in a probe triplet indicates an allelic sequence at the target region corresponding to the probe triplet, and detection of a signal from a reference label but no signal from a second AS label in a probe triplet indicates a wildtype sequence at the target region corresponding to the probe triplet.

In some embodiments, there is provided a method for quantification of wildtype and/or allelic sequences at three target regions in a sample comprising nucleic acid molecules, wherein the nucleic acid molecules are distributed among a plurality of partitions of the sample, wherein substantially all partitions (e.g., all partitions) each comprises three probe triplets corresponding to the three target regions, wherein the three probe triplets comprise:

a first probe triplet comprising:

a first reference probe corresponding to (e.g., comprising) a first reference sequence and a first reference label detectable via a first detection channel, a first AS probe of the first probe triplet ("first AS probe 1") corresponding to (e.g., comprising) a first allelic sequence and a first AS label of the first probe triplet ("first AS label 1") detectable via the first detection channel, and a second AS probe of the first probe triplet ("second AS probe 1") corresponding to (e.g., comprising) the first allelic sequence and a second AS label of the first probe triplet ("second AS label 1") detectable via a second detection channel;

a second probe triplet comprising:

a second reference probe corresponding to (e.g., comprising) a second reference sequence and a second reference label detectable via the second detection channel, a first AS probe of the second probe triplet ("first AS probe 2") corresponding to (e.g., comprising) a second allelic sequence and a first AS label of the second probe triplet ("first AS label 2") detectable via the second detection channel, and a second AS probe of the second probe triplet ("second AS probe 2") corresponding to (e.g., comprising) the first allelic sequence and a second AS label of the second probe triplet ("second AS label 2") detectable via a third detection channel;

a third probe triplet comprising:

a third reference probe corresponding to (e.g., comprising) a third reference sequence and a third reference label detectable via the third detection channel, a first AS probe of the third probe triplet ("first AS probe 3") corresponding to (e.g., comprising) a second allelic sequence and a first AS label of the third probe triplet ("first AS label 3") detectable via the third detection channel, and a second AS probe of the third probe triplet ("second AS probe 3") corresponding to (e.g., comprising) the first allelic sequence and a second AS label of the third probe triplet ("second AS label 3") detectable via the first detection channel;

wherein the first AS probe and the second AS probe of each probe triplet hybridize to the same allelic sequence, different portions within the same allelic sequence, or complementary sequences thereof at a target region corresponding to the respective probe triplet; wherein the reference sequence of each probe triplet is at a reference region corresponding to the respective probe triplet; wherein the first detection channel, the second detection channel and the third detection channel are different with respect to each other; wherein the method comprises detecting hybridization of reference probes of the three probe triplets to nucleic acid molecules or amplicons thereof comprising reference sequences or complementary sequences thereof at the reference regions in the plurality of partitions via each of the first, second, and third detection channels; and detecting hybridization of the first AS probes and the second AS probes of the three probe triplets to nucleic acid molecules or amplicons thereof comprising allelic sequences or complementary sequences thereof at the target regions in the plurality of partitions via each of the first, second, and third detection channels; thereby providing quantification of wildtype and/or allelic sequences at the three of target regions in the sample. In some embodiments, the reference region of a probe triplet is adjacent to (e.g., upstream or downstream) the target region corresponding to the respective probe triplet. In some embodiments, the reference region of a probe triplet overlaps with the target region corresponding to the respective probe triplet. In some embodiments, the reference region of a probe triplet is identical to the target region corresponding to the respective probe triplet. In some embodiments, detection of a signal from a reference label and a signal from a second AS label in a probe triplet indicates an allelic sequence at the target region corresponding to the probe triplet, and detection of a signal from a reference label but no signal from a second AS label in a probe triplet indicates a wildtype sequence at the target region corresponding to the probe triplet. In some embodiments, the target regions are genetic loci associated with CNV. In some embodiments, the target regions are genetic loci associated with rare alleles.

In some embodiments, there is provided a method for quantification of wildtype and/or allelic sequences (e.g., rare allele or CNV) at a plurality of target regions in a sample comprising nucleic acid molecules, wherein the nucleic acid molecules are distributed among a plurality of partitions of the sample, wherein substantially all partitions (e.g., all partitions) each comprises a plurality of probe sets corresponding to the plurality of target regions, wherein each probe set of the plurality of probe sets comprises:

an allele-specific (AS) probe comprising a first AS label, a second AS label and an oligonucleotide AS sequence complementary to an allelic sequence at a target region corresponding to the respective probe set; and a reference probe comprising a reference label and an oligonucleotide sequence complementary to a reference sequence at a reference region corresponding to the respective probe set;

wherein the reference label and the first AS label of each probe set of the plurality of probe sets are detectable via the same detection channel;

wherein the reference label and the second AS label of each probe set of the plurality of probe sets are detectable via different detection channels;

wherein reference labels of the plurality of probe sets are detectable via different detection channels with respect to each other;

wherein the second AS labels of the plurality of probe sets are detectable via different detection channels with respect to each other;

wherein at least one reference label of the plurality of probe sets and at least one second AS label of the plurality of probe sets are detectable via the same detection channel;

wherein the method comprises: detecting hybridization of reference probes of the plurality of probe sets to nucleic acid molecules or amplicons thereof comprising reference sequences at the reference regions in the plurality of partitions; and detecting hybridization of the AS probes of the plurality of probe sets to nucleic acid molecules or amplicons thereof comprising allelic sequences at the target regions in the plurality of partitions; thereby providing quantification of wildtype and/or allelic sequences at the plurality of target regions in the sample. In some embodiments, the reference region of a probe set is adjacent to (e.g., upstream or downstream) the target region corresponding to the respective probe set. In some embodiments, the reference region of a probe set overlaps with the target region corresponding to the respective probe set. In some embodiments, the reference region of a probe set is identical to the target region corresponding to the respective probe set. In some embodiments, detection of a signal from a reference label and no signal from a second AS probe in a probe set indicates a wildtype sequence at the target region corresponding to the probe set, and detection of a signal from a reference label and a signal from a second AS label in a probe set indicates an allelic sequence at the target region corresponding to the probe set. In some embodiments, the reference label and the first AS label of each probe set are identical to each other. In some embodiments, the set of reference labels of the plurality of probe sets and the set of second AS labels of the plurality of probe sets have overlapping labels. In some embodiments, the set of reference labels of the plurality of probe sets and the set of second AS labels of the plurality of probe sets are circular permutations with respect to each other.

In some embodiments, there is provided a method for quantification of wildtype and/or allelic sequences (e.g., rare allele or CNV) at R number of target regions in a sample comprising nucleic acid molecules, wherein the nucleic acid molecules are distributed among a plurality of partitions of the sample, wherein substantially all partitions (e.g., all partitions) each comprises R number of probe pairs corresponding to the R number of target regions, wherein a first probe pair of the R number of probe pairs comprises:

a first reference probe corresponding to (e.g., comprising) a first reference sequence ($w_1$) and a first reference label detectable via a first detection channel ($X_1$), and a first AS probe corresponding to (e.g., comprising) a first allelic sequence ($r_1$), a first AS label of the first probe pair ("first AS label 1") detectable via the first detection channel ($X_1$), and a second AS label of the first probe pair ("second AS label 1") detectable via the second detection channel ($X_2$);

wherein a second probe pair of the R number of probe pairs comprises:

a second reference probe corresponding to (e.g., comprising) a second reference sequence ($w_2$) and a second reference label detectable via the second detection channel ($X_2$), and a second AS probe corresponding to (e.g., comprising) a second allelic sequence ($r_2$), a first AS label of the second probe pair ("AS label 2") detectable via the second detection channel ($X_2$), and a second AS label of the second probe pair ("second AS label 2") detectable via a third detection channel ($X_3$);

wherein, if (e.g., when) R is strictly larger than 3, an i-th probe pair ($2<i<R$) of the R number of probe pair comprises:

an i-th reference probe corresponding to (e.g., comprising) an i-th reference sequence ($w_i$) and an i-th reference label detectable via an i-th detection channel ($X_i$), and an i-th AS probe corresponding to (e.g., comprising) an i-th allelic sequence ($r_i$), a first AS label of the i-th probe pair ("first AS label i") detectable via the i-th detection channel ($X_i$), and a second AS label of the i-th probe pair ("second AS label i") detectable via the (i+1)-th detection channel ($X_{i+1}$);

wherein, if (e.g., when) R is strictly larger than 2, a R-th probe pair of the R number of probe pairs comprises:

a R-th reference probe corresponding to (e.g., comprising) a R-th reference sequence ($w_R$) and a R-th reference label detectable via a R-th detection channel ($X_R$), and a R-th AS probe corresponding to (e.g., comprising) an R-th allelic sequence ($r_R$), a first AS label of the R-th probe pair ("first AS label R") detectable via the R-th detection channel ($X_R$), and a second AS label of the R-th probe pair ("second AS label R") detectable via the first detection channel ($X_1$);

wherein the reference sequence of each probe pair is at a reference region corresponding to the respective probe set;

wherein the detection channels $X_1$-$X_R$ are different from each other;

wherein the method comprises detecting hybridization of reference probes of the R number of probe pairs to nucleic acid molecules or amplicons thereof comprising reference sequences or complementary sequences thereof at the reference regions in the plurality of partitions via each of the detection channels $X_1$-$X_R$; and detecting hybridization of the AS probes of the R number of probe pairs to nucleic acid molecules or amplicons thereof comprising allelic sequences or complementary sequences thereof at the target regions in the plurality of partitions via each of the detection channels $X_1$-$X_R$; thereby providing quantification of wildtype and/or allelic sequences at the R number of target regions in the sample. In some embodiments, the reference region of a probe pair is adjacent to (e.g., upstream or downstream) the target region corresponding to the respective probe pair. In some embodiments, the reference region of a probe pair overlaps with the target region corresponding to the respective probe pair. In some embodiments, the reference region of a probe pair is identical to the target region corresponding to the respective probe pair. R may be any suitable integer of 2 or larger. In some embodiments, R is between 2 and 6. In some embodiments, detection of a signal from a reference label and a signal from a second AS label in a probe pair indicates an allelic sequence at the target region corresponding to the probe pair, and detection of a signal from a reference label but no signal from a second AS label in a probe pair indicates a wildtype sequence at the target region corresponding to the probe pair.

In some embodiments, there is provided a method for quantification of wildtype and/or allelic sequences at three target regions in a sample comprising nucleic acid molecules, wherein the nucleic acid molecules are distributed among a plurality of partitions of the sample, wherein substantially all partitions (e.g., all partitions) each comprises three probe pairs corresponding to the three target regions, wherein the three probe pairs comprise:

- a first probe pair comprising:
  - a first reference probe corresponding to (e.g., comprising) a first reference sequence and
  - a first reference label detectable via a first detection channel, and
  - a first AS probe corresponding to (e.g., comprising) a first allelic sequence, a first AS label of the first probe pair ("first AS label 1") detectable via the first detection channel, and a second AS label of the first probe pair ("second AS label 1") detectable via a second detection channel;
- a second probe pair comprising:
  - a second reference probe corresponding to (e.g., comprising) a second reference sequence and a second reference label detectable via the second detection channel, and
  - a second AS probe corresponding to (e.g., comprising) a second allelic sequence, a first AS label of the second probe pair ("first AS label 2") detectable via the second detection channel, and a second AS label of the second probe pair ("second AS label 2") detectable via a third detection channel;
- a third probe pair comprising:
  - a third reference probe corresponding to (e.g., comprising) a third reference sequence and
  - a third reference label detectable via the third detection channel, and
  - a third AS probe corresponding to (e.g., comprising) a second allelic sequence, a first AS label of the third probe pair ("first AS label 3") detectable via the third detection channel, and a second AS label of the third probe pair ("second AS label 3") detectable via the first detection channel;

wherein the reference sequence of each probe pair is at a reference region corresponding to the respective probe pair; wherein the first detection channel, the second detection channel and the third detection channel are different with respect to each other; wherein the method comprises detecting hybridization of reference probes of the three probe pairs to nucleic acid molecules or amplicons thereof comprising reference sequences or complementary sequences thereof at the reference regions in the plurality of partitions via each of the first, second, and third detection channels; and detecting hybridization of the AS probes of the three probe pairs to nucleic acid molecules or amplicons thereof comprising allelic sequences or complementary sequences thereof at the target regions in the plurality of partitions via each of the first, second, and third detection channels; thereby providing quantification of wildtype and/or allelic sequences at the three of target regions in the sample. In some embodiments, the reference region of a probe pair is adjacent to (e.g., upstream or downstream) the target region corresponding to the respective probe pair. In some embodiments, the reference region of a probe pair overlaps with the target region corresponding to the respective probe pair. In some embodiments, the reference region of a probe pair is identical to the target region corresponding to the respective probe pair. In some embodiments, detection of a signal from a reference label and a signal from a second AS label in a probe pair indicates an allelic sequence at the target region corresponding to the probe pair, and detection of a signal from a reference label but no signal from a second AS label in a probe pair indicates a wildtype sequence at the target region corresponding to the probe pair. In some embodiments, the target regions are genetic loci associated with CNV. In some embodiments, the target regions are genetic loci associated with rare alleles.

The skilled person will know the different practical ways to implement such an approach, as well as the working conditions (concentration of each of the probes, etc.). In particular, illustrations of dual-labelled probes configurations may be found, for example, in U.S. Pat. No. 9,222,128 at FIG. 6 (Target 3), FIG. 9A, FIG. 9B, FIG. 10, and FIG. 11 and later figures, which are incorporated herein by reference in their entirety.

Figure 11A:
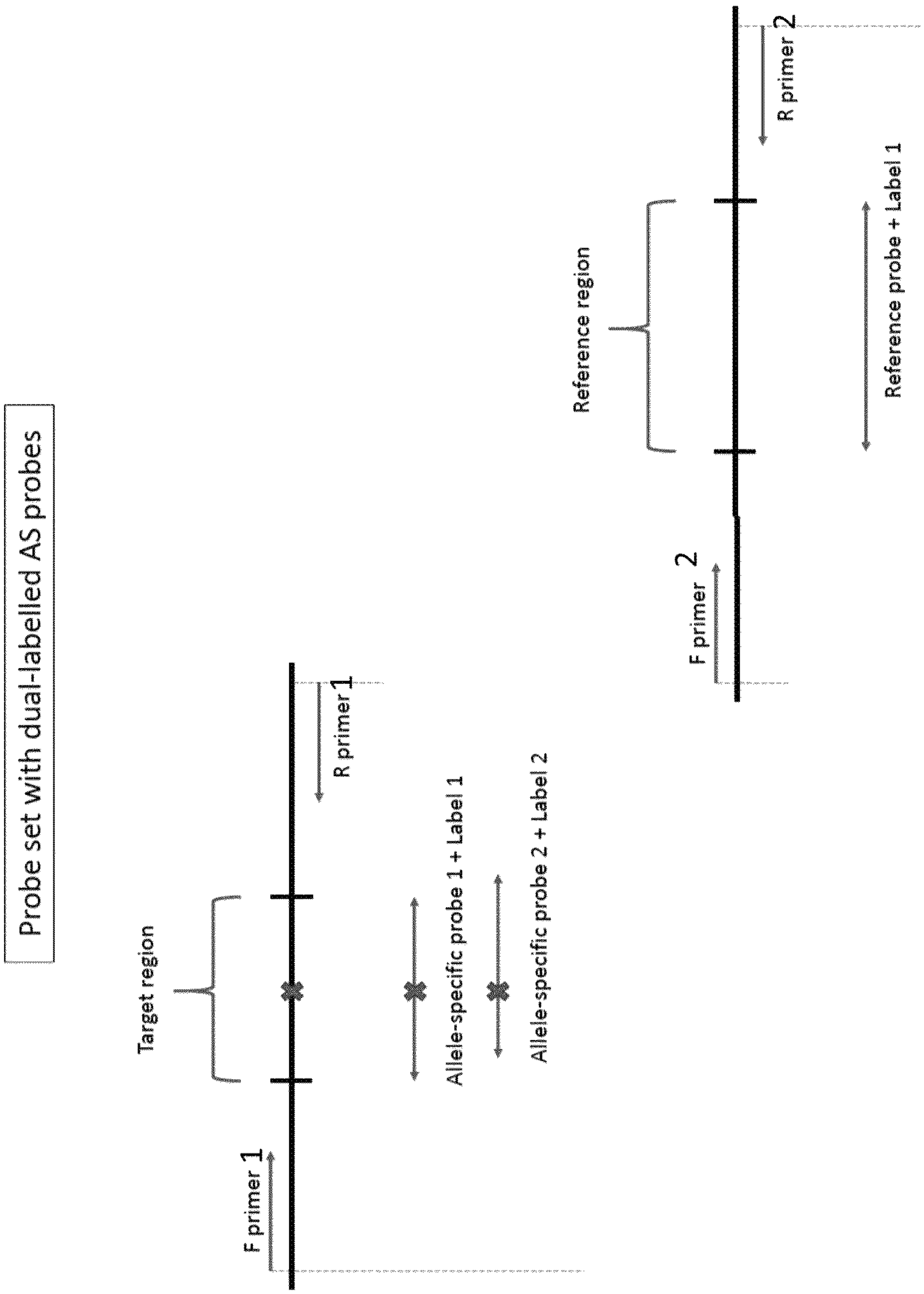
FIG. 11A shows schematics of an exemplary probe set for detecting an allelic sequence at a target region in a nucleic acid molecule. The probe set includes: (a) a first allele-specific (AS) probe with a first label that hybridizes to an allelic sequence (e.g., a sequence containing a mutation, as marked with a cross) at a target region, (b) a second AS probe with a second label that hybridizes to the same allelic sequence at the target region as the first AS probe, and (c) a reference probe that hybridizes to a reference sequence (e.g., a wildtype sequence) at a reference region. The first AS probe and the second AS probe may hybridize to the same sequence or adjacent sequences that contain the allelic sequence, or complementary sequences thereof. A forward primer (F primer 1) and a reverse primer (R primer 1) can be used to amplify a target fragment comprising the target region in the nucleic acid molecule. A forward primer (F primer 2) and a reverse primer (R primer 2) can be used to amplify a reference fragment comprising the reference region in the nucleic acid molecule.
Figure 11B:
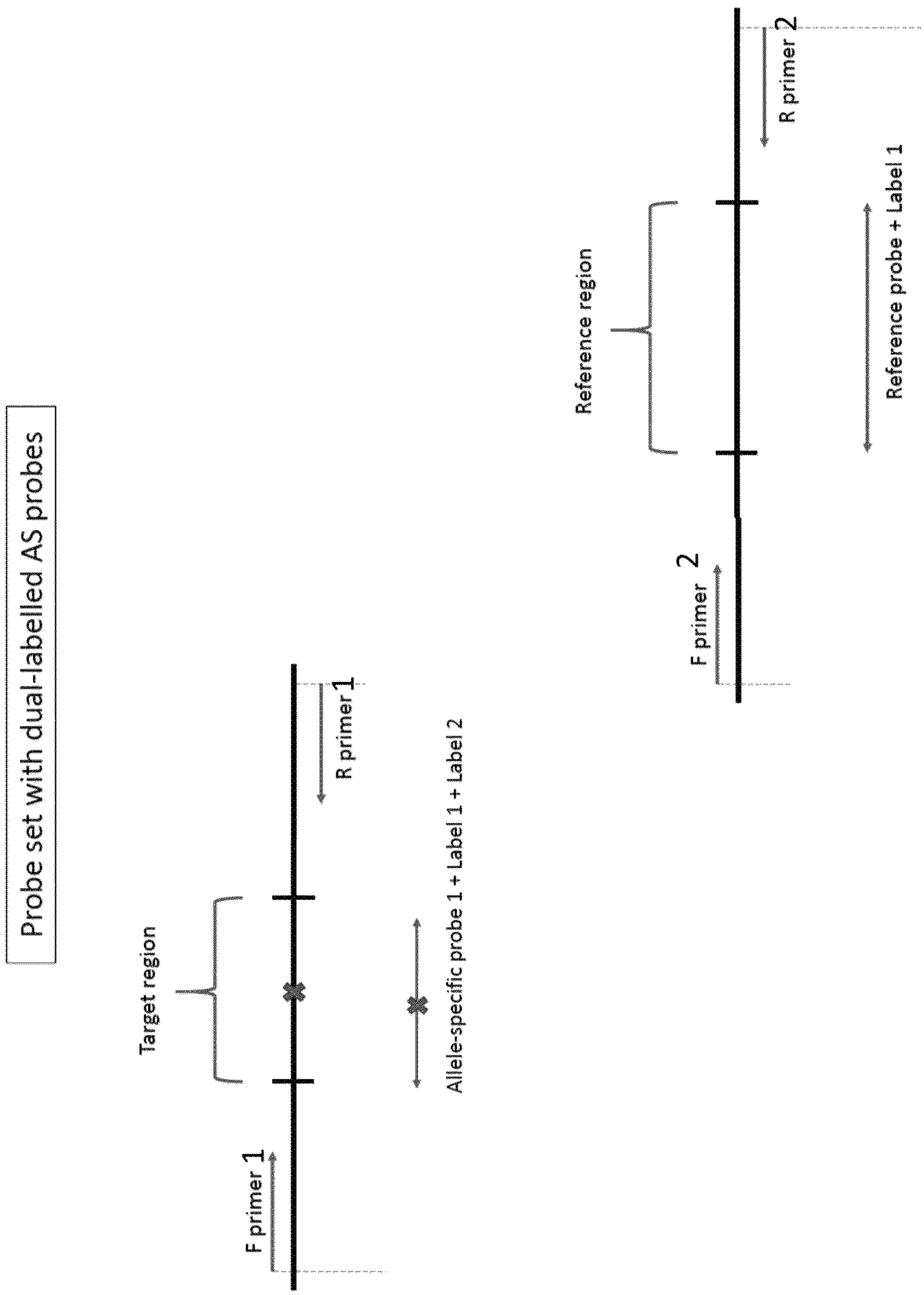
FIG. 11B shows schematics of an exemplary probe set for detecting an allelic sequence at a target region in a nucleic acid molecule. The probe set includes: (a) an allele-specific (AS) probe with a first label and a second label that hybridizes to an allelic sequence (e.g., a sequence containing a mutation) at a target region, and (c) a reference probe that hybridizes to a reference sequence (e.g., a wildtype sequence) at a reference region. The AS probe may hybridize to the same sequence or adjacent sequences that contain the allelic sequence, or complementary sequences thereof. A forward primer (F primer 1) and a reverse primer (R primer 1) can be used to amplify a target fragment comprising the target region in the nucleic acid molecule. A forward primer (F primer 2) and a reverse primer (R primer 2) can be used to amplify a reference fragment comprising the reference region in the nucleic acid molecule.
Figure 11C:
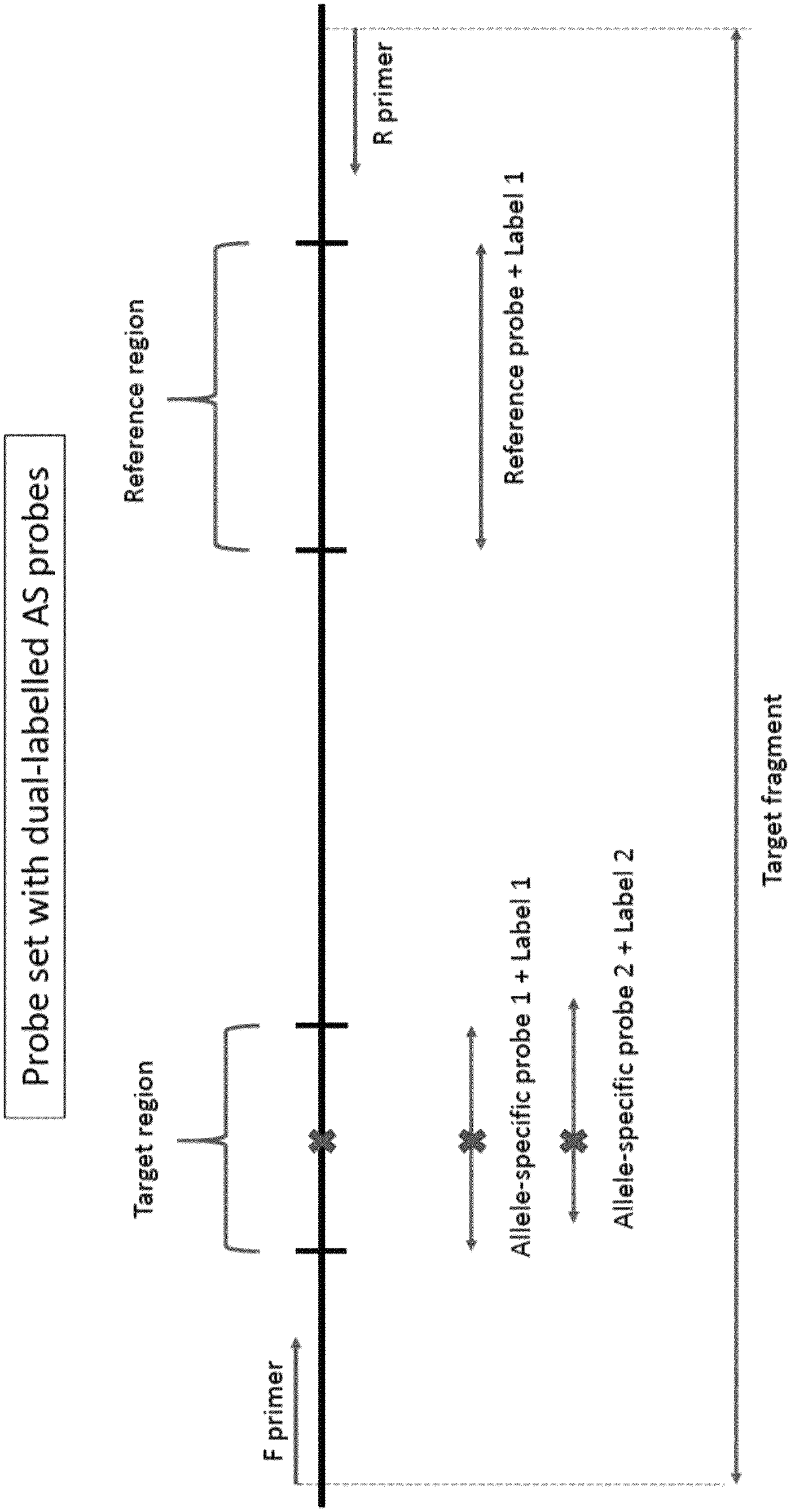
FIG. 11C shows schematics of an exemplary probe set for detecting an allelic sequence at a target region in a nucleic acid molecule. The probe set includes: (a) a first allele-specific (AS) probe with a first label that hybridizes to an allelic sequence (e.g., a sequence containing a mutation) at a target region, (b) a second AS probe with a second label that hybridizes to the same allelic sequence at the target region as the first AS probe, and (c) a reference probe that hybridizes to a reference sequence (e.g., a wildtype sequence) at a reference region. Both the target region and the reference region are found within the same template nucleic acid molecule or amplicons thereof. The reference region can be either upstream or downstream with respect to the target region. The reference probe and the AS probes may be designed to hybridize to the same strand of the nucleic acid molecule or amplicons thereof, or different strands of the nucleic acid molecule or amplicons thereof. A forward primer (F primer) and a reverse primer (R primer) can be used to amplify a target fragment comprising the target region and the reference region in the nucleic acid molecule.
Figure 11D:
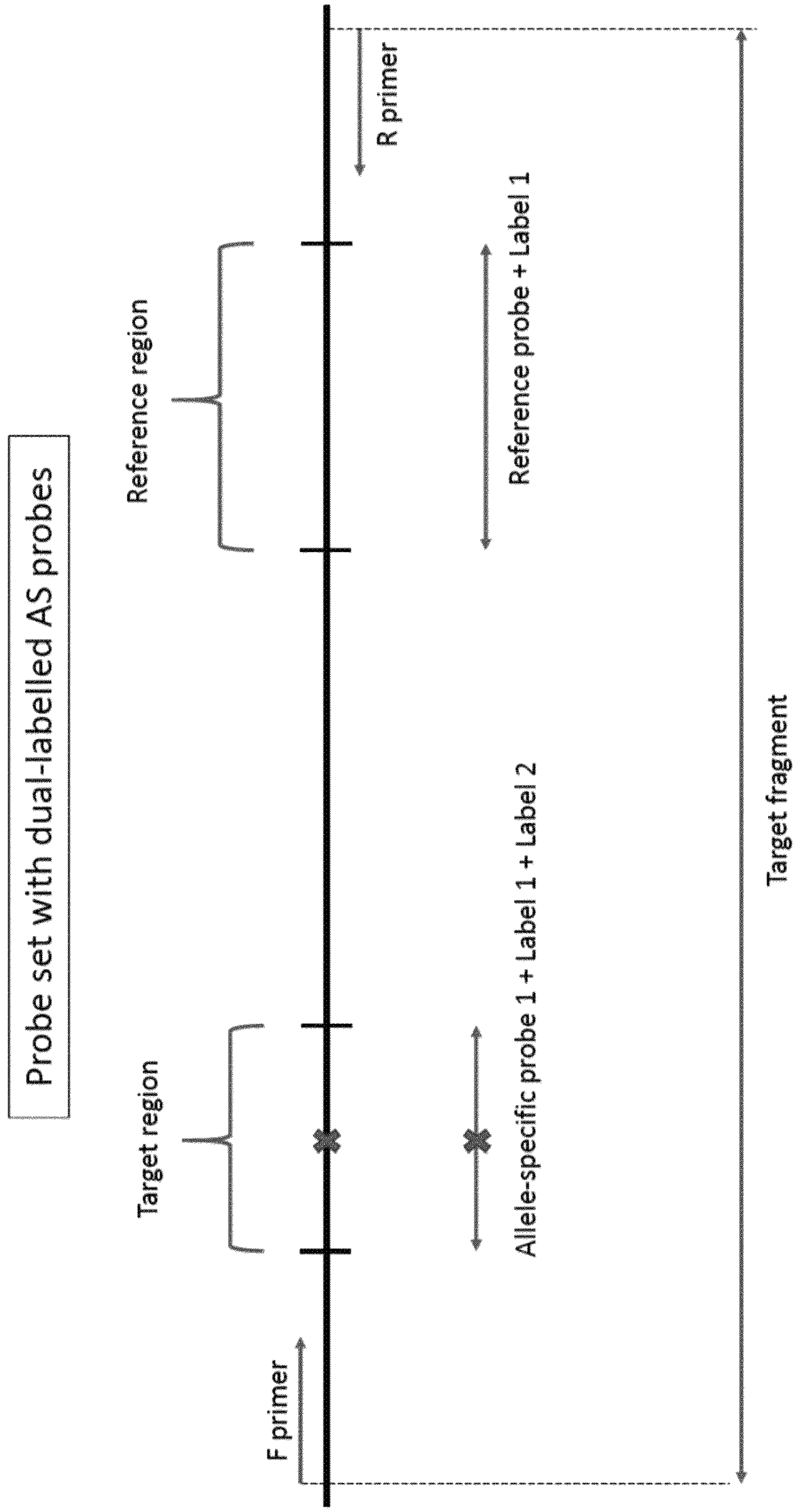
FIG. 11D shows schematics of an exemplary probe set for detecting an allelic sequence at a target region in a nucleic acid molecule. The probe set includes: (a) an allele-specific (AS) probe with a first label and a second label that hybridizes to an allelic sequence (e.g., a sequence containing a mutation) at a target region, and (c) a reference probe that hybridizes to a reference sequence (e.g., a wildtype sequence) at a reference region. Both the target region and the reference region are found within the same template nucleic acid molecule or amplicons thereof. The reference region can be either upstream or downstream with respect to the target region. The reference probe and the AS probe may be designed to hybridize to the same strand of the nucleic acid molecule or amplicons thereof, or different strands of the nucleic acid molecule or amplicons thereof. A forward primer (F primer) and a reverse primer (R primer) can be used to amplify a target fragment comprising the target region and the reference region in the nucleic acid molecule.

FIGS. 11A and 11C provide schematics of exemplary probe sets comprising a reference probe and a dual-labelled AS probe pair. The two AS probes, each using a different detectable label (e.g., different fluorophore) may be directed to the exact same sequence, complementary sequences, or may be designed to bind on nearby regions on the target species bearing them. The AS probes of the same probe set detect the same genetic species. When the genetic species of interest has a unique allelic sequence that is shorter than the AS probes, the two AS probes may hybridize to overlapping sequences, each comprising the unique allelic sequence. When the genetic species of interest has a unique allelic sequence that is longer than the AS probes, the two AS probes may hybridize to non-overlapping sequences, which are comprised by the unique allelic sequence. The two AS probes may be directed to the same strand, or different strands. FIGS. 11B and 11D provide schematics of exemplary probe sets comprising a reference probe and a dual-labeled AS probe.

Figure 11E:
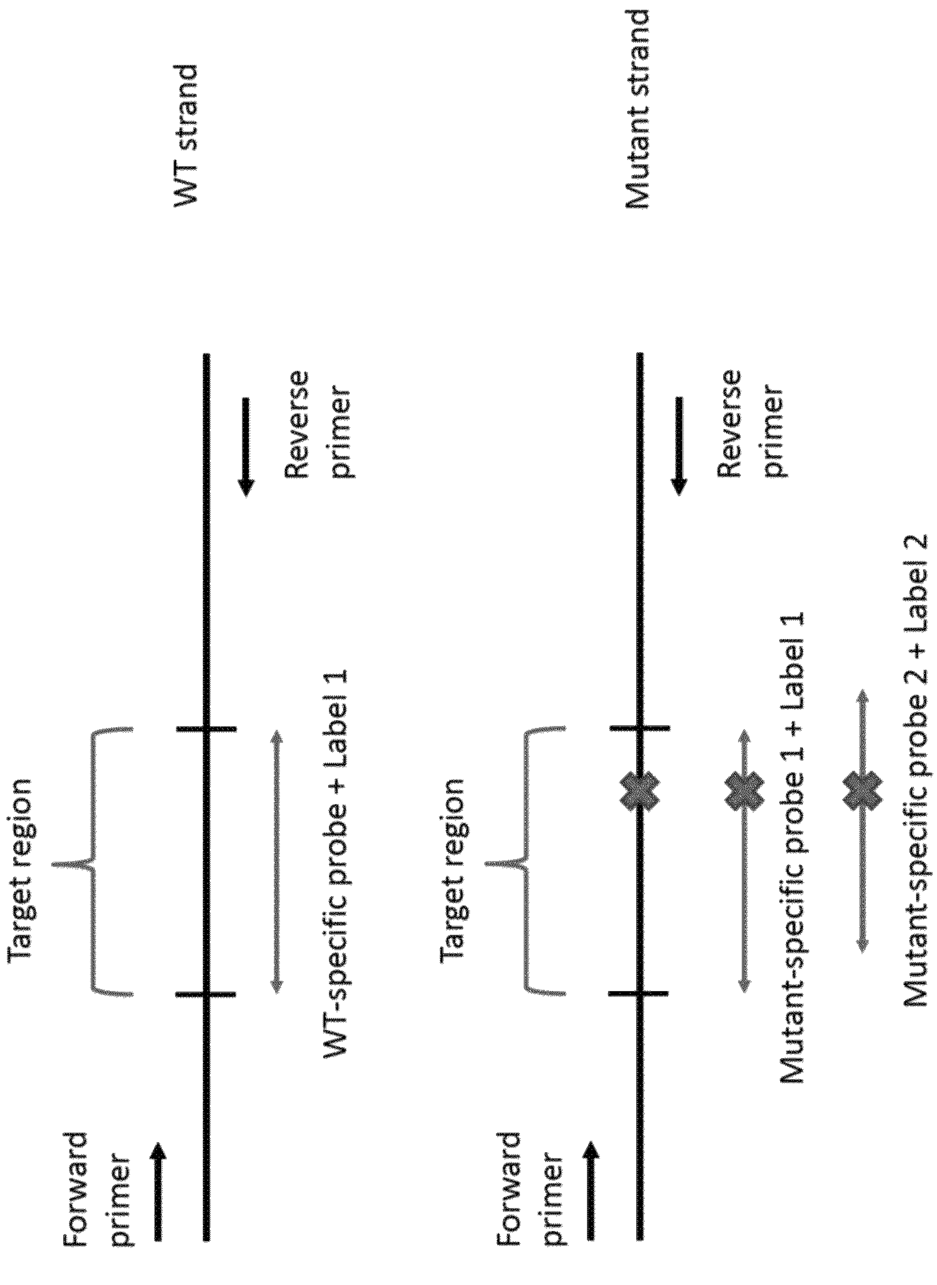
FIG. 11E shows schematics of an exemplary probe set for detecting a mutant sequence at a target region of a nucleic acid molecule. The probe set includes: (a) a first mutant-specific (MS) probe with a first label that hybridizes to a mutant sequence at a target region, (b) a second MS probe with a second label that hybridizes to the same mutant sequence at the target region, and (c) a wildtype-specific (WS) probe that hybridizes to the wildtype sequence at the target region. The WS probe and the MS probes are designed to hybridize to the same or different strands of the nucleic acid molecule or amplicons thereof. A forward primer and a reverse primer can be used to amplify a target fragment comprising the target region in the nucleic acid molecule.
Figure 11F:
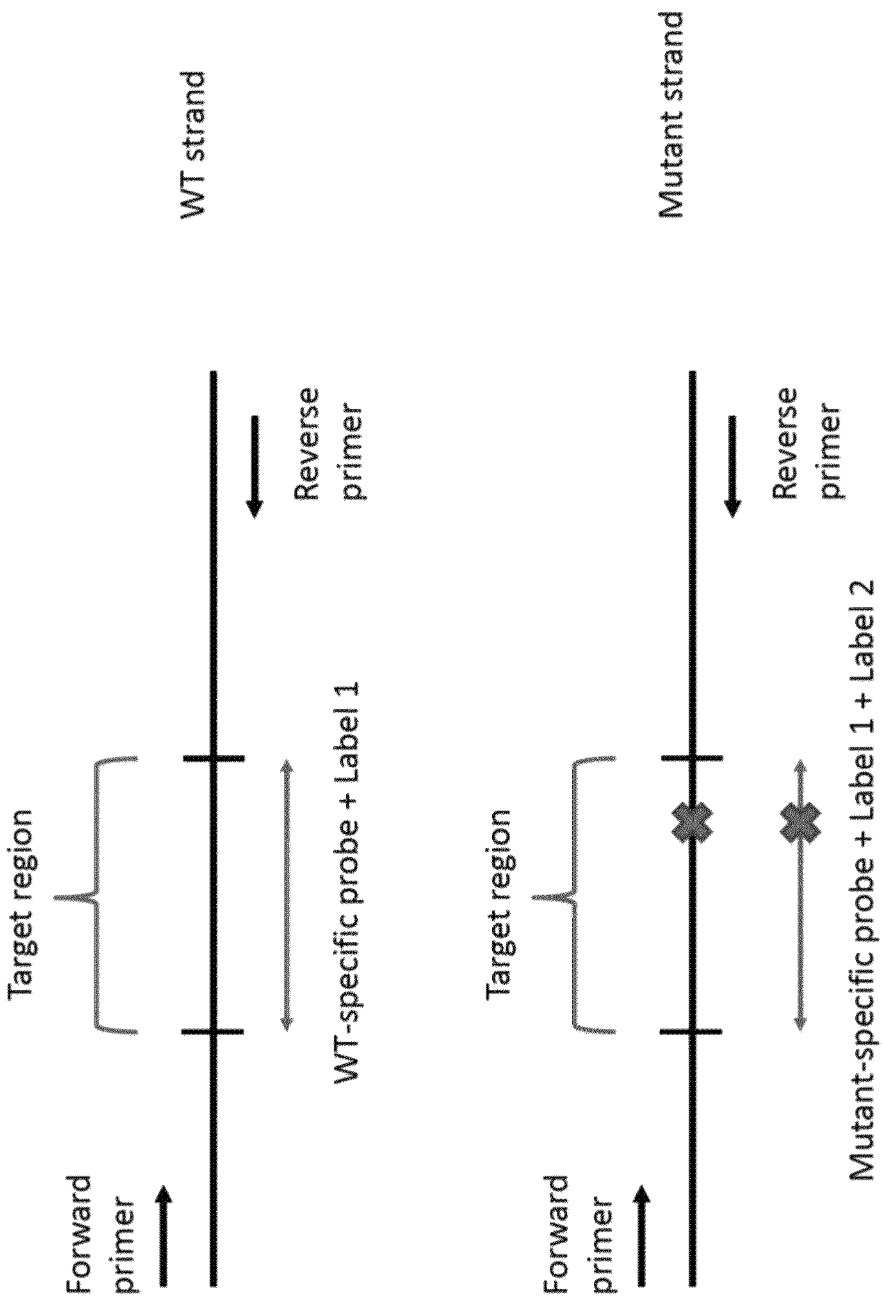
FIG. 11F shows schematics of an exemplary probe set for detecting a mutant sequence at a target region of a nucleic acid molecule. The probe set includes: (a) a mutant-specific (MS) probe with a first label and a second label that hybridizes to a mutant sequence at a target region, and (b) a wildtype-specific (WS) probe that hybridizes to the wildtype sequence at the target region. The WS probe and the MS probe are designed to hybridize to the same strand or different strands of the nucleic acid molecule or amplicons thereof. A forward primer and a reverse primer can be used to amplify a target fragment comprising the target region in the nucleic acid molecule.

In some embodiments, a probe set comprises dual-labelled AS probe(s) and a reference probe that hybridize to overlapping regions, including 100% identical regions in a nucleic acid molecule or amplicons thereof. The AS probe(s) hybridize to a mutant sequence at a target region. The reference probe hybridize to a wildtype sequence at a reference region, which can be identical to the target region as shown in FIGS. 11E-11F. The "WT-specific probes" of FIGS. 11E-11F correspond to reference probes, and the "mutant-specific probes" of FIGS. 11E-11F correspond to AS probes. In some embodiments, a plurality of probe sets of FIGS. 11E-11F are used in multiplex dPCR assays for determining multiple allele frequencies (MAFs).

In FIGS. 11A and 11B, two primer pairs are used, including one pair of forward and reverse primers to amplify a target fragment comprising the target region associated with the genetic species of interest, and one pair of forward and reverse primers to amplify a separate reference fragment comprising the reference region (e.g., a reference region with low mutation or SNP frequency) corresponding to the target region. In FIGS. 11C-11F, a single primer pair is used, including a forward primer and a reverse primer to amplify a target fragment comprising both the target region and the reference region.

The calculations presented herein for a multiplex drop-off dPCR method are directly transferrable to a method using probe sets comprising a dual-labelled AS probes (referred herein as "dual-labelled AS assay", for example with the following assignments:

$m_i$ (mutant i in the context of the drop-off assay)=$ref_i$ (reference species i in the context of dual-labelled AS assay). Labelled with one probe (i.e., reference probe with a detectable label).

and $w_i$ (wild-type i in the context of the drop-off assay)=$target_i$ (target species i in the dual-labelled AS assay). Labelled with two probes (i.e., a first AS probe with a first detectable label, and a second AS probe with a second detectable label), or an AS probe with two detectable labels.

In an exemplary multiplex assay for detecting CNV of three genes, three sets of probes and primers are designed, one for each target gene. Each probe set may include a triplet of a reference probe, a first AS probe and a second AS probe. Each set of primers include a first pair of forward and reverse primers for amplifying reference fragments containing the reference region, and a second pair of forward and reverse primers for amplifying target fragments containing the target region. The first AS probe and the second AS probe hybridize to an allelic sequence comprising a portion of the respective gene. For example, the first AS probe and the second AS probe may hybridize to a portion of a repeated sequence in a mutant gene associated with CNV. The template nucleic acid may be fractionated either physically or by restriction enzyme digestion in the preparation step so that each repeat sequence is cut from the next and partitioned into individual droplets. In other examples, the first AS probe and the second AS probe may hybridize to a junction of two repeats of a mutant gene associated with CNV, but not sequences in a wildtype gene. Other AS probe pairs capable of detecting CNVs may also be used. The reference probe and the AS probes may be TAQMAN™ probes, with the reference probe and the first AS probe labeled with the same fluorophore and the second AS probe labeled with a different fluorophore, which are detectable via different fluorescence detection channels. For a nucleic acid containing CNV of a target gene, the reference probe hybridizes to amplicons of the reference fragment, and the first AS probe and the second AS probe hybridize to amplicons of the target fragment, thereby resulting in positive signals in the fluorescence channels that correspond to both the reference probe and the second AS probe. For a nucleic acid containing wildtype sequences of the target gene, only the reference probe hybridizes to the amplicons of the reference fragment, thereby resulting in positive signals in the fluorescence channel that corresponds to only the reference probe, but no signal in the fluorescence channel that corresponds to the second AS probe. The signals from dPCR droplets can be plotted in three-dimensions. Space segments corresponding to different clusters of signals are determined, and the number of droplets in each space segments is counted. The counts are used to estimate the concentration for each wildtype and CNV populations.

A skilled person in the art would readily appreciate that features and embodiments of multiplex drop-off dPCR methods described herein can be applied to multiplex dPCR methods with dual-labelled AS probes mutatis mutandis according to the assignments above, including, but not limited to, features described in the "Probe sets" and "Digital PCR" sections above and various applications, systems, kits and articles of manufacture in Sections III and IV below.

In the context of the dual-labelled AS assay, which uses two AS probes each having a different detectable label, the mathematical uncertainty is the lowest for the species labelled with two probes. In such assays, it may be preferable to use the dual-labelled AS probe pair to detect target species (e.g., CNV or rare alleles) in order to minimize uncertainty. In some embodiments, where it is desirable to have the lowest mathematical uncertainty attached to the reference sequences in the context of an assay having dual-labeled probes, a pair of dual-labeled reference probes may be used to detect the reference sequences, and a single-label allele-specific probe may be used to detected target species (e.g., CNV or rare alleles) with one probe. The above assignment of species in paragraph to make use of the calculations presented for the multiplex drop-off assay are therefore exchanged in this context, refi corresponding to $w_i$ and $target_i$ corresponding to $m_i$.

Although the mathematical uncertainty is lowest with the dual-labelled probe(s), in certain assays, such as MAF assays (e.g., using probe sets of FIGS. 11E-11F), the single labelled probe is used to detect a mutant sequence, and the dual-labelled probe(s) are used to detect the wildtype sequence. In such situations, the single colored droplets are unambiguously assignable to the mutant sequence, which is likely to be present in the sample in much lower amounts than the wildtype sequence.

Any one of the dual-labelled AS probe assays and methods described herein may be used together with the drop-off assays to simultaneously measure one or more drop-offs and to calculate one or more alleles (e.g., CNVs) as described above. For example, in some embodiments, the method uses a first plurality of probe sets each comprising a reference probe and a drop-off probe, and a second plurality of probe sets each comprising a reference probe, a first AS probe and a second AS probe. In some embodiments, the method uses a first plurality of probe sets each comprising a reference probe and a drop-off probe, and a second plurality of probe sets each comprising a reference probe and a dual-labeled AS probe. In some embodiments, the method further uses one or more standalone AS probes. The set of labels for the plurality of probe sets are permutated to reduce the number of detection channels required for detecting the various genetic species.

In a first example, a multiplex dPCR assay for detecting 2 CNV sequences and 1 drop-off sequence is designed using 3 fluorescence channels represented by 1, 2, 3 that can detect 3 corresponding fluorophores: 1, 2, 3. The two CNVs can be detected using 2 sets of primers and 2 sets of AS probe pairs to quantify their respective targets and 2 sets of primers and 2 sets of single probes to quantify their respective reference. The drop-off is quantified using one set of primers and one probe pair, one probe from said pair being specific to the drop-off sequence and the other probe from said pair being specific to the reference sequence. TABLE 10 below shows an exemplary scheme for this assay. A similar configuration may be used to simultaneously quantify 2 rare allele sequences at two different genetic loci (corresponding to CNV1 and CNV2), and 1 drop-off sequence.

TABLE 10

| CNV | | | Drop-off | |
|---|---|---|---|---|
| Probes | CNV 1 | CNV2 | Probes | Drop off 1 |
| Target (i.e. AS) | 1 + 2 | 2 + 3 | Drop-off | 3 |
| Reference | 2 | 3 | Reference | 1 |

In a second example, a multiplex dPCR assay for detecting 2 drop-off sequences and 1 CNV sequence is designed using 3 fluorescence channels represented by 1, 2, 3 that can detect 3 corresponding fluorophores: 1, 2, 3. TABLE 11 below shows an exemplary scheme for this assay. A similar configuration may be used to simultaneously quantify 2 drop-off sequences and 1 rare allele sequence (corresponding to CNV).

TABLE 11

| CNV | | Drop-off | | |
|---|---|---|---|---|
| Probes | CNV 1 | Probes | Drop off 1 | Drop off 2 |
| Target | 2 + 3 | Drop-off | 1 | 3 |
| Reference | 3 | Reference | 2 | 1 |

III. Applications

The methods and multiplex dPCR assays (e.g., multiplex drop-off dPCR assays) described herein are useful in a variety of applications, including treatment, diagnosis and genome editing. Because of their sensitivity and multiplexing capacity, the methods described herein are particularly useful for detection of predictive mutation biomarkers (e.g., microsatellite instability) in DNA samples containing very low concentrations of target DNA, or for detection of rare NHEJ or HDR-edited sequences at target genomic loci by site-specific genome-editing reagents (e.g., CRISPR/Cas).

Methods of Diagnosis and Treatment

In some embodiments, there is provided a method of diagnosing a disease or condition in an individual, wherein the disease or condition is associated with mutations at a plurality of target genetic loci, comprising detecting mutant sequences at the plurality of target genetic loci in a sample of the individual using any one of the methods described in the "Multiplex dPCR methods" section. In some embodiments, the disease or condition is cancer. In some embodiments, the target genetic loci are selected from the group consisting of EGFR, KRAS, NRAS, ESR1 and BRAF. In some embodiments, the target genetic loci are microsatellite sequence loci. In some embodiments, the target genetic loci are associated with rare alleles or CNVs.

In some embodiments, there is provided a method for prognosis of a disease or condition in an individual, wherein the disease or condition is associated with mutations at a plurality of target genetic loci, comprising detecting mutant sequences at the plurality of target genetic loci in a sample of the individual using any one of the methods described in the "Multiplex dPCR methods" section. In some embodiments, the disease or condition is cancer. In some embodiments, the target genetic loci are selected from the group consisting of EGFR, KRAS, NRAS, ESR1 and BRAF. In some embodiments, the target genetic loci are microsatellite sequence loci. In some embodiments, the target genetic loci are associated with rare alleles or CNVs.

In some embodiments, there is provided a method for predicting the efficacy of a treatment in an individual having a disease or condition, wherein the efficacy of the treatment is associated with mutations at a plurality of target genetic loci, comprising detecting mutant sequences at the plurality of target genetic loci in a sample of the individual using any one of the methods described in the "Multiplex dPCR methods" section. In some embodiments, the disease or condition is cancer. In some embodiments, the target genetic loci are microsatellite sequence loci. In some embodiments, the target genetic loci are selected from the group consisting of EGFR, KRAS, NRAS, ESR1 and BRAF. In some embodiments, the treatment is an immunotherapy, such as an immune checkpoint modulator. In some embodiments, the target genetic loci are associated with rare alleles or CNVs.

In some embodiments, there is provided a method for treating a disease or condition in an individual, wherein the disease or condition is associated with mutations at a plurality of target genetic loci, comprising detecting mutant sequences at the plurality of target genetic loci in a sample of the individual using any one of the methods described in the "Multiplex dPCR methods" section, and administering to the individual an effective amount of a therapeutic agent, if mutant sequences are detected. In some embodiments, the disease or condition is cancer. In some embodiments, the target genetic loci are microsatellite sequence loci. In some embodiments, the target genetic loci are selected from the group consisting of EGFR, KRAS, NRAS, ESR1 and BRAF. In some embodiments, the therapeutic agent is an immunotherapeutic agent, such as an immune checkpoint modulator. In some embodiments, the target genetic loci are associated with rare alleles or CNVs.

In some embodiments, there is provided a method for monitoring an individual diagnosed with a disease or condition associated with a plurality of target genetic loci, comprising detecting mutant sequences at the plurality of target genetic loci in a first sample obtained from the individual at a first time point using any one of the methods described in the "Multiplex dPCR methods" section, detecting mutant sequences at the plurality of target genetic loci in a second sample obtained from the individual at a second time point using the method, and comparing the estimated concentrations of the mutant sequences at one or more of the plurality of target genetic loci in the first sample versus that in the second sample. In some embodiments, the disease or condition is cancer. In some embodiments, the target genetic loci are microsatellite sequence loci. In some embodiments, the target genetic loci are selected from the group consisting of EGFR, KRAS, NRAS, ESR1 and BRAF. In some embodiments, the first time point is before the individual receives a treatment. In some embodiments, the second time point is after the individual receives a treatment. In some embodiments, the treatment is an immunotherapeutic agent, such as an immune checkpoint modulator. In some embodiments, the target genetic loci are associated with rare alleles or CNVs.

The methods described herein are useful for detecting mutations that occur at mutation hotspots in the genome. Because drop-off probes are used to detect the mutations, any mutant sequence at a specific target region can be detected, thereby allowing detection of low-frequency mutations that have similar functional impact on the gene product.

The methods described herein are useful for detecting microsatellite instability (MSI) in a sample of an individual having cancer or at the risk of having cancer.

In some embodiments, there is provided a method of for quantification of mutations at a plurality of microsatellite sequence loci in a sample comprising nucleic acid molecules, wherein the nucleic acid molecules are distributed among a plurality of partitions of the sample, and wherein substantially all partitions (e.g., all partitions) each comprises:

a plurality of primer sets corresponding to the plurality of microsatellite sequence loci, wherein each primer set of the plurality of primer sets comprises:

a forward oligonucleotide primer and a reverse oligonucleotide primer suitable for amplifying target fragments from the nucleic acid molecules, wherein each target fragment comprises the microsatellite sequence locus corresponding to the primer set and an adjacent reference region upstream or downstream to the microsatellite sequence locus;

a plurality of probe pairs corresponding to the plurality of microsatellite sequence loci, wherein each probe pair of the plurality of probe pairs comprises:

a drop-off probe comprising a drop-off label and an oligonucleotide drop-off sequence complementary to a wildtype sequence of a microsatellite sequence locus corresponding to the respective probe pair, a reference probe comprising a reference label and an oligonucleotide reference sequence complementary to a wildtype sequence of the reference region corresponding to the respective probe pair, wherein a reference label and a drop-off label of each probe pair of the plurality of probe pairs are detectable via different detection channels; wherein reference labels of the plurality of probe pairs are detectable via different detection channels with respect to each other; wherein drop-off labels of the plurality of probe pairs are detectable via different detection channels with respect to each other; wherein at least one reference label of the plurality of probe pairs and at least one drop-off label of the plurality of probe pairs are detectable via the same detection channel;

wherein the method comprises amplifying the target fragments in the plurality of partitions; and detecting hybridization of reference probes and drop-off probes of the plurality of probe pairs to amplicons of the target fragments in the plurality of partitions, thereby providing quantification of mutations at the plurality of microsatellite sequence loci in the sample. In some embodiments, the set of reference labels of the plurality of probe pairs and the set of drop-off labels of the plurality of probe pairs are circular permutations with respect to each other. In some embodiments, the methods are carried out in a dPCR format, such as DROPLET DIGITAL™ PCR or CRYSTAL DIGITAL™ PCR. In some embodiments, the nucleic acid molecules are genomic DNA, such as chromosomal DNA, genomic tumor DNA, or circulating tumor DNA.

Microsatellite instability (MSI) is the condition of genetic hypermutability (predisposition to mutation) that results from impaired DNA mismatch repair (MMR). The presence of MSI represents phenotypic evidence that MMR is not functioning normally. Mutations at microsatellite locus commonly typically include deletion(s), addition(s) or substitution of at least one repeat unit at a microsatellite locus. Typically, MSI results in a change in length at a microsatellite locus, due to addition(s) or most frequently deletion(s).

Many microsatellite sequence loci are known. The ability to detect microsatellite expansion mutations at multiple microsatellite sequence loci in a single assay increases the sensitivity of MSI detection. Exemplary microsatellite sequence loci have been described in Bacher et al., 2004 Disease Markers 20, 237-250, as well as in Hause et al., 2016 Nat Medicine November 22(11):1 342-1 350). In some embodiments, the target microsatellite sequence loci (or microsatellite markers) are selected from microsatellites found to be highly associated with MSI positive tumors, based on their frequency of instability in colon, endometrial, rectal and stomach adenocarcinomas. In some embodiments, the target microsatellite sequence loci are located in regions frequently amplified in tumors (e.g. chr8q region of the human genome). In some embodiments, the target microsatellite sequence loci are selected from the group comprising BAT-25, BAT-26, BAT-34c4, BAT-40, NR21, NR24, MONO-27, D2S1 23, D5S346, D 17S250, ACVR2A, DEFB105A, DEFB105B, RNF43, DOCK3, GTF2IP1, LOC100093631, PIP5K1A, MSH3, TRIM43B, PPFIA1 and TDRD1. In some embodiments, the target microsatellite sequence loci are selected among the Bethesda panel, which comprises BAT-25, BAT-26, D2S123, D5S346 and D17S250.

Mononucleotide repeat loci have been shown to be very susceptible to alteration in tumors with dysfunctional DNA mismatch repair systems (Parsons, 1995 supra), making such loci particularly useful for the detection of cancer and other diseases associated with dysfunctional DNA mismatch repair systems, such that mononucleotides MSI markers may be preferred.

In some embodiments, the microsatellite sequence loci are short microsatellite sequences (typically comprising 8 to 30, 8 to 25, 8 to 20, 8 to 15, or 8 to 12 nucleotides) such as the target microsatellite sequence locus exemplified in the group consisting of D2S123, D5S346, D17S250, ACVR2A, DEFB105A, DEFB105B, RNF43, DOCK3, GTF2IP1, LOC100093631, PIP5K1A, MSH3, TRIM43B, PPFIA1 and TDRD1.

The MSI detection methods can be routinely performed on biological samples (or nucleic acid samples derived from biological samples), such as blood samples, plasma samples, urine, or fecal samples. Mutant allele frequency determined using any one of the methods described herein can be compared with a control mutated allele frequency obtained from a control DNA sample. The control DNA sample may be a wildtype sample or a sample of a cell line derived from a subject diagnosed with a MSI positive tumor or with a disease associated with a mutation in the DNA mismatch repair, at a prior time point, during the time-course of the disease and/or during the time course of the treatment.

In some embodiments, a cancer (or a tumor) associated with MSI is also named a MSI positive cancer (or a MSI positive tumor) and relates to a cancer (or tumor) wherein the genomic tumor DNA exhibits at least one mutation in a microsatellite sequence locus. MSI has thus been associated with a great variety of cancers such as but not limited to colorectal cancers, gastric cancer, endometrium cancer, ovarian cancer, urinary tract cancer, brain cancer, and breast cancer. MSI is most prevalent as the consequence of colon cancers. Additionally, MSI is associated with the Constitutional mismatch repair deficiency syndrome (CMMRD syndrome) or the Lynch syndrome. Therefore, detection of mutant sequences at one or more microsatellite sequence loci according to the methods described herein can be used in the diagnostic of cancers, which are associated with impaired DNA mismatch repair, e.g., MSI positive cancers, or in the diagnostic of familial tumor predisposition in an individual.

The MSI phenotype of the cancer (i.e. positive or negative) has important implications in cancer prognosis and rational planning of treatment (Boland and Goel, Gastroenterology 2010). Therefore, even in the case of cancers with low MSI positive prevalence, it remains of high relevance to identify whether the patient is suffering from a MSI positive tumor or a MSI negative tumor. The method of the present invention can be used in the prognosis of various cancers. Identification of a positive MSI cancer is generally associated with a better prognosis.

The present application also relates to a method for predicting the efficacy of a treatment. Reports have shown for example that colorectal cancer patients with MMR deficiency have better responses to immunotherapy by PD-1 immune checkpoint blockade and show improved progression-free survival. Therefore, identification of patients suffering from cancer associated with MSI (i.e. MSI positive cancer or tumor) is of high clinical relevance for selection of an appropriate therapeutic strategy. In some embodiments, the treatment is immunotherapy. Immunotherapy includes but is not limited to immune checkpoint modulators (i.e. inhibitors and/or agonists), monoclonal antibodies, and cancer vaccines. In some embodiments, the treatment comprises administration of immune checkpoint modulators such as anti-PD-1 and/or anti-PDL-1 inhibitors. In some embodiments, immunotherapy is administered to the subject if mutant sequences at one or more microsatellite sequence loci in nucleic acid molecules from a sample is detected.

The methods for detecting microsatellite instability may also be used for monitoring of an individual diagnosed with a tumor associated with impaired DNA mismatch repair. In some embodiments, said monitoring is performed during the time course of the treatment. The method may also be used for the monitoring of cancer relapse in a subject having suffered from a tumor associated with impaired DNA mismatch repair. In an individual having suffered from a tumor associated with impaired DNA mismatch repair, detection of microsatellite instability in circulating tumor DNA may be indicative of a relapse.

Detection of Genome-Editing

The methods described herein are useful for detecting unmodified (i.e., wildtype) and mutant (e.g., NHEJ or HDR-edited) sequences at a plurality of target genomic regions in a cell that is subject to site-specific genome editing.

In some embodiments, there is provided a method for quantification of unmodified and/or NHEJ-edited sequences a plurality of target regions in a sample comprising nucleic acid molecules from cells, wherein the cells have been contacted with a site-specific genome-editing reagent, wherein the site-specific genome-editing reagent is configured to cleave target sites in the plurality of target regions, wherein the nucleic acid molecules are distributed among a plurality of partitions of the sample, and wherein substantially all partitions (e.g., all partitions) each comprises:

an NHEJ drop-off probe comprising an NHEJ drop-off label and an oligonucleotide drop-off sequence complementary to a wildtype sequence of the target region corresponding to the respective probe set, a reference probe comprising a reference label and an oligonucleotide reference sequence complementary to a wildtype sequence at an adjacent reference region upstream or downstream to the target region corresponding to the respective probe set, wherein an NHEJ drop-off label, and a reference label of each probe set of the plurality of probe sets are detectable via different detection channels; wherein NHEJ drop-off labels of the plurality of probe sets are detectable via different detection channels with respect to each other; wherein reference labels of the plurality of probe sets are detectable via different detection channels with respect to each other; wherein at least one reference label of the plurality of probe pairs and at least one NHEJ drop-off label of the plurality of probe pairs are detectable via the same detection channel;

wherein the method comprises detecting hybridization of reference probes of the plurality of probe sets to nucleic acid molecules or amplicons thereof comprising wildtype sequences at the reference regions in the plurality of partitions; and detecting hybridization of NHEJ drop-off probes of the plurality of probe sets to nucleic acid molecules or amplicons thereof comprising wildtype sequences at the target regions in the plurality of partitions; thereby providing quantification of unmodified and/or NHEJ-edited sequences at the plurality of target regions in the sample. In some embodiments, the set of reference labels of the plurality of probe pairs and the set of NHEJ drop-off labels of the plurality of probe pairs are circular permutations with respect to each other.

In some embodiments, there is provided a method for quantification of unmodified, homology directed repair (HDR)-edited, and/or non-homologous end joining (NHEJ)-edited sequences at a plurality of target regions in a sample comprising nucleic acid molecules from cells, wherein the cells have been contacted with a site-specific genome-editing reagent and HDR template nucleic acids comprising HDR replacement sequences, wherein the site-specific genome-editing reagent is configured to cleave target sites in the plurality of target regions, wherein the nucleic acid molecules are distributed among a plurality of partitions of the sample, and wherein substantially all partitions (e.g., all partitions) each comprises: a plurality of probe sets corresponding to the plurality of target regions, wherein each probe set of the plurality of probe sets comprises:

a HDR probe comprising a HDR label and an oligonucleotide HDR sequence complementary to a HDR replacement sequence inserted at a target region corresponding to the respective probe set, an NHEJ drop-off probe comprising an NHEJ drop-off label and an oligonucleotide drop-off sequence complementary to a wildtype sequence of the target region corresponding to the respective probe set, and wherein the drop-off sequence does not hybridize to NHEJ-edited mutant sequences at the target region corresponding to the respective probe set, a reference probe comprising a reference label and an oligonucleotide reference sequence complementary to a wildtype sequence at an adjacent reference region upstream or downstream to the target region corresponding to the respective probe set, wherein a HDR label, an NHEJ drop-off label, and a reference label of each probe set of the plurality of probe sets are detectable via different detection channels; wherein HDR labels of the plurality of probe sets are detectable via different detection channels with respect to each other; wherein NHEJ drop-off labels of the plurality of probe sets are detectable via different detection channels with respect to each other; wherein reference labels of the plurality of probe sets are detectable via different detection channels with respect to each other; wherein at least one reference label of the plurality of probe sets and at least one NHEJ drop-off label of the plurality of probe sets are detectable via the same detection channel, and/or at least one reference label of the plurality of probe sets and at least one HDR label of the plurality of probe sets are detectable via the same detection channel;

wherein the method comprises detecting hybridization of reference probes of the plurality of probe sets to nucleic acid molecules or amplicons thereof comprising wildtype sequences at the reference regions in the plurality of partitions; detecting hybridization of HDR probes of the plurality of probe sets to nucleic acid molecules or amplicons thereof comprising the HDR replacement sequences at the target regions in the plurality of partitions; and detecting hybridization of NHEJ drop-off probes of the plurality of probe sets to nucleic acid molecules or amplicons thereof comprising wildtype sequences at the target regions in the plurality of partitions; thereby providing quantification of unmodified, HDR-edited, and/or NHEJ-edited sequences at the plurality of target regions in the sample. In some embodiments, the set of the reference labels of the plurality of probe sets, the set of the HDR labels of the plurality of probe sets, and the set of the NHEJ drop-off labels of the plurality of probe sets are permutations (e.g., as shown in FIG. 6B) with respect to each other.

In some embodiments, there is provided a method for quantification of unmodified, homology directed repair (HDR)-edited, and/or non-homologous end joining (NHEJ)-edited sequences at (R−1) number of target regions in a sample comprising nucleic acid molecules from cells, wherein the cells have been contacted with a site-specific genome-editing reagent and HDR template nucleic acids comprising HDR replacement sequences, wherein the site-specific genome-editing reagent is configured to cleave target sites in the plurality of target regions, wherein the nucleic acid molecules are distributed among a plurality of partitions of the sample, and wherein substantially all partitions (e.g., all partitions) each comprises (R−1) number of probe triplets corresponding to the (R−1) number of target regions, wherein a first probe triplet of the plurality of probe triplets comprises:

a first reference probe comprising a first reference sequence ($m_1$) and a first reference label detectable via a first detection channel ($X_1$);

a first NHEJ drop-off probe comprising a first NHEJ drop-off sequence ($r_1$) and a first NHEJ drop-off label detectable via a second detection channel ($X_2$); and a first HDR probe comprising a first HDR sequence ($w_1$) and a first HDR label detectable via a third channel ($X_3$);

wherein a second probe triplet of the plurality of probe triplets comprises:

a second reference probe comprising a second reference sequence ($m_2$) and a second reference label detectable via the second detection channel ($X_2$);

a second NHEJ drop-off probe comprising a second drop-off sequence ($r_2$) and a second NHEJ drop-off label detectable via the third detection channel ($X_3$); and a second HDR probe comprising a second HDR sequence ($w_2$) and a second HDR label detectable via a fourth detection channel ($X_4$);

wherein, if (e.g., when) R is strictly larger than 3, an i-th probe triplet (2<i<R−1) of the plurality of probe triplets comprises:

an i-th reference probe comprising an i-th reference sequence ($m_i$) and an i-th reference label detectable via an i-th detection channel ($X_i$);

an i-th NHEJ drop-off probe comprising an i-th drop-off sequence (r) and an i-th NHEJ drop-off label detectable via an (i+1)-th detection channel ($X_{i+1}$); and an i-th HDR probe comprising an i-th HDR sequence ($w_i$) and an i-th HDR label detectable via an (i+2)-th detection channel ($X_{i+2}$);

wherein, if (e.g., when) R is strictly larger than 3, a (R−1)-th probe triplet of the plurality of probe triplets comprises:

a (R−1)-th reference probe comprising a (R−1)-th reference sequence ($m_{R-1}$) and a R-th reference label detectable via a R-th detection channel ($X_R$);

a (R−1)-th NHEJ drop-off probe comprising a (R−1)-th drop-off sequence ($r_{R-1}$) and a (R−1)-th NHEJ drop-off label detectable via a (R−1)-th detection channel ($X_{R-1}$); and a (R−1)-th HDR probe comprising a (R−1)-th HDR sequence ($w_R$-1) and a (R−1)-th HDR label detectable via the first detection channel ($X_1$);

wherein the NHEJ drop-off sequence of each probe triplet is complementary to a wildtype sequence at a target region corresponding to the respective probe triplet; wherein the reference sequence of each probe triplet is complementary to a wildtype sequence at an adjacent reference region upstream or downstream to the target region corresponding to the respective probe triplet; wherein the HDR sequence of each probe triplet is complementary to a HDR replacement sequence at the target region corresponding to the respective probe pair; wherein the detection channels $X_1$-$X_R$ are different from each other;

wherein the method comprises: detecting hybridization of reference probes of the plurality of probe triplets to nucleic acid molecules or amplicons thereof comprising wildtype sequences at the reference regions in the plurality of partitions via each of the detection channels $X_1$-$X_R$; detecting hybridization of HDR probes of the plurality of probe triplets to nucleic acid molecules or amplicons thereof comprising the HDR replacement sequences at the target regions in the plurality of partitions via each of the detection channels $X_1$-$X_R$; and detecting hybridization of NHEJ drop-off probes of the plurality of probe triplets to nucleic acid molecules or amplicons thereof comprising wildtype sequences at the target regions in the plurality of partitions via each of the detection channels $X_1$-$X_R$; thereby providing quantification of unmodified, HDR-edited, and/or NHEJ-edited sequences at the plurality of target regions in the sample.

In some embodiments, the method described herein is carried out in a dPCR, such as CRYSTAL DIGITAL™ PCR assay. In some embodiments, the site-specific genome-editing reagent comprises a Cas nuclease, a TALEN, or a Zinc-finger nuclease. In some embodiments, the method further comprises contacting the cells with the site-specific genome-editing reagent.

In some embodiments, there is provided a method for identifying an optimized condition for genome editing of a cell, comprising: a) performing site specific genome editing of a plurality of cells under a first set of conditions to provide first sample comprising nucleic acid from genome-edited cells; b) performing site specific genome editing of a plurality of cells under a second set of conditions to provide a second sample comprising nucleic acid from genome-edited cells; c) using any one of the methods described in the "Detection of genome-editing" section to quantify NHEJ-edited sequences and/or HDR-edited sequences at a plurality of target genomic regions in the first and second samples to determine a genome editing efficiency for the first and second set of conditions; and d) comparing the genome editing efficiency of the first and second set of conditions, thereby identifying an optimized set of conditions that provide a higher genome editing efficiency. In some embodiments, different set of conditions comprise different site-specific genome editing reagent (e.g., different Cas and/or different gRNA), different target genomic loci, different delivery method, and/or different concentrations of site-specific genome editing reagents. In some embodiments, editing is performed under a third, fourth, fifth, sixth, etc. number of conditions. In some cases, the higher efficiency of HDR editing is identified as the optimized condition for genome editing. In some cases, the higher efficiency of NHEJ editing is identified as the optimized condition for genome editing. In some cases, the higher ratio of the efficiency of NHEJ to HDR editing is identified as the optimized condition for genome editing. In some cases, the higher ratio of the efficiency of HDR to NHEJ editing is identified as the optimized condition for genome editing.

Figure 6A:
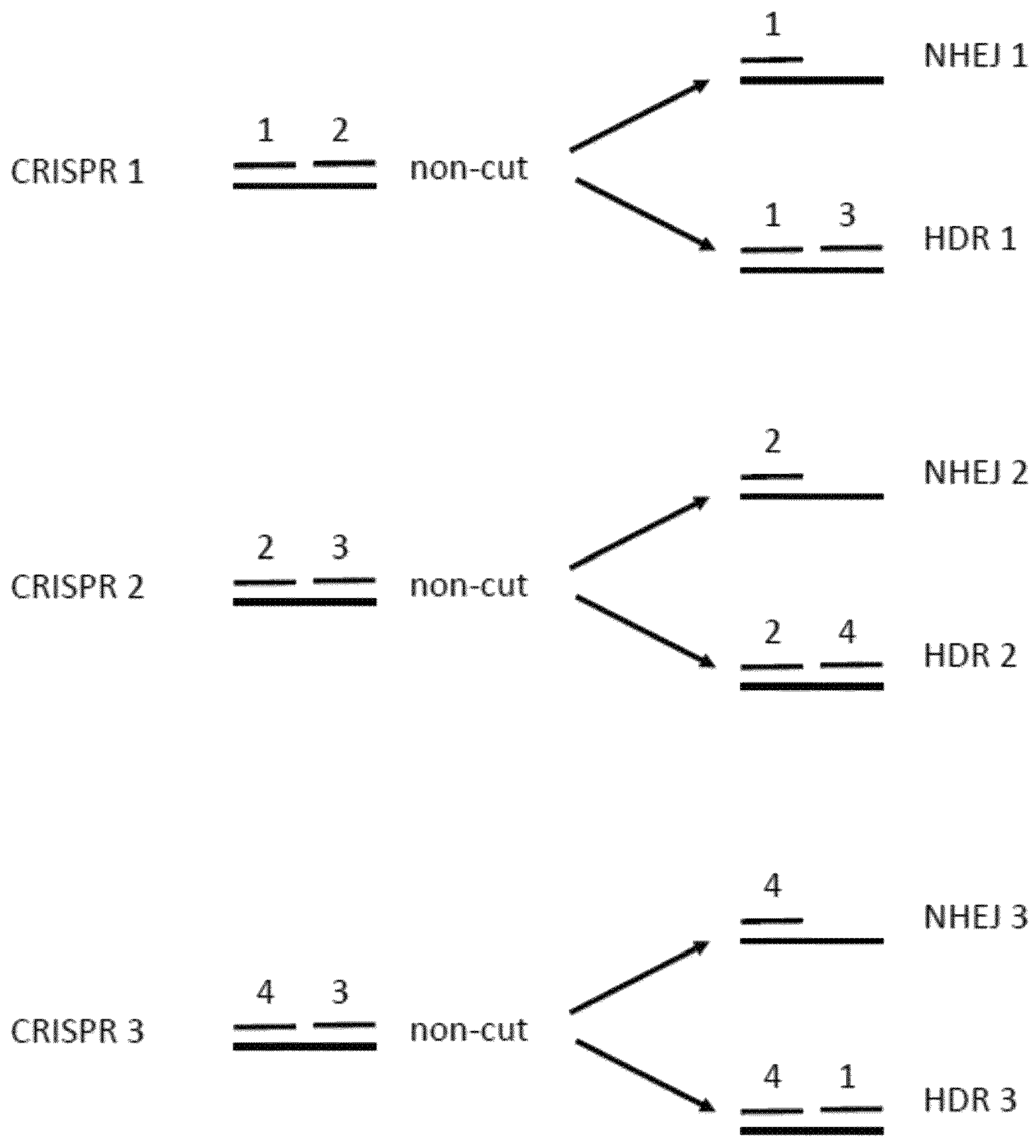
FIG. 6A shows a schematic diagram illustrating a multiplex dPCR assay for simultaneous detection of unmodified, NHEJ-edited and HDR-edited sequences at three target genomic loci in cells subject to CRISPR/Cas genome editing using four detection channels. Each set of CRISPR-Cas genome editing products is detected via a triplet of fluorescently labeled probes. Different numbers indicate different fluorophores.
Figure 6B:
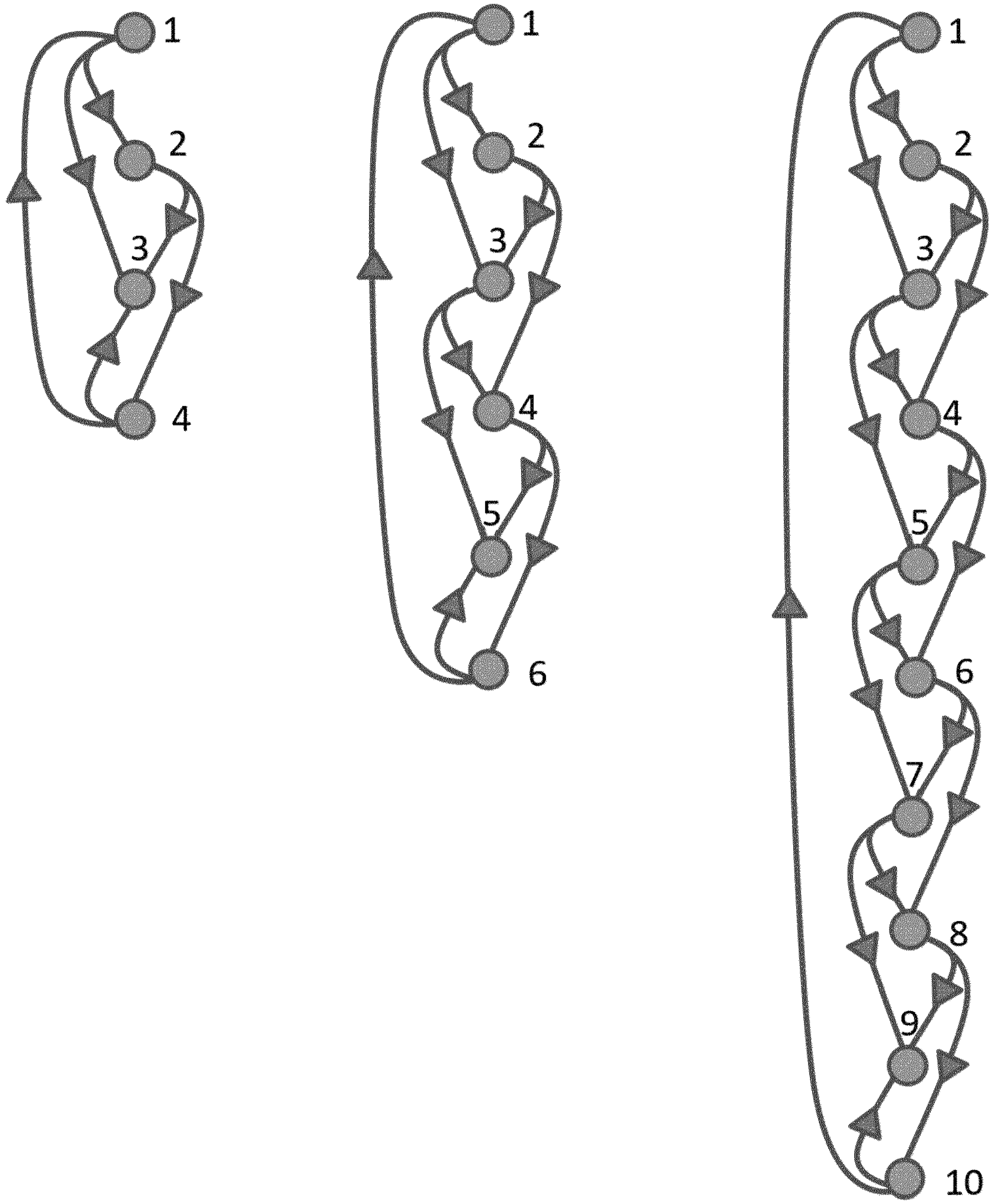
FIG. 6B shows permutation of four, six, or ten labels (e.g., fluorophores) in three probe triplets, five probe triplets, or nine probe triplets for detecting unmodified, NHEJ-edited and HDR-edited sequences at three, five, or nine target genomic loci, respectively. Each enclosed figure with three vertices (represented by a grey circle and marked with a number) corresponds to a probe triplet with probes having three different labels. The arrows show the order from the first label to the second label in each probe triplet. For example, in a set of three probe triplets, the first probe triplet has probes labeled with label 1, label 2 and label 3 respectively; the second probe triplet has probes labeled with label 2, label 3 and label 4 respectively; and the third probe triplet has probes labeled with label 4, label 3 and label 1 respectively. In a set of five probe triplets, the first probe triplet has probes labeled with label 1, label 2 and label 3 respectively; the second probe triplet has probes labeled with label 2, label 3 and label 4 respectively; the third probe triplet has probes labeled with label 3, label 4 and label 5, respectively; the fourth probe triplet has probes labeled with label 4, label 5 and label 6, respectively; and the fifth probe triplet has probes labeled with label 6, label 5 and label 1, respectively. In a set of nine probe triplets, the first probe triplet has probes labeled with label 1, label 2 and label 3 respectively; the second probe triplet has probes labeled with label 2, label 3 and label 4 respectively; the third probe triplet has probes labeled with label 3, label 4 and label 5, respectively; the fourth probe triplet has probes labeled with label 4, label 5 and label 6, respectively; the fifth probe triplet has probes labeled with label 5, label 6 and label 7, respectively; the sixth probe triplet has probes labeled with label 6, label 7 and label 8, respectively; the seventh probe triplet has probes labeled with label 7, label 8 and label 9, respectively; the eighth probe triplet has probes labeled with label 8, label 9 and label 10, respectively; the ninth probe triplet has probes labeled with label 10, label 9 and label 1, respectively.

FIG. 6A illustrates an exemplary method for detecting unmodified, NHEJ-edited, and HDR-edited sequences at three target genomic loci in cells subject to site-specific genome editing using CRISPR/Cas. The reference labels in the CRISPR 1 probe triplet, CRISPR 2 probe triplet, and CRISPR 3 probe triplet have fluorophores 1, 2 and 4 respectively, and they hybridize to all amplicons in a dPCR assay. The NHEJ drop-off probes in the CRISPR 1 probe triplet, CRISPR 2 probe triplet, and CRISPR 3 probe triplet have fluorophores 2, 3 and 3 respectively, and they do not hybridize to NHEJ-edited sequences at the corresponding target genomic loci. The HDR probes in the CRISPR 1 probe triplet, CRISPR 2 probe triplet, and CRISPR 3 probe triplet have fluorophores 3, 4 and 1 respectively, and they hybridize to the HDR replacement sequences at the corresponding target genomic loci. Each genetic species has a unique fluorescence signal signature. A total of four detection channels are required to detect all nine genetic species in the sample. Also refer to "Embodiment Employing (R−1) Number of Probe Triplets" for exemplary methods for detecting unmodified (including non-cut sequences), NHEJ-edited, and HDR-edited sequences at (R−1) number of target genomic loci in cells subject to site-specific genome editing.

FIG. 6B shows permutation of four, six, or ten labels in three sets of probe triplets, five sets of probe triplets, or nine sets of probe triplets respectively.

The methods can be used to determine efficacy of genome editing at a plurality of genomic loci in a sample, for identifying optimal conditions for genome editing, or to guide enrichment of populations of cells for genome editing products (e.g., by sub-selection). For example, genome-editing conditions can be optimized to decrease, or increase, the type or amount of NHEJ mutations in comparison to HDR mutations at a plurality of target genomic regions. As another example, genome editing conditions can be optimized to increase the efficiency of editing, thus allowing the use of a low concentration or activity of genome editing reagent without unduly reducing the amount of editing achieved. Usage of a low concentration or activity of genome editing reagent may be useful for reducing off-target editing events.

In some embodiments, the sample is a sample of cells, a sample of genomes extracted from a sample of cells, or fragments thereof. The cells, or genomes extracted from cells, can be contacted with site-specific genome-editing reagents under conditions suitable for the genome editing of a plurality of target genomic regions. In some cases, the cells or genomes are contacted with a plurality of HDR replacement nucleic acid to introduce a pre-determined HDR mutation into the genome. The genome editing reagents can contain one or more nucleases that introduce double-strand breaks into a DNA.

Site-specific genome editing reagents are known in the art. Generally, such reagents target a genomic region and induce a double stranded cut into the DNA within the target region. Repair of the cutting can proceed via two alternative pathways. In non-homologous end joining (NHEJ), the cut ends of a DNA strand are directly ligated without the need for a homologous template nucleic acid. NHEJ can lead to the addition, the deletion, substitution, or a combination thereof, of one or more nucleotides at the repair site. In homology directed repair, the cut ends of a DNA strand are repaired by polymerization from a homologous template nucleic acid. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid can be introduced to obtain a specific HDR mutation.

As another example, a genome-editing reagent containing an obligate heterodimer nuclease can be used to reduce off-target mutations. Such a genome-editing reagent can be designed to only generate double stranded breaks when obligate heterodimer nucleases are formed at the target genomic region by site-specific recruitment of each monomer component to an adjacent target half-site. Exemplary obligate heterodimer nucleases include, but are not limited to, those described in U.S. patent application Ser. No. 13/812,857. The targeting function can be provided by a nuclease defective Cas9 (dCas9) and appropriate guide RNAs, a pair of TALENs, or any other nucleic acid sequence specific targeting method.

The NHEJ drop-off probes are designed according to the type of the site-specific genome-editing reagent used. For example, if the genome-editing reagent is a Cas9 nuclease and a guide RNA, cut sites are generally 3-5 base pairs directly upstream of a protospacer adjacent motif (PAM). The PAM generally consists of the sequence NGG, although some other PAM sequences can be utilized, such as NGA or NAG. Thus, cut sites can be, for instance, either [5'-20 nt target-NGG-3'] or [5'-CCN-20 nt target-3']. When the target site is 5'-20 nt target-NGG, the predicted cut-site is approximately 3-5 base pairs upstream of the 5' end of the NGG PAM. In such cases, the NHEJ drop-off probe can be designed to hybridize to a subregion containing this predicted cut-site.

As another example, the genome editing reagent can be a pair of guide RNAs targeted to sites adjacent to PAM sequences on opposite strands of the target genomic region, each guide RNA complexed with a nuclease defective, or dead, Cas9 nuclease (dCas9) that is fused to monomer of an obligate heterodimer of a type IIS restriction nuclease (e.g., FokI). In such cases, the cut site is generally from 12 to 21 base pairs between the adjacent PAM sequences on the opposite strands of the targeted genomic region. Thus, the NHEJ drop-off probe can be designed to hybridize to a sub-region containing a predicted cut site from 12 to 21 base pairs between the adjacent PAM sequences. Similar rules can be utilized to design NHEJ drop-off probes for other genome editing reagents.

In some embodiments, the NHEJ drop-off probe is sensitive to (i.e., detects) both HDR mutations and NHEJ mutations. For example, the genome-editing reagent can include an exogenous HDR template nucleic acid. The template nucleic acid can be used as a template to repair a region encompassing, or within, the double strand breaks introduced by the genome-editing reagent. Thus, any mutations present in the HDR template nucleic acid relative to the wildtype genome will be introduced. When the HDR site is proximal to, or at, the target cut site, the NHEJ drop-off probe can hybridize to both potential NHEJ edit sites and the potential HDR edit site. In such cases, the NHEJ drop-off probe can detect both HDR mutations and NHEJ mutations by failing to hybridize to target genomic regions containing such mutations. In some embodiments, NHEJ mutations and HDR mutations are distinguished by including an HDR probe in each probe set. If the NHEJ drop-off probe detects a mutation (HDR or NHEJ), and the HDR probe does not, then the mutation can be classified as NHEJ. Conversely, if the NHEJ probe detects a mutation and the HDR probe also detects a mutation, then the mutation can be classified as HDR.

In some embodiments, the site-specific genome-editing reagent induces double-strand breaks in DNA within the cells. In some embodiments, the site-specific genome-editing reagent comprises a zinc finger nuclease (ZFN), a transcription activator-like effector nuclease (TALEN), a Cas protein, a Cre recombinase, a Hin recombinase, or a Flp recombinase. In some embodiments, the site-specific genome-editing reagent comprises a fusion protein that combine homing endonucleases with the modular DNA binding domains of TALENs (megaTAL). For example, megaTAL may be delivered as a protein or alternatively, an mRNA encoding a megaTAL protein is delivered to the cells. In some embodiments, the site-specific genome-editing reagent comprises one or more RNA molecules, such as a sgRNA, a crRNA, or a crRNA and a tracrRNA. In some embodiments, the site-specific genome-editing reagent is a ribonucleoprotein (RNP), and the RNP comprises a Cas protein and a sgRNA or a crRNA and a tracrRNA.

Non-limiting descriptions relating to gene editing (including HDR repair templates) using the CRISPR-Cas system are discussed in Ran et al. (2013) Nat Protoc. 2013 November; 8(11): 2281-2308, the entire content of which is incorporated herein by reference. Embodiments involving repair templates are not limited to those comprising the CRISPR-Cas system. Various aspects of the CRISPR-Cas system are known in the art. Non-limiting aspects of this system are described, e.g., in U.S. Pat. No. 9,023,649, issued May 5, 2015; U.S. Pat. No. 9,074,199, issued Jul. 7, 2015; U.S. Pat. No. 8,697,359, issued Apr. 15, 2014; U.S. Pat. No. 8,932,814, issued Jan. 13, 2015; PCT International Patent Application Publication No. WO 2015/071474, published Aug. 27, 2015; Cho et al., (2013) Nature Biotechnology Vol 3 1 No 3 pp 230-232 (including supplementary information); and Jinek et al., (2012) Science Vol 337 No 6096 pp 816-821, the entire contents of each of which are incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas1O, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx1O, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2 and in the NCBI database as under accession number Q99ZW2.1. UniProt database accession numbers A0A0G4DEU5 and CDJ55032 provide another example of a Cas9 protein amino acid sequence. Another non-limiting example is a *Streptococcus thermophilus* Cas9 protein, the amino acid sequence of which may be found in the UniProt database under accession number Q03JI6.1. In some embodiments, the unmodified CRISPR enzyme has DNA cleavage activity, such as Cas9. In certain embodiments, the CRISPR enzyme is Cas9, and may be Cas9 from *S. pyogenes* or *S. pneumoniae*. In various embodiments, the CRISPR enzyme directs cleavage of both strands at the location of a target sequence.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some embodiments, the degree of complementarity is 100%.

Gene editing nucleases, including ZFN have been described in Bhakta, M. et al., Genome Research 23:530-538; 2013, and Beerli, R. et al., Proc. Natl. Acad. Sci v. 95 pp 14628-14633; 1998, TAL has been described in Cermak, T. et al., Nucleic Acids Research 2011, v. 39, no. 12, Miller, J. et al., Nature Biotechnology vol. 29 no. 2; 2011, Christian, M. et al., Genetics 186:757-761; 2010, Deng, D. et al, Science 2012: v. 335 p. 720, and Boch, J. et al., Science 2009: v. 326 p. 1509, the entire content of each of which is incorporated herein by reference.

Additionally, Cre has been described in Chevalier, B. et al., Nucleic Acids Research 2001, v. 29 no. 18, the entire content of which is incorporated herein by reference. MegaTal has been described in Sather, B. et al Sci Transl Med 7 (307) 2015, Ibarra, G. et al., Molecular Therapy-Nucleic Acids (2016) 5,e352, Osborn, M. et al., Molecular Therapy v. 24 no. 3, 570-581 (2016); Wang, Y. et al., Nucleic Acid Research 2014; v. 42, 6463-6475; and Gaj, T. et al., Cold Spring Harbor Perspectives in Biology 2015, each of which is incorporated herein by reference.

In some embodiments, the cells are primary cells, cell line, or immortalized cells. For example, the cells may include mesenchymal stem cells, lung cells, neuronal cells, fibroblasts, human umbilical vein (HUVEC) cells, and human embryonic kidney (HEK) cells, primary or immortalized hematopoietic stem cell (HSC), T cells, natural killer (NK) cells, cytokine-induced killer (CIK) cells, human cord blood CD34+ cells, and B cells. Non-limiting examples of T cells may include CD8+ or CD4+ T cells. In some aspects, the CD8+ subpopulation of the CD3+ T cells are used. CD8+ T cells may be purified from the PBMC population by positive isolation using anti-CD8 beads. In some embodiments, primary NK cells are isolated from PBMCs, or NK cell lines, e.g., NK92 may be used. Cell types also include cells that have previously been modified for example T cells, NK cells and MSC to enhance their therapeutic efficacy. For example: T cells or NK cells that express chimeric antigen receptors (CAR T cells, CAR NK cells, respectively); T cells that express modified T cell receptor (TCR); or engineered MSCs.

IV. Systems, Kits and Articles of Manufacture

Also provided are apparatus, devices, systems, compositions, kits, and articles of manufacture for any one of the methods of quantification, multiplex dPCR assays (e.g., multiplex drop-off dPCR assays), methods of treatment, and methods of diagnosis described herein.

Figure 10:
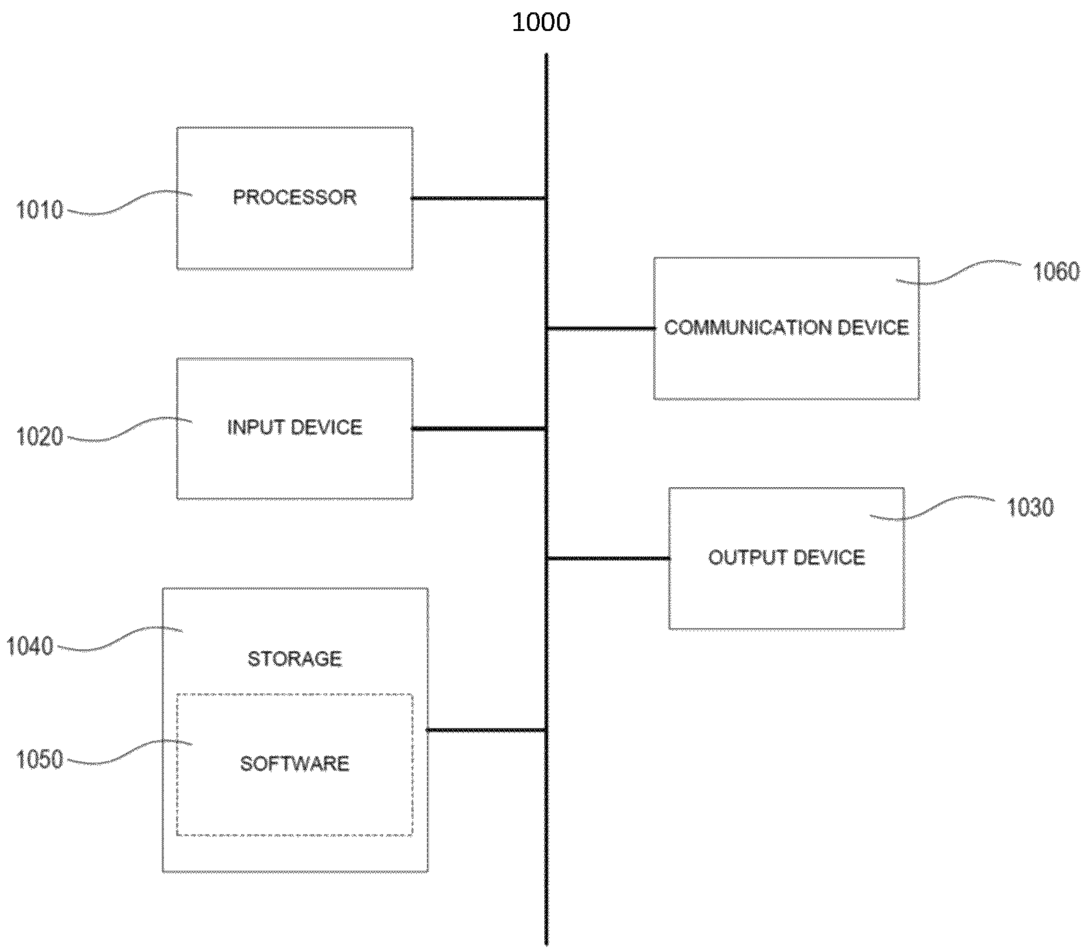
FIG. 10 depicts an exemplary electronic device in accordance with some embodiments.

FIG. 10 illustrates an example of a computing device in accordance with one embodiment. Device 1000 can be a host computer connected to a network. Device 1000 can be a client computer or a server. As shown in FIG. 10, Device 1000 can be any suitable type of microprocessor-based device, such as a personal computer, workstation, server or handheld computing device (portable electronic device) such as a phone or tablet. The device can include, for example, one or more of processor 1010, input device 1020, output device 1030, storage 1040, and communication device 1060. Input device 1020 and output device 1030 can generally correspond to components of Device 1000 described above, and can either be connectable or integrated with the computer.

Input device 1020 can be any suitable device that provides input, such as a touch screen, keyboard or keypad, mouse, or voice-recognition device. Output device 1030 can be any suitable device that provides output, such as a touch screen, haptics device, or speaker.

Storage 1040 can be any suitable device that provides storage, such as an electrical, magnetic or optical memory including a RAM, cache, hard drive, or removable storage disk. Communication device 1060 can include any suitable device capable of transmitting and receiving signals over a network, such as a network interface chip or device. The components of the computer can be connected in any suitable manner, such as via a physical bus or wirelessly.

Software 1050, which can be stored in storage 1040 and executed by processor 1010, can include, for example, the programming that embodies the functionality of the present disclosure (e.g., as embodied in the devices as described above).

Software 1050 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1040, that can contain or store programming for use by or in connection with an instruction execution system, apparatus, or device.

Software 1050 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 1000 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1000 can implement any operating system suitable for operating on the network. Software 1050 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

The exemplary embodiments and examples below are intended to be purely exemplary of the invention and should therefore not be considered to limit the invention in any way. The following exemplary embodiments, examples and detailed description are offered by way of illustration and not by way of limitation.

Exemplary Embodiments

The invention provides the following embodiments:

1. A method for quantification of wildtype and/or mutant sequences at a plurality of target regions in a sample comprising nucleic acid molecules,
   - wherein the nucleic acid molecules are distributed among a plurality of partitions of the sample, and
   - wherein substantially all partitions each comprises:
     - a plurality of probe sets corresponding to the plurality of target regions,
     - wherein each probe set of the plurality of probe sets comprises:
       - a drop-off probe comprising a drop-off label and an oligonucleotide drop-off sequence complementary to a wildtype sequence at a target region corresponding to the respective probe set;
       - a reference probe comprising a reference label and an oligonucleotide reference sequence complementary to a wildtype sequence at an adjacent reference region upstream or downstream to the target region corresponding to the respective probe set;

wherein a reference label and a drop-off label of each probe set of the plurality of probe sets are detectable via different detection channels;

wherein reference labels of the plurality of probe sets are detectable via different detection channels with respect to each other;

wherein drop-off labels of the plurality of probe sets are detectable via different detection channels with respect to each other;

wherein at least one reference label of the plurality of probe sets and at least one drop-off label of the plurality of probe sets are detectable via the same detection channel;

wherein the method comprises:

detecting hybridization of reference probes of the plurality of probe sets to nucleic acid molecules or amplicons thereof comprising wildtype sequences at the reference regions in the plurality of partitions; and detecting hybridization of drop-off probes of the plurality of probe sets to nucleic acid molecules or amplicons thereof comprising wildtype sequences at the target regions in the plurality of partitions;

thereby providing quantification of wildtype and/or mutants sequences at the plurality of target regions in the sample.

2. The method of embodiment 1, wherein each probe set of the plurality of probe sets is a probe pair, and wherein the total number of detection channels is fewer than two times the total number of probe sets.

3. The method of embodiment 2, wherein the total number of detection channels is equal to the total number of probe sets.

4. The method of embodiment 3, wherein the plurality of probe sets are R number of probe pairs, wherein a first probe pair of the R number of probe pairs comprises:

a first reference probe comprising a first reference sequence ($r_1$) and a first reference label detectable via a first detection channel ($X_1$), and a first drop-off probe comprising a first drop-off sequence ($w_1$) and a first drop-off label detectable via a second detection channel ($X_2$);

wherein a second probe pair of the R number of probe pairs comprises:

a second reference probe comprising a second reference sequence ($r_2$) and a second reference label detectable via the second detection channel ($X_2$), and a second drop-off probe comprising a second drop-off sequence ($w_2$) and a second drop-off label detectable via a third detection channel ($X_3$);

wherein, if (e.g., when) R is strictly larger than 3, an i-th probe pair (2<i<R) of the R number of probe pairs comprises:

an i-th reference probe comprising an i-th reference sequence ($r_i$) and an i-th reference label detectable via an i-th detection channel ($X_i$), and an i-th drop-off probe comprising an i-th drop-off sequence ($w_i$) and an i-th drop-off label detectable via an (i+1)-th detection channel ($X_{i+1}$);

wherein, if (e.g., when) R is strictly larger than 2, a R-th probe pair of the R number of probe pairs comprises:

a R-th reference probe comprising a R-th reference sequence (TR) and a R-th reference label associated with a R-th detection channel ($X_R$), and a R-th drop-off probe comprising a R-th drop-off sequence ($w_R$) and a R-th drop-off label detectable by the first detection channel ($X_1$);

wherein the method comprising:

detecting hybridization of reference probes of the R number of probe pairs to nucleic acid molecules or amplicons thereof comprising wildtype sequences at the reference regions in the plurality of partitions via each of the detection channels $X_1$-$X_R$; and detecting hybridization of drop-off probes of the R number of probe pairs to nucleic acid molecules or amplicons thereof comprising wildtype sequences at the target regions in the plurality of partitions via each of the detection channels $X_1$-$X_R$.

5. The method of embodiment 4, further comprising:

obtaining a first count of one or more partitions that each produces a positive signal via the i-th detection channel and negative signals via any other of the detection channels $X_1$-$X_R$;

obtaining a second count of one or more partitions that each produces negative signals via all of the detection channels $X_1$-$X_R$; and calculating a mutant probability ($\hat{P}$(m;)) that a given partition contains a mutant sequence at the target region corresponding to the i-th probe pair, wherein the mutant probability is based on a ratio between the first count and a sum of the first count and the second count.

6. The method of embodiment 5, further comprising determining an estimated concentration of the mutant sequences at the target region corresponding to the i-th probe pair in the sample based on the mutant probability.

7. The method of embodiment 6, wherein the estimated concentration of the mutant sequences at the target region corresponding to the i-th probe pair in the sample is determined according to:

$$\hat{C}(m_i) = -\frac{1}{v}\ln\left(1 - \hat{P}(m_i)\right)$$

wherein C (mt) is indicative of the estimated concentration of mutant sequences at the target region corresponding to the i-the probe pair in the sample, wherein v is indicative of volume of a partition, and wherein $\hat{P}(m_i)$ is indicative of the mutant probability that a given partition contains a mutant sequence at the target region corresponding to the i-th probe pair in the sample.

8. The method of any one of embodiments 4-7, further comprising determining a confidence interval and/or an uncertainty measure associated with the estimated concentration of the mutant sequences at the target region corresponding to the i-th probe pair in the sample.

9. The method of any one of embodiments 4-8, further comprising calculating a wildtype probability that a given partition contains a wildtype sequence at the target region corresponding to the i-th probe pair, wherein the wildtype probability is based on the mutant probability corresponding to the i-th probe pair and the mutant probability corresponding to the (i+1)-th probe pair, wherein the (i+1)-th probe pair refers to the first probe pair if (e.g., when) i=R.

10. The method of embodiment 9, wherein the wildtype probability is calculated according to:

$$\hat{P}(w_i) = \left(\frac{n_{i,(i+1)}}{n_0 + n_i + n_{i+1} + n_{i,(i+1)}} - \hat{P}(m_i)\hat{P}(m_{i+1})\right)\frac{1}{1 - \hat{P}(m_i)\hat{P}(m_{i+1})}$$

wherein $\hat{P}(w_i)$ is indicative of the wildtype probability that a given partition contains a wildtype sequence at the target region corresponding to the i-th probe pair,
wherein $n_{i,(i+1)}$ is indicative of a count of one or more partitions that each produces a positive signal via the $X_i$ detection channel, a positive signal via the $X_{i+1}$ detection channel, and negative signals via any other of the detection channels $X_1$-$X_R$;
wherein $n_{i,(i+1)}$ refers to $n_{R,1}$ if (e.g., when) i=R;
wherein $n_0$ is indicative of a count of one or more partitions that each produces negative signals via all the detection channels $X_1$-$X_R$;
wherein $n_i$ is indicative of a count of one or more partitions that each produces positive signal via the $X_i$ detection channel and negative signals via any other of the detection channels $X_1$-$X_R$;
wherein $n_{i+1}$ is indicative of a count of one or more partitions that each produces positive signal via the $X_{i+1}$ detection channel and negative signals via any other of the detection channels $X_1$-$X_R$;
wherein $n_{i+1}$ refers to $n_1$ if (e.g., when) i=R,
wherein $\hat{P}(m_i)$ is indicative of the mutant probability that a given partition contains a mutant sequence at the target region corresponding to the i-th probe pair,
wherein $\hat{P}(m_{i+1})$ is indicative of the mutant probability that a given partition contains a mutant sequence at the target region corresponding to the (i+1)-th probe pair, and
wherein $\hat{P}(m_{i+1})$ refers to $\hat{P}(m_1)$ if (e.g., when) i=R.

11. The method of embodiment 9 or 10, further comprising determining an estimated concentration of the wildtype sequence at the target region corresponding to the i-th probe pair in the sample based on the wildtype probability.

12. The method of embodiment 11, wherein the estimated concentration of the wildtype sequences at the target region corresponding to the i-th probe pair in the sample is determined according to:

$$\hat{C}(w_1) = -\frac{1}{v}\ln\left(1 - \hat{P}(w_1)\right)$$

wherein $\hat{C}(w_i)$ is indicative of the estimated concentration of wildtype sequences at the target region corresponding to the i-the probe pair in the sample,
wherein v is indicative of volume of a partition, and
wherein $\hat{P}(w_i)$ is indicative of the wildtype probability that a given partition contains a wildtype sequence at the target region corresponding to the i-th probe pair in the sample.

13. The method of any one of embodiments 9-12, further comprising determining a confidence interval and/or a uncertainty measure associated with the estimated concentration of the wildtype sequence at the target region corresponding to the i-th probe pair in the sample 14. The method of any one of embodiments 4-13, further comprising adjusting the concentration of nucleic acid molecules in the sample based on a count of partitions that each produces a positive signal via three or more of the detection channels $X_1$-$X_R$, wherein:
(i) if (e.g., when) the count is larger than a predetermined value, the adjusting is decreasing the concentration of the nucleic acid molecules in the sample by diluting the sample; or
(ii) if (e.g., when) the count is smaller than a predetermined value, the adjusting is increasing the concentration of the nucleic acid molecules in the sample by concentrating the sample.

15. The method of any one of embodiments 4-14, further comprising determining a quality control measure by comparing a count of partitions that each produces a positive signal via each of the detection channels $X_1$-$X_R$ with an estimated count, wherein the estimated count is based on counts of partitions other than the count of partitions that each produces a positive signal via each of the detection channels $X_1$-$X_R$.

16. The method of any one of embodiments 4-15, wherein R is between 2 and 6.

17. The method of embodiment 16, wherein R is 3.

18. The method of embodiment 17, further comprising:
obtaining a first count ($n_{100}$) of one or more partitions that each produces a positive signal via the detection channel $X_1$, a negative signal via the detection channel $X_2$, and a negative signal via the detection channel $X_3$;
obtaining a second count ($n_{000}$) of one or more partitions that each produces negative signals on all of the detection channels $X_1$-$X_3$, and
calculating a mutant probability ($\hat{P}(m_1)$) that a given partition contains a mutant sequence at the target region corresponding to the first probe pair, wherein the mutant probability is based on a ratio between the first count ($n_{100}$) and a sum of the first count ($n_{100}$) and the second count ($n_{000}$).

19. The method of embodiment 18, further comprising determining an estimated concentration $\hat{C}(m_1)$ of the mutant sequences at the target region corresponding to the first probe pair in the sample based on the mutant probability $\hat{P}(m_1)$.

20. The method of embodiment 18 or 19, further comprising determining a confidence interval and/or an uncertainty measure associated with the estimated concentration C ($m_1$) in the sample.

21. The method of any of embodiments 18-20, further comprising calculating a wildtype probability ($\hat{P}(w_1)$) that a given partition contains a wildtype sequence at the target region corresponding to the first probe pair in the sample, wherein the wildtype probability is calculated based on $\hat{P}(m_1)$.

22. The method of embodiment 21, wherein the wildtype probability ($\hat{P}(w_1)$) is determined based on $$\hat{P}(w_1) = \left(\frac{n_{110}}{n_{000} + n_{100} + n_{010} + n_{110}} - \hat{P}(m_1)\hat{P}(m_2)\right)\frac{1}{1 - \hat{P}(m_1)\hat{P}(m_2)},$$

wherein $n_{110}$ is indicative of a count of one or more partitions that each produces a positive signal via the first detection channel, a positive signal via the second detection channel, and a negative signal via the third detection channel,
wherein $n_{010}$ is indicative of a count of one or more partitions that each produces a negative signal via the first detection channel, a positive signal via the second detection channel, and a negative signal via the third detection channel, and wherein $\hat{P}(m_2)$ is indicative of a probability that a given partition contains a mutant sequence at the target region corresponding to the second probe pair.

23. The method of any one of embodiments 1-22, wherein substantially all partitions each further comprises:

an allele-specific (AS) probe comprising an AS label and an oligonucleotide AS sequence complementary to an allelic sequence at a target region, wherein the AS label is detectable via a detection channel that is different from the detection channels corresponding to the reference probes and the drop-off probes of the plurality of probe sets; and wherein the method further comprises:

detecting hybridization of the AS probe to nucleic acid molecules or amplicons thereof comprising the allelic sequence at the target region in the sample, thereby providing quantification of the allelic sequence at the target region in the sample.

24. The method of any one of embodiments 1-23, wherein each of the reference probes and the drop-off probes has a single detectable label.

25. The method of any one of embodiments 1-24, wherein the reference labels and drop-off labels are fluorophores.

26. The method of any one of embodiments 1-25, wherein one or more different detection channels have different excitation wavelength ranges and/or different emission wavelength ranges.

27. The method of any one of embodiments 1-26, wherein one or more different detection channels share the same excitation and/or emission wavelength ranges, but are associated with different fluorescence intensities.

28. The method of embodiment 27, wherein probe sets corresponding to different target regions within a gene of interest comprise drop-off probes having drop-off labels associated with different detection channels that share the same excitation and/or emission wavelength ranges, wherein the drop-off probes are detected at different fluorescence intensities with respect to each other.

29. The method of any one of embodiments 25-28, wherein the reference labels and drop-off labels are selected from the group consisting of fluorescein, FAM, YAKIMA YELLOW®, CY3™, HEX, VIC, ROX, CY5™, CY5.5™, ALEXA FLUOR® 647, ALEXA FLUOR®448, and Quasar705.

30. The method of any one of embodiments 17-29, wherein the first reference label, the second reference label and the third reference label are selected from the group consisting of CY3™, FAM and CY5™, or wherein the first reference label, the second reference label and the third reference label are selected from the group consisting of FAM, HEX and CY5™.

31. The method of any one of embodiments 1-30, wherein the target regions are mutation hotspot regions in one or more genes selected from the group consisting of EGFR, NRAS, KRAS, ESR1, and BRAF.

32. The method of any one of embodiments 1-31, wherein each partition further comprises:

(a) a plurality of primer sets corresponding to the plurality of target regions, and (b) a DNA-dependent DNA polymerase;

wherein each primer set of the plurality of primer sets comprises a forward oligonucleotide primer and a reverse oligonucleotide primer suitable for amplifying a target fragment comprising a target region corresponding to the primer set and the reference region corresponding to the target region;

wherein the method comprises amplifying the target fragments from the nucleic acid molecules in the plurality of partitions; and wherein the detecting comprises detecting hybridization of the reference probes and the drop-off probes to amplicons of the target fragments.

33. The method of embodiment 32, wherein the DNA-dependent DNA polymerase comprises 5' to 3' exonuclease activity and the detecting comprises detecting an increase in fluorescence caused by 5' to 3' exonuclease digestion of the reference labels from hybridized reference probes and/or the drop-off labels from hybridized drop-off probes in the plurality of partitions.

34. The method of any one of embodiments 1-33, wherein the amplicons are about 100 to about 200 nucleotides long.

35. The method of any one of embodiments 1-34, wherein the reference regions are not associated with single nucleotide polymorphisms.

36. The method of any one of embodiments 1-35, further comprising forming a plurality of partitions having a pre-determined volume.

37. The method of any one of embodiments 1-36, wherein the nucleic acid molecules are genomic DNA molecules, tumor DNA molecules, or cDNA molecules.

38. The method of any one of embodiments 1-37, further comprising extracting the nucleic acid molecules from a biological sample.

39. The method of embodiment 38, wherein the nucleic acid molecules are obtained from a formalin-fixed, paraffin-embedded (FFPE) sample, or a liquid biopsy sample.

40. The method of embodiment 38 or 39, comprising fragmenting nucleic acid molecules in the biological sample to provide the sample comprising nucleic acid molecules.

41. The method of any one of embodiments 1-40, wherein the plurality of target regions are microsatellite sequence loci.

42. The method of any one of embodiments 1-41, wherein the nucleic acid molecules are genomic DNA in a sample of cells, wherein the cells have been contacted with a site-specific genome-editing reagent configured to cleave target sites in the plurality of target regions, and wherein the mutant sequences are non-homologous end joining (NHEJ) edited sequences at the plurality of target regions.

43. The method of any one of embodiments 1 and 24-42, wherein each probe set of the plurality of probe sets further comprises:

an allele-specific (AS) probe comprising an AS label and an oligonucleotide AS sequence complementary to an allelic sequence at the target region corresponding to the respective probe set, wherein the AS label is detectable via a detection channel that is different from the detection channel of the respective reference probe or the detection channel of the respective drop-off probe, and wherein AS labels of the plurality of probe sets are detectable via different detection channels with respect to each other, wherein the method further comprises:

detecting hybridization of AS probes of the plurality of probe sets to nucleic acid molecules or amplicons thereof comprising allelic sequences at the target regions in the plurality of partitions;

thereby providing quantification of allelic sequences at the plurality of target regions in the sample.

44. The method of embodiment 43, wherein each probe set of the plurality of probe sets is a probe triplet, wherein the total number of detection channels is fewer than three times the total number of probe sets.

45. The method of embodiment 44, wherein the total number of detection channels is one more than the total number of probe sets.

46. The method of embodiment 45, wherein the nucleic acid molecules are genomic DNA in a sample of cells, wherein the cells have been contacted with a site-specific genome-editing reagent and HDR template nucleic acids comprising HDR replacement sequences, wherein the site-specific genome-editing reagent is configured to cleave target sites in the plurality of target regions, wherein the mutant sequences are non-homologous end joining (NHEJ) edited sequences at the plurality of target regions, and wherein the allelic sequences are HDR replacement sequences inserted at the plurality of target regions.

47. The method of embodiment 45 or 46, wherein the site-specific genome-editing reagent comprises a Cas nuclease, a transcription activator-like effector nuclease (TALEN), or a Zinc-finger nuclease.

48. The method of any one of embodiments 42 and 46-47, further comprising contacting the cells with the site-specific genome-editing reagent.

49. A method for quantification of mutations at a plurality of microsatellite sequence loci in a sample comprising nucleic acid molecules, wherein the nucleic acid molecules are distributed among a plurality of partitions of the sample, and wherein substantially all partitions each comprises:

a plurality of primer sets corresponding to the plurality of microsatellite sequence loci, wherein each primer set of the plurality of primer sets comprises:

a forward oligonucleotide primer and a reverse oligonucleotide primer suitable for amplifying target fragments from the nucleic acid molecules, wherein each target fragment comprises the microsatellite sequence locus corresponding to the primer set and an adjacent reference region upstream or downstream to the microsatellite sequence locus;

a plurality of probe pairs corresponding to the plurality of microsatellite sequence loci, wherein each probe pair of the plurality of probe pairs comprises:

a drop-off probe comprising a drop-off label and an oligonucleotide drop-off sequence complementary to a wildtype sequence of a microsatellite sequence locus corresponding to the respective probe pair, a reference probe comprising a reference label and an oligonucleotide reference sequence complementary to a wildtype sequence of the reference region corresponding to the respective probe pair, wherein a reference label and a drop-off label of each probe pair of the plurality of probe pairs are detectable via different detection channels;

wherein reference labels of the plurality of probe pairs are detectable via different detection channels with respect to each other;

wherein drop-off labels of the plurality of probe pairs are detectable via different detection channels with respect to each other;

wherein at least one reference label of the plurality of probe pairs and at least one drop-off label of the plurality of probe pairs are detectable via the same detection channel;

wherein the method comprises:

amplifying the target fragments in the plurality of partitions; and detecting hybridization of reference probes and drop-off probes of the plurality of probe pairs to amplicons of the target fragments in the plurality of partitions, thereby providing quantification of mutations at the plurality of microsatellite sequence loci in the sample.

50. A method for quantification of unmodified, homology directed repair (HDR)-edited, and/or non-homologous end joining (NHEJ)-edited sequences at a plurality of target regions in nucleic acid molecules from a sample of cells, wherein the cells have been contacted with a site-specific genome-editing reagent and HDR template nucleic acids comprising HDR replacement sequences, wherein the site-specific genome-editing reagent is configured to cleave target sites in the plurality of target regions, wherein the nucleic acid molecules are distributed among a plurality of partitions of the sample, and wherein substantially all partitions each comprises:

a plurality of probe sets corresponding to the plurality of target regions, wherein each probe set of the plurality of probe sets comprises:

a HDR probe comprising a HDR label and an oligonucleotide HDR sequence complementary to a HDR replacement sequence inserted at a target region corresponding to the respective probe set, an NHEJ drop-off probe comprising an NHEJ drop-off label and an oligonucleotide drop-off sequence complementary to a wildtype sequence of the target region corresponding to the respective probe set, and wherein the drop-off sequence does not hybridize to NHEJ-edited mutant sequences at the target region corresponding to the respective probe set, a reference probe comprising a reference label and an oligonucleotide reference sequence complementary to a wildtype sequence at an adjacent reference region upstream or downstream to the target region corresponding to the respective probe set, wherein a HDR label, an NHEJ drop-off label, and a reference label of each probe set of the plurality of probe sets are detectable via different detection channels;

wherein HDR labels of the plurality of probe sets are detectable via different detection channels with respect to each other;

wherein NHEJ drop-off labels of the plurality of probe sets are detectable via different detection channels with respect to each other;

wherein reference labels of the plurality of probe sets are detectable via different detection channels with respect to each other;

wherein at least one reference label of the plurality of probe sets and at least one NHEJ drop-off label of the plurality of probe sets are detectable via the same detection channel, and/or at least one reference label of the plurality of probe sets and at least one HDR label of the plurality of probe sets are detectable via the same detection channel;

wherein the method comprises:

detecting hybridization of reference probes of the plurality of probe sets to nucleic acid molecules or amplicons thereof comprising wildtype sequences at the reference regions in the plurality of partitions;

detecting hybridization of HDR probes of the plurality of probe sets to nucleic acid molecules or amplicons thereof comprising the HDR replacement sequences at the target regions in the plurality of partitions; and detecting hybridization of NHEJ drop-off probes of the plurality of probe sets to nucleic acid molecules or amplicons thereof comprising wildtype sequences at the target regions in the plurality of partitions;

thereby providing quantification of unmodified, HDR-edited, and/or NHEJ-edited sequences at the plurality of target regions in the sample.

51. The method of embodiment 50, wherein the plurality of probe sets are (R−1) number of probe triplets, wherein a first probe triplet of the (R−1) number of probe triplets comprises:

a first reference probe comprising a first reference sequence ($m_1$) and a first reference label detectable via a first detection channel ($X_1$);

a first NHEJ drop-off probe comprising a first NHEJ drop-off sequence ($r_1$) and a first NHEJ drop-off label detectable via a second detection channel ($X_2$); and a first HDR probe comprising a first HDR sequence ($w_1$) and a first HDR label detectable via a third channel ($X_3$);

wherein a second probe triplet of the (R−1) number of probe triplets comprises:

a second reference probe comprising a second reference sequence ($m_2$) and a second reference label detectable via the second detection channel ($X_2$);

a second NHEJ drop-off probe comprising a second drop-off sequence ($r_2$) and a second NHEJ drop-off label detectable via the third detection channel ($X_3$); and a second HDR probe comprising a second HDR sequence ($w_2$) and a second HDR label detectable via a fourth detection channel ($X_4$);

wherein, if (e.g., when) R is strictly larger than 3, an i-th probe triplet ($2<i<R-1$) of the (R−1) number of probe triplets comprises:

an i-th reference probe comprising an i-th reference sequence ($m_i$) and an i-th reference label detectable via an i-th detection channel ($X_i$);

an i-th NHEJ drop-off probe comprising an i-th drop-off sequence ($r_i$) and an i-th NHEJ drop-off label detectable via an (i+1)-th detection channel ($X_{i+1}$); and an i-th HDR probe comprising an i-th HDR sequence ($w_i$) and an i-th HDR label detectable via an (i+2)-th detection channel ($X_{i+2}$);

wherein, if (e.g., when) R is strictly larger than 3, a (R−1)-th probe triplet of the (R−1) number of probe triplets comprises:

a (R−1)-th reference probe comprising a (R−1)-th reference sequence ($m_{R-1}$) and a R-th reference label detectable via a R-th detection channel ($X_R$);

a (R−1)-th NHEJ drop-off probe comprising a (R−1)-th drop-off sequence ($r_{R-1}$) and a (R−1)-th NHEJ drop-off label detectable via a (R−1)-th detection channel ($X_{R-1}$); and a (R−1)-th HDR probe comprising a (R−1)-th HDR sequence ($w_R$-1) and a (R−1)-th HDR label detectable via the first detection channel ($X_1$);

the method comprises:

detecting hybridization of reference probes of the (R−1) number of probe triplets to nucleic acid molecules or amplicons thereof comprising wildtype sequences at the reference regions in the plurality of partitions via each of the detection channels $X_1$-$X_{R-2}$ and $X_R$;

detecting hybridization of NHEJ drop-off probes of the (R−1) number of probe triplets to nucleic acid molecules or amplicons thereof comprising wildtype sequences at the target regions in the plurality of partitions via each of the detection channels $X_2$-$X_{R-1}$; and detecting hybridization of HDR probes of the (R−1) number of probe triplets to nucleic acid molecules or amplicons thereof comprising the HDR replacement sequences at the target regions in the plurality of partitions via each of the detection channels $X_1$ and $X_3$-$X_R$.

52. The method of embodiment 51, further comprising:

if (e.g., when) $1 \leq i \leq R-2$:

obtaining a first count of one or more partitions that each produces a positive signal via the $X_i$ detection channel and negative signals via any other of the detection channels $X_1$-$X_R$;

obtaining a second count of one or more partitions that each produces negative signals via all of the detection channels $X_1$-$X_R$;

or if (e.g., when) i is R−1:

obtaining a first count of one or more partitions that each produces a positive signal via the $X_R$ detection channel and negative signals via any other of the detection channel $X_1$-$X_R$;

obtaining a second count of one or more partitions that each produces negative signals via all of the detection channels $X_1$-$X_R$; and calculating an NHEJ-edited probability ($\hat{P}(r_i)$) that a given partition contains an NHEJ-edited sequence at the target region corresponding to the i-th probe triplet, wherein the NHEJ-edited probability is based on a ratio between the first count and a sum of the first count and the second count.

53. The method of embodiment 51 or 52, further comprising:

if (e.g., when) $1 \leq i < R-2$:

obtaining a first count of one or more partitions that each produces a positive signal via the $X_i$ detection channel, a positive signal via the $X_{i+1}$ detection channel and negative signals via any other of the detection channels $X_1$-$X_R$;

obtaining a second count of one or more partitions that each produces negative signals via each of the detection channels $X_1$-$X_{i-1}$, and negative signals via each of the detection channels $X_{i+2}$-$X_R$; and calculating an unmodified probability ($\hat{P}(m;)$) that a given partition contains a wildtype sequence at the target region corresponding to the i-th probe triplet, wherein the unmodified probability is based on $\hat{P}(r_i)$, $\hat{P}(r_{i+1})$ and a ratio between the first count and a sum of the first count and the second count;

or if (e.g., when) i is R−1:

obtaining a first count of one or more partitions that each produces a positive signal via the $X_R$ detection channel, a positive signal at the $X_{R-1}$ detection channel and negative signals via any other of the detection channel $X_1$-$X_R$;

obtaining a second count of one or more partitions that each produces negative signals via each of the detection channels $X_1$-$X_{R-2}$; and calculating an unmodified probability ($\hat{P}(MR-1)$) that a given partition contains a wildtype sequence at the target region corresponding to the (R−1)-th probe triplet, wherein the unmodified probability is based on a ratio between the first count and a sum of the first count and the second count.

54. The method of any of embodiments 51-53, further comprising:

if (e.g., when) $1 \leq i < R-2$:

obtaining a first count of one or more partitions that each produces a positive signal via the $X_i$ detection channel, a positive signal via the $X_{i+2}$ detection channel and negative signals via any other of the detection channels $X_1$-$X_R$;

obtaining a second count of one or more partitions that each produces negative signals via each of the detection channels $X_1$-$X_{i-1}$, negative signal in $X_{i+1}$, and negative signals via each of the detection channels $X_{i+3}$-$X_R$; and calculating a HDR-edited probability ($\hat{P}(w;)$) that a given partition contains a HDR replacement sequence at the target region corresponding to the i-th probe triplet, wherein the HDR-edited probability is based on $\hat{P}(r_i)$, $\hat{P}(r_{i+2})$, and a ratio between the first count and a sum of the first count and the second count;

or if (e.g., when) i is R−1:

obtaining a first count of one or more partitions that each produces a positive signal via the $X_R$ detection channel, a positive signal at the $X_1$ detection channel and negative signals via any other of the detection channel $X_1$-$X_R$;

obtaining a second count of one or more partitions that each produces negative signals via each of the detection channels $X_2$-$X_{R-1}$; and calculating a HDR-edited probability ($\hat{P}(w_R\text{-}1)$) that a given partition contains a wildtype sequence at the target region corresponding to the (R−1)-th probe triplet, wherein the HDR-edited probability is based on $\hat{P}(r_{R-1})$, $\hat{P}(r_1)$, and a ration between the first count and a sum of the first count and the second count.

55. A method for quantification of wildtype and/or allelic sequences at R number of target regions in a sample comprising nucleic acid molecules, wherein the nucleic acid molecules are distributed among a plurality of partitions of the sample, wherein substantially all partitions each comprises R number of probe triplets corresponding to the R number of target regions, wherein a first probe triplet of the R number of probe triplets comprises:

a first reference probe corresponding to (e.g., comprising) a first reference sequence ($w_1$) and a first reference label detectable via a first detection channel ($X_1$), a first AS probe of the first probe triplet ("first AS probe 1") corresponding to (e.g., comprising) a first allelic sequence ($r_1$) and a first AS label of the first probe triplet ("first AS label 1") detectable via the first detection channel ($X_1$), and a second AS probe of the first probe triplet ("second AS probe 1") corresponding to (e.g., comprising) the first allelic sequence ($r_1$) and a second AS label of the first probe triplet ("second AS label 1") detectable via the second detection channel ($X_2$);

wherein a second probe triplet of the R number of probe triplets comprises:

a second reference probe corresponding to (e.g., comprising) a second reference sequence ($w_2$) and a second reference label detectable via the second detection channel ($X_2$), a first AS probe of the second probe triplet ("first AS probe 2") corresponding to (e.g., comprising) a second allelic sequence ($r_2$) and a first AS label of the second probe triplet ("AS label 2") detectable via the second detection channel ($X_2$), and a second AS probe of the second probe triplet ("second AS probe 2") corresponding to (e.g., comprising) the second allelic sequence second allelic sequence ($r_2$) and a second AS label of the second probe triplet ("second AS label 2") detectable via a third detection channel ($X_3$);

wherein, if (e.g., when) R is strictly larger than 3, an i-th probe triplet ($2<i<R$) of the R number of probe triplet comprises:

an i-th reference probe corresponding to (e.g., comprising) an i-th reference sequence ($w_i$) and an i-th reference label detectable via an i-th detection channel ($X_i$), a first AS probe of the i-th probe triplet ("first AS probe i") corresponding to (e.g., comprising) an i-th allelic sequence ($r_i$) and a first AS label of the i-th probe triplet ("first AS label i") detectable via the i-th detection channel ($X_i$), and a second AS probe of the i-th probe triplet ("second AS probe i") corresponding to (e.g., comprising) an i-th allelic sequence ($r_i$) and a second AS label of the i-th probe triplet ("second AS label i") detectable via the (i+1)-th detection channel ($X_{i+1}$);

wherein, if (e.g., when) R is strictly larger than 2, a R-th probe triplet of the R number of probe triplets comprises:

a R-th reference probe corresponding to (e.g., comprising) a R-th reference sequence ($w_R$) and a R-th reference label detectable via a R-th detection channel ($X_R$), a first AS probe of the R-th probe triplet ("first AS probe R") corresponding to (e.g., comprising) an R-th allelic sequence (TR) and a first AS label of the R-th probe triplet ("first AS label R") detectable via the R-th detection channel ($X_R$), and a second AS probe of the R-th probe triplet ("second AS probe R") corresponding to (e.g., comprising) a R-th allelic sequence ($r_R$) and a second AS label of the R-th probe triplet ("second AS label R") detectable via the first detection channel ($X_1$);

wherein the first AS probe and the second AS probe of each probe triplet hybridize to the same allelic sequence, different portions within the same allelic sequence, or complementary sequences thereof at a target region corresponding to the respective probe triplet;

wherein the reference sequence of each probe triplet is at a reference region corresponding to the respective probe triplet;

wherein the detection channels $X_1$-$X_R$ are different from each other;

wherein the method comprises detecting hybridization of reference probes of the R number of probe triplets to nucleic acid molecules or amplicons thereof comprising reference sequences or complementary sequences thereof at the reference regions in the plurality of partitions via each of the detection channels $X_1$-$X_R$; and detecting hybridization of the first AS probes and the second AS probes of the R number of probe triplets to nucleic acid molecules or amplicons thereof comprising allelic sequences or complementary sequences thereof at the target regions in the plurality of partitions via each of the detection channels $X_1$-$X_R$; thereby providing quantification of wildtype and/or allelic sequences at the R number of target regions in the sample.

56. The method of embodiment 55, wherein the reference region of a probe triplet is adjacent to (e.g., upstream or downstream) the target region corresponding to the respective probe set.

57. The method of embodiment 55 or 56, further comprising:

obtaining a first count of one or more partitions that each produces a positive signal via the i-th detection channel and negative signals via any other of the detection channels $X_1$-$X_R$;

obtaining a second count of one or more partitions that each produces negative signals via all of the detection channels $X_1$-$X_R$; and calculating a wildtype probability ($\hat{P}(m_i)$) that a given partition contains a wildtype sequence at the target region corresponding to the i-th probe triplet, wherein the wildtype probability is based on a ratio between the first count and a sum of the first count and the second count.

58. The method of embodiment 57, further comprising determining an estimated concentration of the wildtype sequences at the target region corresponding to the i-th probe triplet in the sample based on the wildtype probability.

59. The method of embodiment 58, wherein the estimated concentration of the wildtype sequences at the target region corresponding to the i-th probe triplet in the sample is determined according to:

$$\hat{C}(m_i) = -\frac{1}{v}\ln\left(1 - \hat{P}(m_i)\right)$$

wherein $\hat{C}(m_i)$ is indicative of the estimated concentration of wildtype sequences at the target region corresponding to the i-the probe triplet in the sample, wherein v is indicative of volume of a partition, and wherein $\hat{P}(m_i)$ is indicative of the wildtype probability that a given partition contains a wildtype sequence at the target region corresponding to the i-th probe triplet in the sample.

60. The method of any one of embodiments 55-59, further comprising determining a confidence interval and/or an uncertainty measure associated with the estimated concentration of the wildtype sequences at the target region corresponding to the i-th probe triplet in the sample.

61. The method of any one of embodiments 55-60, further comprising calculating an allele-specific (AS) probability that a given partition contains an allelic sequence at the target region corresponding to the i-th probe triplet, wherein the AS probability is based on the wildtype probability corresponding to the i-th probe triplet and the wildtype probability corresponding to the (i+1)-th probe triplet, wherein the (i+1)-th probe triplet refers to the first probe triplet if (e.g., when) i=R.

62. The method of embodiment 61, wherein the AS probability is calculated according to:

$$\hat{P}(w_i) = \left(\frac{n_{i,(i+1)}}{n_0 + n_i + n_{i+1} + n_{i,(i+1)}} - \hat{P}(m_i)\hat{P}(m_{i+1})\right)\frac{1}{1 - \hat{P}(m_i)\hat{P}(m_{i+1})}$$

wherein $\hat{P}(w_i)$ is indicative of the AS probability that a given partition contains an allelic sequence at the target region corresponding to the i-th probe triplet, wherein $n_{i,(i+1)}$ is indicative of a count of one or more partitions that each produces a positive signal via the $X_i$ detection channel, a positive signal via the $X_{i+1}$ detection channel, and negative signals via any other of the detection channels $X_1$-$X_R$;

wherein $n_{i,(i+1)}$ refers to $n_{R,1}$ if (e.g., when) i=R;

wherein $n_0$ is indicative of a count of one or more partitions that each produces negative signals via all the detection channels $X_1$-$X_R$;

wherein $n_i$ is indicative of a count of one or more partitions that each produces positive signal via the $X_i$ detection channel and negative signals via any other of the detection channels $X_1$-$X_R$;

wherein $n_{i+1}$ is indicative of a count of one or more partitions that each produces positive signal via the $X_{i+1}$ detection channel and negative signals via any other of the detection channels $X_1$-$X_R$;

wherein $n_{i+1}$ refers to $n_1$ if (e.g., when) i=R, wherein $\hat{P}(m_i)$ is indicative of the wildtype probability that a given partition contains a wildtype sequence at the target region corresponding to the i-th probe triplet, wherein $\hat{P}(m_{i+1})$ is indicative of the wildtype probability that a given partition contains a wildtype sequence at the target region corresponding to the (i+1)-th probe triplet, and wherein $\hat{P}(m_{i+1})$ refers to $\hat{P}(m_1)$ if (e.g., when) i=R.

63. The method of embodiment 61 or 62, further comprising determining an estimated concentration of the allelic sequence at the target region corresponding to the i-th probe triplet in the sample based on the AS probability.

64. The method of embodiment 63, wherein the estimated concentration of the allelic sequences at the target region corresponding to the i-th probe triplet in the sample is determined according to:

$$\hat{C}(w_1) = -\frac{1}{v}\ln(1 - \hat{P}(w_1))$$

wherein $\hat{C}(w_i)$ is indicative of the estimated concentration of allelic sequences at the target region corresponding to the i-the probe triplet in the sample, wherein v is indicative of volume of a partition, and wherein $\hat{P}(w_i)$ is indicative of the AS probability that a given partition contains an allelic sequence at the target region corresponding to the i-th probe triplet in the sample.

65. The method of any one of embodiments 61-64, further comprising determining a confidence interval and/or a uncertainty measure associated with the estimated concentration of the allelic sequence at the target region corresponding to the i-th probe triplet in the sample 66. The method of any one of embodiments 55-65, further comprising adjusting the concentration of nucleic acid molecules in the sample based on a count of partitions that each produces a positive signal via three or more of the detection channels $X_1$-$X_R$, wherein: (i) if (e.g., when) the count is larger than a pre-determined value, the adjusting is decreasing the concentration of the nucleic acid molecules in the sample by diluting the sample; or (ii) if (e.g., when) the count is smaller than a pre-determined value, the adjusting is increasing the concentration of the nucleic acid molecules in the sample by concentrating the sample.

67. The method of any one of embodiments 55-66, further comprising determining a quality control measure by comparing a count of partitions that each produces a positive signal via each of the detection channels $X_1$-$X_R$ with an estimated count, wherein the estimated count is based on counts of partitions other than the count of partitions that each produces a positive signal via each of the detection channels $X_1$-$X_R$.

68. The method of any one of embodiments 55-67, wherein R is between 2 and 6.

69. The method of embodiment 68, wherein R is 3.

70. The method of embodiment 69, further comprising:

obtaining a first count ($n_{100}$) of one or more partitions that each produces a positive signal via the detection channel $X_1$, a negative signal via the detection channel $X_2$, and a negative signal via the detection channel $X_3$;

obtaining a second count ($n_{000}$) of one or more partitions that each produces negative signals on all of the detection channels $X_1$-$X_3$, and calculating a wildtype probability ($\hat{P}(m_1)$) that a given partition contains a wildtype sequence at the target region corresponding to the first probe triplet, wherein the wildtype probability is based on a ratio between the first count ($n_{100}$) and a sum of the first count ($n_{100}$) and the second count ($n_{000}$).

71. The method of embodiment 70, further comprising determining an estimated concentration $\hat{C}(m_1)$ of the wildtype sequences at the target region corresponding to the first probe triplet in the sample based on the wildtype probability $\hat{P}(m_1)$.

72. The method of embodiment 70 or 71, further comprising determining a confidence interval and/or an uncertainty measure associated with the estimated concentration $\hat{C}(m_1)$ in the sample.

73. The method of any of embodiments 70-72, further comprising calculating an AS probability ($\hat{P}(w_1)$) that a given partition contains an allelic sequence at the target region corresponding to the first probe triplet in the sample, wherein the AS probability is calculated based on $\hat{P}(m_1)$.

74. The method of embodiment 73, wherein the AS probability ($\hat{P}(w_1)$) is determined based on $$\hat{P}(w_1) = \left(\frac{n_{110}}{n_{000} + n_{100} + n_{010} + n_{110}} - \hat{P}(m_1)\hat{P}(m_2)\right)\frac{1}{1 - \hat{P}(m_1)\hat{P}(m_2)},$$

wherein $n_{110}$ is indicative of a count of one or more partitions that each produces a positive signal via the first detection channel, a positive signal via the second detection channel, and a negative signal via the third detection channel, wherein $n_{010}$ is indicative of a count of one or more partitions that each produces a negative signal via the first detection channel, a positive signal via the second detection channel, and a negative signal via the third detection channel, and wherein $\hat{P}(m_2)$ is indicative of a probability that a given partition contains a wildtype sequence at the target region corresponding to the second probe pair.

75. The method of any one of embodiments 55-74, wherein each of the reference probes, the first AS probes and the second AS probes has a single detectable label.

76. The method of any one of embodiments 55-75, wherein the reference labels, the first AS labels and the second AS labels are fluorophores.

77. The method of any one of embodiments 55-76, wherein one or more different detection channels have different excitation wavelength ranges and/or different emission wavelength ranges.

78. The method of embodiment 76 or 77, wherein the reference labels, the first AS labels and the second AS labels are selected from the group consisting of fluorescein, FAM, YAKIMA YELLOW®, CY3™, HEX, VIC, ROX, CY5™, CY5.5™, ALEXA FLUOR® 647, ALEXA FLUOR®448, and Quasar705.

79. The method of any one of embodiments 69-78, wherein the first reference label, the second reference label and the third reference label are selected from the group consisting of CY3™, FAM and CY5™, or wherein the first reference label, the second reference label and the third reference label are selected from the group consisting of FAM, HEX and CY5™.

80. The method of any one of embodiments 55-79, wherein the target regions are associated with rare alleles and/or copy number variations (CNVs).

81. The method of any one of embodiments 55-80, wherein each partition further comprises:

(a) a plurality of primer sets corresponding to the plurality of target regions and the plurality of reference regions; and (b) a DNA-dependent DNA polymerase;

wherein each primer set of the plurality of primer sets comprises a forward oligonucleotide primer and a reverse oligonucleotide primer suitable for amplifying a target fragment comprising a target region corresponding to the primer set;

wherein each primer set of the plurality of primer sets comprises a forward oligonucleotide primer and a reverse oligonucleotide primer suitable for amplifying a reference fragment comprising the reference region corresponding to the target region;

wherein the method comprises amplifying the target fragments and the reference regions from the nucleic acid molecules in the plurality of partitions; and wherein the detecting comprises detecting hybridization of the reference probes to amplicons of the reference regions, and detecting hybridization of the first AS probes and the second AS probes to amplicons of the target fragments.

82. The method of any one of embodiments 56-80, wherein each partition further comprises:

(a) a plurality of primer sets corresponding to the plurality of target regions, and (b) a DNA-dependent DNA polymerase;

wherein each primer set of the plurality of primer sets comprises a forward oligonucleotide primer and a reverse oligonucleotide primer suitable for amplifying a target fragment comprising a target region corresponding to the primer set and the reference region corresponding to the target region;

wherein the method comprises amplifying the target fragments from the nucleic acid molecules in the plurality of partitions; and wherein the detecting comprises detecting hybridization of the reference probes, the first AS probes and the second AS probes to amplicons of the target fragments.

83. The method of embodiment 81 or 82, wherein the DNA-dependent DNA polymerase comprises 5' to 3' exonuclease activity and the detecting comprises detecting an increase in fluorescence caused by 5' to 3' exonuclease digestion of the reference labels from hybridized reference probes and/or the first AS labels from hybridized first AS probes and/or the second AS labels from hybridized second AS probes in the plurality of partitions.

84. The method of any one of embodiments 55-83, wherein the amplicons are about 100 to about 200 nucleotides long.

85. The method of any one of embodiments 55-84, wherein the reference regions are not associated with single nucleotide polymorphisms.

86. The method of any one of embodiments 55-85, further comprising forming a plurality of partitions having a pre-determined volume.

87. The method of any one of embodiments 55-86, wherein the nucleic acid molecules are genomic DNA molecules, tumor DNA molecules, or cDNA molecules.

88. The method of any one of embodiments 55-87, further comprising extracting the nucleic acid molecules from a biological sample.

89. The method of embodiment 88, wherein the nucleic acid molecules are obtained from a formalin-fixed, paraffin-embedded (FFPE) sample, or a liquid biopsy sample.

90. The method of embodiment 88 or 89, comprising fragmenting nucleic acid molecules in the biological sample to provide the sample comprising nucleic acid molecules.

EXAMPLES

Example 1. Triplex Drop-Off Digital PCR Assay for Detection of KRAS, NRAS and EGFR Mutations In clinical settings, a set of predictive genetic markers are routinely monitored for diagnosis and to track therapy efficacy. For example, in non-small cell lung cancer the presence of deletions in the epidermal growth factor (EGFR) exon 19 confers sensitivity to first generation tyrosine kinase inhibitors. Moreover, in colorectal carcinoma, KRAS and NRAS proto-oncogene mutations are strong indicators of resistance to anti-EGFR antibodies.

A triplex drop-off dPCR assay was developed to detect wildtype and mutant sequences at the G13 locus (e.g., G13D) of KRAS, the Q61 locus (e.g., Q61K) of NRAS and the E19 locus (e.g., E19 deletion) of EGFR. Previously, drop-off dPCR assays have been developed to detect individual pairs of wildtype and mutant sequences at each genetic locus in individual assays. The ability to multiplex three mutation hotspots in a single dPCR assay greatly facilitates detection of predictive biomarkers such as KRAS, NRAS and EGFR in samples from cancer patients. The triplex drop-off assay may be used on any dPCR system with at least three fluorescence channels, such as the NAICA™ System (Stilla Technologies).

Figure 3:
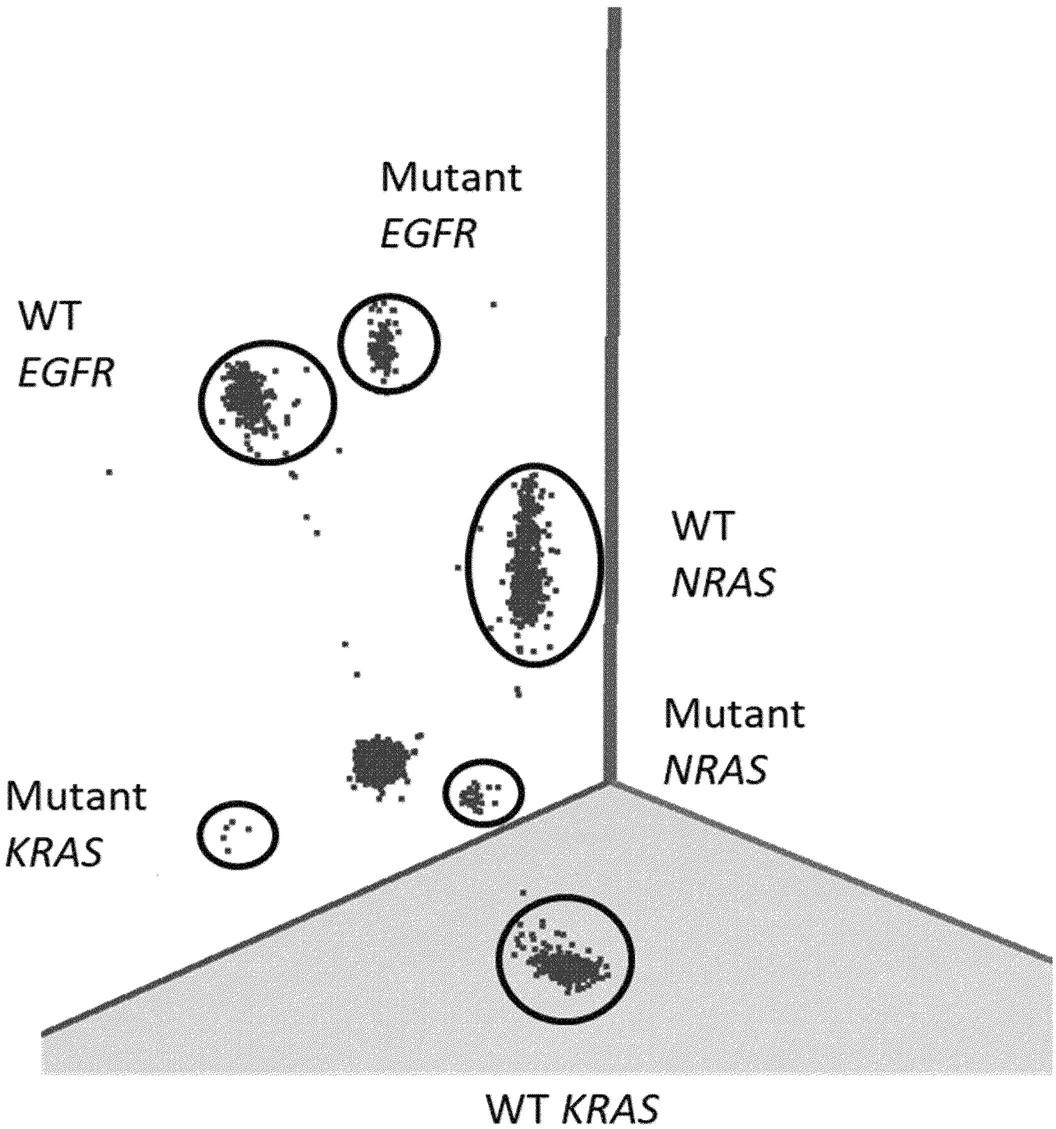
FIG. 3 shows a three-dimensional plot of fluorescent signals from dPCR reaction droplets of a sample in a triplex drop-off dPCR assay for detection of KRAS, NRAS and EGFR mutations. The dPCR assay was performed on a sample containing three mutant DNA species mixed together at different concentrations with wildtype DNA molecules. The first mutant DNA species has a G13D mutation in KRAS, the second mutant DNA species has a Q61K mutation in NRAS, and the third DNA species has an E19 deletion mutation in EGFR. TABLE 12 shows an exemplary set of forward and reverse primers, reference probes and drop-off probes for KRAS, NRAS and EGFR in a triplex drop-off dPCR assay. TABLE 13 shows the expected concentration, measured concentration, and standard deviation of the measured concentration for each genetic population in the sample.

A DNA sample was prepared by mixing three mutant DNA species (i.e., G13D KRAS, Q61K NRAS and E19 deletion EGFR) at different concentrations with wildtype DNA. The sample was subject to the triplex drop-off dPCR assay with primers, reference and drop-off probes as shown in TABLE 12. The experiment was carried out according to the methods described below. FIG. 3 shows a three-dimensional plot of fluorescence signals from each dPCR droplet, which demonstrates well-resolved droplet clusters having distinct fluorescence signal signatures. TABLE 13 shows the actual and estimated concentrations of the various genetic species in the sample. The triplex dPCR assay allows accurate and simultaneous quantification of all six genetic species in the sample

TABLE 12

| Primers/ Probes | 5' Fluoro phore | Sequence | 3' modifi- cation | SEQ ID NO |
|---|---|---|---|---|
| KRAS-Forward | — | TGAAAATGACTGAATATAAACTTGTG | — | 1 |
| KRAS-Reverse | — | CTCTATTGTTGGATCATATTCGTC | — | 2 |
| KRAS Ref. Probe | FAM | AGTGCCTTGACGATACAG | MGB-NFQ | 3 |
| KRAS Drop-off | Cy5 | CCTACGCCACCAGCTC | MGB-NFQ | 4 |

TABLE 12-continued

| Primers/ Probes | 5' Fluoro phore | Sequence | 3' modifi-cation | SEQ ID NO |
|---|---|---|---|---|
| NRAS-Forward | — | CAAGTGGTTATAGATGGTGAAAC | — | 5 |
| NRAS-Reverse | — | CCTTCGCCTGTCCTCAT | — | 6 |
| NRAS Ref. Probe | Cy5 | TTTGTTGGACATACTGGATA | MGB-NFQ | 7 |
| NRAS Drop-off | Cy3 | AG{C}TG{G}ACAA{G}AAGAGTA | BHQ-2 | 8 |
| EGFR Del19-Forward | — | GTGAGAAAGTTAAAATTCCCG | — | 9 |
| EGFR Del19-Reverse | — | CACACAGCAAAGCAGAAAC | — | 10 |
| EGFR Del19 Ref. Probe | FAM | CACATCGAGGATTTCCTTGTTGGC | BHQ-1 | 11 |
| EGFR Del19 Drop-off | Cy5 | AGGAATTA{A}GA{G}AAG{C}AACAT C | BHQ-3 | 12 |

Bases between { } are Locked Nucleic Acid (LNA) bases.

TABLE 13

| Mutant/WT | Cp/μl expected | Cp/μl measured | Standard deviation |
|---|---|---|---|
| KRAS G13D | 1 | 0.44 | 0.2879 |
| KRAS WT | 40 | 37.18 | 2.3779 |
| NRAS Q61K | 2 | 3.83 | 0.362 |
| NRAS WT | 40 | 40.89 | 2.4673 |
| EGFR E19-dels | 10 | 8.81 | 0.8972 |
| EGFR WT | 40 | 33.57 | 0.3234 |

Materials and Methods

The following materials were used:

1. Barrier/filter tips (sterile and aerosol resistant)
2. Micropipettes
3. Powder-free gloves
4. Microcentrifuge
5. Vortex
6. PCR reaction microtubes (sterile, 1.5 mL)
7. PCR and DNA free flowhood for PCR mix assembly
8. PCR and DNA free flowhood for DNA template addition
9. digital PCR sapphire chips (Stilla Technologies)
10. pressurized Geode thermocycler (Stilla Technologies)
11. 6-color digital PCR reader.
12. CRYSTAL™ Reader software (Stilla Technologies), including CRYSTAL™ Miner Software and scripts for thresholding and data acquisition in 3D plots.
13. NANODROP® ND-3300 Spectrophotometer or QUBIT® fluorometer (Thermo Scientific) or real-time thermocycler.

The following reagents were used:

1. PERFECTA™ Multiplex qPCR ToughMix 5X (Quanta Biosciences), containing DNA Hot Start polymerase with 5'-3' exonuclease activity, DNA polymerase buffer and optimized concentrations of deoxynucleoside triphosphate (dNTPs) and magnesium chloride ($MgCl_2$)
2. Fluorescein solution (Sigma, Saint Louis, MO, USA)
3. Genomic DNA template
4. Molecular biology grade water
5. Restriction enzyme (in case of using non fragmented high molecular weight DNA)
6. Primers and TAQMAN™ oligoprobes in 100 μM stock solution Primers and probes were designed using three distinct fluorophores that can be detected using three channels of detection. Three drop-off assays each comprising a forward and a reverse primer and a probe pair consisting of a reference probe and a drop-off probe were designed. Each drop-off assay targeted a genetic region ("target genetic locus") known to host genetic alterations, including single mutations, insertions, and deletions. The primers were designed in order to generate an amplicon as short as possible for the assay to be suitable for the analysis of fragmented DNA template. Both reference probes and drop-off probes were designed to anneal within the region delimited by the forward and the reverse primer. The reference probe was designed to anneal to amplicons with either wildtype or mutant sequences at the target genetic locus. For example, the reference probe was designed to anneal to a sequence upstream or downstream of the target genetic locus, and such sequence did not include a single nucleotide polymorphism (SNP) site. The drop-off probe was designed to anneal only to the wildtype sequence at the target genetic locus. The drop-off probe annealing site includes the region where genetic alterations of interest occurs. The reference probes and the drop-off probes could additionally contain modified nucleotides (e.g., locked nucleic acids) that increase the specificity of the probes.

Each reference probe was labeled with a reference fluorophore. Each drop-off probe was labeled with a drop-off fluorophore that was distinct from the reference fluorophore in the same probe pair. The three reference probes were designed to have distinct fluorophores. Each combination of reference/drop-off fluorophores corresponding to each probe pair was unique, and the set of reference fluorophores and the set of drop-off fluorophores were designed to be circular permutations with respect to each other. For example, the three probe pairs were labeled with fluorophores in the following manner:

Assay 1: reference probe (fluorophore 1), drop-off probe (fluorophore 3)

Assay 2: reference probe (fluorophore 2), drop-off probe (fluorophore 1)

Assay 3: reference probe (fluorophore 3), drop-off probe (fluorophore 2)

An exemplary set of primers and probes for the triplex drop-off dPCR assay is shown in TABLE 12.

General considerations: Special caution was exercised to prevent DNA carry-over contamination, which could lead to false positives. All reagents and plastic consumables were sterile, DNA- and DNAse-free, and of molecular biology grade. Gloves were worn while handling reagents, materials, and equipment. Commercially available DNA decontamination solutions were used to clean all surfaces dedicated to protocol handling. Areas dedicated to sample extraction, digital PCR mixture assembly, and digital PCR amplification were separated. As PCR products are the leading cause of contamination, reagents and consumables brought in the post amplification area must not be reintroduced in the pre amplification areas.

DNA template preparation, quantification and quality monitoring: The DNA template was prepared as follows. High quality DNA or cDNA templates suitable for PCR amplification were obtained using a standard phenol/chloroform extraction method or commercial extraction kits. The DNA quantity and quality obtained were assessed prior to digital PCR amplification and control samples were first accessed to ensure compatibility with the NAICA™ System. High molecular weight DNA was fragmented using sonication or restriction enzyme digestion. The DNA templates were quantified using a NANODROP™ ND-3300 Spectrophotometer, a QUBIT™ fluorometer or using real-time PCR quantification. DNA quantities compatible within the detection range of the NAICA™ System were used: e.g., 0.0165 to 1650 ng of human DNA per digital PCR reaction for the sapphire chip (equivalent to 5 to 500 000 copies of DNA per 25 μL reaction). A DNA template is deemed as high quality when a 260 nm/280 nm absorbance ratio of ~1.8-2 and a 260 nm/230 nm absorbance ratio in the range of 2.0-2.2 are obtained.

Set-up of dPCR reactions: The digital PCR reaction was set up as follows. Reagents were thawed on ice, mixed thoroughly before use. In the pre-PCR "clean room", the primer pool was prepared by mixing all of the forward and the reverse primers at 100 M in a stock solution to obtain 20 μM working solutions. Individual 20 μM working solutions for each probe was prepared, and a 1 μM fluorescein working solution. In a clean 1.5 mL microcentrifuge tube, the digital PCR reaction mix was prepared by assembling the reagents (5X PERFECTA™ ToughMix, Fluorescein, Primers, Probes) in a 25 μl final volume using the following final concentrations: 1X PERFECTA™ ToughMix, 100 nM fluorescein, 500-1000 nM each primer pair and 250-750 nM each probe. The digital PCR reaction mix was dispensed in separate microcentrifuge tubes and the lids were closed. Opening only one tube at a time to avoid cross-contamination, the DNA template was added individually to each reaction tube. The lids were closed and the tubes were vertexed thoroughly. The microcentrifuge tubes were briefly centrifuged to collect the entire volume at the bottom of each tube. The white caps of the inlet ports of the sapphire chip were removed and 25 μL of the reaction mixture were gently pipetted over the oil phase in each inlet port, being extremely careful not to introduce air bubbles. A tall PCR-ready white cap was placed on each inlet port. Care was taken to avoid preparing too many chips at a time to prevent evaporation of the oil contained within the chips. The chips were subsequently placed on the thermal plate of the NAICA™ Geode. The lid of the Geode was closed and the following thermocycling program was run:

–95° C. 3 min

–50 cycles of

–95° C. 30 s

–55-65° C. 30 s

End of thermocycling

Data acquisition and analysis of test samples: Following digital PCR amplification and Geode depressurization, the sapphire chips were placed in the NAICA™ 6-color prototype reader and the reading program was launched. After the reading step, the data was analyzed using the CRYSTAL™ Miner software. Briefly, the numbers of positive and negative droplets in each channel of detection corresponding to the labels in the reference and drop-off probes were counted. The mutant and wildtype targets concentrations were calculated according to the formula in the "Embodiment Employing Three (3) Probe Pairs" section.

What is claimed is:

1. A method for quantification of wildtype and allelic sequences at a plurality of target regions in a sample comprising nucleic acid molecules distributed among a plurality of partitions of the sample, wherein 70% or more of the total number of partitions each comprises a plurality of probe sets corresponding to the plurality of target regions, wherein each probe set of the plurality of probe sets comprises:

a drop-off probe comprising a drop-off label and an oligonucleotide drop-off sequence complementary to a wildtype sequence at a target region corresponding to the respective probe set;

a reference probe comprising a reference label and an oligonucleotide reference sequence complementary to a wildtype sequence at an adjacent reference region upstream or downstream to the target region corresponding to the respective probe set;

an allele-specific (AS) probe comprising an AS label and an oligonucleotide AS sequence complementary to an allelic sequence at the target region corresponding to the respective probe set, wherein the reference label, the drop-off label, and the AS label of each probe set of the plurality of probe sets are detectable via different detection channels;

wherein reference labels of the plurality of probe sets are detectable via different detection channels with respect to each other;

wherein at least one reference label of the plurality of probe sets and at least one drop-off label of the plurality of probe sets are detectable via the same detection channel; and wherein the set of reference labels of the plurality of probe sets, the set of drop-off labels of the plurality of probe sets, and the set of the AS labels of the plurality of probe sets have overlapping labels;

the method comprising:

detecting hybridization of reference probes of the plurality of probe sets to nucleic acid molecules or amplicons thereof comprising wildtype sequences at the reference regions in the plurality of partitions;

detecting hybridization of drop-off probes of the plurality of probe sets to nucleic acid molecules or amplicons thereof comprising wildtype sequences at the target regions in the plurality of partitions; and detecting hybridization of AS probes of the plurality of probe sets to nucleic acid molecules or amplicons thereof comprising allelic sequences at the target regions in the plurality of partitions to provide quantification of wildtype sequences and allelic sequences at the plurality of target regions in the sample.

2. The method of claim 1, wherein drop-off labels of the plurality of probe sets are detectable via different detection channels with respect to each other.

3. The method of claim 1, wherein AS labels of the plurality of probe sets are detectable via different detection channels with respect to each other.

4. The method of claim 1, wherein reference labels of the plurality of probe sets are detectable via different detection channels with respect to each other; drop-off labels of the plurality of probe sets are detectable via different detection channels with respect to each other; and wherein AS labels of the plurality of probe sets are detectable via different detection channels with respect to each other.

5. The method of claim 1, wherein the total number of detection channels is fewer than the total number of probes.

6. The method of claim 5, wherein the plurality of probe sets is a plurality of probe triplets, and the total number of detection channels is fewer than three times the total number of probe triplets.

7. The method of claim 6, wherein the total number of detection channels is equal to the total number of probe triplets plus 1.

8. The method of claim 1, wherein the plurality of probe sets are 2 probe triplets, wherein a first probe triplet of the 2 probe triplets comprises:

a first reference probe comprising a first reference sequence ($m_1$) and a first reference label detectable via a first detection channel ($X_1$);

a first drop-off probe comprising a first drop-off sequence ($r_1$) and a first drop-off label detectable via a second detection channel ($X_2$); and a first allele-specific (AS) probe comprising a first AS sequence ($w_1$) and a first AS label detectable via a third channel ($X_3$);

wherein a second probe triplet of the 2 probe triplets comprises:

a second reference probe comprising a second reference sequence ($m_2$) and a second reference label detectable via the second detection channel ($X_2$);

a second drop-off probe comprising a second drop-off sequence ($r_2$) and a second drop-off label detectable via the third detection channel ($X_3$); and a second AS probe comprising a second AS sequence ($w_2$) and a second AS label detectable via a fourth detection channel ($X_4$);

wherein the drop-off sequence of each probe triplet is complementary to a wildtype sequence at a target region corresponding to the respective probe triplet;

wherein the reference sequence of each probe triplet is complementary to a wildtype sequence at an adjacent reference region upstream or downstream to the target region corresponding to the respective probe triplet;

wherein the AS sequence of each probe triplet is complementary to an allelic sequence at the target region corresponding to the respective probe triplet; and wherein the detection channels $X_1$, $X_2$, $X_3$, and $X_4$ are different from each other;

the method comprising:

detecting hybridization of reference probes of the 2 probe triplets to nucleic acid molecules or amplicons thereof comprising wildtype sequences at the reference regions in the plurality of partitions;

detecting hybridization of AS probes of the 2 probe triplets to nucleic acid molecules or amplicons thereof comprising the allelic sequences at the target regions in the plurality of partitions; and detecting hybridization of drop-off probes of the 2 probe triplets to nucleic acid molecules or amplicons thereof comprising wildtype sequences at the target regions in the plurality of partitions to provide quantification of wildtype and allelic sequences at the plurality of target regions in the sample.

9. The method of claim 1, wherein the plurality of probe sets are (R−1) number of probe triplets, wherein R is an integer of 4 or more, wherein a first probe triplet of the (R−1) number of probe triplets comprises:

a first reference probe comprising a first reference sequence ($m_1$) and a first reference label detectable via a first detection channel ($X_1$);

a first drop-off probe comprising a first drop-off sequence ($r_1$) and a first drop-off label detectable via a second detection channel ($X_2$); and a first allele-specific (AS) probe comprising a first AS sequence ($w_1$) and a first AS label detectable via a third channel ($X_3$);

wherein a second probe triplet of the (R−1) number of probe triplets comprises:

a second reference probe comprising a second reference sequence ($m_2$) and a second reference label detectable via the second detection channel ($X_2$);

a second drop-off probe comprising a second drop-off sequence ($r_2$) and a second drop-off label detectable via the third detection channel ($X_3$); and a second AS probe comprising a second AS sequence ($w_2$) and a second AS label detectable via a fourth detection channel ($X_4$);

wherein, an i-th probe triplet ($2<i<R-1$) of the (R−1) number of probe triplets comprises:

an i-th reference probe comprising an i-th reference sequence ($m_i$) and an i-th reference label detectable via an i-th detection channel ($X_i$);

an i-th drop-off probe comprising an i-th drop-off sequence ($r_i$) and an i-th drop-off label detectable via an (i+1)-th detection channel ($X_{i+1}$); and an i-th AS probe comprising an i-th AS sequence ($w_i$) and an i-th AS label detectable via an (i+2)-th detection channel ($X_{i+2}$);

wherein, a (R−1)-th probe triplet of the (R−1) number of probe triplets comprises:

a (R−1)-th reference probe comprising a (R−1)-th reference sequence ($m_{R-1}$) and a R-th reference label detectable via a R-th detection channel ($X_R$);

a (R−1)-th drop-off probe comprising a (R−1)-th drop-off sequence ($r_{R-1}$) and a (R−1)-th drop-off label detectable via a (R−1)-th detection channel ($X_{R-1}$); and a (R−1)-th AS probe comprising a (R−1)-th AS sequence ($w_{R-1}$) and a (R−1)-th AS label detectable via the first detection channel ($X_1$);

wherein the drop-off sequence of each probe triplet is complementary to a wildtype sequence at a target region corresponding to the respective probe triplet;

wherein the reference sequence of each probe triplet is complementary to a wildtype sequence at an adjacent reference region upstream or downstream to the target region corresponding to the respective probe triplet;

wherein the AS sequence of each probe triplet is complementary to an allelic sequence at the target region corresponding to the respective probe triplet;

wherein the detection channels $X_1$-$X_R$ are different from each other;

the method comprising:

detecting hybridization of reference probes of the (R−1) number of probe triplets to nucleic acid molecules or amplicons thereof comprising wildtype sequences at the reference regions in the plurality of partitions via each of the detection channels $X_1$-$X_R$;

detecting hybridization of AS probes of the (R−1) number of probe triplets to nucleic acid molecules or amplicons thereof comprising the allelic sequences at the target regions in the plurality of partitions via each of the detection channels $X_1$-$X_R$; and detecting hybridization of drop-off probes of the (R−1) number of probe triplets to nucleic acid molecules or amplicons thereof comprising wildtype sequences at the target regions in the plurality of partitions via each of the detection channels $X_1$-$X_R$ to provide quantification of wildtype and allelic sequences at the plurality of target regions in the sample.

10. The method of claim 1, wherein each of the reference probes, drop-off probes and AS probes has a single detectable label.

11. The method of claim 1, wherein the reference labels, drop-off labels, and AS labels are fluorophores.

12. The method of claim 1, wherein one or more different detection channels have different excitation wavelength ranges and/or different emission wavelength ranges.

13. The method of claim 1, wherein one or more different detection channels share the same excitation and/or emission wavelength ranges, but are associated with different fluorescence intensities.

14. The method of claim 1, wherein one or more detection channels are associated with different excitation wavelengths or wavelength ranges, and/or different emission wavelengths or wavelength ranges, and one or more detection channels are associated with different fluorescence intensities.

15. The method of claim 1, wherein the reference labels, drop-off labels and/or AS labels are selected from the group consisting of fluorescein, fluorescein amidite (FAM), hexachlorofluorescein (HEX), and carboxy-X-rhodamine (ROX).

16. The method of claim 1, wherein at least one reference label of the plurality of probe sets and at least one AS label of the plurality of probe sets are detectable via the same detection channel.

17. A method for quantification of wildtype and allelic sequences at a plurality of target regions in a sample comprising nucleic acid molecules distributed among a plurality of partitions of the sample, wherein 70% or more of the total number of partitions each comprises a plurality of probe sets corresponding to the plurality of target regions, wherein each probe set of the plurality of probe sets comprises:

a drop-off probe comprising a drop-off label and an oligonucleotide drop-off sequence complementary to a wildtype sequence at a target region corresponding to the respective probe set;

a reference probe comprising a reference label and an oligonucleotide reference sequence complementary to a wildtype sequence at an adjacent reference region upstream or downstream to the target region corresponding to the respective probe set; and an allele-specific (AS) probe comprising an AS label and an oligonucleotide AS sequence complementary to an allelic sequence at the target region corresponding to the respective probe set, wherein the reference label, the drop-off label, and the AS label of each probe set of the plurality of probe sets are detectable via different detection channels;

wherein drop-off labels of the plurality of probe sets are detectable via different detection channels with respect to each other;

wherein at least one reference label of the plurality of probe sets and at least one drop-off label of the plurality of probe sets are detectable via the same detection channel; and wherein the set of reference labels of the plurality of probe sets, the set of drop-off labels of the plurality of probe sets, and set of the AS labels of the plurality of probe sets have overlapping labels;

the method comprising:

detecting hybridization of reference probes of the plurality of probe sets to nucleic acid molecules or amplicons thereof comprising wildtype sequences at the reference regions in the plurality of partitions;

detecting hybridization of drop-off probes of the plurality of probe sets to nucleic acid molecules or amplicons thereof comprising wildtype sequences at the target regions in the plurality of partitions; and detecting hybridization of AS probes of the plurality of probe sets to nucleic acid molecules or amplicons thereof comprising allelic sequences at the target regions in the plurality of partitions to provide quantification of wildtype sequences and allelic sequences at the plurality of target regions in the sample.

18. A method for quantification of wildtype and allelic sequences at a plurality of target regions in a sample comprising nucleic acid molecules distributed among a plurality of partitions of the sample, wherein 70% or more of the total number of partitions each comprises a plurality of probe sets corresponding to the plurality of target regions, wherein each probe set of the plurality of probe sets comprises:

a drop-off probe comprising a drop-off label and an oligonucleotide drop-off sequence complementary to a wildtype sequence at a target region corresponding to the respective probe set;

a reference probe comprising a reference label and an oligonucleotide reference sequence complementary to a wildtype sequence at an adjacent reference region upstream or downstream to the target region corresponding to the respective probe set; and an allele-specific (AS) probe comprising an AS label and an oligonucleotide AS sequence complementary to an allelic sequence at the target region corresponding to the respective probe set, wherein the reference label, the drop-off label, and the AS label of each probe set of the plurality of probe sets are detectable via different detection channels;

wherein reference labels of the plurality of probe sets are detectable via different detection channels with respect to each other;

wherein drop-off labels of the plurality of probe sets are detectable via different detection channels with respect to each other;

wherein AS labels of the plurality of probe sets are detectable via different detection channels with respect to each other;

wherein at least one reference label of the plurality of probe sets and at least one drop-off label of the plurality of probe sets are detectable via the same detection channel; and wherein the set of reference labels of the plurality of probe sets, the set of drop-off labels of the plurality of probe sets, and set of the AS labels of the plurality of probe sets have overlapping labels;

the method comprising:

detecting hybridization of reference probes of the plurality of probe sets to nucleic acid molecules or amplicons thereof comprising wildtype sequences at the reference regions in the plurality of partitions;

detecting hybridization of drop-off probes of the plurality of probe sets to nucleic acid molecules or amplicons thereof comprising wildtype sequences at the target regions in the plurality of partitions; and detecting hybridization of AS probes of the plurality of probe sets to nucleic acid molecules or amplicons thereof comprising allelic sequences at the target regions in the plurality of partitions to provide quantification of wildtype sequences and allelic sequences at the plurality of target regions in the sample.

* * * * *

SEQUENCE LISTING

```
<160> NUMBER OF SEQ ID NOS: 12

<210> SEQ ID NO 1
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1

tgaaaatgac tgaatataaa cttgtg                                          26


<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2

ctctattgtt ggatcatatt cgtc                                            24
```

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct

<400> SEQUENCE: 3
agtgccttga cgatacag 18

<210> SEQ ID NO 4
<211> LENGTH: 16
<212> TYPE: DNA
<213> ORGANISM: Artificial Sequence
<220> FEATURE:
<223> OTHER INFORMATION: Synthetic Construct

<400> SEQUENCE: 4
cctacgccac cagctc 16

<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
caagtggtta tagatggtga aac 23

<210> SEQ ID NO 6
<211> LENGTH: 17
<212> TYPE: DNA
<213> ORGANISM: Artificial Sequence
<220> FEATURE:
<223> OTHER INFORMATION: Synthetic Construct

<400> SEQUENCE: 6
ccttcgcctg tcctcat 17

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
tttgttggac atactggata 20

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: 3
<223> OTHER INFORMATION: Locked Nucleic Acid (LNA) base
<220> FEATURE:
<221> NAME/KEY: modified_base
<222> LOCATION: 6
<223> OTHER INFORMATION: Locked Nucleic Acid (LNA) base
<220> FEATURE:
<221> NAME/KEY: modified_base
<222> LOCATION: 11
<223> OTHER INFORMATION: Locked Nucleic Acid (LNA) base -continued

```
<400> SEQUENCE: 8

agctggacaa gaagagta                                                   18


<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9

gtgagaaagt taaaattccc g                                               21


<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10

cacacagcaa agcagaaac                                                  19


<210> SEQ ID NO 11
<211> LENGTH: 24
<212> TYPE: DNA
<213> ORGANISM: Artificial Sequence
<220> FEATURE:
<223> OTHER INFORMATION: Synthetic Construct

<400> SEQUENCE: 11

cacatcgagg atttccttgt tggc                                            24


<210> SEQ ID NO 12
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: 9
<223> OTHER INFORMATION: Locked Nucleic Acid (LNA) base
<220> FEATURE:
<221> NAME/KEY: modified_base
<222> LOCATION: 12
<223> OTHER INFORMATION: Locked Nucleic Acid (LNA) base
<220> FEATURE:
<221> NAME/KEY: modified_base
<222> LOCATION: 16
<223> OTHER INFORMATION: Locked Nucleic Acid (LNA) base

<400> SEQUENCE: 12

aggaattaag agaagcaaca tc                                              22
```